US008652455B2

(12) United States Patent

DiCosimo et al.

(10) Patent No.: US 8,652,455 B2
(45) Date of Patent: Feb. 18, 2014

(54) TARGETED PERHYDROLASES

(75) Inventors: Robert DiCosimo, Chadds Ford, PA (US); Scott D. Cunningham, Chadds Ford, PA (US); Stephen R. Fahnestock, Wilmington, DE (US); Tanja Maria Gruber, Media, PA (US); Mark S. Payne, Wilmington, DE (US); Pierre E. Rouviere, Wilmington, DE (US); Linda Jane Solomon, Wilmington, DE (US); Hong Wang, Kennett Square, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/330,171

(22) Filed: Dec. 19, 2011

(65) Prior Publication Data

US 2012/0321581 A1 Dec. 20, 2012

Related U.S. Application Data

(60) Provisional application No. 61/424,916, filed on Dec. 20, 2010.

(51) Int. Cl.

*A61L 9/00* (2006.01)
*C12P 7/40* (2006.01)
*C12N 9/96* (2006.01)
*C12N 9/18* (2006.01)

(52) U.S. Cl.

USPC ........... 424/76.1; 435/136; 435/188; 435/197

(58) Field of Classification Search

None
See application file for complete search history.

(56) References Cited

U.S. PATENT DOCUMENTS

| | | | |
|---|---|---|---|
| 3,901,819 | A | 8/1975 | Nakagawa et al. |
| 3,974,082 | A | 8/1976 | Weyn |
| 4,444,886 | A | 4/1984 | Esders et al. |
| 5,116,575 | A | 5/1992 | Badertscher et al. |
| 5,296,161 | A | 3/1994 | Wiersema et al. |
| 5,364,554 | A | 11/1994 | Stanislowski et al. |
| 5,398,846 | A | 3/1995 | Corba et al. |
| 5,552,018 | A | 9/1996 | Devenyns |
| 5,624,634 | A | 4/1997 | Brougham et al. |
| 5,683,724 | A | 11/1997 | Hei et al. |
| 5,871,714 | A | 2/1999 | Budny |
| 6,210,639 | B1 | 4/2001 | Vlass et al. |
| 6,265,366 | B1 | 7/2001 | Bonett et al. |
| 6,319,888 | B2 | 11/2001 | Wei et al. |
| 6,391,840 | B1 | 5/2002 | Thompson et al. |
| 6,410,498 | B1 | 6/2002 | Smets et al. |
| 6,465,410 | B1 | 10/2002 | Bettiol et al. |
| 6,468,955 | B1 | 10/2002 | Smets et al. |
| 6,579,842 | B2 | 6/2003 | Howell et al. |
| 6,586,384 | B2 | 7/2003 | Hemmington et al. |
| 6,635,286 | B2 | 10/2003 | Hei et al. |
| 6,830,745 | B1 | 12/2004 | Budny |
| 6,906,024 | B1 | 6/2005 | Baeck et al. |
| 6,995,125 | B2 | 2/2006 | Dasque et al. |
| 7,041,793 | B2 | 5/2006 | Davis et al. |
| 7,361,487 | B2 | 4/2008 | Alapuranen et al. |
| 7,384,787 | B2 | 6/2008 | Kazlauskas et al. |
| 7,510,859 | B2 | 3/2009 | Wieland et al. |
| 7,632,919 | B2 | 12/2009 | Cunningham et al. |
| 7,700,716 | B2 | 4/2010 | Cunningham et al. |
| 7,709,601 | B2 | 5/2010 | Cunningham et al. |
| 7,754,460 | B2 | 7/2010 | Amin et al. |
| 7,858,581 | B2 | 12/2010 | Cunningham et al. |
| 7,906,617 | B2 | 3/2011 | Cunningham et al. |
| 7,910,347 | B1 | 3/2011 | DiCosimo et al. |
| 7,923,233 | B1 | 4/2011 | DiCosimo et al. |
| 7,927,854 | B1 | 4/2011 | DiCosimo et al. |
| 7,928,076 | B2 | 4/2011 | Cunningham et al. |
| 7,932,072 | B1 | 4/2011 | DiCosimo et al. |
| 7,960,528 | B1 | 6/2011 | DiCosimo et al. |
| 2002/0098524 | A1 | 7/2002 | Murray et al. |
| 2005/0008526 | A1 | 1/2005 | Bianchetti et al. |
| 2005/0054752 | A1 | 3/2005 | O'Brien et al. |
| 2005/0139608 | A1 | 6/2005 | Muehlhausen et al. |
| 2005/0158253 | A1 | 7/2005 | Budny et al. |
| 2005/0281773 | A1 * | 12/2005 | Wieland et al. ............ 424/70.14 |
| 2006/0171885 | A1 | 8/2006 | Janssen et al. |
| 2006/0246566 | A1 | 11/2006 | Vehmaanpera et al. |
| 2007/0042924 | A1 | 2/2007 | DiCosimo et al. |

(Continued)

FOREIGN PATENT DOCUMENTS

| | | | |
|---|---|---|---|
| CN | 101591648 | A | 12/2009 |
| DE | 19733841 | A1 | 2/1999 |

(Continued)

OTHER PUBLICATIONS

International Search Report, PCT/US2011/065902, Mail date Aug. 1, 2012.

Vincent et al, Multifunctinal xylooligosaccharide/cephalosporin C deacetylase revealed by the hemameric structure of the *Bacillus subtilis* enzyme at 1.9 A resolution, J.Mol.Biol., 2003, 330, 593-606, Science Direct.

Tomme et al., Characterization and affinity applications of cellulose-binding domains, J. of Chromatography B, 1998, 715, 283-296, Elsevier.

Han et al., Screening of Cellulose Binding Motif (CMB) from phage peptides library, Acta Biochimica et Biophysica Sinica, 1998, 30, 263-266.

(Continued)

*Primary Examiner* — Tekchand Saidha
*Assistant Examiner* — Younus Meah

(57) ABSTRACT

Disclosed herein are compositions and methods to target enzymatic peracid production to a target surface. The peracid benefit agent produced by the targeted perhydrolytic enzyme can be use for a variety of applications such as bleaching, whitening, disinfecting, destaining, deodorizing, and combinations thereof. Specifically, a fusion protein comprising a perhydrolytic enzyme and at least one peptidic component having affinity for a target surface (excluding body surfaces and oral care surfaces) is used in combination with a suitable substrate and a source of peroxygen to enzymatically produce a peracid on or near the surface of the target material. In a preferred aspect, the target surface is a cellulosic material.

27 Claims, 1 Drawing Sheet

(56) References Cited

U.S. PATENT DOCUMENTS

| | | | | |
|---|---|---|---|---|
| 2007/0072185 | A1 | 3/2007 | Schnorr et al. | |
| 2007/0082832 | A1 | 4/2007 | DiCosimo et al. | |
| 2007/0105740 | A1 | 5/2007 | DiCosimo et al. | |
| 2007/0184999 | A1 | 8/2007 | DiCosimo et al. | |
| 2008/0145353 | A1 | 6/2008 | Amin et al. | |
| 2008/0176299 | A1 | 7/2008 | DiCosimo et al. | |
| 2008/0176783 | A1 * | 7/2008 | DiCosimo et al. ............ | 510/374 |
| 2009/0005590 | A1 | 1/2009 | DiCosimo et al. | |
| 2009/0031198 | A1 | 1/2009 | Johansson | |
| 2010/0041752 | A1 | 2/2010 | DiCosimo et al. | |
| 2010/0048448 | A1 | 2/2010 | DiCosimo et al. | |
| 2010/0086510 | A1 | 4/2010 | Ben-Bassat et al. | |
| 2010/0086534 | A1 | 4/2010 | DiCosimo et al. | |
| 2010/0086535 | A1 | 4/2010 | DiCosimo et al. | |
| 2010/0086621 | A1 | 4/2010 | Ben-Bassat et al. | |
| 2010/0087528 | A1 | 4/2010 | DiCosimo et al. | |
| 2010/0087529 | A1 | 4/2010 | DiCosimo et al. | |
| 2010/0158823 | A1 | 6/2010 | Cheng et al. | |
| 2010/0298231 | A1 | 11/2010 | Schneider et al. | |
| 2010/0298240 | A1 | 11/2010 | Schneider et al. | |
| 2010/0298241 | A1 | 11/2010 | Schneider et al. | |
| 2010/0298531 | A1 | 11/2010 | Schneider et al. | |
| 2010/0298532 | A1 | 11/2010 | Schneider et al. | |
| 2010/0298533 | A1 | 11/2010 | Schneider et al. | |
| 2010/0298534 | A1 | 11/2010 | Schneider et al. | |
| 2010/0298535 | A1 | 11/2010 | Schneider et al. | |
| 2010/0310495 | A1 | 12/2010 | Schneider et al. | |
| 2011/0081693 | A1 | 4/2011 | DiCosimo et al. | |
| 2011/0236335 | A1 | 9/2011 | DiCosimo et al. | |
| 2011/0250673 | A1 | 10/2011 | DiCosimo et al. | |

FOREIGN PATENT DOCUMENTS

| | | | |
|---|---|---|---|
| EP | 491782 | B1 | 12/1993 |
| EP | 0450800 | B1 | 6/1996 |
| EP | 0479600 | B1 | 8/1997 |
| EP | 1224270 | B1 | 9/2005 |
| EP | 1115828 | B1 | 4/2006 |
| EP | 1040222 | B1 | 2/2008 |
| EP | 1689859 | B1 | 3/2011 |
| GB | 692478 | | 4/1940 |
| GB | 1560399 | | 12/1976 |
| WO | 9724106 | A1 | 7/1997 |
| WO | 9724109 | A1 | 7/1997 |
| WO | 9740127 | A1 | 10/1997 |
| WO | 9740229 | A1 | 10/1997 |
| WO | 0018865 | A1 | 4/2000 |
| WO | 0107009 | A1 | 2/2001 |
| WO | 2005051997 | A1 | 6/2005 |

OTHER PUBLICATIONS

Hahn et al., Some New Hair Removal: Part 1, New depilation methods, Leder, 1967, 18, 184-192.

Guillen et al., Carbohydrate-binding domains: multiplicity of biological roles, Appl. Microbiolo. Biotechnology, 2010, 85, 1241-1249, Springer.

Muyldermans, Single domain camel antibodies: current status, Molecular Biotechnology, 2001, 74, 277-302, Elsevier.

Hosse et al., A new generation of protein display scaffolds for molecular recognition, Protein Science, 2006, 15, 14-27, Cold spring Harbor Laboratory Press.

Binz et al., Engineering novel binding proteins from nonimmunoglobulin domains, Nature Biotechnology, 2005, 23(10), 1257-1268, Nature Publishing Group.

Cantarel et al., The carbohydrate-active enzymes database : an expert resource for glycogenomics, Nucleic Acids Research, 2009, 37, D233-D238.

Kirk et al., Metal Free Haloperoxidases: Fact or Artifact?, Angew Chem. Int. Ed. 1999, 38, 977-979.

Bernard et al., Molecular basis of perhydrolase activity in serine hydrolases, Angew.chem.Int.Ed., 2005, 44, 2742-2746; Wiley-VCH Verlag GmbH & Co.

Lillie et al., Metachromatic basophilia of keratin after oxidation-cleavage of disulfide bonds, J. HistochemCytochem, 1954, 2, 95-102.

U.S. Appl. No. 61/318,016, filed Mar. 26, 2010, DiCosimo.

U.S. Appl. No. 13/330,261, filed Dec. 19, 2011, Butterick.

U.S. Appl. No. 13/330,105, filed Dec. 19, 2011, Chisholm.

* cited by examiner

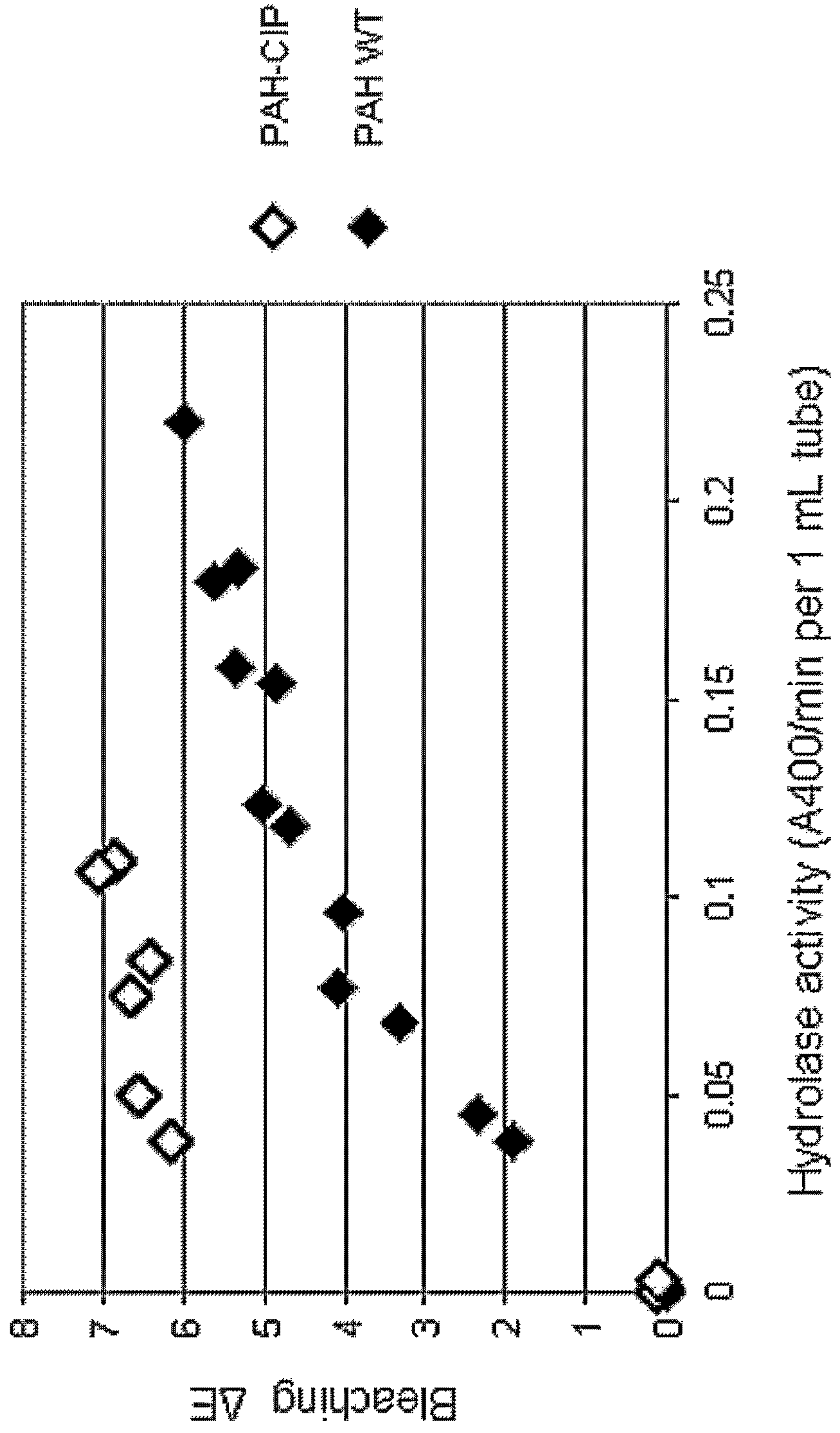
PAH-CIP
PAH WT
Bleaching ΔE
Hydrolase activity (A400/min per 1 mL tube)
0
1
2
3
4
5
6
7
8
0
0.05
0.1
0.15
0.2
0.25

SEQUENCE LISTING

```
<160> NUMBER OF SEQ ID NOS: 181

<210> SEQ ID NO 1
<211> LENGTH: 960
<212> TYPE: DNA
```

```
<213> ORGANISM: Bacillus subtilis
<220> FEATURE:
<221> NAME/KEY: CDS
<222> LOCATION: (1)..(960)

<400> SEQUENCE: 1

atg caa cta ttc gat ctg ccg ctc gac caa ttg caa aca tat aag cct       48
Met Gln Leu Phe Asp Leu Pro Leu Asp Gln Leu Gln Thr Tyr Lys Pro
1               5                   10                  15

gaa aaa aca gca ccg aaa gat ttt tct gag ttt tgg aaa ttg tct ttg       96
Glu Lys Thr Ala Pro Lys Asp Phe Ser Glu Phe Trp Lys Leu Ser Leu
            20                  25                  30

gag gaa ctt gca aaa gtc caa gca gaa cct gat tta cag ccg gtt gac      144
Glu Glu Leu Ala Lys Val Gln Ala Glu Pro Asp Leu Gln Pro Val Asp
        35                  40                  45

tat cct gct gac gga gta aaa gtg tac cgt ctc aca tat aaa agc ttc      192
Tyr Pro Ala Asp Gly Val Lys Val Tyr Arg Leu Thr Tyr Lys Ser Phe
    50                  55                  60

gga aac gcc cgc att acc gga tgg tac gcg gtg cct gac aag caa ggc      240
Gly Asn Ala Arg Ile Thr Gly Trp Tyr Ala Val Pro Asp Lys Gln Gly
65                  70                  75                  80

ccg cat ccg gcg atc gtg aaa tat cat ggc tac aat gca agc tat gat      288
Pro His Pro Ala Ile Val Lys Tyr His Gly Tyr Asn Ala Ser Tyr Asp
                85                  90                  95

ggt gag att cat gaa atg gta aac tgg gca ctc cat ggc tac gcc gca      336
Gly Glu Ile His Glu Met Val Asn Trp Ala Leu His Gly Tyr Ala Ala
            100                 105                 110

ttc ggc atg ctt gtc cgc ggc cag cag agc agc gag gat acg agt att      384
Phe Gly Met Leu Val Arg Gly Gln Gln Ser Ser Glu Asp Thr Ser Ile
        115                 120                 125

tca ctg cac ggt cac gct ttg ggc tgg atg acg aaa gga att ctt gat      432
Ser Leu His Gly His Ala Leu Gly Trp Met Thr Lys Gly Ile Leu Asp
    130                 135                 140

aaa gat aca tac tat tac cgc ggt gtt tat ttg gac gcc gtc cgc gcg      480
Lys Asp Thr Tyr Tyr Tyr Arg Gly Val Tyr Leu Asp Ala Val Arg Ala
145                 150                 155                 160

ctt gag gtc atc agc agc ttc gac gag gtt gac gaa aca agg atc ggt      528
Leu Glu Val Ile Ser Ser Phe Asp Glu Val Asp Glu Thr Arg Ile Gly
                165                 170                 175

gtg aca gga gga agc caa ggc gga ggt tta acc att gcc gca gca gcg      576
Val Thr Gly Gly Ser Gln Gly Gly Gly Leu Thr Ile Ala Ala Ala Ala
            180                 185                 190

ctg tca gac att cca aaa gcc gcg gtt gcc gat tat cct tat tta agc      624
Leu Ser Asp Ile Pro Lys Ala Ala Val Ala Asp Tyr Pro Tyr Leu Ser
        195                 200                 205

aac ttc gaa cgg gcc att gat gtg gcg ctt gaa cag ccg tac ctt gaa      672
Asn Phe Glu Arg Ala Ile Asp Val Ala Leu Glu Gln Pro Tyr Leu Glu
    210                 215                 220

atc aat tcc ttc ttc aga aga aat ggc agc ccg gaa aca gaa gtg cag      720
Ile Asn Ser Phe Phe Arg Arg Asn Gly Ser Pro Glu Thr Glu Val Gln
225                 230                 235                 240

gcg atg aag aca ctt tca tat ttc gat att atg aat ctc gct gac cga      768
Ala Met Lys Thr Leu Ser Tyr Phe Asp Ile Met Asn Leu Ala Asp Arg
                245                 250                 255

gtg aag gtg cct gtc ctg atg tca atc ggc ctg att gac aag gtc acg      816
Val Lys Val Pro Val Leu Met Ser Ile Gly Leu Ile Asp Lys Val Thr
            260                 265                 270

ccg ccg tcc acc gtg ttt gcc gcc tac aat cat ttg gaa aca gag aaa      864
Pro Pro Ser Thr Val Phe Ala Ala Tyr Asn His Leu Glu Thr Glu Lys
        275                 280                 285

gag ctg aag gtg tac cgc tac ttc gga cat gag tat atc cct gct ttt      912
```

```
Glu Leu Lys Val Tyr Arg Tyr Phe Gly His Glu Tyr Ile Pro Ala Phe
    290                 295                 300

caa acg gaa aaa ctt gct ttc ttt aag cag cat ctt aaa ggc tga taa      960
Gln Thr Glu Lys Leu Ala Phe Phe Lys Gln His Leu Lys Gly
305                 310                 315


<210> SEQ ID NO 2
<211> LENGTH: 318
<212> TYPE: PRT
<213> ORGANISM: Bacillus subtilis

<400> SEQUENCE: 2

Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Gln Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Leu His Gly His Ala Leu Gly Trp Met Thr Lys Gly Ile Leu Asp
    130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315


<210> SEQ ID NO 3
<211> LENGTH: 957
<212> TYPE: DNA
<213> ORGANISM: Bacillus subtilis
```

<400> SEQUENCE: 3

```
atgcaactat tcgatctgcc gctcgaccaa ttgcaaacat ataagcctga aaaaacagca     60
ccgaaagatt tttctgagtt ttggaaattg tctttggagg aacttgcaaa agtccaagca    120
gaacctgatt tacagccggt tgactatcct gctgacggag taaaagtgta ccgtctcaca    180
tataaaagct tcggaaacgc ccgcattacc ggatggtacg cggtgcctga caaggaaggc    240
ccgcatccgg cgatcgtgaa atatcatggc tacaatgcaa gctatgatgg tgagattcat    300
gaaatggtaa actgggcact ccatggctac gccacattcg gcatgcttgt ccgcggccag    360
cagagcagcg aggatacgag tatttcaccg cacggtcacg ctttgggctg gatgacgaaa    420
ggaattcttg ataaagatac atactattac cgcggtgttt atttggacgc cgtccgcgcg    480
cttgaggtca tcagcagctt cgacgaggtt gacgaaacaa ggatcggtgt gacaggagga    540
agccaaggcg gaggtttaac cattgccgca gcagcgctgt cagacattcc aaaagccgcg    600
gttgccgatt atccttattt aagcaacttc gaacgggcca ttgatgtggc gcttgaacag    660
ccgtaccttg aaatcaattc cttcttcaga agaaatggca gcccggaaac agaagtgcag    720
gcgatgaaga cactttcata tttcgatatt atgaatctcg ctgaccgagt gaaggtgcct    780
gtcctgatgt caatcggcct gattgacaag gtcacgccgc cgtccaccgt gtttgccgcc    840
tacaatcatt tggaaacaaa gaaagagctg aaggtgtacc gctacttcgg acatgagtat    900
atccctgctt ttcaaactga aaaacttgct ttctttaagc agcatcttaa aggctga       957
```

<210> SEQ ID NO 4
<211> LENGTH: 318
<212> TYPE: PRT
<213> ORGANISM: Bacillus subtilis

<400> SEQUENCE: 4

```
Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Glu Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Thr
            100                 105                 110

Phe Gly Met Leu Val Arg Gly Gln Gln Ser Ser Glu Asp Thr Ser Ile
        115                 120                 125

Ser Pro His Gly His Ala Leu Gly Trp Met Thr Lys Gly Ile Leu Asp
    130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
```

-continued

```
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Lys Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315
```

<210> SEQ ID NO 5
<211> LENGTH: 957
<212> TYPE: DNA
<213> ORGANISM: Bacillus subtilis

<400> SEQUENCE: 5

```
atgcaactat tcgatctgcc gctcgaccaa ttgcaaacgt ataagcctga aaaaacaaca      60

ccgaacgatt tttctgagtt ttggaaatcg tctttggacg aacttgcgaa agtcaaagca     120

gcacctgatt tacagctggt tgattatcct gctgatggag tcaaggtgta ccgcctcaca     180

tataaaagct tcggaaacgc ccgcattacc ggatggtacg cagtgcctga caaggaagga     240

ccgcatccgg cgatcgtcaa atatcatggc tacaacgcta gctatgacgg tgagattcat     300

gaaatggtaa actgggcgct ccacggttac gccgcattcg gcatgctagt ccgcggccag     360

cagagcagcg aggatacgag tatttctcca catggccatg ctttgggctg gatgacgaaa     420

ggaatccttg ataaagatac atactattac cggggcgttt atttggacgc tgtccgcgcg     480

cttgaggtca tcagcagctt tgacgaagtt gacgaaacaa gaatcggtgt gacaggcgga     540

agccaaggag gcggcttaac cattgccgca gccgctctgt cagacattcc aaaagccgcg     600

gttgccgatt atccttattt aagcaacttt gaacgggcca ttgatgtggc gcttgaacag     660

ccgtaccttg aaatcaattc cttctttaga agaaatggaa gcccggaaac ggaagagaag     720

gcgatgaaga cactttcata tttcgatatt atgaatctcg ctgaccgagt gaaggtccct     780

gtcctgatgt cgatcggtct gattgacaag gtcacgccgc cgtccaccgt gtttgccgca     840

tacaaccact tggagacaga gaaagagctc aaagtgtacc gctacttcgg gcatgagtat     900

atccctgcct ttcaaacaga aaaacttgct ttctttaagc agcatcttaa aggctga        957
```

<210> SEQ ID NO 6
<211> LENGTH: 318
<212> TYPE: PRT
<213> ORGANISM: Bacillus subtilis

<400> SEQUENCE: 6

```
Met Gln Leu Phe Asp Leu Pro Leu Asp Gln Leu Gln Thr Tyr Lys Pro
1               5                   10                  15

Glu Lys Thr Thr Pro Asn Asp Phe Ser Glu Phe Trp Lys Ser Ser Leu
            20                  25                  30

Asp Glu Leu Ala Lys Val Lys Ala Ala Pro Asp Leu Gln Leu Val Asp
        35                  40                  45
```

```
Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Glu Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Pro His Gly His Ala Leu Gly Trp Met Thr Lys Gly Ile Leu Asp
    130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Glu Lys
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315
```

<210> SEQ ID NO 7
<211> LENGTH: 957
<212> TYPE: DNA
<213> ORGANISM: Bacillus licheniformis

<400> SEQUENCE: 7

```
atgcagcagc cttatgatat gccgcttgaa cagctttatc agtataaacc tgaacggacg      60

gcaccggccg attttaaaga gttctggaag ggttcattgg aggaattggc aaatgaaaaa     120

gcgggaccgc agcttgaacc gcatgaatat ccggctgacg gggtaaaagt ctactggctt     180

acatacagaa gcatcggggg agcgcgaatt aaaggctggt acgcagtacc cgaccgccaa     240

gggcctcatc ctgcgatcgt caaataccac ggctataacg caagctatga cggagacatt     300

cacgatattg tcaattgggc tcttcacggc tatgcggcat tcggtatgct ggtccgcgga     360

cagaacagca gtgaagatac agagatctct catcacggac atgtacccgg ctggatgaca     420

aaaggaatcc tcgatccgaa aacatattac tacagagggg tctatttaga tgccgtacga     480

gcagtcgaag tggtcagcgg ttttgctgaa gtcgatgaaa agcggatcgg ggtgatcggg     540

gcaagccaag gaggcgggct ggccgtcgcg gtttcggcgc tgtccgatat tccaaaagca     600

gccgtgtcag aataccctta tttaagcaat tttcaacgag cgatcgatac agcgatcgac     660
```

-continued

```
cagccatatc tcgaaatcaa ctcctttttc agaagaaaca ccagtccgga tattgagcag    720

gcggccatgc ataccctgtc ttatttcgat gtcatgaacc ttgcccaatt ggtcaaagcg    780

accgtactca tgtcgatcgg actggttgac accatcactc cgccatccac cgtctttgcg    840

gcttacaatc acttggaaac ggataaagaa ataaaagtgt accgttattt tggacacgaa    900

tacatcccgc cgttccaaac cgaaaagctg gcgtttctga gaaagcatct gaaataa       957


<210> SEQ ID NO 8
<211> LENGTH: 318
<212> TYPE: PRT
<213> ORGANISM: Bacillus licheniformis

<400> SEQUENCE: 8

Met Gln Gln Pro Tyr Asp Met Pro Leu Glu Gln Leu Tyr Gln Tyr Lys
1               5                   10                  15

Pro Glu Arg Thr Ala Pro Ala Asp Phe Lys Glu Phe Trp Lys Gly Ser
            20                  25                  30

Leu Glu Glu Leu Ala Asn Glu Lys Ala Gly Pro Gln Leu Glu Pro His
        35                  40                  45

Glu Tyr Pro Ala Asp Gly Val Lys Val Tyr Trp Leu Thr Tyr Arg Ser
    50                  55                  60

Ile Gly Gly Ala Arg Ile Lys Gly Trp Tyr Ala Val Pro Asp Arg Gln
65                  70                  75                  80

Gly Pro His Pro Ala Ile Val Lys Tyr His Gly Tyr Asn Ala Ser Tyr
                85                  90                  95

Asp Gly Asp Ile His Asp Ile Val Asn Trp Ala Leu His Gly Tyr Ala
            100                 105                 110

Ala Phe Gly Met Leu Val Arg Gly Gln Asn Ser Ser Glu Asp Thr Glu
        115                 120                 125

Ile Ser His His Gly His Val Pro Gly Trp Met Thr Lys Gly Ile Leu
    130                 135                 140

Asp Pro Lys Thr Tyr Tyr Tyr Arg Gly Val Tyr Leu Asp Ala Val Arg
145                 150                 155                 160

Ala Val Glu Val Val Ser Gly Phe Ala Glu Val Asp Glu Lys Arg Ile
                165                 170                 175

Gly Val Ile Gly Ala Ser Gln Gly Gly Gly Leu Ala Val Ala Val Ser
            180                 185                 190

Ala Leu Ser Asp Ile Pro Lys Ala Ala Val Ser Glu Tyr Pro Tyr Leu
        195                 200                 205

Ser Asn Phe Gln Arg Ala Ile Asp Thr Ala Ile Asp Gln Pro Tyr Leu
    210                 215                 220

Glu Ile Asn Ser Phe Phe Arg Arg Asn Thr Ser Pro Asp Ile Glu Gln
225                 230                 235                 240

Ala Ala Met His Thr Leu Ser Tyr Phe Asp Val Met Asn Leu Ala Gln
                245                 250                 255

Leu Val Lys Ala Thr Val Leu Met Ser Ile Gly Leu Val Asp Thr Ile
            260                 265                 270

Thr Pro Pro Ser Thr Val Phe Ala Ala Tyr Asn His Leu Glu Thr Asp
        275                 280                 285

Lys Glu Ile Lys Val Tyr Arg Tyr Phe Gly His Glu Tyr Ile Pro Pro
    290                 295                 300

Phe Gln Thr Glu Lys Leu Ala Phe Leu Arg Lys His Leu Lys
305                 310                 315
```

<210> SEQ ID NO 9
<211> LENGTH: 963
<212> TYPE: DNA
<213> ORGANISM: Bacillus pumilis

<400> SEQUENCE: 9

```
atgcaattgt tcgatttatc actagaagag ctaaaaaaat ataaaccaaa gaaaacagca     60

cgtcctgatt tctcagactt ttggaagaaa tcgctcgaag aactgcgcca agtggaggca    120

gagccaacac ttgaatctta tgactatcca gtgaaaggcg tcaaggtgta ccgcctgacg    180

tatcaaagct ttggacattc taaaattgaa ggcttttatg ctgtgcctga tcaaactggt    240

ccgcatccag cgctcgttcg ttttcatggc tataatgcca gctatgacgg cggcattcac    300

gacatcgtca actgggcgct gcacggctat gcaacatttg gtatgctcgt ccgcggtcaa    360

ggtggcagtg aagacacatc agtgacacca ggcgggcatg cattagggtg gatgacaaaa    420

ggcattttat cgaaagatac gtactattat cgaggcgttt atctagatgc tgttcgtgca    480

cttgaagtca ttcagtcttt ccccgaagta gatgaacacc gtatcggcgt gatcggtgga    540

agtcaggggg gtgcgttagc gattgcggcc gcagcccttt cagacattcc aaaagtcgtt    600

gtggcagact atccttactt atcaaatttt gagcgtgcag ttgatgttgc cttggagcag    660

ccttatttag aaatcaattc atactttcgc agaaacagtg atccgaaagt ggaggaaaag    720

gcatttgaga cattaagcta ttttgattta atcaatttag ctggatgggt gaaacagcca    780

acattgatgg cgatcggtct gattgacaaa ataaccccac catctactgt gtttgcggca    840

tacaaccatt tagaaacaga taaagacctg aaagtatatc gctattttgg acacgagttt    900

atccctgctt ttcaaacaga gaagctgtcc tttttacaaa agcatttgct tctatcaaca    960

taa                                                                  963
```

<210> SEQ ID NO 10
<211> LENGTH: 320
<212> TYPE: PRT
<213> ORGANISM: Bacillus pumilis

<400> SEQUENCE: 10

```
Met Gln Leu Phe Asp Leu Ser Leu Glu Glu Leu Lys Lys Tyr Lys Pro
1               5                   10                  15

Lys Lys Thr Ala Arg Pro Asp Phe Ser Asp Phe Trp Lys Lys Ser Leu
            20                  25                  30

Glu Glu Leu Arg Gln Val Glu Ala Glu Pro Thr Leu Glu Ser Tyr Asp
        35                  40                  45

Tyr Pro Val Lys Gly Val Lys Val Tyr Arg Leu Thr Tyr Gln Ser Phe
    50                  55                  60

Gly His Ser Lys Ile Glu Gly Phe Tyr Ala Val Pro Asp Gln Thr Gly
65                  70                  75                  80

Pro His Pro Ala Leu Val Arg Phe His Gly Tyr Asn Ala Ser Tyr Asp
                85                  90                  95

Gly Gly Ile His Asp Ile Val Asn Trp Ala Leu His Gly Tyr Ala Thr
            100                 105                 110

Phe Gly Met Leu Val Arg Gly Gln Gly Gly Ser Glu Asp Thr Ser Val
        115                 120                 125

Thr Pro Gly Gly His Ala Leu Gly Trp Met Thr Lys Gly Ile Leu Ser
    130                 135                 140

Lys Asp Thr Tyr Tyr Tyr Arg Gly Val Tyr Leu Asp Ala Val Arg Ala
145                 150                 155                 160

Leu Glu Val Ile Gln Ser Phe Pro Glu Val Asp Glu His Arg Ile Gly
```

-continued

```
                165                 170                 175

Val Ile Gly Gly Ser Gln Gly Gly Ala Leu Ala Ile Ala Ala Ala Ala
            180                 185                 190

Leu Ser Asp Ile Pro Lys Val Val Val Ala Asp Tyr Pro Tyr Leu Ser
        195                 200                 205

Asn Phe Glu Arg Ala Val Asp Val Ala Leu Glu Gln Pro Tyr Leu Glu
    210                 215                 220

Ile Asn Ser Tyr Phe Arg Arg Asn Ser Asp Pro Lys Val Glu Glu Lys
225                 230                 235                 240

Ala Phe Glu Thr Leu Ser Tyr Phe Asp Leu Ile Asn Leu Ala Gly Trp
                245                 250                 255

Val Lys Gln Pro Thr Leu Met Ala Ile Gly Leu Ile Asp Lys Ile Thr
            260                 265                 270

Pro Pro Ser Thr Val Phe Ala Ala Tyr Asn His Leu Glu Thr Asp Lys
        275                 280                 285

Asp Leu Lys Val Tyr Arg Tyr Phe Gly His Glu Phe Ile Pro Ala Phe
    290                 295                 300

Gln Thr Glu Lys Leu Ser Phe Leu Gln Lys His Leu Leu Leu Ser Thr
305                 310                 315                 320
```

<210> SEQ ID NO 11
<211> LENGTH: 963
<212> TYPE: DNA
<213> ORGANISM: Clostridium thermocellum

<400> SEQUENCE: 11

```
atggcacaat tatatgatat gcctttggag gaattaaaaa aatataagcc tgcgcttaca      60

aaacagaaag attttgatga gttttgggaa aaaagcctta aagagctggc tgaaattcct     120

ttaaaatatc aacttatacc ttatgatttt ccggcccgga gggtaaaagt tttcagagtt     180

gaatatcttg gttttaaagg tgcaaatatt gaagggtggc ttgccgttcc cgagggagaa     240

gggttgtatc ccgggcttgt acagtttcac ggatacaact gggcgatgga tggatgtgtt     300

cccgatgtgg taaattgggc tttgaatgga tatgccgcat ttcttatgct tgttcgggga     360

cagcagggaa gaagcgtgga caatattgtg cccggcagcg gtcatgcttt gggatggatg     420

tcgaaaggta ttttgtcacc ggaggaatat tattatagag gagtatatat ggatgcggtt     480

cgtgctgttg aaattttggc ttcgcttcct tgtgtggatg aatcgagaat aggagtgaca     540

gggggcagcc agggtggagg acttgcactg gcggtggctg ctctgtccgg cataccgaaa     600

gttgcagccg tgcattatcc gtttctggca cattttgagc gtgccattga cgttgcgccg     660

gacggccctt atcttgaaat taacgaatat ttaagaagaa acagcggtga agaaatagaa     720

agacaggtaa agaaaaccct ttcctatttt gatatcatga atcttgctcc ccgtataaaa     780

tgccgtactt ggatttgcac tggtcttgtg gatgagatta ctcctccgtc aacggttttt     840

gcagtgtaca atcacctcaa atgcccaaag gaaatttcgg tattcagata ttttgggcat     900

gaacatatgc caggaagcgt tgaaatcaag ctgaggatac ttatggatga gctgaatccg     960

taa                                                                    963
```

<210> SEQ ID NO 12
<211> LENGTH: 320
<212> TYPE: PRT
<213> ORGANISM: Clostridium thermocellum

<400> SEQUENCE: 12

```
Met Ala Gln Leu Tyr Asp Met Pro Leu Glu Glu Leu Lys Lys Tyr Lys
```

```
1               5                   10                  15

Pro Ala Leu Thr Lys Gln Lys Asp Phe Asp Glu Phe Trp Glu Lys Ser
            20                  25                  30

Leu Lys Glu Leu Ala Glu Ile Pro Leu Lys Tyr Gln Leu Ile Pro Tyr
        35                  40                  45

Asp Phe Pro Ala Arg Arg Val Lys Val Phe Arg Val Glu Tyr Leu Gly
    50                  55                  60

Phe Lys Gly Ala Asn Ile Glu Gly Trp Leu Ala Val Pro Glu Gly Glu
65                  70                  75                  80

Gly Leu Tyr Pro Gly Leu Val Gln Phe His Gly Tyr Asn Trp Ala Met
                85                  90                  95

Asp Gly Cys Val Pro Asp Val Val Asn Trp Ala Leu Asn Gly Tyr Ala
            100                 105                 110

Ala Phe Leu Met Leu Val Arg Gly Gln Gln Gly Arg Ser Val Asp Asn
        115                 120                 125

Ile Val Pro Gly Ser Gly His Ala Leu Gly Trp Met Ser Lys Gly Ile
    130                 135                 140

Leu Ser Pro Glu Glu Tyr Tyr Tyr Arg Gly Val Tyr Met Asp Ala Val
145                 150                 155                 160

Arg Ala Val Glu Ile Leu Ala Ser Leu Pro Cys Val Asp Glu Ser Arg
                165                 170                 175

Ile Gly Val Thr Gly Gly Ser Gln Gly Gly Gly Leu Ala Leu Ala Val
            180                 185                 190

Ala Ala Leu Ser Gly Ile Pro Lys Val Ala Ala Val His Tyr Pro Phe
        195                 200                 205

Leu Ala His Phe Glu Arg Ala Ile Asp Val Ala Pro Asp Gly Pro Tyr
    210                 215                 220

Leu Glu Ile Asn Glu Tyr Leu Arg Arg Asn Ser Gly Glu Glu Ile Glu
225                 230                 235                 240

Arg Gln Val Lys Lys Thr Leu Ser Tyr Phe Asp Ile Met Asn Leu Ala
                245                 250                 255

Pro Arg Ile Lys Cys Arg Thr Trp Ile Cys Thr Gly Leu Val Asp Glu
            260                 265                 270

Ile Thr Pro Pro Ser Thr Val Phe Ala Val Tyr Asn His Leu Lys Cys
        275                 280                 285

Pro Lys Glu Ile Ser Val Phe Arg Tyr Phe Gly His Glu His Met Pro
    290                 295                 300

Gly Ser Val Glu Ile Lys Leu Arg Ile Leu Met Asp Glu Leu Asn Pro
305                 310                 315                 320
```

<210> SEQ ID NO 13
<211> LENGTH: 978
<212> TYPE: DNA
<213> ORGANISM: Thermotoga neapolitana

<400> SEQUENCE: 13

```
atggccttct tcgatatgcc ccttgaggaa ctgaaaaagt accggcctga aaggtacgag     60

gagaaagatt tcgatgagtt ctggagggaa acacttaaag aaagcgaagg attccctctg    120

gatcccgtct ttgaaaaggt ggactttcat ctcaaaacgg ttgaaacgta cgatgttact    180

ttctctggat acagggggca gagaataaag ggctggcttc ttgttccgaa gttggcggaa    240

gaaaagcttc catgcgtcgt gcagtacata ggttacaatg gtggaagggg ttttccacac    300

gactggctgt tctggccgtc aatgggttac atctgttttg tcatggacac cagggggcag    360

ggaagcggct ggatgaaggg agacacaccg gattaccctg agggtccagt cgatccacag    420
```

```
taccccggat tcatgacgag gggcattctg gatccgggaa cctattacta caggcgagtc    480

ttcgtggatg cggtcagggc ggtggaagca gccatttcct tcccgagagt ggattccagg    540

aaggtggtgg tggccggagg cagtcagggt gggggaatcg cccttgcggt gagtgccctg    600

tcgaacaggg tgaaggctct gctctgcgat gtgccgtttc tgtgccactt cagaagggcc    660

gtgcaacttg tcgacacaca cccatacgtg gagatcacca acttcctcaa aacccacagg    720

gacaaagagg agattgtttt cagaacactt tcctacttcg atggtgtgaa ctttgcagca    780

agggcaaagg tgcccgccct gttttccgtt gggctcatgg acaccatctg tcctccctcg    840

acggtcttcg ccgcttacaa ccactacgcc ggtccaaagg agatcagaat ctatccgtac    900

aacaaccacg aaggtggagg ttctttccag gcaattgagc aggtgaaatt cttgaagaga    960

ctatttgagg aaggctag                                                  978
```

<210> SEQ ID NO 14
<211> LENGTH: 325
<212> TYPE: PRT
<213> ORGANISM: Thermotoga neapolitana

<400> SEQUENCE: 14

```
Met Ala Phe Phe Asp Met Pro Leu Glu Glu Leu Lys Lys Tyr Arg Pro
1               5                   10                  15

Glu Arg Tyr Glu Glu Lys Asp Phe Asp Glu Phe Trp Arg Glu Thr Leu
            20                  25                  30

Lys Glu Ser Glu Gly Phe Pro Leu Asp Pro Val Phe Glu Lys Val Asp
        35                  40                  45

Phe His Leu Lys Thr Val Glu Thr Tyr Asp Val Thr Phe Ser Gly Tyr
    50                  55                  60

Arg Gly Gln Arg Ile Lys Gly Trp Leu Leu Val Pro Lys Leu Ala Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Gly Thr Tyr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Val Ala Gly Gly Ser Gln Gly Gly Gly
            180                 185                 190

Ile Ala Leu Ala Val Ser Ala Leu Ser Asn Arg Val Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
            260                 265                 270
```

-continued

```
Met Asp Thr Ile Cys Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Glu Gly
                325


<210> SEQ ID NO 15
<211> LENGTH: 978
<212> TYPE: DNA
<213> ORGANISM: Thermotoga maritima

<400> SEQUENCE: 15

atggccttct tcgatttacc actcgaagaa ctgaagaaat atcgtccaga gcggtacgaa      60

gagaaagact tcgatgagtt ctgggaagag acactcgcag agagcgaaaa gttcccctta     120

gaccccgtct tcgagaggat ggagtctcac ctcaaaacag tcgaagcgta cgatgtcacc     180

ttctccggat acaggggaca gaggatcaaa gggtggctcc ttgttccaaa actggaagaa     240

gaaaaacttc cctgcgttgt gcagtacata ggatacaacg gtggaagagg attccctcac     300

gactggctgt tctggccttc tatgggttac atatgtttcg tcatggatac tcgaggtcag     360

ggaagcggct ggctgaaagg agacacaccg gattaccctg agggtcccgt tgaccctcag     420

tatccaggat tcatgacaag aggaatactg gatcccagaa cttactacta cagacgagtc     480

ttcacggacg ctgtcagagc cgttgaagct gctgcttctt ttcctcaggt agatcaagaa     540

agaatcgtga tagctggagg cagtcagggt ggcggaatag cccttgcggt gagcgctctc     600

tcaaagaaag caaaggctct tctgtgcgat gtgccgtttc tgtgtcactt cagaagagca     660

gtacagcttg tggatacgca tccatacgcg gagatcacga actttctaaa gacccacaga     720

gacaaggaag aaatcgtgtt caggactctt tcctatttcg atggagtgaa cttcgcagcc     780

agagcgaaga tccctgcgct gttttctgtg ggtctcatgg acaacatttg tcctccttca     840

acggttttcg ctgcctacaa ttactacgct ggaccgaagg aaatcagaat ctatccgtac     900

aacaaccacg agggaggagg ctctttccaa gcggttgaac aggtgaaatt cttgaaaaaa     960

ctatttgaga aaggctaa                                                   978


<210> SEQ ID NO 16
<211> LENGTH: 325
<212> TYPE: PRT
<213> ORGANISM: Thermotoga maritima

<400> SEQUENCE: 16

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95
```

```
Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Cys Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 17
<211> LENGTH: 963
<212> TYPE: DNA
<213> ORGANISM: Thermoanaerobacterium sp.

<400> SEQUENCE: 17

atgggacttt tcgacatgcc attacaaaaa cttagagaat acactggtac aaatccatgc      60

cctgaagatt tcgatgagta ttggaatagg gctttagatg agatgaggtc agttgatcct     120

aaaattgaat tgaaagaaag tagctttcaa gtatcctttg cagaatgcta tgacttgtac     180

tttacaggtg ttcgtggtgc cagaattcat gcaaagtata taaaacctaa gacagaaggg     240

aaacatccag cgttgataag atttcatgga tattcgtcaa attcaggcga ctggaacgac     300

aaattaaatt acgtggcggc aggcttcacc gttgtggcta tggatgtaag aggtcaagga     360

gggcagtctc aagatgttgg cggtgtaact gggaatactt taaatgggca tattataaga     420

gggctagacg atgatgctga taatatgctt ttcaggcata ttttcttaga cactgcccaa     480

ttggctggaa tagttatgaa catgccagaa gttgatgaag atagagtggg agtcatggga     540

ccttctcaag gcggagggct gtcgttggcg tgtgctgcat tggagccaag ggtacgcaaa     600

gtagtatctg aatatccttt tttatctgac tacaagagag tttgggactt agaccttgca     660

aaaaacgcct atcaagagat tacggactat ttcaggcttt ttgacccaag gcatgaaagg     720

gagaatgagg tatttacaaa gcttggatat atagacgtta aaaaccttgc gaaaaggata     780

aaaggcgatg tcttaatgtg cgttgggctt atggaccaag tatgtccgcc atcaactgtt     840
```

-continued

```
tttgcagcct acaacaacat acagtcaaaa aaagatataa aagtgtatcc tgattatgga    900

catgaaccta tgagaggatt tggagattta gcgatgcagt ttatgttgga actatattca    960

taa                                                                  963
```

<210> SEQ ID NO 18
<211> LENGTH: 320
<212> TYPE: PRT
<213> ORGANISM: Thermoanaerobacterium sp.

<400> SEQUENCE: 18

```
Met Gly Leu Phe Asp Met Pro Leu Gln Lys Leu Arg Glu Tyr Thr Gly
1               5                   10                  15

Thr Asn Pro Cys Pro Glu Asp Phe Asp Glu Tyr Trp Asn Arg Ala Leu
            20                  25                  30

Asp Glu Met Arg Ser Val Asp Pro Lys Ile Glu Leu Lys Glu Ser Ser
        35                  40                  45

Phe Gln Val Ser Phe Ala Glu Cys Tyr Asp Leu Tyr Phe Thr Gly Val
    50                  55                  60

Arg Gly Ala Arg Ile His Ala Lys Tyr Ile Lys Pro Lys Thr Glu Gly
65                  70                  75                  80

Lys His Pro Ala Leu Ile Arg Phe His Gly Tyr Ser Ser Asn Ser Gly
                85                  90                  95

Asp Trp Asn Asp Lys Leu Asn Tyr Val Ala Ala Gly Phe Thr Val Val
            100                 105                 110

Ala Met Asp Val Arg Gly Gln Gly Gly Gln Ser Gln Asp Val Gly Gly
        115                 120                 125

Val Thr Gly Asn Thr Leu Asn Gly His Ile Ile Arg Gly Leu Asp Asp
    130                 135                 140

Asp Ala Asp Asn Met Leu Phe Arg His Ile Phe Leu Asp Thr Ala Gln
145                 150                 155                 160

Leu Ala Gly Ile Val Met Asn Met Pro Glu Val Asp Glu Asp Arg Val
                165                 170                 175

Gly Val Met Gly Pro Ser Gln Gly Gly Gly Leu Ser Leu Ala Cys Ala
            180                 185                 190

Ala Leu Glu Pro Arg Val Arg Lys Val Val Ser Glu Tyr Pro Phe Leu
        195                 200                 205

Ser Asp Tyr Lys Arg Val Trp Asp Leu Asp Leu Ala Lys Asn Ala Tyr
    210                 215                 220

Gln Glu Ile Thr Asp Tyr Phe Arg Leu Phe Asp Pro Arg His Glu Arg
225                 230                 235                 240

Glu Asn Glu Val Phe Thr Lys Leu Gly Tyr Ile Asp Val Lys Asn Leu
                245                 250                 255

Ala Lys Arg Ile Lys Gly Asp Val Leu Met Cys Val Gly Leu Met Asp
            260                 265                 270

Gln Val Cys Pro Pro Ser Thr Val Phe Ala Ala Tyr Asn Asn Ile Gln
        275                 280                 285

Ser Lys Lys Asp Ile Lys Val Tyr Pro Asp Tyr Gly His Glu Pro Met
    290                 295                 300

Arg Gly Phe Gly Asp Leu Ala Met Gln Phe Met Leu Glu Leu Tyr Ser
305                 310                 315                 320
```

<210> SEQ ID NO 19
<211> LENGTH: 978
<212> TYPE: DNA
<213> ORGANISM: Bacillus sp.

```
<220> FEATURE:
<221> NAME/KEY: CDS
<222> LOCATION: (1)..(978)

<400> SEQUENCE: 19

atg aac ctt ttt gat atg ccc ctt gag gag ctg cag cat tac aag cct       48
Met Asn Leu Phe Asp Met Pro Leu Glu Glu Leu Gln His Tyr Lys Pro
1               5                   10                  15

gcc cag acc agg cag gat gat ttt gag tca ttc tgg aaa aag cgg att       96
Ala Gln Thr Arg Gln Asp Asp Phe Glu Ser Phe Trp Lys Lys Arg Ile
            20                  25                  30

gag gag aac agt caa tat ccg ctg aat ata gaa gta atg gag cgg gtt      144
Glu Glu Asn Ser Gln Tyr Pro Leu Asn Ile Glu Val Met Glu Arg Val
        35                  40                  45

tat ccg gtt ccg gga gtg aga gta tat gat att tat ttt gac ggg ttc      192
Tyr Pro Val Pro Gly Val Arg Val Tyr Asp Ile Tyr Phe Asp Gly Phe
    50                  55                  60

cgg aat tcc cgc atc cat ggg gtg tat gtt act cca gaa act ccg gga      240
Arg Asn Ser Arg Ile His Gly Val Tyr Val Thr Pro Glu Thr Pro Gly
65                  70                  75                  80

gcg gac act cct gcg gca gtg att ttt cac ggc tat aac tgg aac acg      288
Ala Asp Thr Pro Ala Ala Val Ile Phe His Gly Tyr Asn Trp Asn Thr
                85                  90                  95

ctg cag ccg cat tac agc ttc aag cac gtg att cag ggg att cct gta      336
Leu Gln Pro His Tyr Ser Phe Lys His Val Ile Gln Gly Ile Pro Val
            100                 105                 110

ctg atg gtg gag gtg cgg gga caa aat ctc ttg tct cca gat aga aat      384
Leu Met Val Glu Val Arg Gly Gln Asn Leu Leu Ser Pro Asp Arg Asn
        115                 120                 125

cat tat ggg aat gga ggt ccg gga ggc tgg atg aca ctc ggc gtg atg      432
His Tyr Gly Asn Gly Gly Pro Gly Gly Trp Met Thr Leu Gly Val Met
    130                 135                 140

gat ccc gat caa tat tat tac agc ctg gta tat atg gac tgc ttc cgc      480
Asp Pro Asp Gln Tyr Tyr Tyr Ser Leu Val Tyr Met Asp Cys Phe Arg
145                 150                 155                 160

agc att gat gct gtc agg gaa ctg tcg agg aag aga agt gtg ttt gtg      528
Ser Ile Asp Ala Val Arg Glu Leu Ser Arg Lys Arg Ser Val Phe Val
                165                 170                 175

gaa ggc gga agc cag gga ggt gca ctg gcg att gcc gca gcc gcc ctg      576
Glu Gly Gly Ser Gln Gly Gly Ala Leu Ala Ile Ala Ala Ala Ala Leu
            180                 185                 190

cag gat gac atc ctg ctt gca ctc gcc gac atc cct ttt ctc acc cat      624
Gln Asp Asp Ile Leu Leu Ala Leu Ala Asp Ile Pro Phe Leu Thr His
        195                 200                 205

ttc aag cgt tcc gtg gag ctt tcc tcg gat gga ccg tat cag gag att      672
Phe Lys Arg Ser Val Glu Leu Ser Ser Asp Gly Pro Tyr Gln Glu Ile
    210                 215                 220

tcc cac tac ttc aaa gtt cat gat cct ctt cat caa acg gaa gag cag      720
Ser His Tyr Phe Lys Val His Asp Pro Leu His Gln Thr Glu Glu Gln
225                 230                 235                 240

gta tat cag acg ctc agc tat gtg gac tgc atg aac atg gcc agc atg      768
Val Tyr Gln Thr Leu Ser Tyr Val Asp Cys Met Asn Met Ala Ser Met
                245                 250                 255

gtt gaa tgt cca gtc ctt ctt tca gcc ggt ctg gaa gac atc gtt tgt      816
Val Glu Cys Pro Val Leu Leu Ser Ala Gly Leu Glu Asp Ile Val Cys
            260                 265                 270

ccc ccg tcc agt gca ttt gca ctg ttc aac cat ctc ggc ggg cca aaa      864
Pro Pro Ser Ser Ala Phe Ala Leu Phe Asn His Leu Gly Gly Pro Lys
        275                 280                 285

gaa ata cgg gcc tat ccg gaa tac gcc cat gaa gta ccg gct gtc cat      912
Glu Ile Arg Ala Tyr Pro Glu Tyr Ala His Glu Val Pro Ala Val His
```

```
    290                 295                 300

gaa gag gaa aag ctg aag ttt ata tct tca agg cta aaa aat aga gaa      960
Glu Glu Glu Lys Leu Lys Phe Ile Ser Ser Arg Leu Lys Asn Arg Glu
305                 310                 315                 320

aag agg tgc cgg cca tga                                              978
Lys Arg Cys Arg Pro
                325


<210> SEQ ID NO 20
<211> LENGTH: 325
<212> TYPE: PRT
<213> ORGANISM: Bacillus sp.

<400> SEQUENCE: 20

Met Asn Leu Phe Asp Met Pro Leu Glu Glu Leu Gln His Tyr Lys Pro
1               5                   10                  15

Ala Gln Thr Arg Gln Asp Asp Phe Glu Ser Phe Trp Lys Lys Arg Ile
            20                  25                  30

Glu Glu Asn Ser Gln Tyr Pro Leu Asn Ile Glu Val Met Glu Arg Val
        35                  40                  45

Tyr Pro Val Pro Gly Val Arg Val Tyr Asp Ile Tyr Phe Asp Gly Phe
    50                  55                  60

Arg Asn Ser Arg Ile His Gly Val Tyr Val Thr Pro Glu Thr Pro Gly
65                  70                  75                  80

Ala Asp Thr Pro Ala Ala Val Ile Phe His Gly Tyr Asn Trp Asn Thr
                85                  90                  95

Leu Gln Pro His Tyr Ser Phe Lys His Val Ile Gln Gly Ile Pro Val
            100                 105                 110

Leu Met Val Glu Val Arg Gly Gln Asn Leu Leu Ser Pro Asp Arg Asn
        115                 120                 125

His Tyr Gly Asn Gly Gly Pro Gly Gly Trp Met Thr Leu Gly Val Met
    130                 135                 140

Asp Pro Asp Gln Tyr Tyr Tyr Ser Leu Val Tyr Met Asp Cys Phe Arg
145                 150                 155                 160

Ser Ile Asp Ala Val Arg Glu Leu Ser Arg Lys Arg Ser Val Phe Val
                165                 170                 175

Glu Gly Gly Ser Gln Gly Gly Ala Leu Ala Ile Ala Ala Ala Ala Leu
            180                 185                 190

Gln Asp Asp Ile Leu Leu Ala Leu Ala Asp Ile Pro Phe Leu Thr His
        195                 200                 205

Phe Lys Arg Ser Val Glu Leu Ser Ser Asp Gly Pro Tyr Gln Glu Ile
    210                 215                 220

Ser His Tyr Phe Lys Val His Asp Pro Leu His Gln Thr Glu Glu Gln
225                 230                 235                 240

Val Tyr Gln Thr Leu Ser Tyr Val Asp Cys Met Asn Met Ala Ser Met
                245                 250                 255

Val Glu Cys Pro Val Leu Leu Ser Ala Gly Leu Glu Asp Ile Val Cys
            260                 265                 270

Pro Pro Ser Ser Ala Phe Ala Leu Phe Asn His Leu Gly Gly Pro Lys
        275                 280                 285

Glu Ile Arg Ala Tyr Pro Glu Tyr Ala His Glu Val Pro Ala Val His
    290                 295                 300

Glu Glu Glu Lys Leu Lys Phe Ile Ser Ser Arg Leu Lys Asn Arg Glu
305                 310                 315                 320

Lys Arg Cys Arg Pro
                325
```

<210> SEQ ID NO 21
<211> LENGTH: 960
<212> TYPE: DNA
<213> ORGANISM: Bacillus halodurans

<400> SEQUENCE: 21
ttagagatca gataaaaatt gaaaaatccg atcacgatgg cctggcaaat cttcgtgagc 60
aaagtctgga tataactcga tactttttgt cgtcgtgagt ttgttataca tggcaaattg 120
tgtagacggc gggcaaaccg tatccattaa cccaacagca agtaagactt ctccctttac 180
gagtggagca agatgctgaa tatcaatata gcctagcttc gtaaagattt cagcctcacg 240
tcggtgctgt ggatcaaagc gacgaaaata cgtttgcaat tcgtcataag ctttctcggc 300
taaatccatc tcccatacgc gttggtaatc gctaaggaaa ggataaacag gagctacctt 360
tttaattttc ggttccaaag ccgcacaagc aatcgctaag gcccctcctt gtgaccaacc 420
tgtcactgcc acgcgctctt catcgacttc aggaaggttc atcacaatgt tggcaagctg 480
agccgtatca agaaacacat gacggaacaa taattgatca gcattatcat cgagtccgcg 540
tattatatga ccggaatgag tattcccctt cacgcctcct gtgtcttcag acaagcctcc 600
ttgcccgcga acgtccattg caagaacaga atatccgagg gctgcgtaat gaagtaaacc 660
cgtccattcc cccgcattca tcgtatatcc gtgaaaatga ataaccgccg ggtgtgtccc 720
gctcgtgtgt cttgggcgca cgtattttgc gtgaattcta gcacccctaa cccctgtaaa 780
atataggtgg aagcattctg catacgtggt ttgaaaatca ctcggtatga gctctacgtt 840
tggatttacc tttctcatct cttgtaaagc acgatcccaa tactcagtaa agtcatctgg 900
ctttggatta cgtcccatgt actcttttaa ttcggttaac ggcatgtcta ttagtggcat 960

<210> SEQ ID NO 22
<211> LENGTH: 319
<212> TYPE: PRT
<213> ORGANISM: Bacillus halodurans

<400> SEQUENCE: 22

Met Pro Leu Ile Asp Met Pro Leu Thr Glu Leu Lys Glu Tyr Met Gly
1 5 10 15

Arg Asn Pro Lys Pro Asp Asp Phe Thr Glu Tyr Trp Asp Arg Ala Leu
20 25 30

Gln Glu Met Arg Lys Val Asn Pro Asn Val Glu Leu Ile Pro Ser Asp
35 40 45

Phe Gln Thr Thr Tyr Ala Glu Cys Phe His Leu Tyr Phe Thr Gly Val
50 55 60

Arg Gly Ala Arg Ile His Ala Lys Tyr Val Arg Pro Arg His Thr Ser
65 70 75 80

Gly Thr His Pro Ala Val Ile His Phe His Gly Tyr Thr Met Asn Ala
85 90 95

Gly Glu Trp Thr Gly Leu Leu His Tyr Ala Ala Leu Gly Tyr Ser Val
100 105 110

Leu Ala Met Asp Val Arg Gly Gln Gly Gly Leu Ser Glu Asp Thr Gly
115 120 125

Gly Val Lys Gly Asn Thr His Ser Gly His Ile Ile Arg Gly Leu Asp
130 135 140

Asp Asn Ala Asp Gln Leu Leu Phe Arg His Val Phe Leu Asp Thr Ala
145 150 155 160

Gln Leu Ala Asn Ile Val Met Asn Leu Pro Glu Val Asp Glu Glu Arg

```
                165                 170                 175

Val Ala Val Thr Gly Trp Ser Gln Gly Gly Ala Leu Ala Ile Ala Cys
            180                 185                 190

Ala Ala Leu Glu Pro Lys Ile Lys Lys Val Ala Pro Val Tyr Pro Phe
        195                 200                 205

Leu Ser Asp Tyr Gln Arg Val Trp Glu Met Asp Leu Ala Glu Lys Ala
    210                 215                 220

Tyr Asp Glu Leu Gln Thr Tyr Phe Arg Arg Phe Asp Pro Gln His Arg
225                 230                 235                 240

Arg Glu Ala Glu Ile Phe Thr Lys Leu Gly Tyr Ile Asp Ile Gln His
                245                 250                 255

Leu Ala Pro Leu Val Lys Gly Glu Val Leu Leu Ala Val Gly Leu Met
            260                 265                 270

Asp Thr Val Cys Pro Pro Ser Thr Gln Phe Ala Met Tyr Asn Lys Leu
        275                 280                 285

Thr Thr Thr Lys Ser Ile Glu Leu Tyr Pro Asp Phe Ala His Glu Asp
    290                 295                 300

Leu Pro Gly His Arg Asp Arg Ile Phe Gln Phe Leu Ser Asp Leu
305                 310                 315


<210> SEQ ID NO 23
<211> LENGTH: 954
<212> TYPE: DNA
<213> ORGANISM: Bacillus clausii

<400> SEQUENCE: 23

atgccattag tcgatatgcc gttgcgcgag ttgttagctt atgaaggaat aaaccctaaa      60

ccagcagatt ttgaccaata ctggaaccgg gccaaaacgg aaattgaagc gattgatccc     120

gaagtcactc tagtcgaatc ttctttccag tgttcgtttg caaactgtta ccatttctat     180

tatcgaagcg ctggaaatgc aaaaatccat gcgaaatacg tacagccaaa agcaggggag     240

aagacgccag cagtttttat gttccatggg tatgggggc gttcagccga atggagcagc      300

ttgttaaatt atgtagcggc gggtttttct gttttctata tggacgtgcg tggacaaggt     360

ggaacttcag aggatcctgg gggcgtaagg gggaatacat ataggggcca cattattcgc     420

ggcctcgatg ccgggccaga cgcacttttt taccgcagcg ttttcttgga caccgtccaa     480

ttggttcgtg ctgctaaaac attgcctcac atcgataaaa cacggcttat ggccacaggg     540

tggtcgcaag gggcgcctt aacgcttgcc tgtgctgccc ttgttcctga aatcaagcgt      600

cttgctccag tatacccgtt tttaagcgat tacaagcgag tgtggcaaat ggatttagcg     660

gttcgttcgt ataaagaatt ggctgattat ttccgttcat acgatccgca acataaacgc     720

catggcgaaa tttttgaacg ccttggctac atcgatgtcc agcatcttgc tgaccggatt     780

caaggagatg tcctaatggg agttggttta atggatacag aatgcccgcc gtctacccaa     840

tttgctgctt ataataaaat aaaggctaaa aaatcgtatg agctctatcc tgattttggc     900

catgagcacc ttccaggaat gaacgatcat atttttcgct tttcactag ttga            954


<210> SEQ ID NO 24
<211> LENGTH: 317
<212> TYPE: PRT
<213> ORGANISM: Bacillus clausii

<400> SEQUENCE: 24

Met Pro Leu Val Asp Met Pro Leu Arg Glu Leu Leu Ala Tyr Glu Gly
1               5                   10                  15
```

-continued

```
Ile Asn Pro Lys Pro Ala Asp Phe Asp Gln Tyr Trp Asn Arg Ala Lys
            20                  25                  30

Thr Glu Ile Glu Ala Ile Asp Pro Glu Val Thr Leu Val Glu Ser Ser
        35                  40                  45

Phe Gln Cys Ser Phe Ala Asn Cys Tyr His Phe Tyr Tyr Arg Ser Ala
    50                  55                  60

Gly Asn Ala Lys Ile His Ala Lys Tyr Val Gln Pro Lys Ala Gly Glu
65                  70                  75                  80

Lys Thr Pro Ala Val Phe Met Phe His Gly Tyr Gly Gly Arg Ser Ala
                85                  90                  95

Glu Trp Ser Ser Leu Leu Asn Tyr Val Ala Ala Gly Phe Ser Val Phe
            100                 105                 110

Tyr Met Asp Val Arg Gly Gln Gly Gly Thr Ser Glu Asp Pro Gly Gly
        115                 120                 125

Val Arg Gly Asn Thr Tyr Arg Gly His Ile Ile Arg Gly Leu Asp Ala
    130                 135                 140

Gly Pro Asp Ala Leu Phe Tyr Arg Ser Val Phe Leu Asp Thr Val Gln
145                 150                 155                 160

Leu Val Arg Ala Ala Lys Thr Leu Pro His Ile Asp Lys Thr Arg Leu
                165                 170                 175

Met Ala Thr Gly Trp Ser Gln Gly Gly Ala Leu Thr Leu Ala Cys Ala
            180                 185                 190

Ala Leu Val Pro Glu Ile Lys Arg Leu Ala Pro Val Tyr Pro Phe Leu
        195                 200                 205

Ser Asp Tyr Lys Arg Val Trp Gln Met Asp Leu Ala Val Arg Ser Tyr
    210                 215                 220

Lys Glu Leu Ala Asp Tyr Phe Arg Ser Tyr Asp Pro Gln His Lys Arg
225                 230                 235                 240

His Gly Glu Ile Phe Glu Arg Leu Gly Tyr Ile Asp Val Gln His Leu
                245                 250                 255

Ala Asp Arg Ile Gln Gly Asp Val Leu Met Gly Val Gly Leu Met Asp
            260                 265                 270

Thr Glu Cys Pro Pro Ser Thr Gln Phe Ala Ala Tyr Asn Lys Ile Lys
        275                 280                 285

Ala Lys Lys Ser Tyr Glu Leu Tyr Pro Asp Phe Gly His Glu His Leu
    290                 295                 300

Pro Gly Met Asn Asp His Ile Phe Arg Phe Phe Thr Ser
305                 310                 315


<210> SEQ ID NO 25
<211> LENGTH: 960
<212> TYPE: DNA
<213> ORGANISM: Bacillus subtilis
<220> FEATURE:
<221> NAME/KEY: CDS
<222> LOCATION: (1)..(960)

<400> SEQUENCE: 25

atg caa cta ttc gat ctg ccg ctc gac caa ttg caa aca tat aag cct       48
Met Gln Leu Phe Asp Leu Pro Leu Asp Gln Leu Gln Thr Tyr Lys Pro
1               5                   10                  15

gaa aaa aca gca ccg aaa gat ttt tct gag ttt tgg aaa ttg tct ttg       96
Glu Lys Thr Ala Pro Lys Asp Phe Ser Glu Phe Trp Lys Leu Ser Leu
            20                  25                  30

gag gaa ctt gca aaa gtc caa gca gaa cct gat cta cag ccg gtt gac      144
Glu Glu Leu Ala Lys Val Gln Ala Glu Pro Asp Leu Gln Pro Val Asp
        35                  40                  45
```

-continued

```
tat cct gct gac gga gta aaa gtg tac cgt ctc aca tat aaa agc ttc      192
Tyr Pro Ala Asp Gly Val Lys Val Tyr Arg Leu Thr Tyr Lys Ser Phe
    50                  55                  60

gga aac gcc cgc att acc gga tgg tac gcg gtg cct gac aag caa ggc      240
Gly Asn Ala Arg Ile Thr Gly Trp Tyr Ala Val Pro Asp Lys Gln Gly
65                  70                  75                  80

ccg cat ccg gcg atc gtg aaa tat cat ggc tac aat gca agc tat gat      288
Pro His Pro Ala Ile Val Lys Tyr His Gly Tyr Asn Ala Ser Tyr Asp
                85                  90                  95

ggt gag att cat gaa atg gta aac tgg gca ctc cat ggc tac gcc gca      336
Gly Glu Ile His Glu Met Val Asn Trp Ala Leu His Gly Tyr Ala Ala
            100                 105                 110

ttc ggc atg ctt gtc cgc ggc cag cag agc agc gag gat acg agt att      384
Phe Gly Met Leu Val Arg Gly Gln Gln Ser Ser Glu Asp Thr Ser Ile
        115                 120                 125

tca ccg cac ggt cac gct ttg ggc tgg atg acg aaa gga att ctt gat      432
Ser Pro His Gly His Ala Leu Gly Trp Met Thr Lys Gly Ile Leu Asp
    130                 135                 140

aaa gat aca tac tat tac cgc ggt gtt tat ttg gac gcc gtc cgc gcg      480
Lys Asp Thr Tyr Tyr Tyr Arg Gly Val Tyr Leu Asp Ala Val Arg Ala
145                 150                 155                 160

ctt gag gtc atc agc agc ttc gac gag gtt gac gaa aca agg atc ggt      528
Leu Glu Val Ile Ser Ser Phe Asp Glu Val Asp Glu Thr Arg Ile Gly
                165                 170                 175

gtg aca gga gga agc caa ggc gga ggt tta acc att gcc gca gca gcg      576
Val Thr Gly Gly Ser Gln Gly Gly Gly Leu Thr Ile Ala Ala Ala Ala
            180                 185                 190

ctg tca gac att cca aaa gcc gcg gtt gcc gat tat cct tat tta agc      624
Leu Ser Asp Ile Pro Lys Ala Ala Val Ala Asp Tyr Pro Tyr Leu Ser
        195                 200                 205

aac ttc gaa cgg gcc att gat gtg gcg ctt gaa cag ccg tac ctt gaa      672
Asn Phe Glu Arg Ala Ile Asp Val Ala Leu Glu Gln Pro Tyr Leu Glu
    210                 215                 220

atc aat tcc ttc ttc aga aga aat ggc agc ccg gaa aca gaa gtg cag      720
Ile Asn Ser Phe Phe Arg Arg Asn Gly Ser Pro Glu Thr Glu Val Gln
225                 230                 235                 240

gcg atg aag aca ctt tca tat ttc gat att atg aat ctc gct gac cga      768
Ala Met Lys Thr Leu Ser Tyr Phe Asp Ile Met Asn Leu Ala Asp Arg
                245                 250                 255

gtg aag gtg cct gtc ctg atg tca atc ggc ctg att gac aag gtc acg      816
Val Lys Val Pro Val Leu Met Ser Ile Gly Leu Ile Asp Lys Val Thr
            260                 265                 270

ccg cca tcc acc gtg ttt gcc gcc tac aat cat ttg gaa aca gag aaa      864
Pro Pro Ser Thr Val Phe Ala Ala Tyr Asn His Leu Glu Thr Glu Lys
        275                 280                 285

gag ctg aag gtg tac cgc tac ttc gga cat gag tat atc cct gct ttt      912
Glu Leu Lys Val Tyr Arg Tyr Phe Gly His Glu Tyr Ile Pro Ala Phe
    290                 295                 300

caa acg gaa aaa ctt gct ttc ttt aag cag cat ctt aaa ggc tga taa      960
Gln Thr Glu Lys Leu Ala Phe Phe Lys Gln His Leu Lys Gly
305                 310                 315
```

<210> SEQ ID NO 26
<211> LENGTH: 318
<212> TYPE: PRT
<213> ORGANISM: Bacillus subtilis

<400> SEQUENCE: 26

```
Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
```

```
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Gln Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Pro His Gly His Ala Leu Gly Trp Met Thr Lys Gly Ile Leu Asp
    130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315


<210> SEQ ID NO 27
<211> LENGTH: 325
<212> TYPE: PRT
<213> ORGANISM: Thermotoga neapolitana
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 27

Met Ala Phe Phe Asp Met Pro Leu Glu Glu Leu Lys Lys Tyr Arg Pro
1               5                   10                  15

Glu Arg Tyr Glu Glu Lys Asp Phe Asp Glu Phe Trp Arg Glu Thr Leu
            20                  25                  30

Lys Glu Ser Glu Gly Phe Pro Leu Asp Pro Val Phe Glu Lys Val Asp
        35                  40                  45

Phe His Leu Lys Thr Val Glu Thr Tyr Asp Val Thr Phe Ser Gly Tyr
    50                  55                  60
```

```
Arg Gly Gln Arg Ile Lys Gly Trp Leu Leu Val Pro Lys Leu Ala Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Gly Thr Tyr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Val Ala Gly Gly Ser Gln Gly Gly Gly
            180                 185                 190

Ile Ala Leu Ala Val Ser Ala Leu Ser Asn Arg Val Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
            260                 265                 270

Met Asp Thr Ile Xaa Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Glu Gly
                325


<210> SEQ ID NO 28
<211> LENGTH: 325
<212> TYPE: PRT
<213> ORGANISM: Thermotoga maritima
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 28

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95
```

```
Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Xaa Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 29
<211> LENGTH: 326
<212> TYPE: PRT
<213> ORGANISM: Thermotoga lettingae
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 29

Met Val Tyr Phe Asp Met Pro Leu Glu Asp Leu Arg Lys Tyr Leu Pro
1               5                   10                  15

Gln Arg Tyr Glu Glu Lys Asp Phe Asp Asp Phe Trp Lys Gln Thr Ile
            20                  25                  30

His Glu Thr Arg Gly Tyr Phe Gln Glu Pro Ile Leu Lys Lys Val Asp
        35                  40                  45

Phe Tyr Leu Gln Asn Val Glu Thr Phe Asp Val Thr Phe Ser Gly Tyr
    50                  55                  60

Arg Gly Gln Lys Ile Lys Gly Trp Leu Ile Leu Pro Lys Phe Arg Asn
65                  70                  75                  80

Gly Lys Leu Pro Cys Val Val Glu Phe Val Gly Tyr Gly Gly Gly Arg
                85                  90                  95

Gly Phe Pro Tyr Asp Trp Leu Leu Trp Ser Ala Ala Gly Tyr Ala His
            100                 105                 110

Phe Ile Met Asp Thr Arg Gly Gln Gly Ser Asn Trp Met Lys Gly Asp
```

```
        115                 120                 125

Thr Pro Asp Tyr Glu Asp Asn Pro Ser Asp Pro Gln Tyr Pro Gly Phe
    130                 135                 140

Leu Thr Lys Gly Val Leu Asn Pro Glu Thr Tyr Tyr Tyr Arg Arg Val
145                 150                 155                 160

Phe Met Asp Ala Phe Met Ala Val Glu Thr Ile Ser Gln Leu Glu Gln
                165                 170                 175

Ile Asp Ser Gln Thr Ile Ile Leu Ser Gly Ala Ser Gln Gly Gly Gly
            180                 185                 190

Ile Ala Leu Ala Val Ser Ala Leu Ser Ser Lys Val Met Ala Leu Leu
        195                 200                 205

Cys Asp Val Pro Phe Leu Cys His Tyr Lys Arg Ala Val Gln Ile Thr
    210                 215                 220

Asp Ser Met Pro Tyr Ala Glu Ile Thr Arg Tyr Cys Lys Thr His Ile
225                 230                 235                 240

Asp Lys Ile Gln Thr Val Phe Arg Thr Leu Ser Tyr Phe Asp Gly Val
                245                 250                 255

Asn Phe Ala Ala Arg Ala Lys Cys Pro Ala Leu Phe Ser Val Gly Leu
            260                 265                 270

Met Asp Asp Ile Xaa Pro Pro Ser Thr Val Phe Ala Ala Tyr Asn Tyr
        275                 280                 285

Tyr Ala Gly Glu Lys Asp Ile Arg Ile Tyr Pro Tyr Asn Asn His Glu
    290                 295                 300

Gly Gly Gly Ser Phe His Thr Leu Glu Lys Leu Lys Phe Val Lys Lys
305                 310                 315                 320

Thr Ile Ser Met Arg Glu
                325


<210> SEQ ID NO 30
<211> LENGTH: 325
<212> TYPE: PRT
<213> ORGANISM: Thermotoga petrophilia
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 30

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Gly Thr Leu
            20                  25                  30

Ala Glu Asn Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Met Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Asp Pro Val Asp Pro Gln Tyr Pro Gly Phe
    130                 135                 140
```

```
Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270

Met Asp Asn Ile Xaa Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Lys Gly
                325


<210> SEQ ID NO 31
<211> LENGTH: 325
<212> TYPE: PRT
<213> ORGANISM: Thermotoga sp.
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 31

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Lys Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Val Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Arg
                165                 170                 175
```

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270

Met Asp Asn Ile Xaa Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 32
<211> LENGTH: 329
<212> TYPE: PRT
<213> ORGANISM: Thermotoga sp.
<220> FEATURE:
<221> NAME/KEY: MISC_FEATURE
<222> LOCATION: (278)..(278)
<223> OTHER INFORMATION: Xaa is Ala, Val, Ser, or Thr.

<400> SEQUENCE: 32

Met Ala Leu Phe Asp Met Pro Leu Glu Lys Leu Arg Ser Tyr Leu Pro
1               5                   10                  15

Asp Arg Tyr Glu Glu Glu Asp Phe Asp Leu Phe Trp Lys Glu Thr Leu
            20                  25                  30

Glu Glu Ser Arg Lys Phe Pro Leu Asp Pro Ile Phe Glu Arg Val Asp
        35                  40                  45

Tyr Leu Leu Glu Asn Val Glu Val Tyr Asp Val Thr Phe Ser Gly Tyr
    50                  55                  60

Arg Gly Gln Arg Ile Lys Ala Trp Leu Ile Leu Pro Val Val Lys Lys
65                  70                  75                  80

Glu Glu Arg Leu Pro Cys Ile Val Glu Phe Ile Gly Tyr Arg Gly Gly
                85                  90                  95

Arg Gly Phe Pro Phe Asp Trp Leu Phe Trp Ser Ser Ala Gly Tyr Ala
            100                 105                 110

His Phe Val Met Asp Thr Arg Gly Gln Gly Thr Ser Arg Val Lys Gly
        115                 120                 125

Asp Thr Pro Asp Tyr Cys Asp Glu Pro Ile Asn Pro Gln Phe Pro Gly
    130                 135                 140

Phe Met Thr Arg Gly Ile Leu Asp Pro Arg Thr Tyr Tyr Tyr Arg Arg
145                 150                 155                 160

Val Phe Thr Asp Ala Val Arg Ala Val Glu Thr Ala Ser Ser Phe Pro
                165                 170                 175

Gly Ile Asp Pro Glu Arg Ile Ala Val Val Gly Thr Ser Gln Gly Gly
            180                 185                 190

Gly Ile Ala Leu Ala Val Ala Ala Leu Ser Glu Ile Pro Lys Ala Leu

```
        195                 200                 205

Val Ser Asn Val Pro Phe Leu Cys His Phe Arg Arg Ala Val Gln Ile
    210                 215                 220

Thr Asp Asn Ala Pro Tyr Ser Glu Ile Val Asn Tyr Leu Lys Val His
225                 230                 235                 240

Arg Asp Lys Glu Glu Ile Val Phe Arg Thr Leu Ser Tyr Phe Asp Gly
                245                 250                 255

Val Asn Phe Ala Ala Arg Ala Lys Ile Pro Ala Leu Phe Ser Val Ala
            260                 265                 270

Leu Met Asp Lys Thr Xaa Pro Pro Ser Thr Val Phe Ala Ala Tyr Asn
        275                 280                 285

His Tyr Ala Gly Pro Lys Glu Ile Lys Val Tyr Pro Phe Asn Glu His
    290                 295                 300

Glu Gly Gly Glu Ser Phe Gln Arg Met Glu Glu Leu Arg Phe Met Lys
305                 310                 315                 320

Arg Ile Leu Lys Gly Glu Phe Lys Ala
                325


<210> SEQ ID NO 33
<211> LENGTH: 326
<212> TYPE: PRT
<213> ORGANISM: Thermotoga lettingae

<400> SEQUENCE: 33

Met Val Tyr Phe Asp Met Pro Leu Glu Asp Leu Arg Lys Tyr Leu Pro
1               5                   10                  15

Gln Arg Tyr Glu Glu Lys Asp Phe Asp Asp Phe Trp Lys Gln Thr Ile
            20                  25                  30

His Glu Thr Arg Gly Tyr Phe Gln Glu Pro Ile Leu Lys Lys Val Asp
        35                  40                  45

Phe Tyr Leu Gln Asn Val Glu Thr Phe Asp Val Thr Phe Ser Gly Tyr
    50                  55                  60

Arg Gly Gln Lys Ile Lys Gly Trp Leu Ile Leu Pro Lys Phe Arg Asn
65                  70                  75                  80

Gly Lys Leu Pro Cys Val Val Glu Phe Val Gly Tyr Gly Gly Gly Arg
                85                  90                  95

Gly Phe Pro Tyr Asp Trp Leu Leu Trp Ser Ala Ala Gly Tyr Ala His
            100                 105                 110

Phe Ile Met Asp Thr Arg Gly Gln Gly Ser Asn Trp Met Lys Gly Asp
        115                 120                 125

Thr Pro Asp Tyr Glu Asp Asn Pro Ser Asp Pro Gln Tyr Pro Gly Phe
    130                 135                 140

Leu Thr Lys Gly Val Leu Asn Pro Glu Thr Tyr Tyr Tyr Arg Arg Val
145                 150                 155                 160

Phe Met Asp Ala Phe Met Ala Val Glu Thr Ile Ser Gln Leu Glu Gln
                165                 170                 175

Ile Asp Ser Gln Thr Ile Ile Leu Ser Gly Ala Ser Gln Gly Gly Gly
            180                 185                 190

Ile Ala Leu Ala Val Ser Ala Leu Ser Ser Lys Val Met Ala Leu Leu
        195                 200                 205

Cys Asp Val Pro Phe Leu Cys His Tyr Lys Arg Ala Val Gln Ile Thr
    210                 215                 220

Asp Ser Met Pro Tyr Ala Glu Ile Thr Arg Tyr Cys Lys Thr His Ile
225                 230                 235                 240

Asp Lys Ile Gln Thr Val Phe Arg Thr Leu Ser Tyr Phe Asp Gly Val
```

-continued

```
                245                 250                 255

Asn Phe Ala Ala Arg Ala Lys Cys Pro Ala Leu Phe Ser Val Gly Leu
            260                 265                 270

Met Asp Asp Ile Cys Pro Pro Ser Thr Val Phe Ala Ala Tyr Asn Tyr
        275                 280                 285

Tyr Ala Gly Glu Lys Asp Ile Arg Ile Tyr Pro Tyr Asn Asn His Glu
    290                 295                 300

Gly Gly Gly Ser Phe His Thr Leu Glu Lys Leu Lys Phe Val Lys Lys
305                 310                 315                 320

Thr Ile Ser Met Arg Glu
                325


<210> SEQ ID NO 34
<211> LENGTH: 325
<212> TYPE: PRT
<213> ORGANISM: Thermotoga petrophilia

<400> SEQUENCE: 34

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Gly Thr Leu
            20                  25                  30

Ala Glu Asn Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Met Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270

Met Asp Asn Ile Cys Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
```

-continued

```
    290                 295                 300

Gly Gly Gly Ser Phe Gln Ala Ile Glu Gln Val Lys Phe Leu Lys Arg
305                 310                 315                 320

Leu Phe Glu Lys Gly
                325


<210> SEQ ID NO 35
<211> LENGTH: 325
<212> TYPE: PRT
<213> ORGANISM: Thermotoga sp.

<400> SEQUENCE: 35

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Lys Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Val Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270

Met Asp Asn Ile Cys Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Lys Gly
                325
```

-continued

<210> SEQ ID NO 36
<211> LENGTH: 329
<212> TYPE: PRT
<213> ORGANISM: Thermotoga sp.

<400> SEQUENCE: 36

```
Met Ala Leu Phe Asp Met Pro Leu Glu Lys Leu Arg Ser Tyr Leu Pro
1               5                   10                  15

Asp Arg Tyr Glu Glu Glu Asp Phe Asp Leu Phe Trp Lys Glu Thr Leu
            20                  25                  30

Glu Glu Ser Arg Lys Phe Pro Leu Asp Pro Ile Phe Glu Arg Val Asp
        35                  40                  45

Tyr Leu Leu Glu Asn Val Glu Val Tyr Asp Val Thr Phe Ser Gly Tyr
    50                  55                  60

Arg Gly Gln Arg Ile Lys Ala Trp Leu Ile Leu Pro Val Val Lys Lys
65                  70                  75                  80

Glu Glu Arg Leu Pro Cys Ile Val Glu Phe Ile Gly Tyr Arg Gly Gly
                85                  90                  95

Arg Gly Phe Pro Phe Asp Trp Leu Phe Trp Ser Ser Ala Gly Tyr Ala
            100                 105                 110

His Phe Val Met Asp Thr Arg Gly Gln Gly Thr Ser Arg Val Lys Gly
        115                 120                 125

Asp Thr Pro Asp Tyr Cys Asp Glu Pro Ile Asn Pro Gln Phe Pro Gly
    130                 135                 140

Phe Met Thr Arg Gly Ile Leu Asp Pro Arg Thr Tyr Tyr Tyr Arg Arg
145                 150                 155                 160

Val Phe Thr Asp Ala Val Arg Ala Val Glu Thr Ala Ser Ser Phe Pro
                165                 170                 175

Gly Ile Asp Pro Glu Arg Ile Ala Val Val Gly Thr Ser Gln Gly Gly
            180                 185                 190

Gly Ile Ala Leu Ala Val Ala Ala Leu Ser Glu Ile Pro Lys Ala Leu
        195                 200                 205

Val Ser Asn Val Pro Phe Leu Cys His Phe Arg Arg Ala Val Gln Ile
    210                 215                 220

Thr Asp Asn Ala Pro Tyr Ser Glu Ile Val Asn Tyr Leu Lys Val His
225                 230                 235                 240

Arg Asp Lys Glu Glu Ile Val Phe Arg Thr Leu Ser Tyr Phe Asp Gly
                245                 250                 255

Val Asn Phe Ala Ala Arg Ala Lys Ile Pro Ala Leu Phe Ser Val Ala
            260                 265                 270

Leu Met Asp Lys Thr Cys Pro Pro Ser Thr Val Phe Ala Ala Tyr Asn
        275                 280                 285

His Tyr Ala Gly Pro Lys Glu Ile Lys Val Tyr Pro Phe Asn Glu His
    290                 295                 300

Glu Gly Gly Glu Ser Phe Gln Arg Met Glu Glu Leu Arg Phe Met Lys
305                 310                 315                 320

Arg Ile Leu Lys Gly Glu Phe Lys Ala
                325
```

<210> SEQ ID NO 37
<211> LENGTH: 960
<212> TYPE: DNA
<213> ORGANISM: Thermoanaerobacterium saccharolyticum

<400> SEQUENCE: 37

```
atgggtctgt tcgatatgcc actgcaaaaa ctgcgtgaat ataccggtac caacccatgt      60
```

-continued

```
cctgaggatt tcgatgaata ctgggatcgc gcactggacg aaatgcgtag cgttgatcct    120

aaaatcaaga tgaagaagag ctcctttcaa gttccgttcg cggaatgtta cgatctgtat    180

tttaccggcg ttcgtggtgc ccgcattcac gcgaaataca ttcgtccgaa aaccgaaggc    240

aaacacccgg cgctgattcg cttccatggt tactccagca actctggtga ttggaacgac    300

aagctgaact acgttgcggc tggttttacc gtagtagcga tggacgctcg tggccagggt    360

ggccaatctc aggacgtcgg cggtgttaat ggcaacaccc tgaacggtca catcatccgt    420

ggcctggacg atgatgcaga taacatgctg ttccgtcata ttttcctgga caccgcgcag    480

ctggctggta tcgttatgaa catgccggaa atcgatgagg accgcgtagc tgttatgggt    540

ccgtcccagg gcggcggtct gtccctggcg tgtgcggctc tggaacctaa aatccgtaaa    600

gtagtgtccg aatatccgtt cctgagcgac tacaagcgtg tgtgggatct ggatctggcc    660

aaaaatgcgt accaagaaat cactgactat ttccgtctgt tcgacccacg ccacgaacgt    720

gagaacgagg tttttactaa actgggttac attgacgtaa agaacctggc gaaacgtatc    780

aaaggtgatg ttctgatgtg cgtgggcctg atggatcagg tctgcccgcc gagcaccgta    840

tttgcagcat acaacaacat ccagtccaag aaggacatca aagtctaccc ggactatggt    900

cacgaaccga tgcgtggctt cggtgacctg gctatgcagt tcatgctgga actgtattct    960
```

```
<210> SEQ ID NO 38
<211> LENGTH: 320
<212> TYPE: PRT
<213> ORGANISM: Thermoanaerobacterium saccharolyticum

<400> SEQUENCE: 38

Met Gly Leu Phe Asp Met Pro Leu Gln Lys Leu Arg Glu Tyr Thr Gly
1               5                   10                  15

Thr Asn Pro Cys Pro Glu Asp Phe Asp Glu Tyr Trp Asp Arg Ala Leu
            20                  25                  30

Asp Glu Met Arg Ser Val Asp Pro Lys Ile Lys Met Lys Lys Ser Ser
        35                  40                  45

Phe Gln Val Pro Phe Ala Glu Cys Tyr Asp Leu Tyr Phe Thr Gly Val
    50                  55                  60

Arg Gly Ala Arg Ile His Ala Lys Tyr Ile Arg Pro Lys Thr Glu Gly
65                  70                  75                  80

Lys His Pro Ala Leu Ile Arg Phe His Gly Tyr Ser Ser Asn Ser Gly
                85                  90                  95

Asp Trp Asn Asp Lys Leu Asn Tyr Val Ala Ala Gly Phe Thr Val Val
            100                 105                 110

Ala Met Asp Ala Arg Gly Gln Gly Gly Gln Ser Gln Asp Val Gly Gly
        115                 120                 125

Val Asn Gly Asn Thr Leu Asn Gly His Ile Ile Arg Gly Leu Asp Asp
    130                 135                 140

Asp Ala Asp Asn Met Leu Phe Arg His Ile Phe Leu Asp Thr Ala Gln
145                 150                 155                 160

Leu Ala Gly Ile Val Met Asn Met Pro Glu Ile Asp Glu Asp Arg Val
                165                 170                 175

Ala Val Met Gly Pro Ser Gln Gly Gly Gly Leu Ser Leu Ala Cys Ala
            180                 185                 190

Ala Leu Glu Pro Lys Ile Arg Lys Val Val Ser Glu Tyr Pro Phe Leu
        195                 200                 205

Ser Asp Tyr Lys Arg Val Trp Asp Leu Asp Leu Ala Lys Asn Ala Tyr
    210                 215                 220
```

Gln Glu Ile Thr Asp Tyr Phe Arg Leu Phe Asp Pro Arg His Glu Arg
225 230 235 240

Glu Asn Glu Val Phe Thr Lys Leu Gly Tyr Ile Asp Val Lys Asn Leu
245 250 255

Ala Lys Arg Ile Lys Gly Asp Val Leu Met Cys Val Gly Leu Met Asp
260 265 270

Gln Val Cys Pro Pro Ser Thr Val Phe Ala Ala Tyr Asn Asn Ile Gln
275 280 285

Ser Lys Lys Asp Ile Lys Val Tyr Pro Asp Tyr Gly His Glu Pro Met
290 295 300

Arg Gly Phe Gly Asp Leu Ala Met Gln Phe Met Leu Glu Leu Tyr Ser
305 310 315 320

<210> SEQ ID NO 39
<211> LENGTH: 939
<212> TYPE: DNA
<213> ORGANISM: Lactococcus lactis

<400> SEQUENCE: 39
atgacaaaaa taaacaattg gcaagattat caaggaagtt cacttaaacc agaggatttt 60
gataaatttt gggatgaaaa aattaatttg gtttcaaatc atcaatttga atttgaatta 120
atagaaaaaa atctttcctc taaggtagtt aacttttatc atttgtggtt tacagctatt 180
gatggagcta aaattcatgc tcagttaatt gttcccaaga atttgaaaga gaaataccca 240
gccatcttac aatttcatgg ttatcattgc gatagtgggg attgggtcga taaaataggg 300
atagttgccg aagggaatgt agttcttgcg cttgattgtc gaggacaagg tggtttaagt 360
caagataata ttcaaactat ggggatgaca atgaagggac tcattgttcg aggaattgat 420
gaagggtatg aaaatctcta ttacgttcgc caatttatgg acttaataac tgcaaccaaa 480
attttatccg agtttgattt tgttgatgaa acaaatataa gtgcacaagg tgcttctcaa 540
ggtggagcgc ttgccgttgc ttgcgccgca ctttctcctc ttataaaaaa ggtgactgcc 600
acttacccct ttctttcaga ttatcgcaaa gcttatgagc ttggtgccga ggaatctgct 660
ttcgaagaac ttccatattg gtttcagttt aaagatccac ttcatctaag agaagactgg 720
ttttttaatc agttggaata cattgatatt caaaatttag caccaagaat taaggctgag 780
gtcatttgga tcctaggcgg caaagatact gttgttcctc cgattacgca aatggcggct 840
tacaataaaa tacaaagtaa aaaatctctc tatgtcttac ctgaatacgg ccatgaatat 900
cttcctaaaa ttagcgactg gttaagagag aatcaataa 939

<210> SEQ ID NO 40
<211> LENGTH: 312
<212> TYPE: PRT
<213> ORGANISM: Lactococcus lactis

<400> SEQUENCE: 40

Met Thr Lys Ile Asn Asn Trp Gln Asp Tyr Gln Gly Ser Ser Leu Lys
1 5 10 15

Pro Glu Asp Phe Asp Lys Phe Trp Asp Glu Lys Ile Asn Leu Val Ser
20 25 30

Asn His Gln Phe Glu Phe Glu Leu Ile Glu Lys Asn Leu Ser Ser Lys
35 40 45

Val Val Asn Phe Tyr His Leu Trp Phe Thr Ala Ile Asp Gly Ala Lys
50 55 60

Ile His Ala Gln Leu Ile Val Pro Lys Asn Leu Lys Glu Lys Tyr Pro
65 70 75 80

```
Ala Ile Leu Gln Phe His Gly Tyr His Cys Asp Ser Gly Asp Trp Val
                85                  90                  95

Asp Lys Ile Gly Ile Val Ala Glu Gly Asn Val Val Leu Ala Leu Asp
            100                 105                 110

Cys Arg Gly Gln Gly Gly Leu Ser Gln Asp Asn Ile Gln Thr Met Gly
        115                 120                 125

Met Thr Met Lys Gly Leu Ile Val Arg Gly Ile Asp Glu Gly Tyr Glu
    130                 135                 140

Asn Leu Tyr Tyr Val Arg Gln Phe Met Asp Leu Ile Thr Ala Thr Lys
145                 150                 155                 160

Ile Leu Ser Glu Phe Asp Phe Val Asp Glu Thr Asn Ile Ser Ala Gln
                165                 170                 175

Gly Ala Ser Gln Gly Gly Ala Leu Ala Val Ala Cys Ala Ala Leu Ser
            180                 185                 190

Pro Leu Ile Lys Lys Val Thr Ala Thr Tyr Pro Phe Leu Ser Asp Tyr
        195                 200                 205

Arg Lys Ala Tyr Glu Leu Gly Ala Glu Glu Ser Ala Phe Glu Glu Leu
    210                 215                 220

Pro Tyr Trp Phe Gln Phe Lys Asp Pro Leu His Leu Arg Glu Asp Trp
225                 230                 235                 240

Phe Phe Asn Gln Leu Glu Tyr Ile Asp Ile Gln Asn Leu Ala Pro Arg
                245                 250                 255

Ile Lys Ala Glu Val Ile Trp Ile Leu Gly Gly Lys Asp Thr Val Val
            260                 265                 270

Pro Pro Ile Thr Gln Met Ala Ala Tyr Asn Lys Ile Gln Ser Lys Lys
        275                 280                 285

Ser Leu Tyr Val Leu Pro Glu Tyr Gly His Glu Tyr Leu Pro Lys Ile
    290                 295                 300

Ser Asp Trp Leu Arg Glu Asn Gln
305                 310


<210> SEQ ID NO 41
<211> LENGTH: 972
<212> TYPE: DNA
<213> ORGANISM: Mesorhizobium loti

<400> SEQUENCE: 41

atgccgttcc cggatctgat ccagcccgaa ctgggcgctt atgtcagcag tgtcggcatg      60

ccggacgact ttgcccaatt ctggacgtcg accatcgccg aggctcgcca ggccggcggt     120

gaggtcagta tcgtgcaggc gcagacgaca ctgaaggcgg tccagtcctt cgatgtcacg     180

tttccaggat acggcggtca tccaatcaaa ggatggctga tcttgccgac gcaccacaag     240

gggcggcttc ccctcgtcgt gcagtatatc ggctatggcg gcggccgcgg cttggcgcat     300

gagcaactgc attgggcggc gtcaggcttt gcctatttcc gaatggatac acgcgggcag     360

ggaagcgact ggagcgtcgg tgagaccgcc gatcccgtcg gctcgacctc gtccattccc     420

ggctttatga cgcgtggcgt gctggacaag aatgactact attaccggcg cctgttcacc     480

gatgccgtga gggcgataga tgctctgctc ggactggact tcgtcgatcc cgaacgcatc     540

gcggtttgcg gtgacagtca gggaggcggt atttcgctcg ccgttggcgg catcgacccg     600

cgcgtcaagg ccgtaatgcc cgacgttcca tttctgtgcg actttccgcg cgctgtgcag     660

actgccgtgc gcgatcccta tttggaaatc gttcgctttc tggcccagca tcgcgaaaag     720

aaggcggcag tctttgaaac gctcaactat ttcgactgcg tcaacttcgc ccggcggtcc     780
```

-continued

```
aaggcgccgg cgctgttttc ggtggccctg atggacgaag tctgcccgcc ctctaccgtg    840

tatggcgcat tcaatgccta tgcaggcgaa aagaccatca cagagtacga attcaacaat    900

catgaaggcg ggcaaggcta tcaagagcgc caacagatga cgtggctcag caggctgttc    960

ggtgtcggct ga                                                        972


<210> SEQ ID NO 42
<211> LENGTH: 323
<212> TYPE: PRT
<213> ORGANISM: Mesorhizobium loit

<400> SEQUENCE: 42

Met Pro Phe Pro Asp Leu Ile Gln Pro Glu Leu Gly Ala Tyr Val Ser
1               5                   10                  15

Ser Val Gly Met Pro Asp Asp Phe Ala Gln Phe Trp Thr Ser Thr Ile
            20                  25                  30

Ala Glu Ala Arg Gln Ala Gly Gly Glu Val Ser Ile Val Gln Ala Gln
        35                  40                  45

Thr Thr Leu Lys Ala Val Gln Ser Phe Asp Val Thr Phe Pro Gly Tyr
    50                  55                  60

Gly Gly His Pro Ile Lys Gly Trp Leu Ile Leu Pro Thr His His Lys
65                  70                  75                  80

Gly Arg Leu Pro Leu Val Val Gln Tyr Ile Gly Tyr Gly Gly Gly Arg
                85                  90                  95

Gly Leu Ala His Glu Gln Leu His Trp Ala Ala Ser Gly Phe Ala Tyr
            100                 105                 110

Phe Arg Met Asp Thr Arg Gly Gln Gly Ser Asp Trp Ser Val Gly Glu
        115                 120                 125

Thr Ala Asp Pro Val Gly Ser Thr Ser Ser Ile Pro Gly Phe Met Thr
    130                 135                 140

Arg Gly Val Leu Asp Lys Asn Asp Tyr Tyr Tyr Arg Arg Leu Phe Thr
145                 150                 155                 160

Asp Ala Val Arg Ala Ile Asp Ala Leu Leu Gly Leu Asp Phe Val Asp
                165                 170                 175

Pro Glu Arg Ile Ala Val Cys Gly Asp Ser Gln Gly Gly Gly Ile Ser
            180                 185                 190

Leu Ala Val Gly Gly Ile Asp Pro Arg Val Lys Ala Val Met Pro Asp
        195                 200                 205

Val Pro Phe Leu Cys Asp Phe Pro Arg Ala Val Gln Thr Ala Val Arg
    210                 215                 220

Asp Pro Tyr Leu Glu Ile Val Arg Phe Leu Ala Gln His Arg Glu Lys
225                 230                 235                 240

Lys Ala Ala Val Phe Glu Thr Leu Asn Tyr Phe Asp Cys Val Asn Phe
                245                 250                 255

Ala Arg Arg Ser Lys Ala Pro Ala Leu Phe Ser Val Ala Leu Met Asp
            260                 265                 270

Glu Val Cys Pro Pro Ser Thr Val Tyr Gly Ala Phe Asn Ala Tyr Ala
        275                 280                 285

Gly Glu Lys Thr Ile Thr Glu Tyr Glu Phe Asn Asn His Glu Gly Gly
    290                 295                 300

Gln Gly Tyr Gln Glu Arg Gln Gln Met Thr Trp Leu Ser Arg Leu Phe
305                 310                 315                 320

Gly Val Gly


<210> SEQ ID NO 43
```

-continued

<211> LENGTH: 990
<212> TYPE: DNA
<213> ORGANISM: Geobacillus stearothermophilus

<400> SEQUENCE: 43
atgttcgata tgccgttagc acaattacag aaatacatgg ggacaaatcc gaagccggct 60
gattttgctg acttttggag tcgagcgttg gaggaattat ctgcccaatc gttgcattat 120
gagctgattc cggcaacatt tcaaacgaca gtggcgagtt gctaccattt gtatttcacg 180
ggagtcggcg gggctagagt ccattgtcag ttagtaaaac cgagagagca gaagcagaaa 240
ggcccggggt tggtatggtt tcatggctac catacgaata gcggcgattg ggtcgataaa 300
ctggcatatg ctgcggcagg ttttactgta ttggcgatgg attgccgcgg ccaaggagga 360
aaatcagagg ataatttgca agtgaaaggc ccaacattga agggccatat tattcgcgga 420
attgaggatc caaatcctca tcatctttat tatcgaaatg ttttttttaga tacagttcag 480 gcggtaagaa ttttatgctc tatggatcat attgatcgtg aacgaattgg tgtatatggc 540
gcttcccaag gaggagcgtt ggcattagcg tgtgctgctc tggaaccatc ggtggtgaaa 600
aaagcggttg tgctctatcc atttttatcg gattataagc gggcgcaaga gttggatatg 660
aaaaataccg cgtatgagga aattcattat tattttcgat ttttagatcc cacacatgag 720
cgggaagaag aagtatttta caaactaggc tatattgata ttcaactctt agccgatcgg 780
atttgtgccg atgttttatg ggctgttgcg ctagaagacc atatttgtcc cccgtccaca 840
caatttgctg tttataataa aattaagtca aaaaaagaca tggttttgtt ttacgagtat 900
ggtcatgagt atttaccgac tatgggagac cgtgcttatc tgttttttttg cccgatcttc 960 tttccaatcc aaaagagaaa cgttaagtaa 990

<210> SEQ ID NO 44
<211> LENGTH: 329
<212> TYPE: PRT
<213> ORGANISM: Geobacillus stearothermophilus

<400> SEQUENCE: 44

Met Phe Asp Met Pro Leu Ala Gln Leu Gln Lys Tyr Met Gly Thr Asn
1 5 10 15

Pro Lys Pro Ala Asp Phe Ala Asp Phe Trp Ser Arg Ala Leu Glu Glu
20 25 30

Leu Ser Ala Gln Ser Leu His Tyr Glu Leu Ile Pro Ala Thr Phe Gln
35 40 45

Thr Thr Val Ala Ser Cys Tyr His Leu Tyr Phe Thr Gly Val Gly Gly
50 55 60

Ala Arg Val His Cys Gln Leu Val Lys Pro Arg Glu Gln Lys Gln Lys
65 70 75 80

Gly Pro Gly Leu Val Trp Phe His Gly Tyr His Thr Asn Ser Gly Asp
85 90 95

Trp Val Asp Lys Leu Ala Tyr Ala Ala Ala Gly Phe Thr Val Leu Ala
100 105 110

Met Asp Cys Arg Gly Gln Gly Gly Lys Ser Glu Asp Asn Leu Gln Val
115 120 125

Lys Gly Pro Thr Leu Lys Gly His Ile Ile Arg Gly Ile Glu Asp Pro
130 135 140

Asn Pro His His Leu Tyr Tyr Arg Asn Val Phe Leu Asp Thr Val Gln
145 150 155 160

Ala Val Arg Ile Leu Cys Ser Met Asp His Ile Asp Arg Glu Arg Ile
165 170 175

-continued

```
Gly Val Tyr Gly Ala Ser Gln Gly Gly Ala Leu Ala Leu Ala Cys Ala
            180                 185                 190

Ala Leu Glu Pro Ser Val Val Lys Lys Ala Val Val Leu Tyr Pro Phe
        195                 200                 205

Leu Ser Asp Tyr Lys Arg Ala Gln Glu Leu Asp Met Lys Asn Thr Ala
    210                 215                 220

Tyr Glu Glu Ile His Tyr Tyr Phe Arg Phe Leu Asp Pro Thr His Glu
225                 230                 235                 240

Arg Glu Glu Glu Val Phe Tyr Lys Leu Gly Tyr Ile Asp Ile Gln Leu
                245                 250                 255

Leu Ala Asp Arg Ile Cys Ala Asp Val Leu Trp Ala Val Ala Leu Glu
            260                 265                 270

Asp His Ile Cys Pro Pro Ser Thr Gln Phe Ala Val Tyr Asn Lys Ile
        275                 280                 285

Lys Ser Lys Lys Asp Met Val Leu Phe Tyr Glu Tyr Gly His Glu Tyr
    290                 295                 300

Leu Pro Thr Met Gly Asp Arg Ala Tyr Leu Phe Phe Cys Pro Ile Phe
305                 310                 315                 320

Phe Pro Ile Gln Lys Arg Asn Val Lys
                325
```

<210> SEQ ID NO 45
<211> LENGTH: 978
<212> TYPE: DNA
<213> ORGANISM: artificial sequence
<220> FEATURE:
<223> OTHER INFORMATION: synthetic construct

<400> SEQUENCE: 45

```
atggcgttct tcgacctgcc tctggaagaa ctgaagaaat accgtccaga gcgttacgaa      60

gagaaggaca tcgacgagtt ctgggaggaa actctggcgg agaccgaaaa gtttccgctg     120

gacccagtgt tcgagcgtat ggaatctcac ctgaaaaccg tggaggcata tgacgttact     180

ttttctggtt accgtggcca gcgtatcaaa ggctggctgc tggttccgaa actggaggaa     240

gaaaaactgc cgtgcgtagt tcagtacatc ggttacaacg gtggccgtgg ctttccgcac     300

gattggctgt tctggccgtc tatgggctac atttgcttcg tcatggatac tcgtggtcag     360

ggttccggct ggctgaaagg cgatactccg gattatccgg agggcccggt agacccgcag     420

taccctggct tcatgacgcg tggtattctg gatccgcgta cctattacta tcgccgcgtt     480

tttaccgatg cagttcgtgc cgtagaggcc gcggcttctt tccctcaggt tgacctggag     540

cgtattgtta tcgctggtgg ctcccagggt ggcggcatcg ccctggcggt atctgcgctg     600

agcaagaaag ctaaggcact gctgtgtgac gtcccgttcc tgtgtcactt ccgtcgcgct     660

gttcagctgg tagataccca tccgtacgcg gagattacta acttcctgaa aactcaccgc     720

gacaaagaag aaatcgtttt ccgcaccctg tcctatttcg acggcgttaa cttcgcggct     780

cgtgcaaaaa ttccggcact gttctctgtt ggtctgatgg acgacatcag ccctccttct     840

accgttttcg cggcatataa ctattatgcg ggtccgaaag aaatccgtat ctatccgtac     900

aacaaccacg aaggcggtgg tggctttcag gctgttgaac aagtgaaatc cctgaagaaa     960

ctgtttgaga agggctaa                                                   978
```

<210> SEQ ID NO 46
<211> LENGTH: 325
<212> TYPE: PRT
<213> ORGANISM: artificial sequence -continued
<220> FEATURE:
<223> OTHER INFORMATION: synthetic construct

<400> SEQUENCE: 46

```
Met Ala Phe Phe Asp Leu Pro Leu Glu Glu Leu Lys Lys Tyr Arg Pro
1               5                   10                  15

Glu Arg Tyr Glu Glu Lys Asp Ile Asp Glu Phe Trp Glu Glu Thr Leu
            20                  25                  30

Ala Glu Thr Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Leu Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asp Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Gly Phe Gln Ala Val Glu Gln Val Lys Ser Leu Lys Lys
305                 310                 315                 320

Leu Phe Glu Lys Gly
                325
```

<210> SEQ ID NO 47
<211> LENGTH: 978
<212> TYPE: DNA
<213> ORGANISM: artificial sequence
<220> FEATURE:
<223> OTHER INFORMATION: synthetic construct

<400> SEQUENCE: 47

```
atggcgttct tcgacctgcc tctggaagaa ctgaagaaat accgtccaga gcgttacgaa     60
```

-continued

```
gagaaggact tcgacgagtt ctgggaggaa actctggcgg agagcgaaaa gtttccgctg    120

gacccagtgt tcgagcgtat ggaatctcac ctgaaaaccg tggaggcata tgacgttact    180

ttttctggtt accgtggcca gcgtatcaaa ggctggctgc tggttccgaa actggaggaa    240

gaaaaactgc cgtgcgtagt tcagtacatc ggttacaacg gtggccgtgg ctttccgcac    300

gattggctgt tctggccgtc tatgggctac atttgcttcg tcatggatac tcgtggtcag    360

ggttccggct ggctgaaagg cgatactccg gattatccgg agggcccggt agacccgcag    420

taccctggct tcatgacgcg tggtattctg gatccgcgta cctattacta tcgccgcgtt    480

tttaccgatg cagttcgtgc cgtagaggcc gcggcttctt tccctcaggt tgaccaggag    540

cgtattgtta tcgctggtgg ctcccagggt ggcggcatcg ccctggcggt atctgcgctg    600

agcaagaaag ctaaggcact gctgtgtgac gtcccgttcc tgtgtcactt ccgtcgcgct    660

gttcagctgg tagataccca tccgtacgcg gagattacta acttcctgaa aactcaccgc    720

gacaaagaag aaatcgtttt ccgcaccctg tcctatttcg acggcgttaa cttcgcggct    780

cgtgcaaaaa ttccggcact gttctctgtt ggtctgatgg acgacatcag ccctccttct    840

accgttttcg cggcatataa ctattatgcg ggtccgaaag aaatccgtat ctatccgtac    900

aacaaccacg aaggcggtgg tagctttcag gctgttgaac aagtgaaatt cctgaagaaa    960

ctgtttgaga agggctaa                                                  978
```

```
<210> SEQ ID NO 48
<211> LENGTH: 325
<212> TYPE: PRT
<213> ORGANISM: artificial sequence
<220> FEATURE:
<223> OTHER INFORMATION: synthetic construct

<400> SEQUENCE: 48

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205
```

```
Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asp Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325
```

<210> SEQ ID NO 49
<211> LENGTH: 978
<212> TYPE: DNA
<213> ORGANISM: Artificial sequence
<220> FEATURE:
<223> OTHER INFORMATION: synthetic construct

<400> SEQUENCE: 49

```
atggcgttct tcgacctgcc tctggaagaa ctgaagaaat accgtccaga gcgttacgaa      60

gagaaggact tcgacgagtt ctgggaggaa actctggcgg agagcgaaaa gtttccgctg     120

gacccagtgt tcgagcgtat ggaatctcac ctgaaaaccg tggaggcata tgacgttact     180

ttttctggtt accgtggcca gcgtatcaaa ggctggctgc tggttccgaa actggaggaa     240

gaaaaactgc cgtgcgtagt tcagtacatc ggttacaacg gtggccgtgg ctttccgcac     300

gattggctgt tctggccgtc tatgggctac atttgcttcg tcatggatac tcgtggtcag     360

ggttccggct ggctgaaagg cgatactccg gattatccgg agggcccggt agacccgcag     420

taccctggct tcatgacgcg tggtattctg gatccgcgta cctattacta tcgccgcgtt     480

tttaccgatg cagttcgtgc cgtagaggcc gcggcttctt tccctcaggt tgaccaggag     540

cgtattgtta tcgctggtgg ctcccagggt ggcggcatcg ccctggcggt atctgcgctg     600

agcaagaaag ctaaggcact gctgtgtgac gtcccgttcc tgtgtcactt ccgtcgcgct     660

gttcagctgg tagataccca tccgtacgcg gagattacta acttcctgaa aactcaccgc     720

gacaaagaag aaatcgtttt ccgcaccctg tcctatttcg acggcgttaa cttcgcggct     780

cgtgcaaaaa ttccggcact gttctctgtt ggtctgatgg acaacatcag ccctccttct     840

accgttttcg cggcatataa ctattatgcg ggtccgaaag aaatccgtat ctatccgtac     900

aacaaccacg aaggcggtgg tagctttcag gctgttgaac aagtgaaatc cctgaagaaa     960

ctgtttgaga agggctaa                                                   978
```

<210> SEQ ID NO 50
<211> LENGTH: 325
<212> TYPE: PRT
<213> ORGANISM: Artificial sequence
<220> FEATURE:
<223> OTHER INFORMATION: synthetic construct

<400> SEQUENCE: 50

```
Met Ala Phe Phe Asp Leu Pro Leu Glu Glu Leu Lys Lys Tyr Arg Pro
```

-continued

```
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Ser Leu Lys Lys
305                 310                 315                 320

Leu Phe Glu Lys Gly
                325
```

<210> SEQ ID NO 51
<211> LENGTH: 978
<212> TYPE: DNA
<213> ORGANISM: Artificial sequence
<220> FEATURE:
<223> OTHER INFORMATION: synthetic construct

<400> SEQUENCE: 51

```
atggcgttct tcgacctgcc tctggaagaa ctgaagaaat accgtccaga gcgttacgaa      60

gagaaggact tcgacgagtt ctgggaggaa actctggcgg agaccgaaaa gtttccgctg     120

gacccagtgt tcgagcgtat ggaatctcac ctgaaaaccg tggaggcata tgacgttact     180

ttttctggtt accgtggcca gcgtatcaaa ggctggctgc tggttccgaa actggaggaa     240
```

```
gaaaaactgc cgtgcgtagt tcagtacatc ggttacaacg gtggccgtgg ctttccgcac    300

gattggctgt tctggccgtc tatgggctac atttgcttcg tcatggatac tcgtggtcag    360

ggttccggct ggctgaaagg cgatactccg gattatccgg agggcccggt agacccgcag    420

taccctggct tcatgacgcg tggtattctg gatccgcgta cctattacta tcgccgcgtt    480

tttaccgatg cagttcgtgc cgtagaggcc gcggcttctt tccctcaggt tgaccaggag    540

cgtattgtta tcgctggtgg ctcccagggt ggcggcatcg ccctggcggt atctgcgctg    600

agcaagaaag ctaaggcact gctgtgtgac gtcccgttcc tgtgtcactt ccgtcgcgct    660

gttcagctgg tagataccca tccgtacgcg gagattacta acttcctgaa aactcaccgc    720

gacaaagaag aaatcgtttt ccgcaccctg tcctatttcg acggcgttaa cttcgcggct    780

cgtgcaaaaa ttccggcact gttctctgtt ggtctgatgg acaacatcag ccctccttct    840

accgttttcg cggcatataa ctattatgcg ggtccgaaag aaatccgtat ctatccgtac    900

aacaaccacg aaggcggtgg tagctttcag gctgttgaac aagtgaaatt cctgaagaaa    960

ctgtttgaga agggctaa                                                  978
```

<210> SEQ ID NO 52
<211> LENGTH: 325
<212> TYPE: PRT
<213> ORGANISM: Artificial sequence
<220> FEATURE:
<223> OTHER INFORMATION: synthetic construct

<400> SEQUENCE: 52

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Thr Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240
```

Asp Lys Glu Glu Ile Val Phe Arg Thr Leu Ser Tyr Phe Asp Gly Val
245 250 255

Asn Phe Ala Ala Arg Ala Lys Ile Pro Ala Leu Phe Ser Val Gly Leu
260 265 270

Met Asp Asn Ile Ser Pro Pro Ser Thr Val Phe Ala Ala Tyr Asn Tyr
275 280 285

Tyr Ala Gly Pro Lys Glu Ile Arg Ile Tyr Pro Tyr Asn Asn His Glu
290 295 300

Gly Gly Gly Ser Phe Gln Ala Val Glu Gln Val Lys Phe Leu Lys Lys
305 310 315 320

Leu Phe Glu Lys Gly
325

<210> SEQ ID NO 53
<211> LENGTH: 978
<212> TYPE: DNA
<213> ORGANISM: Artificial sequence
<220> FEATURE:
<223> OTHER INFORMATION: synthetic construct

<400> SEQUENCE: 53
atggcgttct tcgacctgcc tctggaagaa ctgaagaaat accgtccaga gcgttacgaa 60
gagaaggact tcgacgagtt ctgggaggaa actctggcgg agagcgaaaa gtttccgctg 120
gacccagtgt tcgagcgtat ggaatctcac ctgaaaaccg tggaggcata tgacgttact 180
ttttctggtt accgtggcca gcgtatcaaa ggctggctgc tggttccgaa actggaggaa 240
gaaaaactgc cgtgcgtagt tcagtacatc ggttacaacg gtggccgtgg ctttccgcac 300
gattggctgt tctggccgtc tatgggctac atttgcttcg tcatggatac tcgtggtcag 360
ggttccggct ggctgaaagg cgatactccg gattatccgg agggcccggt agacccgcag 420
taccctggct tcatgacgcg tggtattctg gatccgcgta cctattacta tcgccgcgtt 480
tttaccgatg cagttcgtgc cgtagaggcc gcggcttctt tccctcaggt tgacctggag 540
cgtattgtta tcgctggtgg ctcccagggt ggcggcatcg ccctggcggt atctgcgctg 600
agcaagaaag ctaaggcact gctgtgtgac gtcccgttcc tgtgtcactt ccgtcgcgct 660
gttcagctgg tagataccca tccgtacgcg gagattacta acttcctgaa aactcaccgc 720
gacaaagaag aaatcgtttt ccgcaccctg tcctatttcg acggcgttaa cttcgcggct 780
cgtgcaaaaa ttccggcact gttctctgtt ggtctgatgg acaacatcag ccctccttct 840
accgttttcg cggcatataa ctattatgcg ggtccgaaag aaatccgtat ctatccgtac 900
aacaaccacg aaggcggtgg tagctttcag gctgttgaac aagtgaaatt cctgaagaaa 960
ctgtttgaga agggctaa 978

<210> SEQ ID NO 54
<211> LENGTH: 325
<212> TYPE: PRT
<213> ORGANISM: Artificial sequence
<220> FEATURE:
<223> OTHER INFORMATION: synthetic construct

<400> SEQUENCE: 54

Met Ala Phe Phe Asp Leu Pro Leu Glu Glu Leu Lys Lys Tyr Arg Pro
1 5 10 15

Glu Arg Tyr Glu Glu Lys Asp Phe Asp Glu Phe Trp Glu Glu Thr Leu
20 25 30

Ala Glu Ser Glu Lys Phe Pro Leu Asp Pro Val Phe Glu Arg Met Glu

```
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Leu Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 55
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 55

atg gcg ttc ttc gac ctg cct cgg gaa gaa ctg aag aaa tac cgt cca       48
Met Ala Phe Phe Asp Leu Pro Arg Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45
```

-continued

```
tct cac ctg aaa acc gtg gag gca tat gac gtt act ttt tct ggt tac       192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa       240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt       288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc       336
Gly Phe Pro His Asp Trp Leu Phe Trp Pro Ser Met Gly Tyr Ile Cys
            100                 105                 110

ttc gtc atg gat act cgt ggt cag ggt tcc ggc tgg cag aaa ggc gat       384
Phe Val Met Asp Thr Arg Gly Gln Gly Ser Gly Trp Gln Lys Gly Asp
        115                 120                 125

act ccg gat tat ccg gag ggc ccg gta gac ccg cag tac cct ggc ttc       432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt       480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct ctg       528
Phe Thr Asp Ala Val Arg Ala Val Glu Ala Ala Ala Ser Phe Pro Leu
                165                 170                 175

gtt gac cag gag cgt att gat atc gct ggt ggc tcc cag ggt ggc ggc       576
Val Asp Gln Glu Arg Ile Asp Ile Ala Gly Gly Ser Gln Gly Gly Gly
            180                 185                 190

atc gcc ctg gcg gta tct gcg ctg agc aag aaa gct aag gca ctg ctg       624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta       672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc       720
Asp Thr His Pro Tyr Ala Glu Ile Thr Asn Phe Leu Lys Thr His Arg
225                 230                 235                 240

gac aaa gaa gaa atc gtt atc cgc acc ctg tcc tat ttc gac ggc gtt       768
Asp Lys Glu Glu Ile Val Ile Arg Thr Leu Ser Tyr Phe Asp Gly Val
                245                 250                 255

aac ttc gcg gct cgt gca aaa att ccg gca ctg ttc tct gtt ggt ctg       816
Asn Phe Ala Ala Arg Ala Lys Ile Pro Ala Leu Phe Ser Val Gly Leu
            260                 265                 270

atg gac aac atc agc cct cct tct acc gtt ttc gcg gca tat aac tat       864
Met Asp Asn Ile Ser Pro Pro Ser Thr Val Phe Ala Ala Tyr Asn Tyr
        275                 280                 285

tat gcg ggt ctg aaa gaa atc cgt atc tat ccg tac aac aac cac gaa       912
Tyr Ala Gly Leu Lys Glu Ile Arg Ile Tyr Pro Tyr Asn Asn His Glu
    290                 295                 300

ggc ggt ggt agc ttt cag gct gtt gaa caa gtg aaa ttc ctg aag aaa       960
Gly Gly Gly Ser Phe Gln Ala Val Glu Gln Val Lys Phe Leu Lys Lys
305                 310                 315                 320

ctg ttt gag aag ggc taa                                               978
Leu Phe Glu Lys Gly
                325
```

<210> SEQ ID NO 56
<211> LENGTH: 325
<212> TYPE: PRT
<213> ORGANISM: artificial sequence
<220> FEATURE:
<223> OTHER INFORMATION: Synthetic Construct

<400> SEQUENCE: 56

```
Met Ala Phe Phe Asp Leu Pro Arg Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Gln Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Leu
                165                 170                 175

Val Asp Gln Glu Arg Ile Asp Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Ile Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Leu Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325
```

<210> SEQ ID NO 57
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 57

```
atg gcg ttc ttc gac ctg cct ctg gaa gaa ctg aag aaa tac cgt cca       48
```

-continued

```
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg      96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa     144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac     192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg gaa ctg gag gaa     240
Arg Gly Gln Arg Ile Lys Gly Trp Leu Leu Val Pro Glu Leu Glu Glu
65                  70                  75                  80

gaa aaa ctg ccg tgc gta gtt cag tac atc ggt tac aac ggt ggc cgt     288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc     336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat     384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc     432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt     480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag     528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc     576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg     624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta     672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc     720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt     768
Asp Lys Glu Glu Ile Val Phe Arg Thr Leu Ser Tyr Phe Asp Gly Val
                245                 250                 255

aac ttc gcg gct cgt gca aaa att ccg gaa ctg ttc tct gtt ggt ctg     816
Asn Phe Ala Ala Arg Ala Lys Ile Pro Glu Leu Phe Ser Val Gly Leu
            260                 265                 270

atg gac aac atc agc cct cct tct acc gtt ttc gcg gca tat aac tat     864
Met Asp Asn Ile Ser Pro Pro Ser Thr Val Phe Ala Ala Tyr Asn Tyr
        275                 280                 285

tat gcg ggt ccg aaa gaa atc cgt atc tat ccg tac aac aac cac gaa     912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa     960
Gly Gly Gly Ser Phe Gln Ala Val Glu Gln Val Lys Phe Leu Lys Lys
305                 310                 315                 320

ctg ttt gag aag ggc taa                                             978
```

Leu Phe Glu Lys Gly
325

<210> SEQ ID NO 58
<211> LENGTH: 325
<212> TYPE: PRT
<213> ORGANISM: artificial sequence
<220> FEATURE:
<223> OTHER INFORMATION: Synthetic Construct

<400> SEQUENCE: 58

Met Ala Phe Phe Asp Leu Pro Leu Glu Glu Leu Lys Lys Tyr Arg Pro
1 5 10 15

Glu Arg Tyr Glu Glu Lys Asp Phe Asp Glu Phe Trp Glu Glu Thr Leu
20 25 30

Ala Glu Ser Glu Lys Phe Pro Leu Asp Pro Val Phe Glu Arg Met Glu
35 40 45

Ser His Leu Lys Thr Val Glu Ala Tyr Asp Val Thr Phe Ser Gly Tyr
50 55 60

Arg Gly Gln Arg Ile Lys Gly Trp Leu Leu Val Pro Glu Leu Glu Glu
65 70 75 80

Glu Lys Leu Pro Cys Val Val Gln Tyr Ile Gly Tyr Asn Gly Gly Arg
85 90 95

Gly Phe Pro His Asp Trp Leu Phe Trp Pro Ser Met Gly Tyr Ile Cys
100 105 110

Phe Val Met Asp Thr Arg Gly Gln Gly Ser Gly Trp Leu Lys Gly Asp
115 120 125

Thr Pro Asp Tyr Pro Glu Gly Pro Val Asp Pro Gln Tyr Pro Gly Phe
130 135 140

Met Thr Arg Gly Ile Leu Asp Pro Arg Thr Tyr Tyr Tyr Arg Arg Val
145 150 155 160

Phe Thr Asp Ala Val Arg Ala Val Glu Ala Ala Ala Ser Phe Pro Gln
165 170 175

Val Asp Gln Glu Arg Ile Val Ile Ala Gly Gly Ser Gln Gly Gly Gly
180 185 190

Ile Ala Leu Ala Val Ser Ala Leu Ser Lys Lys Ala Lys Ala Leu Leu
195 200 205

Cys Asp Val Pro Phe Leu Cys His Phe Arg Arg Ala Val Gln Leu Val
210 215 220

Asp Thr His Pro Tyr Ala Glu Ile Thr Asn Phe Leu Lys Thr His Arg
225 230 235 240

Asp Lys Glu Glu Ile Val Phe Arg Thr Leu Ser Tyr Phe Asp Gly Val
245 250 255

Asn Phe Ala Ala Arg Ala Lys Ile Pro Glu Leu Phe Ser Val Gly Leu
260 265 270

Met Asp Asn Ile Ser Pro Pro Ser Thr Val Phe Ala Ala Tyr Asn Tyr
275 280 285

Tyr Ala Gly Pro Lys Glu Ile Arg Ile Tyr Pro Tyr Asn Asn His Glu
290 295 300

Gly Gly Gly Ser Phe Gln Ala Val Glu Gln Val Lys Phe Leu Lys Lys
305 310 315 320

Leu Phe Glu Lys Gly
325

<210> SEQ ID NO 59
<211> LENGTH: 978
<212> TYPE: DNA

-continued

```
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 59

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag tac tgg gag gaa act ctg       96
Glu Arg Tyr Glu Glu Lys Asp Phe Asp Glu Tyr Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt gtt ctg gat ccg cgt acc tat tac tat cgc cgc gtt      480
Met Thr Arg Gly Val Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gta ctg ttc tct gtt ggt ctg      816
Asn Phe Ala Ala Arg Ala Lys Ile Pro Val Leu Phe Ser Val Gly Leu
            260                 265                 270

atg gac aac atc agc cct cct tct acc gtt ttc gcg gca tat aac tat      864
Met Asp Asn Ile Ser Pro Pro Ser Thr Val Phe Ala Ala Tyr Asn Tyr
        275                 280                 285
```

```
tat gcg ggt ccg aaa gaa acc cgt atc tat ccg tac aac agc cac gaa      912
Tyr Ala Gly Pro Lys Glu Thr Arg Ile Tyr Pro Tyr Asn Ser His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 60
<211> LENGTH: 325
<212> TYPE: PRT
<213> ORGANISM: artificial sequence
<220> FEATURE:
<223> OTHER INFORMATION: Synthetic Construct

<400> SEQUENCE: 60

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Tyr Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Val Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Val Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Thr Arg Ile Tyr Pro Tyr Asn Ser His Glu
    290                 295                 300
```

-continued

```
Gly Gly Gly Ser Phe Gln Ala Val Glu Gln Val Lys Phe Leu Lys Lys
305                 310                 315                 320

Leu Phe Glu Lys Gly
                325


<210> SEQ ID NO 61
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 61

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc cag gcg gta tct gcg ctg agc aag aaa gct aag gca ctg ctg      624
Ile Ala Gln Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
```

```
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc agc cct cct tct acc gtt ttc gcg gca tat aac tat      864
Met Asp Asn Ile Ser Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 62
<211> LENGTH: 325
<212> TYPE: PRT
<213> ORGANISM: artificial sequence
<220> FEATURE:
<223> OTHER INFORMATION: Synthetic Construct

<400> SEQUENCE: 62

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Gln Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255
```

```
Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 63
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 63

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc ttc att tgc      336
Gly Phe Pro His Asp Trp Leu Phe Trp Pro Ser Met Gly Phe Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205
```

```
tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc agc cct cct tct acc gtt ttc gcg gca tat aac tat      864
Met Asp Asn Ile Ser Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325
```

<210> SEQ ID NO 64
<211> LENGTH: 325
<212> TYPE: PRT
<213> ORGANISM: artificial sequence
<220> FEATURE:
<223> OTHER INFORMATION: Synthetic Construct

<400> SEQUENCE: 64

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Phe Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
```

-continued

```
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 65
<211> LENGTH: 12
<212> TYPE: PRT
<213> ORGANISM: Artificial Sequence
<220> FEATURE:
<223> OTHER INFORMATION: synthetic construct

<400> SEQUENCE: 65

Ala Pro Trp His Leu Ser Ser Gln Tyr Ser Gly Thr
1               5                   10


<210> SEQ ID NO 66
<211> LENGTH: 14
<212> TYPE: PRT
<213> ORGANISM: Artificial Sequence
<220> FEATURE:
<223> OTHER INFORMATION: synthetic construct

<400> SEQUENCE: 66

Gly Tyr Cys Leu Arg Val Asp Glu Pro Thr Val Cys Ser Gly
1               5                   10


<210> SEQ ID NO 67
<211> LENGTH: 15
<212> TYPE: PRT
<213> ORGANISM: Artificial Sequence
<220> FEATURE:
<223> OTHER INFORMATION: synthetic construct

<400> SEQUENCE: 67

His Ile His Pro Ser Asp Asn Phe Pro His Lys Asn Arg Thr His
1               5                   10                  15


<210> SEQ ID NO 68
<211> LENGTH: 20
<212> TYPE: PRT
<213> ORGANISM: Artificial Sequence
<220> FEATURE:
<223> OTHER INFORMATION: synthetic construct

<400> SEQUENCE: 68

His Thr His His Asp Thr His Lys Pro Trp Pro Thr Asp Asp His Arg
1               5                   10                  15

Asn Ser Ser Val
            20
```

<210> SEQ ID NO 69
<211> LENGTH: 20
<212> TYPE: PRT
<213> ORGANISM: Artificial Sequence
<220> FEATURE:
<223> OTHER INFORMATION: synthetic construct

<400> SEQUENCE: 69

Pro Glu Asp Arg Pro Ser Arg Thr Asn Ala Leu His His Asn Ala His
1 5 10 15

His His Asn Ala
20

<210> SEQ ID NO 70
<211> LENGTH: 15
<212> TYPE: PRT
<213> ORGANISM: Artificial Sequence
<220> FEATURE:
<223> OTHER INFORMATION: synthetic construct

<400> SEQUENCE: 70

Thr Pro His Asn His Ala Thr Thr Asn His His Ala Gly Lys Lys
1 5 10 15

<210> SEQ ID NO 71
<211> LENGTH: 15
<212> TYPE: PRT
<213> ORGANISM: Artificial Sequence
<220> FEATURE:
<223> OTHER INFORMATION: synthetic construct

<400> SEQUENCE: 71

Glu Met Val Lys Asp Ser Asn Gln Arg Asn Thr Arg Ile Ser Ser
1 5 10 15

<210> SEQ ID NO 72
<211> LENGTH: 12
<212> TYPE: PRT
<213> ORGANISM: Artificial Sequence
<220> FEATURE:
<223> OTHER INFORMATION: synthetic construct

<400> SEQUENCE: 72

His Tyr Ser Arg Tyr Asn Pro Gly Pro His Pro Leu
1 5 10

<210> SEQ ID NO 73
<211> LENGTH: 12
<212> TYPE: PRT
<213> ORGANISM: Artificial Sequence
<220> FEATURE:
<223> OTHER INFORMATION: synthetic construct

<400> SEQUENCE: 73

Ile Asp Thr Phe Tyr Met Ser Thr Met Ser His Ser
1 5 10

<210> SEQ ID NO 74
<211> LENGTH: 20
<212> TYPE: PRT
<213> ORGANISM: Artificial Sequence
<220> FEATURE:
<223> OTHER INFORMATION: synthetic construct

<400> SEQUENCE: 74

Pro Met Lys Glu Ala Thr His Pro Val Pro Pro His Lys His Ser Glu

```
1               5                   10                  15

Thr Pro Thr Ala
            20


<210> SEQ ID NO 75
<211> LENGTH: 12
<212> TYPE: PRT
<213> ORGANISM: Artificial Sequence
<220> FEATURE:
<223> OTHER INFORMATION: synthetic construct

<400> SEQUENCE: 75

Tyr Gln Thr Ser Ser Pro Ala Lys Gln Ser Val Gly
1               5                   10


<210> SEQ ID NO 76
<211> LENGTH: 15
<212> TYPE: PRT
<213> ORGANISM: Artificial Sequence
<220> FEATURE:
<223> OTHER INFORMATION: synthetic construct

<400> SEQUENCE: 76

His Leu Pro Ser Tyr Gln Ile Thr Gln Thr His Ala Gln Tyr Arg
1               5                   10                  15


<210> SEQ ID NO 77
<211> LENGTH: 20
<212> TYPE: PRT
<213> ORGANISM: Artificial Sequence
<220> FEATURE:
<223> OTHER INFORMATION: synthetic construct

<400> SEQUENCE: 77

Thr Thr Pro Lys Thr Thr Tyr His Gln Ser Arg Ala Pro Val Thr Ala
1               5                   10                  15

Met Ser Glu Val
            20


<210> SEQ ID NO 78
<211> LENGTH: 15
<212> TYPE: PRT
<213> ORGANISM: Artificial Sequence
<220> FEATURE:
<223> OTHER INFORMATION: synthetic construct

<400> SEQUENCE: 78

Asp Arg Ile His His Lys Ser His His Val Thr Thr Asn His Phe
1               5                   10                  15


<210> SEQ ID NO 79
<211> LENGTH: 12
<212> TYPE: PRT
<213> ORGANISM: Artificial Sequence
<220> FEATURE:
<223> OTHER INFORMATION: synthetic construct

<400> SEQUENCE: 79

Trp Ala Pro Glu Lys Asp Tyr Met Gln Leu Met Lys
1               5                   10


<210> SEQ ID NO 80
<211> LENGTH: 12
<212> TYPE: PRT
<213> ORGANISM: Artificial sequence
<220> FEATURE:
<223> OTHER INFORMATION: synthetic construct
```

<400> SEQUENCE: 80

Thr Ser Asp Ile Lys Ser Arg Ser Pro His His Arg
1 5 10

<210> SEQ ID NO 81
<211> LENGTH: 12
<212> TYPE: PRT
<213> ORGANISM: Artificial Sequence
<220> FEATURE:
<223> OTHER INFORMATION: synthetic construct

<400> SEQUENCE: 81

His Thr Gln Asn Met Arg Met Tyr Glu Pro Trp Phe
1 5 10

<210> SEQ ID NO 82
<211> LENGTH: 7
<212> TYPE: PRT
<213> ORGANISM: Artificial Sequence
<220> FEATURE:
<223> OTHER INFORMATION: synthetic construct

<400> SEQUENCE: 82

Leu Pro Pro Gly Ser Leu Ala
1 5

<210> SEQ ID NO 83
<211> LENGTH: 12
<212> TYPE: PRT
<213> ORGANISM: Artificial Sequence
<220> FEATURE:
<223> OTHER INFORMATION: synthetic construct

<400> SEQUENCE: 83

Met Pro Ala Val Met Ser Ser Ala Gln Val Pro Arg
1 5 10

<210> SEQ ID NO 84
<211> LENGTH: 12
<212> TYPE: PRT
<213> ORGANISM: Artificial Sequence
<220> FEATURE:
<223> OTHER INFORMATION: synthetic construct

<400> SEQUENCE: 84

Asn Gln Ser Phe Leu Pro Leu Asp Phe Pro Phe Arg
1 5 10

<210> SEQ ID NO 85
<211> LENGTH: 12
<212> TYPE: PRT
<213> ORGANISM: Artificial Sequence
<220> FEATURE:
<223> OTHER INFORMATION: synthetic construct

<400> SEQUENCE: 85

Ser Ile Leu Ser Thr Met Ser Pro His Gly Ala Thr
1 5 10

<210> SEQ ID NO 86
<211> LENGTH: 12
<212> TYPE: PRT
<213> ORGANISM: Artificial Sequence
<220> FEATURE:
<223> OTHER INFORMATION: synthetic construct

<400> SEQUENCE: 86

Ser Met Lys Tyr Ser His Ser Thr Ala Pro Ala Leu
1 5 10

<210> SEQ ID NO 87
<211> LENGTH: 12
<212> TYPE: PRT
<213> ORGANISM: Artificial sequence
<220> FEATURE:
<223> OTHER INFORMATION: synthetic construct

<400> SEQUENCE: 87

Glu Ser Ser Tyr Ser Trp Ser Pro Ala Arg Leu Ser
1 5 10

<210> SEQ ID NO 88
<211> LENGTH: 12
<212> TYPE: PRT
<213> ORGANISM: Artificial Sequence
<220> FEATURE:
<223> OTHER INFORMATION: synthetic construct

<400> SEQUENCE: 88

Gly Pro Leu Lys Leu Leu His Ala Trp Trp Gln Pro
1 5 10

<210> SEQ ID NO 89
<211> LENGTH: 7
<212> TYPE: PRT
<213> ORGANISM: Artificial Sequence
<220> FEATURE:
<223> OTHER INFORMATION: synthetic construct

<400> SEQUENCE: 89

Asn Ala Leu Thr Arg Pro Val
1 5

<210> SEQ ID NO 90
<211> LENGTH: 7
<212> TYPE: PRT
<213> ORGANISM: Artificial Sequence
<220> FEATURE:
<223> OTHER INFORMATION: synthetic construct

<400> SEQUENCE: 90

Ser Ala Pro Ser Ser Lys Asn
1 5

<210> SEQ ID NO 91
<211> LENGTH: 12
<212> TYPE: PRT
<213> ORGANISM: Artificial Sequence
<220> FEATURE:
<223> OTHER INFORMATION: synthetic construct

<400> SEQUENCE: 91

Ser Val Ser Val Gly Met Lys Pro Ser Pro Arg Pro
1 5 10

<210> SEQ ID NO 92
<211> LENGTH: 12
<212> TYPE: PRT
<213> ORGANISM: Artificial Sequence
<220> FEATURE:
<223> OTHER INFORMATION: synthetic construct

<400> SEQUENCE: 92

Ser Tyr Tyr Ser Leu Pro Pro Ile Phe His Ile Pro

-continued 1 5 10

<210> SEQ ID NO 93
<211> LENGTH: 12
<212> TYPE: PRT
<213> ORGANISM: Artificial Sequence
<220> FEATURE:
<223> OTHER INFORMATION: synthetic construct

<400> SEQUENCE: 93

Thr Phe Thr Pro Tyr Ser Ile Thr His Ala Leu Leu
1 5 10

<210> SEQ ID NO 94
<211> LENGTH: 12
<212> TYPE: PRT
<213> ORGANISM: Artificial Sequence
<220> FEATURE:
<223> OTHER INFORMATION: synthetic construct

<400> SEQUENCE: 94

Thr Met Gly Phe Thr Ala Pro Arg Phe Pro His Tyr
1 5 10

<210> SEQ ID NO 95
<211> LENGTH: 12
<212> TYPE: PRT
<213> ORGANISM: Artificial Sequence
<220> FEATURE:
<223> OTHER INFORMATION: synthetic construct

<400> SEQUENCE: 95

Thr Asn Pro Phe Pro Pro Pro Pro Ser Ser Pro Ala
1 5 10

<210> SEQ ID NO 96
<211> LENGTH: 12
<212> TYPE: PRT
<213> ORGANISM: Artificial sequence
<220> FEATURE:
<223> OTHER INFORMATION: synthetic construct

<400> SEQUENCE: 96

His Asn Lys Ser Ser Pro Leu Thr Ala Ala Leu Pro
1 5 10

<210> SEQ ID NO 97
<211> LENGTH: 12
<212> TYPE: PRT
<213> ORGANISM: Artificial Sequence
<220> FEATURE:
<223> OTHER INFORMATION: synthetic construct

<400> SEQUENCE: 97

Leu Pro Pro Trp Lys His Lys Thr Ser Gly Val Ala
1 5 10

<210> SEQ ID NO 98
<211> LENGTH: 12
<212> TYPE: PRT
<213> ORGANISM: Artificial Sequence
<220> FEATURE:
<223> OTHER INFORMATION: synthetic construct

<400> SEQUENCE: 98

Leu Pro Trp Trp Leu Arg Asp Ser Tyr Leu Leu Pro
1 5 10

<210> SEQ ID NO 99
<211> LENGTH: 12
<212> TYPE: PRT
<213> ORGANISM: Artificial Sequence
<220> FEATURE:
<223> OTHER INFORMATION: synthetic construct

<400> SEQUENCE: 99

Val Pro Trp Trp Lys His Pro Pro Leu Pro Val Pro
1 5 10

<210> SEQ ID NO 100
<211> LENGTH: 12
<212> TYPE: PRT
<213> ORGANISM: Artificial Sequence
<220> FEATURE:
<223> OTHER INFORMATION: synthetic construct

<400> SEQUENCE: 100

His His Lys Gln Trp His Asn His Pro His His Ala
1 5 10

<210> SEQ ID NO 101
<211> LENGTH: 12
<212> TYPE: PRT
<213> ORGANISM: Artificial Sequence
<220> FEATURE:
<223> OTHER INFORMATION: synthetic construct

<400> SEQUENCE: 101

His Ile Phe Ser Ser Trp His Gln Met Trp His Arg
1 5 10

<210> SEQ ID NO 102
<211> LENGTH: 12
<212> TYPE: PRT
<213> ORGANISM: Artificial Sequence
<220> FEATURE:
<223> OTHER INFORMATION: synthetic construct

<400> SEQUENCE: 102

Trp Pro Ala Trp Lys Thr His Pro Ile Leu Arg Met
1 5 10

<210> SEQ ID NO 103
<211> LENGTH: 7
<212> TYPE: PRT
<213> ORGANISM: Artificial sequence
<220> FEATURE:
<223> OTHER INFORMATION: synthetic construct

<400> SEQUENCE: 103

Lys Thr Pro Pro Thr Arg Pro
1 5

<210> SEQ ID NO 104
<211> LENGTH: 7
<212> TYPE: PRT
<213> ORGANISM: Artificial Sequence
<220> FEATURE:
<223> OTHER INFORMATION: synthetic construct

<400> SEQUENCE: 104

Val Ile Asn Pro Asn Leu Asp
1 5

<210> SEQ ID NO 105

-continued

<211> LENGTH: 7
<212> TYPE: PRT
<213> ORGANISM: Artificial Sequence
<220> FEATURE:
<223> OTHER INFORMATION: synthetic construct

<400> SEQUENCE: 105

Lys Val Trp Ile Val Ser Thr
1               5

<210> SEQ ID NO 106
<211> LENGTH: 7
<212> TYPE: PRT
<213> ORGANISM: Artificial Sequence
<220> FEATURE:
<223> OTHER INFORMATION: synthetic construct

<400> SEQUENCE: 106

Ala Glu Pro Val Ala Met Leu
1               5

<210> SEQ ID NO 107
<211> LENGTH: 7
<212> TYPE: PRT
<213> ORGANISM: Artificial Sequence
<220> FEATURE:
<223> OTHER INFORMATION: synthetic construct

<400> SEQUENCE: 107

Ala Glu Leu Val Ala Met Leu
1               5

<210> SEQ ID NO 108
<211> LENGTH: 7
<212> TYPE: PRT
<213> ORGANISM: Artificial Sequence
<220> FEATURE:
<223> OTHER INFORMATION: synthetic construct

<400> SEQUENCE: 108

His Ser Leu Arg Leu Asp Trp
1               5

<210> SEQ ID NO 109
<211> LENGTH: 13
<212> TYPE: PRT
<213> ORGANISM: Artificial sequence
<220> FEATURE:
<223> OTHER INFORMATION: synthetic construct

<400> SEQUENCE: 109

Thr Ser Thr Ala Ser Pro Thr Met Gln Ser Lys Ile Arg
1               5                   10

<210> SEQ ID NO 110
<211> LENGTH: 12
<212> TYPE: PRT
<213> ORGANISM: Artificial Sequence
<220> FEATURE:
<223> OTHER INFORMATION: synthetic construct

<400> SEQUENCE: 110

Lys Arg Asn His Trp Gln Arg Met His Leu Ser Ala
1               5                   10

<210> SEQ ID NO 111
<211> LENGTH: 12
<212> TYPE: PRT

<213> ORGANISM: Artificial Sequence
<220> FEATURE:
<223> OTHER INFORMATION: synthetic construct

<400> SEQUENCE: 111

Ser His Ala Thr Pro Pro Gln Gly Leu Gly Pro Gln
1 5 10

<210> SEQ ID NO 112
<211> LENGTH: 20
<212> TYPE: PRT
<213> ORGANISM: artificial sequence
<220> FEATURE:
<223> OTHER INFORMATION: synthetic construct

<400> SEQUENCE: 112

Ala Thr Thr Pro Pro Ser Gly Lys Ala Ala Ala His Ser Ala Ala Arg
1 5 10 15

Gln Lys Gly Asn
20

<210> SEQ ID NO 113
<211> LENGTH: 15
<212> TYPE: PRT
<213> ORGANISM: artificial sequence
<220> FEATURE:
<223> OTHER INFORMATION: synthetic construct

<400> SEQUENCE: 113

Asp Thr Ile His Pro Asn Lys Met Lys Ser Pro Ser Ser Pro Leu
1 5 10 15

<210> SEQ ID NO 114
<211> LENGTH: 20
<212> TYPE: PRT
<213> ORGANISM: artificial sequence
<220> FEATURE:
<223> OTHER INFORMATION: synthetic construct

<400> SEQUENCE: 114

Asn Gly Asn Asn His Thr Asp Ile Pro Asn Arg Ser Ser Tyr Thr Gly
1 5 10 15

Gly Ser Phe Ala
20

<210> SEQ ID NO 115
<211> LENGTH: 15
<212> TYPE: PRT
<213> ORGANISM: ARTIFICIAL SEQUENCE
<220> FEATURE:
<223> OTHER INFORMATION: synthetic construct

<400> SEQUENCE: 115

Ser Asp Glu Thr Gly Pro Gln Ile Pro His Arg Arg Pro Thr Trp
1 5 10 15

<210> SEQ ID NO 116
<211> LENGTH: 7
<212> TYPE: PRT
<213> ORGANISM: Artificial Sequence
<220> FEATURE:
<223> OTHER INFORMATION: synthetic construct

<400> SEQUENCE: 116

Ser Ile Leu Pro Tyr Pro Tyr
1 5

<210> SEQ ID NO 117
<211> LENGTH: 7
<212> TYPE: PRT
<213> ORGANISM: Artificial Sequence
<220> FEATURE:
<223> OTHER INFORMATION: synthetic construct

<400> SEQUENCE: 117

Ser Thr Ala Ser Tyr Thr Arg
1               5

<210> SEQ ID NO 118
<211> LENGTH: 7
<212> TYPE: PRT
<213> ORGANISM: Artificial Sequence
<220> FEATURE:
<223> OTHER INFORMATION: synthetic construct

<400> SEQUENCE: 118

Leu Pro Val Arg Pro Trp Thr
1               5

<210> SEQ ID NO 119
<211> LENGTH: 7
<212> TYPE: PRT
<213> ORGANISM: Artificial Sequence
<220> FEATURE:
<223> OTHER INFORMATION: synthetic construct

<400> SEQUENCE: 119

Gly Asn Thr Pro Ser Arg Ala
1               5

<210> SEQ ID NO 120
<211> LENGTH: 7
<212> TYPE: PRT
<213> ORGANISM: Artificial Sequence
<220> FEATURE:
<223> OTHER INFORMATION: synthetic construct

<400> SEQUENCE: 120

His Ala Ile Tyr Pro Arg His
1               5

<210> SEQ ID NO 121
<211> LENGTH: 7
<212> TYPE: PRT
<213> ORGANISM: Artificial Sequence
<220> FEATURE:
<223> OTHER INFORMATION: synthetic construct

<400> SEQUENCE: 121

Tyr Gln Asp Ser Ala Lys Thr
1               5

<210> SEQ ID NO 122
<211> LENGTH: 7
<212> TYPE: PRT
<213> ORGANISM: Artificial Sequence
<220> FEATURE:
<223> OTHER INFORMATION: synthetic construct

<400> SEQUENCE: 122

Val Pro Arg Val Thr Ser Ile
1               5

<210> SEQ ID NO 123

<211> LENGTH: 7
<212> TYPE: PRT
<213> ORGANISM: Artificial Sequence
<220> FEATURE:
<223> OTHER INFORMATION: synthetic construct

<400> SEQUENCE: 123

Met Ala Asn His Asn Leu Ser
1               5

<210> SEQ ID NO 124
<211> LENGTH: 7
<212> TYPE: PRT
<213> ORGANISM: Artificial Sequence
<220> FEATURE:
<223> OTHER INFORMATION: synthetic construct

<400> SEQUENCE: 124

Phe His Glu Asn Trp Pro Ser
1               5

<210> SEQ ID NO 125
<211> LENGTH: 12
<212> TYPE: PRT
<213> ORGANISM: Artificial Sequence
<220> FEATURE:
<223> OTHER INFORMATION: synthetic construct

<400> SEQUENCE: 125

Thr His Lys Thr Ser Thr Gln Arg Leu Leu Ala Ala
1               5                   10

<210> SEQ ID NO 126
<211> LENGTH: 12
<212> TYPE: PRT
<213> ORGANISM: Artificial Sequence
<220> FEATURE:
<223> OTHER INFORMATION: synthetic construct

<400> SEQUENCE: 126

Lys Cys Cys Tyr Val Asn Val Gly Ser Val Phe Ser
1               5                   10

<210> SEQ ID NO 127
<211> LENGTH: 12
<212> TYPE: PRT
<213> ORGANISM: Artificial Sequence
<220> FEATURE:
<223> OTHER INFORMATION: synthetic construct

<400> SEQUENCE: 127

Ala His Met Gln Phe Arg Thr Ser Leu Thr Pro His
1               5                   10

<210> SEQ ID NO 128
<211> LENGTH: 8
<212> TYPE: PRT
<213> ORGANISM: Artificial Sequence
<220> FEATURE:
<223> OTHER INFORMATION: Synthetic construct - caspace 3 cleavable
      linker

<400> SEQUENCE: 128

Leu Glu Ser Gly Asp Glu Val Asp
1               5

<210> SEQ ID NO 129
<211> LENGTH: 37

-continued

<212> TYPE: PRT
<213> ORGANISM: Artificial Sequence
<220> FEATURE:
<223> OTHER INFORMATION: synthetic construct

<400> SEQUENCE: 129

```
Thr Ser Thr Ser Lys Ala Ser Thr Thr Thr Thr Ser Ser Lys Thr Thr
1               5                   10                  15

Thr Thr Ser Ser Lys Thr Thr Thr Thr Thr Ser Lys Thr Ser Thr Thr
            20                  25                  30

Ser Ser Ser Ser Thr
        35
```

<210> SEQ ID NO 130
<211> LENGTH: 22
<212> TYPE: PRT
<213> ORGANISM: Artificial Sequence
<220> FEATURE:
<223> OTHER INFORMATION: synthetic construct

<400> SEQUENCE: 130

```
Gly Gln Gly Gly Tyr Gly Gly Leu Gly Ser Gln Gly Ala Gly Arg Gly
1               5                   10                  15

Gly Leu Gly Gly Gln Gly
            20
```

<210> SEQ ID NO 131
<211> LENGTH: 10
<212> TYPE: PRT
<213> ORGANISM: Artificial Sequence
<220> FEATURE:
<223> OTHER INFORMATION: synthetic construct

<400> SEQUENCE: 131

```
Gly Pro Gly Gly Tyr Gly Pro Gly Gln Gln
1               5                   10
```

<210> SEQ ID NO 132
<211> LENGTH: 9
<212> TYPE: PRT
<213> ORGANISM: Artificial Sequence
<220> FEATURE:
<223> OTHER INFORMATION: synthetic construct

<400> SEQUENCE: 132

```
Gly Gly Ser Gly Pro Gly Ser Gly Gly
1               5
```

<210> SEQ ID NO 133
<211> LENGTH: 5
<212> TYPE: PRT
<213> ORGANISM: Artificial Sequence
<220> FEATURE:
<223> OTHER INFORMATION: synthetic construct

<400> SEQUENCE: 133

```
Gly Gly Pro Lys Lys
1               5
```

<210> SEQ ID NO 134
<211> LENGTH: 5
<212> TYPE: PRT
<213> ORGANISM: Artificial Sequence
<220> FEATURE:
<223> OTHER INFORMATION: synthetic construct

<400> SEQUENCE: 134

```
Gly Pro Gly Val Gly
1               5


<210> SEQ ID NO 135
<211> LENGTH: 7
<212> TYPE: PRT
<213> ORGANISM: Artificial Sequence
<220> FEATURE:
<223> OTHER INFORMATION: synthetic construct

<400> SEQUENCE: 135

Gly Gly Gly Cys Gly Gly Gly
1               5


<210> SEQ ID NO 136
<211> LENGTH: 4
<212> TYPE: PRT
<213> ORGANISM: Artificial Sequence
<220> FEATURE:
<223> OTHER INFORMATION: synthetic construct

<400> SEQUENCE: 136

Gly Gly Gly Cys
1


<210> SEQ ID NO 137
<211> LENGTH: 14
<212> TYPE: PRT
<213> ORGANISM: Artificial Sequence
<220> FEATURE:
<223> OTHER INFORMATION: synthetic construct

<400> SEQUENCE: 137

Pro His Met Ala Ser Met Thr Gly Gly Gln Gln Met Gly Ser
1               5                   10


<210> SEQ ID NO 138
<211> LENGTH: 16
<212> TYPE: PRT
<213> ORGANISM: Artificial Sequence
<220> FEATURE:
<223> OTHER INFORMATION: synthetic construct

<400> SEQUENCE: 138

Gly Pro Glu Glu Ala Ala Lys Lys Glu Glu Ala Ala Lys Lys Pro Ala
1               5                   10                  15


<210> SEQ ID NO 139
<211> LENGTH: 14
<212> TYPE: PRT
<213> ORGANISM: Artificial Sequence
<220> FEATURE:
<223> OTHER INFORMATION: synthetic construct

<400> SEQUENCE: 139

Gly Ser Gly Gly Gly Gly Ser Gly Ser Gly Gly Gly Gly Ser
1               5                   10


<210> SEQ ID NO 140
<211> LENGTH: 37
<212> TYPE: PRT
<213> ORGANISM: Artificial Sequence
<220> FEATURE:
<223> OTHER INFORMATION: synthetic construct

<400> SEQUENCE: 140

Gly Pro Glu Pro Glu Pro Glu Pro Glu Pro Ile Pro Glu Pro Pro Lys
```

-continued

```
1               5                   10                  15

Glu Ala Pro Val Val Ile Glu Lys Pro Lys Pro Lys Pro Lys Pro Lys
            20                  25                  30

Pro Lys Pro Pro Ala
        35
```

<210> SEQ ID NO 141
<211> LENGTH: 6368
<212> TYPE: DNA
<213> ORGANISM: artificial sequence
<220> FEATURE:
<223> OTHER INFORMATION: synthetic construct

<400> SEQUENCE: 141

```
agatctcgat cccgcgaaat taatacgact cactataggg agaccacaac ggtttccctc     60

tagaaataat tttgtttaac tttaagaagg agatatacat atgcacactc cagaacatat    120

caccgcagta gtacagcgtt ttgtggcagc tctgaacgcg ggcgagctgg aaggtattgt    180

ggcgctgttc gcggaagaag ccaccgtgga agaaccggtg ggttctgaac cgcgttccgg    240

caccgcagcc tgccgtgaat tttacgcaaa cagcctgaag ctgccgctgg cggttgaact    300

gacccaagaa tgtcgtgcgg tggctaacga agccgctttc gcgttcaccg tgtccttcga    360

ataccagggt cgtaagaccg ttgtggcgcc atgcgaacac tttcgtttca acggcgcagg    420

caaagtggtt tccatccgcg cactgttcgg tgaaaagaac atccatgctt gtcagggatc    480

cgatccgact ccgccgacga atgtactgat gctggcaacc aaaggcggtg gtacgcattc    540

cacgcacaac catggcagcc cgcgccacac gaatgctgac gcaggcaatc cgggcggcgg    600

caccccacca accaatgtcc tgatgctggc tactaaaggc ggcggcacgc attctaccca    660

caaccatggt agcccgcgcc atactaatgc agatgccggc aacccgggcg gtggtacccc    720

gccaaccaac gttctgatgc tggcgacgaa aggtggcggt acccattcca cgcataatca    780

tggcagccct cgccacacca acgctgatgc tggtaatcct ggtggcggta agaagaaata    840

ataaggcgcg ccgacccagc tttcttgtac aaagtggttg attcgaggct gctaacaaag    900

cccgaaagga agctgagttg gctgctgcca ccgctgagca ataactagca taaccccttg    960

gggcctctaa acgggtcttg aggggttttt tgctgaaagg aggaactata tccggatatc   1020

cacaggacgg gtgtggtcgc catgatcgcg tagtcgatag tggctccaag tagcgaagcg   1080

agcaggactg ggcggcggcc aaagcggtcg gacagtgctc cgagaacggg tgcgcataga   1140

aattgcatca acgcatatag cgctagcagc acgccatagt gactggcgat gctgtcggaa   1200

tggacgatat cccgcaagag gcccggcagt accggcataa ccaagcctat gcctacagca   1260

tccagggtga cggtgccgag gatgacgatg agcgcattgt tagatttcat acacggtgcc   1320

tgactgcgtt agcaatttaa ctgtgataaa ctaccgcatt aaagcttgca gtggcggttt   1380

tcatggcttg ttatgactgt ttttttgggg tacagtctat gcctcgggca tccaagcagc   1440

aagcgcgtta cgccgtgggt cgatgtttga tgttatggag cagcaacgat gttacgcagc   1500

agggcagtcg ccctaaaaca aagttaaaca tcatgaggga agcggtgatc gccgaagtat   1560

cgactcaact atcagaggta gttggcgtca tcgagcgcca tctcgaaccg acgttgctgg   1620

ccgtacattt gtacggctcc gcagtggatg gcggcctgaa gccacacagt gatattgatt   1680

tgctggttac ggtgaccgta aggcttgatg aaacaacgcg gcgagctttg atcaacgacc   1740

ttttggaaac ttcggcttcc cctggagaga gcgagattct ccgcgctgta gaagtcacca   1800

ttgttgtgca cgacgacatc attccgtggc gttatccagc taagcgcgaa ctgcaatttg   1860
```

-continued

```
gagaatggca gcgcaatgac attcttgcag gtatcttcga gccagccacg atcgacattg   1920
atctggctat cttgctgaca aaagcaagag aacatagcgt tgccttggta ggtccagcgg   1980
cggaggaact ctttgatccg gttcctgaac aggatctatt tgaggcgcta aatgaaacct   2040
taacgctatg gaactcgccg cccgactggg ctggcgatga gcgaaatgta gtgcttacgt   2100
tgtcccgcat ttggtacagc gcagtaaccg gcaaaatcgc gccgaaggat gtcgctgccg   2160
actgggcaat ggagcgcctg ccggcccagt atcagcccgt catacttgaa gctagacagg   2220
cttatcttgg acaagaagaa gatcgcttgg cctcgcgcgc agatcagttg gaagaatttg   2280
tccactacgt gaaaggcgag atcaccaagg tagtcggcaa ataatgtcta acaattcgtt   2340
caagcttatc gatgataagc tgtcaaacat gagaattctt gaagacgaaa gggcctcgtg   2400
atacgcctat ttttataggt taatgtcatg ataataatgg tttcttagac gtcaggtggc   2460
acttttcggg gaaatgtgcg cggaacccct atttgtttat ttttctaaat acattcaaat   2520
atgtatccgc tcatgagaca ataaccctga taaatgcttc aataatattg aaaaaggaag   2580
agtatgagta ttcaacattt ccgtgtcgcc cttattccct tttttgcggc attttgcctt   2640
cctgtttttg ctcacccaga aacgctggtg aaagtaaaag atgctgaaga tcagttgggt   2700
gcacgagtgg gttacatcga actggatctc aacagcggta agatccttga gagttttcgc   2760
cccgaagaac gttttccaat gatgagcact tttaaagttc tgctatgtgg cgcggtatta   2820
tcccgtgttg acgccgggca agagcaactc ggtcgccgca tacactattc tcagaatgac   2880
ttggttgagt actcaccagt cacagaaaag catcttacgg atggcatgac agtaagagaa   2940
ttatgcagtg ctgccataac catgagtgat aacactgcgg ccaacttact tctgacaacg   3000
atcggaggac cgaaggagct aaccgctttt ttgcacaaca tgggggatca tgtaactcgc   3060
cttgatcgtt gggaaccgga gctgaatgaa gccataccaa acgacgagcg tgacaccacg   3120
atgcctgcag caatggcaac aacgttgcgc aaactattaa ctggcgaact acttactcta   3180
gcttcccggc aacaattaat agactggatg gaggcggata aagttgcagg accacttctg   3240
cgctcggccc ttccggctgg ctggtttatt gctgataaat ctggagccgg tgagcgtggg   3300
tctcgcggta tcattgcagc actggggcca gatggtaagc cctcccgtat cgtagttatc   3360
tacacgacgg ggagtcaggc aactatggat gaacgaaata gacagatcgc tgagataggt   3420
gcctcactga ttaagcattg gtaactgtca gaccaagttt actcatatat actttagatt   3480
gatttaaaac ttcattttta atttaaaagg atctaggtga agatcctttt tgataatctc   3540
atgaccaaaa tcccttaacg tgagttttcg ttccactgag cgtcagaccc cgtagaaaag   3600
atcaaaggat cttcttgaga tccttttttt ctgcgcgtaa tctgctgctt gcaaacaaaa   3660
aaaccaccgc taccagcggt ggtttgtttg ccggatcaag agctaccaac tctttttccg   3720
aaggtaactg gcttcagcag agcgcagata ccaaatactg tccttctagt gtagccgtag   3780
ttaggccacc acttcaagaa ctctgtagca ccgcctacat acctcgctct gctaatcctg   3840
ttaccagtgg ctgctgccag tggcgataag tcgtgtctta ccgggttgga ctcaagacga   3900
tagttaccgg ataaggcgca gcggtcgggc tgaacggggg gttcgtgcac acagcccagc   3960
ttggagcgaa cgacctacac cgaactgaga tacctacagc gtgagctatg agaaagcgcc   4020
acgcttcccg aagggagaaa ggcggacagg tatccggtaa gcggcagggt cggaacagga   4080
gagcgcacga gggagcttcc agggggaaac gcctggtatc tttatagtcc tgtcgggttt   4140
cgccacctct gacttgagcg tcgatttttg tgatgctcgt caggggggcg gagcctatgg   4200
aaaaacgcca gcaacgcggc ctttttacgg ttcctggcct tttgctggcc ttttgctcac   4260
```

-continued

```
atgttctttc ctgcgttatc ccctgattct gtggataacc gtattaccgc ctttgagtga   4320

gctgataccg ctcgccgcag ccgaacgacc gagcgcagcg agtcagtgag cgaggaagcg   4380

gaagagcgcc tgatgcggta ttttctcctt acgcatctgt gcggtatttc acaccgcata   4440

tatggtgcac tctcagtaca atctgctctg atgccgcata gttaagccag tatacactcc   4500

gctatcgcta cgtgactggg tcatggctgc gccccgacac ccgccaacac ccgctgacgc   4560

gccctgacgg gcttgtctgc tcccggcatc cgcttacaga caagctgtga ccgtctccgg   4620

gagctgcatg tgtcagaggt tttcaccgtc atcaccgaaa cgcgcgaggc agctgcggta   4680

aagctcatca gcgtggtcgt gaagcgattc acagatgtct gcctgttcat ccgcgtccag   4740

ctcgttgagt ttctccagaa gcgttaatgt ctggcttctg ataaagcggg ccatgttaag   4800

ggcggttttt tcctgtttgg tcactgatgc ctccgtgtaa gggggatttc tgttcatggg   4860

ggtaatgata ccgatgaaac gagagaggat gctcacgata cgggttactg atgatgaaca   4920

tgcccggtta ctggaacgtt gtgagggtaa acaactggcg gtatggatgc ggcgggacca   4980

gagaaaaatc actcagggtc aatgccagcg cttcgttaat acagatgtag gtgttccaca   5040

gggtagccag cagcatcctg cgatgcagat ccggaacata atggtgcagg gcgctgactt   5100

ccgcgtttcc agactttacg aaacacggaa accgaagacc attcatgttg ttgctcaggt   5160

cgcagacgtt ttgcagcagc agtcgcttca cgttcgctcg cgtatcggtg attcattctg   5220

ctaaccagta aggcaacccc gccagcctag ccgggtcctc aacgacagga gcacgatcat   5280

gcgcacccgt ggccaggacc caacgctgcc cgagatgcgc cgcgtgcggc tgctggagat   5340

ggcggacgcg atggatatgt tctgccaagg gttggtttgc gcattcacag ttctccgcaa   5400

gaattgattg gctccaattc ttggagtggt gaatccgtta gcgaggtgcc gccggcttcc   5460

attcaggtcg aggtggcccg gctccatgca ccgcgacgca acgcggggag gcagacaagg   5520

tatagggcgg cgcctacaat ccatgccaac ccgttccatg tgctcgccga ggcggcataa   5580

atcgccgtga cgatcagcgg tccagtgatc gaagttaggc tggtaagagc cgcgagcgat   5640

ccttgaagct gtccctgatg gtcgtcatct acctgcctgg acagcatggc ctgcaacgcg   5700

ggcatcccga tgccgccgga agcgagaaga atcataatgg ggaaggccat ccagcctcgc   5760

gtcgcgaacg ccagcaagac gtagcccagc gcgtcggccg ccatgccggc gataatggcc   5820

tgcttctcgc cgaaacgttt ggtggcggga ccagtgacga aggcttgagc gagggcgtgc   5880

aagattccga ataccgcaag cgacaggccg atcatcgtcg cgctccagcg aaagcggtcc   5940

tcgccgaaaa tgacccagag cgctgccggc acctgtccta cgagttgcat gataaagaag   6000

acagtcataa gtgcggcgac gatagtcatg ccccgcgccc accggaagga gctgactggg   6060

ttgaaggctc tcaagggcat cggtcgatcg acgctctccc ttatgcgact cctgcattag   6120

gaagcagccc agtagtaggt tgaggccgtt gagcaccgcc gccgcaagga atggtgcatg   6180

caaggagatg gcgcccaaca gtcccccggc cacggggcct gccaccatac ccacgccgaa   6240

acaagcgctc atgagcccga agtggcgagc ccgatcttcc ccatcggtga tgtcggcgat   6300

ataggcgcca gcaaccgcac ctgtggcgcc ggtgatgccg gccacgatgc gtccggcgta   6360

gaggatcg                                                            6368
```

<210> SEQ ID NO 142
<211> LENGTH: 325
<212> TYPE: PRT
<213> ORGANISM: Thermotoga maritima

<400> SEQUENCE: 142

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 143
<211> LENGTH: 18
<212> TYPE: PRT
<213> ORGANISM: artificial sequence
<220> FEATURE:
<223> OTHER INFORMATION: synthetic construct

<400> SEQUENCE: 143

Gly Pro Gly Ser Gly Gly Ala Gly Ser Pro Gly Ser Ala Gly Gly Pro
1               5                   10                  15

Gly Ser


<210> SEQ ID NO 144
```

<211> LENGTH: 1293
<212> TYPE: DNA
<213> ORGANISM: artificial sequence
<220> FEATURE:
<223> OTHER INFORMATION: synthetic construct

<400> SEQUENCE: 144
atggcattct tcgacctgcc actggaggag ctgaagaaat atcgtcctga gcgctatgaa 60
gaaaaggatt ttgatgagtt ctgggaggaa actctggcag aaagcgagaa attcccgctg 120
gacccggtgt ttgaacgtat ggagagccat ttgaaaaccg tggaagccta cgatgtgacc 180
tttagcggct atcgtggtca acgcattaaa ggttggctgc tggtgcctaa gctggaagaa 240
gagaagttgc cttgcgtggt gcaatacatt ggttacaacg gtggtcgtgg ttttccgcac 300
gattggttgt tctggccgag catgggttac atttgctttg tgatggatac ccgcggtcaa 360
ggtagcggtt ggctgaaagg cgacaccccg gattacccgg agggtccagt cgacccacag 420
tacccgggtt ttatgacccg tggtatcctt gacccgcgta cctactacta ccgtcgtgtg 480
ttcaccgacg cggtacgtgc agttgaggca gccgcgtcct tcccacaggt tgaccaggaa 540
cgcatcgtga ttgcgggtgg ctcgcaaggt ggtggtatcg cattggcggt tagcgctctg 600
tccaagaaag caaaagcact gctgtgcgac gtgccgtttc tgtgtcactt ccgtcgtgca 660
gttcagctgg ttgatacgca cccttacgcc gaaattacca actttctgaa aacgcaccgc 720
gataaggaag aaatcgtgtt ccgcaccctg agctattttg acggcgtcaa tttcgcagcg 780
cgtgcgaaga ttccagcgtt gttcagcgtt ggtctgatgg ataacatttc cccgccttct 840
accgttttcg cggcctacaa ctactacgca ggcccgaaag agattcgcat ctacccatat 900
aacaaccatg agggtggcgg tagcttccag gcagttgagc aagttaagtt cctgaagaag 960
ctgttcgaaa agggtggtcc gggttcgggt ggtgcgggca gcccgggtag cgccggtggc 1020
cctggatccc ctagcgcaca aagccaactg ccggacaagc atagcggcct gcacgaacgt 1080
gctccgcagc gttacggtcc ggaaccggaa ccggaaccgg agccgatccc agaaccgccg 1140
aaagaggccc cagttgttat tgaaaagccg aagccgaaac cgaagccgaa gccgaagccg 1200
cctgcgcatg atcataagaa tcagaaggaa acccatcagc gtcacgccgc tggttcgggc 1260
ggtggtggta gcccgcacca tcaccaccac cac 1293

<210> SEQ ID NO 145
<211> LENGTH: 431
<212> TYPE: PRT
<213> ORGANISM: artificial sequence
<220> FEATURE:
<223> OTHER INFORMATION: synthetic construct

<400> SEQUENCE: 145

Met Ala Phe Phe Asp Leu Pro Leu Glu Glu Leu Lys Lys Tyr Arg Pro
1 5 10 15

Glu Arg Tyr Glu Glu Lys Asp Phe Asp Glu Phe Trp Glu Glu Thr Leu
20 25 30

Ala Glu Ser Glu Lys Phe Pro Leu Asp Pro Val Phe Glu Arg Met Glu
35 40 45

Ser His Leu Lys Thr Val Glu Ala Tyr Asp Val Thr Phe Ser Gly Tyr
50 55 60

Arg Gly Gln Arg Ile Lys Gly Trp Leu Leu Val Pro Lys Leu Glu Glu
65 70 75 80

Glu Lys Leu Pro Cys Val Val Gln Tyr Ile Gly Tyr Asn Gly Gly Arg
85 90 95

```
Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Gly Ala Gly Ser Pro Gly
                325                 330                 335

Ser Ala Gly Gly Pro Gly Ser Pro Ser Ala Gln Ser Gln Leu Pro Asp
            340                 345                 350

Lys His Ser Gly Leu His Glu Arg Ala Pro Gln Arg Tyr Gly Pro Glu
        355                 360                 365

Pro Glu Pro Glu Pro Glu Pro Ile Pro Glu Pro Pro Lys Glu Ala Pro
    370                 375                 380

Val Val Ile Glu Lys Pro Lys Pro Lys Pro Lys Pro Lys Pro Lys Pro
385                 390                 395                 400

Pro Ala His Asp His Lys Asn Gln Lys Glu Thr His Gln Arg His Ala
                405                 410                 415

Ala Gly Ser Gly Gly Gly Gly Ser Pro His His His His His His
            420                 425                 430
```

<210> SEQ ID NO 146
<211> LENGTH: 88
<212> TYPE: PRT
<213> ORGANISM: artificial sequence
<220> FEATURE:
<223> OTHER INFORMATION: synthetic construct

<400> SEQUENCE: 146

```
Pro Ser Ala Gln Ser Gln Leu Pro Asp Lys His Ser Gly Leu His Glu
1               5                   10                  15

Arg Ala Pro Gln Arg Tyr Gly Pro Glu Pro Glu Pro Glu Pro Glu Pro
            20                  25                  30

Ile Pro Glu Pro Pro Lys Glu Ala Pro Val Val Ile Glu Lys Pro Lys
```

-continued

```
        35                  40                  45

Pro Lys Pro Lys Pro Lys Pro Lys Pro Pro Ala His Asp His Lys Asn
    50                  55                  60

Gln Lys Glu Thr His Gln Arg His Ala Ala Gly Ser Gly Gly Gly Gly
65                  70                  75                  80

Ser Pro His His His His His His
                85
```

<210> SEQ ID NO 147
<211> LENGTH: 1560
<212> TYPE: DNA
<213> ORGANISM: artificial sequence
<220> FEATURE:
<223> OTHER INFORMATION: synthetic construct

<400> SEQUENCE: 147

```
atggcattct tcgacctgcc actggaggag ctgaagaaat atcgtcctga gcgctatgaa      60

gaaaaggatt ttgatgagtt ctgggaggaa actctggcag aaagcgagaa attcccgctg     120

gacccggtgt ttgaacgtat ggagagccat ttgaaaaccg tggaagccta cgatgtgacc     180

tttagcggct atcgtggtca acgcattaaa ggttggctgc tggtgcctaa gctggaagaa     240

gagaagttgc cttgcgtggt gcaatacatt ggttacaacg gtggtcgtgg ttttccgcac     300

gattggttgt tctggccgag catgggttac atttgctttg tgatggatac ccgcggtcaa     360

ggtagcggtt ggctgaaagg cgacaccccg gattacccgg agggtccagt cgacccacag     420

tacccgggtt ttatgacccg tggtatcctt gacccgcgta cctactacta ccgtcgtgtg     480

ttcaccgacg cggtacgtgc agttgaggca gccgcgtcct tcccacaggt tgaccaggaa     540

cgcatcgtga ttgcgggtgg ctcgcaaggt ggtggtatcg cattggcggt tagcgctctg     600

tccaagaaag caaaagcact gctgtgcgac gtgccgtttc tgtgtcactt ccgtcgtgca     660

gttcagctgg ttgatacgca cccttacgcc gaaattacca actttctgaa aacgcaccgc     720

gataaggaag aaatcgtgtt ccgcaccctg agctattttg acggcgtcaa tttcgcagcg     780

cgtgcgaaga ttccagcgtt gttcagcgtt ggtctgatgg ataacatttc cccgccttct     840

accgttttcg cggcctacaa ctactacgca ggcccgaaag agattcgcat ctacccatat     900

aacaaccatg agggtggcgg tagcttccag gcagttgagc aagttaagtt cctgaagaag     960

ctgttcgaaa agggtggtcc gggttcgggt ggtgcgggca gcccgggtag cgccggtggc    1020

cctggatcca tggcgaatac gccggtgtct ggcaatctga aagtggagtt ttacaatagc    1080

aacccgagcg ataccacgaa ttccatcaac ccacaattca aggtgacgaa tacgggcagc    1140

agcgcgattg atctgagcaa attgacgctg cgctattact ataccgttga tggtcagaag    1200

gaccagacct tttgggcgga tcatgcggca atcatcggca gcaatggcag ctacaacggc    1260

attacctcta atgtgaaggg tactttcgtc aaaatgagca gcagcaccaa caacgctgac    1320

acctacctgg aaatcagctt caccggtggc actctggagc cgggtgccca cgtgcagatc    1380

cagggccgtt tcgcgaagaa tgactggtcc aattacaccc aaagcaatga ttacagcttt    1440

aagagccgct cgcaatttgt tgagtgggac caggttaccg cgtatctgaa cggtgtcttg    1500

gtttggggta aagagccagg cggttcggtg gtgggtggcg gtcaccatca ccaccatcac    1560
```

<210> SEQ ID NO 148
<211> LENGTH: 520
<212> TYPE: PRT
<213> ORGANISM: artificial sequence
<220> FEATURE:
<223> OTHER INFORMATION: synthetic construct

<400> SEQUENCE: 148

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Gly Ala Gly Ser Pro Gly
                325                 330                 335

Ser Ala Gly Gly Pro Gly Ser Met Ala Asn Thr Pro Val Ser Gly Asn
            340                 345                 350

Leu Lys Val Glu Phe Tyr Asn Ser Asn Pro Ser Asp Thr Thr Asn Ser
        355                 360                 365

Ile Asn Pro Gln Phe Lys Val Thr Asn Thr Gly Ser Ser Ala Ile Asp
    370                 375                 380

Leu Ser Lys Leu Thr Leu Arg Tyr Tyr Tyr Thr Val Asp Gly Gln Lys
385                 390                 395                 400

Asp Gln Thr Phe Trp Ala Asp His Ala Ala Ile Ile Gly Ser Asn Gly
                405                 410                 415

Ser Tyr Asn Gly Ile Thr Ser Asn Val Lys Gly Thr Phe Val Lys Met
420 425 430

Ser Ser Ser Thr Asn Asn Ala Asp Thr Tyr Leu Glu Ile Ser Phe Thr
435 440 445

Gly Gly Thr Leu Glu Pro Gly Ala His Val Gln Ile Gln Gly Arg Phe
450 455 460

Ala Lys Asn Asp Trp Ser Asn Tyr Thr Gln Ser Asn Asp Tyr Ser Phe
465 470 475 480

Lys Ser Arg Ser Gln Phe Val Glu Trp Asp Gln Val Thr Ala Tyr Leu
485 490 495

Asn Gly Val Leu Val Trp Gly Lys Glu Pro Gly Gly Ser Val Val Gly
500 505 510

Gly Gly His His His His His His
515 520

<210> SEQ ID NO 149
<211> LENGTH: 177
<212> TYPE: PRT
<213> ORGANISM: Clostridium thermocellum

<400> SEQUENCE: 149

Met Ala Asn Thr Pro Val Ser Gly Asn Leu Lys Val Glu Phe Tyr Asn
1 5 10 15

Ser Asn Pro Ser Asp Thr Thr Asn Ser Ile Asn Pro Gln Phe Lys Val
20 25 30

Thr Asn Thr Gly Ser Ser Ala Ile Asp Leu Ser Lys Leu Thr Leu Arg
35 40 45

Tyr Tyr Tyr Thr Val Asp Gly Gln Lys Asp Gln Thr Phe Trp Ala Asp
50 55 60

His Ala Ala Ile Ile Gly Ser Asn Gly Ser Tyr Asn Gly Ile Thr Ser
65 70 75 80

Asn Val Lys Gly Thr Phe Val Lys Met Ser Ser Ser Thr Asn Asn Ala
85 90 95

Asp Thr Tyr Leu Glu Ile Ser Phe Thr Gly Gly Thr Leu Glu Pro Gly
100 105 110

Ala His Val Gln Ile Gln Gly Arg Phe Ala Lys Asn Asp Trp Ser Asn
115 120 125

Tyr Thr Gln Ser Asn Asp Tyr Ser Phe Lys Ser Arg Ser Gln Phe Val
130 135 140

Glu Trp Asp Gln Val Thr Ala Tyr Leu Asn Gly Val Leu Val Trp Gly
145 150 155 160

Lys Glu Pro Gly Gly Ser Val Val Gly Gly Gly His His His His His
165 170 175

His

<210> SEQ ID NO 150
<211> LENGTH: 1647
<212> TYPE: DNA
<213> ORGANISM: artificial sequence
<220> FEATURE:
<223> OTHER INFORMATION: synthetic construct

<400> SEQUENCE: 150
atggcattct tcgacctgcc actggaggag ctgaagaaat atcgtcctga gcgctatgaa 60
gaaaaggatt ttgatgagtt ctgggaggaa actctggcag aaagcgagaa attcccgctg 120
gacccggtgt ttgaacgtat ggagagccat ttgaaaaccg tggaagccta cgatgtgacc 180

```
tttagcggct atcgtggtca acgcattaaa ggttggctgc tggtgcctaa gctggaagaa    240
gagaagttgc cttgcgtggt gcaatacatt ggttacaacg gtggtcgtgg ttttccgcac    300
gattggttgt tctggccgag catgggttac atttgctttg tgatggatac ccgcggtcaa    360
ggtagcggtt ggctgaaagg cgacaccccg gattacccgg agggtccagt cgacccacag    420
tacccgggtt ttatgacccg tggtatcctt gacccgcgta cctactacta ccgtcgtgtg    480
ttcaccgacg cggtacgtgc agttgaggca gccgcgtcct tcccacaggt tgaccaggaa    540
cgcatcgtga ttgcgggtgg ctcgcaaggt ggtggtatcg cattggcggt tagcgctctg    600
tccaagaaag caaaagcact gctgtgcgac gtgccgtttc tgtgtcactt ccgtcgtgca    660
gttcagctgg ttgatacgca cccttacgcc gaaattacca actttctgaa aacgcaccgc    720
gataaggaag aaatcgtgtt ccgcaccctg agctattttg acggcgtcaa tttcgcagcg    780
cgtgcgaaga ttccagcgtt gttcagcgtt ggtctgatgg ataacatttc cccgccttct    840
accgttttcg cggcctacaa ctactacgca ggcccgaaag agattcgcat ctacccatat    900
aacaaccatg agggtggcgg tagcttccag gcagttgagc aagttaagtt cctgaagaag    960
ctgttcgaaa agggtggtcc gggttcgggt ggtgcgggca gcccgggtag cgccggtggc   1020
cctggatcca tggcaagcta tgctacccct gttgatccag ttacgaacca gccgacggca   1080
ccgaaagact ttagcagcgg cttttgggac ttcaatgacg gcaccaccca gggttttggc   1140
gtgaatccgg atagcccgat tactgccatt aacgtcgaga acgctaacaa tgcgctgaag   1200
atcagcaacc tgaacagcaa aggtagcaat gatctgtctg aaggcaattt ctgggctaac   1260
gttcgcatca gcgcagacat ctggggtcaa tcgatcaaca tttacggcga taccaagttg   1320
actatggacg tgatcgcgcc gactccggtg aacgtgtcca ttgcagccat cccgcagagc   1380
tccacccacg gctggggtaa tccgacgcgt gcgattcgtg tctggaccaa taacttcgtt   1440
gcgcaaacgg acggtacgta caaagcgacc ctgaccatta gcaccaatga ttccccgaat   1500
ttcaatacca ttgcgacgga tgccgcagac tctgtcgtta ccaacatgat tctgttcgtg   1560
ggtagcaata gcgacaatat cagcctggat aacatcaagt ttacgaaagg tccgtctggt   1620
ccgggtaccc accaccatca ccatcac                                       1647
```

<210> SEQ ID NO 151
<211> LENGTH: 549
<212> TYPE: PRT
<213> ORGANISM: artificial sequence
<220> FEATURE:
<223> OTHER INFORMATION: synthetic construct

<400> SEQUENCE: 151

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
```

```
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Gly Ala Gly Ser Pro Gly
                325                 330                 335

Ser Ala Gly Gly Pro Gly Ser Met Ala Ser Tyr Ala Thr Pro Val Asp
            340                 345                 350

Pro Val Thr Asn Gln Pro Thr Ala Pro Lys Asp Phe Ser Ser Gly Phe
        355                 360                 365

Trp Asp Phe Asn Asp Gly Thr Thr Gln Gly Phe Gly Val Asn Pro Asp
    370                 375                 380

Ser Pro Ile Thr Ala Ile Asn Val Glu Asn Ala Asn Asn Ala Leu Lys
385                 390                 395                 400

Ile Ser Asn Leu Asn Ser Lys Gly Ser Asn Asp Leu Ser Glu Gly Asn
                405                 410                 415

Phe Trp Ala Asn Val Arg Ile Ser Ala Asp Ile Trp Gly Gln Ser Ile
            420                 425                 430

Asn Ile Tyr Gly Asp Thr Lys Leu Thr Met Asp Val Ile Ala Pro Thr
        435                 440                 445

Pro Val Asn Val Ser Ile Ala Ala Ile Pro Gln Ser Ser Thr His Gly
    450                 455                 460

Trp Gly Asn Pro Thr Arg Ala Ile Arg Val Trp Thr Asn Asn Phe Val
465                 470                 475                 480

Ala Gln Thr Asp Gly Thr Tyr Lys Ala Thr Leu Thr Ile Ser Thr Asn
                485                 490                 495

Asp Ser Pro Asn Phe Asn Thr Ile Ala Thr Asp Ala Ala Asp Ser Val
            500                 505                 510

Val Thr Asn Met Ile Leu Phe Val Gly Ser Asn Ser Asp Asn Ile Ser
        515                 520                 525
```

Leu Asp Asn Ile Lys Phe Thr Lys Gly Pro Ser Gly Pro Gly Thr His
    530                 535                 540

His His His His His
545

<210> SEQ ID NO 152
<211> LENGTH: 206
<212> TYPE: PRT
<213> ORGANISM: Clostridium cellulovorans

<400> SEQUENCE: 152

Met Ala Ser Tyr Ala Thr Pro Val Asp Pro Val Thr Asn Gln Pro Thr
1               5                   10                  15

Ala Pro Lys Asp Phe Ser Ser Gly Phe Trp Asp Phe Asn Asp Gly Thr
            20                  25                  30

Thr Gln Gly Phe Gly Val Asn Pro Asp Ser Pro Ile Thr Ala Ile Asn
        35                  40                  45

Val Glu Asn Ala Asn Asn Ala Leu Lys Ile Ser Asn Leu Asn Ser Lys
    50                  55                  60

Gly Ser Asn Asp Leu Ser Glu Gly Asn Phe Trp Ala Asn Val Arg Ile
65                  70                  75                  80

Ser Ala Asp Ile Trp Gly Gln Ser Ile Asn Ile Tyr Gly Asp Thr Lys
                85                  90                  95

Leu Thr Met Asp Val Ile Ala Pro Thr Pro Val Asn Val Ser Ile Ala
            100                 105                 110

Ala Ile Pro Gln Ser Ser Thr His Gly Trp Gly Asn Pro Thr Arg Ala
        115                 120                 125

Ile Arg Val Trp Thr Asn Asn Phe Val Ala Gln Thr Asp Gly Thr Tyr
    130                 135                 140

Lys Ala Thr Leu Thr Ile Ser Thr Asn Asp Ser Pro Asn Phe Asn Thr
145                 150                 155                 160

Ile Ala Thr Asp Ala Ala Asp Ser Val Val Thr Asn Met Ile Leu Phe
                165                 170                 175

Val Gly Ser Asn Ser Asp Asn Ile Ser Leu Asp Asn Ile Lys Phe Thr
            180                 185                 190

Lys Gly Pro Ser Gly Pro Gly Thr His His His His His His
        195                 200                 205

<210> SEQ ID NO 153
<211> LENGTH: 1653
<212> TYPE: DNA
<213> ORGANISM: artificial sequence
<220> FEATURE:
<223> OTHER INFORMATION: synthetic construct

<400> SEQUENCE: 153
atggcattct tcgacctgcc actggaggag ctgaagaaat atcgtcctga gcgctatgaa      60
gaaaaggatt ttgatgagtt ctgggaggaa actctggcag aaagcgagaa attcccgctg     120
gacccggtgt ttgaacgtat ggagagccat ttgaaaaccg tggaagccta cgatgtgacc     180
tttagcggct atcgtggtca acgcattaaa ggttggctgc tggtgcctaa gctggaagaa     240
gagaagttgc cttgcgtggt gcaatacatt ggttacaacg gtggtcgtgg ttttccgcac     300
gattggttgt tctggccgag catgggttac atttgctttg tgatggatac ccgcggtcaa     360
ggtagcggtt ggctgaaagg cgacaccccg gattacccgg agggtccagt cgacccacag     420
tacccgggtt ttatgacccg tggtatcctt gacccgcgta cctactacta ccgtcgtgtg     480
ttcaccgacg cggtacgtgc agttgaggca gccgcgtcct tcccacaggt tgaccaggaa     540

```
cgcatcgtga ttgcgggtgg ctcgcaaggt ggtggtatcg cattggcggt tagcgctctg    600

tccaagaaag caaaagcact gctgtgcgac gtgccgtttc tgtgtcactt ccgtcgtgca    660

gttcagctgg ttgatacgca cccttacgcc gaaattacca actttctgaa aacgcaccgc    720

gataaggaag aaatcgtgtt ccgcaccctg agctattttg acggcgtcaa tttcgcagcg    780

cgtgcgaaga ttccagcgtt gttcagcgtt ggtctgatgg ataacatttc cccgccttct    840

accgttttcg cggcctacaa ctactacgca ggcccgaaag agattcgcat ctacccatat    900

aacaaccatg agggtggcgg tagcttccag gcagttgagc aagttaagtt cctgaagaag    960

ctgttcgaaa agggtggtcc gggttcgggt ggtgcgggca gcccgggtag cgccggtggc   1020

cctggatcca tggctagcgg tacggaggtg gaaatcccgg ttgtgcacga tcctaagggc   1080

gaggcggtgt tgccgagcgt ttttgaggac ggcacgcgtc agggttggga ctgggcgggt   1140

gagagcggcg tgaaaacggc gctgaccatt gaagaggcga acggctcgaa cgcactgagc   1200

tgggaatttg gctacccgga ggttaaaccg tccgataact gggcaaccgc cccacgtctg   1260

gatttctgga agtctgacct ggttcgtggt gagaatgact atgtgacgtt cgatttctat   1320

ctggacccgg ttcgcgcaac cgaaggtgcg atgaacatta acctggtctt tcagccgccg   1380

accaatggtt actgggtgca ggcgccgaaa acctatacta tcaatttcga tgaattggaa   1440

gaaccgaatc aagtcaacgg cctgtaccat tacgaggtta agattaacgt ccgtgacatt   1500

accaacatcc aagacgacac gctgctgcgc aatatgatga tcattttcgc ggacgtcgag   1560

agcgatttcg ccggtcgtgt ctttgttgac aatgtccgct ttgagggcgc tgcgggtccg   1620

agcggtcctg gtacccacca ccatcaccat cac                                1653
```

<210> SEQ ID NO 154
<211> LENGTH: 551
<212> TYPE: PRT
<213> ORGANISM: artificial sequence
<220> FEATURE:
<223> OTHER INFORMATION: synthetic construct

<400> SEQUENCE: 154

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
```

```
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Gly Ala Gly Ser Pro Gly
                325                 330                 335

Ser Ala Gly Gly Pro Gly Ser Met Ala Ser Gly Thr Glu Val Glu Ile
            340                 345                 350

Pro Val Val His Asp Pro Lys Gly Glu Ala Val Leu Pro Ser Val Phe
        355                 360                 365

Glu Asp Gly Thr Arg Gln Gly Trp Asp Trp Ala Gly Glu Ser Gly Val
    370                 375                 380

Lys Thr Ala Leu Thr Ile Glu Glu Ala Asn Gly Ser Asn Ala Leu Ser
385                 390                 395                 400

Trp Glu Phe Gly Tyr Pro Glu Val Lys Pro Ser Asp Asn Trp Ala Thr
                405                 410                 415

Ala Pro Arg Leu Asp Phe Trp Lys Ser Asp Leu Val Arg Gly Glu Asn
            420                 425                 430

Asp Tyr Val Thr Phe Asp Phe Tyr Leu Asp Pro Val Arg Ala Thr Glu
        435                 440                 445

Gly Ala Met Asn Ile Asn Leu Val Phe Gln Pro Pro Thr Asn Gly Tyr
    450                 455                 460

Trp Val Gln Ala Pro Lys Thr Tyr Thr Ile Asn Phe Asp Glu Leu Glu
465                 470                 475                 480

Glu Pro Asn Gln Val Asn Gly Leu Tyr His Tyr Glu Val Lys Ile Asn
                485                 490                 495

Val Arg Asp Ile Thr Asn Ile Gln Asp Asp Thr Leu Leu Arg Asn Met
            500                 505                 510

Met Ile Ile Phe Ala Asp Val Glu Ser Asp Phe Ala Gly Arg Val Phe
        515                 520                 525

Val Asp Asn Val Arg Phe Glu Gly Ala Ala Gly Pro Ser Gly Pro Gly
    530                 535                 540

Thr His His His His His His
545                 550
```

<210> SEQ ID NO 155
<211> LENGTH: 208
<212> TYPE: PRT
<213> ORGANISM: Bacillus sp.

<400> SEQUENCE: 155

Met Ala Ser Gly Thr Glu Val Glu Ile Pro Val Val His Asp Pro Lys
1 5 10 15

Gly Glu Ala Val Leu Pro Ser Val Phe Glu Asp Gly Thr Arg Gln Gly
20 25 30

Trp Asp Trp Ala Gly Glu Ser Gly Val Lys Thr Ala Leu Thr Ile Glu
35 40 45

Glu Ala Asn Gly Ser Asn Ala Leu Ser Trp Glu Phe Gly Tyr Pro Glu
50 55 60

Val Lys Pro Ser Asp Asn Trp Ala Thr Ala Pro Arg Leu Asp Phe Trp
65 70 75 80

Lys Ser Asp Leu Val Arg Gly Glu Asn Asp Tyr Val Thr Phe Asp Phe
85 90 95

Tyr Leu Asp Pro Val Arg Ala Thr Glu Gly Ala Met Asn Ile Asn Leu
100 105 110

Val Phe Gln Pro Pro Thr Asn Gly Tyr Trp Val Gln Ala Pro Lys Thr
115 120 125

Tyr Thr Ile Asn Phe Asp Glu Leu Glu Glu Pro Asn Gln Val Asn Gly
130 135 140

Leu Tyr His Tyr Glu Val Lys Ile Asn Val Arg Asp Ile Thr Asn Ile
145 150 155 160

Gln Asp Asp Thr Leu Leu Arg Asn Met Met Ile Ile Phe Ala Asp Val
165 170 175

Glu Ser Asp Phe Ala Gly Arg Val Phe Val Asp Asn Val Arg Phe Glu
180 185 190

Gly Ala Ala Gly Pro Ser Gly Pro Gly Thr His His His His His His
195 200 205

<210> SEQ ID NO 156
<211> LENGTH: 1599
<212> TYPE: DNA
<213> ORGANISM: artificial sequence
<220> FEATURE:
<223> OTHER INFORMATION: synthetic construct

<400> SEQUENCE: 156
atggcattct tcgacctgcc actggaggag ctgaagaaat atcgtcctga gcgctatgaa 60
gaaaaggatt ttgatgagtt ctgggaggaa actctggcag aaagcgagaa attcccgctg 120
gacccggtgt ttgaacgtat ggagagccat ttgaaaaccg tggaagccta cgatgtgacc 180
tttagcggct atcgtggtca acgcattaaa ggttggctgc tggtgcctaa gctggaagaa 240
gagaagttgc cttgcgtggt gcaatacatt ggttacaacg gtggtcgtgg ttttccgcac 300
gattggttgt tctggccgag catgggttac atttgctttg tgatggatac ccgcggtcaa 360
ggtagcggtt ggctgaaagg cgacaccccg gattacccgg agggtccagt cgacccacag 420
tacccgggtt ttatgacccg tggtatcctt gacccgcgta cctactacta ccgtcgtgtg 480
ttcaccgacg cggtacgtgc agttgaggca gccgcgtcct tcccacaggt tgaccaggaa 540
cgcatcgtga ttgcgggtgg ctcgcaaggt ggtggtatcg cattggcggt tagcgctctg 600
tccaagaaag caaaagcact gctgtgcgac gtgccgtttc tgtgtcactt ccgtcgtgca 660
gttcagctgg ttgatacgca cccttacgcc gaaattacca actttctgaa aacgcaccgc 720
gataaggaag aaatcgtgtt ccgcaccctg agctattttg acggcgtcaa tttcgcagcg 780
cgtgcgaaga ttccagcgtt gttcagcgtt ggtctgatgg ataacatttc cccgccttct 840
accgttttcg cggcctacaa ctactacgca ggcccgaaag agattcgcat ctacccatat 900

```
aacaaccatg agggtggcgg tagcttccag gcagttgagc aagttaagtt cctgaagaag    960

ctgttcgaaa agggtggtcc gggttcgggt ggtgcgggca gcccgggtag cgccggtggc   1020

cctggatccg tggcaactgc taagtatggc acgcctgtta ttgacggcga gattgatgag   1080

atctggaata ccaccgaaga gattgaaacg aaggcagtcg cgatgggttc tttggataag   1140

aatgcgactg cgaaagttcg tgtgctgtgg gacgaaaact acctgtacgt gctggcgatt   1200

gtgaaagatc cggttctgaa caaggataac agcaatccgt gggaacagga ctccgtcgag   1260

attttcattg acgagaacaa tcacaaaacc ggttactatg aggacgacga cgcacagttc   1320

cgcgttaact atatgaacga gcaaaccttt ggtacgggcg gtagcccggc tcgtttcaag   1380

acggccgtta aactgatcga gggcggttac attgtcgaag cggcgatcaa atggaaaacg   1440

atcaaaccaa ccccgaatac cgtcatcggc ttcaatatcc aggtgaatga tgccaatgaa   1500

aagggtcaac gtgtgggcat cattagctgg agcgatccga ccaacaacag ctggcgcgac   1560

ccgagcaagt ttggtaacct gcgtctgatc aaataatga                          1599
```

<210> SEQ ID NO 157
<211> LENGTH: 531
<212> TYPE: PRT
<213> ORGANISM: artificial sequence
<220> FEATURE:
<223> OTHER INFORMATION: synthetic construct

<400> SEQUENCE: 157

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240
```

```
Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Gly Ala Gly Ser Pro Gly
                325                 330                 335

Ser Ala Gly Gly Pro Gly Ser Val Ala Thr Ala Lys Tyr Gly Thr Pro
            340                 345                 350

Val Ile Asp Gly Glu Ile Asp Glu Ile Trp Asn Thr Thr Glu Glu Ile
        355                 360                 365

Glu Thr Lys Ala Val Ala Met Gly Ser Leu Asp Lys Asn Ala Thr Ala
    370                 375                 380

Lys Val Arg Val Leu Trp Asp Glu Asn Tyr Leu Tyr Val Leu Ala Ile
385                 390                 395                 400

Val Lys Asp Pro Val Leu Asn Lys Asp Asn Ser Asn Pro Trp Glu Gln
                405                 410                 415

Asp Ser Val Glu Ile Phe Ile Asp Glu Asn Asn His Lys Thr Gly Tyr
            420                 425                 430

Tyr Glu Asp Asp Asp Ala Gln Phe Arg Val Asn Tyr Met Asn Glu Gln
        435                 440                 445

Thr Phe Gly Thr Gly Gly Ser Pro Ala Arg Phe Lys Thr Ala Val Lys
    450                 455                 460

Leu Ile Glu Gly Gly Tyr Ile Val Glu Ala Ala Ile Lys Trp Lys Thr
465                 470                 475                 480

Ile Lys Pro Thr Pro Asn Thr Val Ile Gly Phe Asn Ile Gln Val Asn
                485                 490                 495

Asp Ala Asn Glu Lys Gly Gln Arg Val Gly Ile Ile Ser Trp Ser Asp
            500                 505                 510

Pro Thr Asn Asn Ser Trp Arg Asp Pro Ser Lys Phe Gly Asn Leu Arg
        515                 520                 525

Leu Ile Lys
    530


<210> SEQ ID NO 158
<211> LENGTH: 187
<212> TYPE: PRT
<213> ORGANISM: artificial sequence
<220> FEATURE:
<223> OTHER INFORMATION: synthetic construct

<400> SEQUENCE: 158

Val Ala Thr Ala Lys Tyr Gly Thr Pro Val Ile Asp Gly Glu Ile Asp
1               5                   10                  15

Glu Ile Trp Asn Thr Thr Glu Glu Ile Glu Thr Lys Ala Val Ala Met
            20                  25                  30

Gly Ser Leu Asp Lys Asn Ala Thr Ala Lys Val Arg Val Leu Trp Asp
        35                  40                  45

Glu Asn Tyr Leu Tyr Val Leu Ala Ile Val Lys Asp Pro Val Leu Asn
    50                  55                  60

Lys Asp Asn Ser Asn Pro Trp Glu Gln Asp Ser Val Glu Ile Phe Ile
```

```
65                  70                  75                  80

Asp Glu Asn Asn His Lys Thr Gly Tyr Tyr Glu Asp Asp Asp Ala Gln
                85                  90                  95

Phe Arg Val Asn Tyr Met Asn Glu Gln Thr Phe Gly Thr Gly Gly Ser
            100                 105                 110

Pro Ala Arg Phe Lys Thr Ala Val Lys Leu Ile Glu Gly Gly Tyr Ile
        115                 120                 125

Val Glu Ala Ala Ile Lys Trp Lys Thr Ile Lys Pro Thr Pro Asn Thr
    130                 135                 140

Val Ile Gly Phe Asn Ile Gln Val Asn Asp Ala Asn Glu Lys Gly Gln
145                 150                 155                 160

Arg Val Gly Ile Ile Ser Trp Ser Asp Pro Thr Asn Asn Ser Trp Arg
                165                 170                 175

Asp Pro Ser Lys Phe Gly Asn Leu Arg Leu Ile
            180                 185


<210> SEQ ID NO 159
<211> LENGTH: 1521
<212> TYPE: DNA
<213> ORGANISM: artificial sequence
<220> FEATURE:
<223> OTHER INFORMATION: synthetic construct

<400> SEQUENCE: 159

atggcattct tcgacctgcc actggaggag ctgaagaaat atcgtcctga gcgctatgaa     60

gaaaaggatt ttgatgagtt ctgggaggaa actctggcag aaagcgagaa attcccgctg    120

gacccggtgt ttgaacgtat ggagagccat ttgaaaaccg tggaagccta cgatgtgacc    180

tttagcggct atcgtggtca acgcattaaa ggttggctgc tggtgcctaa gctggaagaa    240

gagaagttgc cttgcgtggt gcaatacatt ggttacaacg gtggtcgtgg ttttccgcac    300

gattggttgt tctggccgag catgggttac atttgctttg tgatggatac ccgcggtcaa    360

ggtagcggtt ggctgaaagg cgacaccccg gattacccgg agggtccagt cgacccacag    420

tacccgggtt ttatgacccg tggtatcctt gacccgcgta cctactacta ccgtcgtgtg    480

ttcaccgacg cggtacgtgc agttgaggca gccgcgtcct tcccacaggt tgaccaggaa    540

cgcatcgtga ttgcgggtgg ctcgcaaggt ggtggtatcg cattggcggt tagcgctctg    600

tccaagaaag caaaagcact gctgtgcgac gtgccgtttc tgtgtcactt ccgtcgtgca    660

gttcagctgg ttgatacgca cccttacgcc gaaattacca actttctgaa aacgcaccgc    720

gataaggaag aaatcgtgtt ccgcaccctg agctattttg acggcgtcaa tttcgcagcg    780

cgtgcgaaga ttccagcgtt gttcagcgtt ggtctgatgg ataacatttc cccgccttct    840

accgttttcg cggcctacaa ctactacgca ggcccgaaag agattcgcat ctacccatat    900

aacaaccatg agggtggcgg tagcttccag gcagttgagc aagttaagtt cctgaagaag    960

ctgttcgaaa agggtggtcc gggttcgggt ggtgcgggca gcccgggtag cgccggtggc   1020

cctggatcca ccccagcgac gtctggtcaa atcaaggttc tgtatgcgaa caaagagact   1080

aattccacca cgaacactat ccgtccgtgg ctgaaagtgg tcaatagcgg tagcagcagc   1140

attgatctga gccgtgtcac gattcgctat tggtacacgg tcgacggcga gcgtgcgcag   1200

agcgcgatct ccgattgggc tcaaattggc gcgtccaacg ttacctttaa gtttgtgaaa   1260

ctgagctcta gcgtgagcgg tgcagactac tatttggaaa ttggtttcaa gagcggtgcc   1320

ggccaactgc agccgggtaa agataccggc gagatccaga tccgtttcaa caaggacgac   1380

tggagcaatt acaatcaggg taatgattgg agctggattc agtcgatgac cagctacggt   1440
```

```
gaaaacgaaa aagtgaccgc ctacatcgac ggcgttctgg tttggggtca agagccgagc   1500

ggcaccaccc cggcataatg a                                             1521


<210> SEQ ID NO 160
<211> LENGTH: 505
<212> TYPE: PRT
<213> ORGANISM: artificial sequence
<220> FEATURE:
<223> OTHER INFORMATION: synthetic construct

<400> SEQUENCE: 160

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Gly Ala Gly Ser Pro Gly
                325                 330                 335

Ser Ala Gly Gly Pro Gly Ser Thr Pro Ala Thr Ser Gly Gln Ile Lys
            340                 345                 350
```

Val Leu Tyr Ala Asn Lys Glu Thr Asn Ser Thr Thr Asn Thr Ile Arg
355 360 365

Pro Trp Leu Lys Val Val Asn Ser Gly Ser Ser Ser Ile Asp Leu Ser
370 375 380

Arg Val Thr Ile Arg Tyr Trp Tyr Thr Val Asp Gly Glu Arg Ala Gln
385 390 395 400

Ser Ala Ile Ser Asp Trp Ala Gln Ile Gly Ala Ser Asn Val Thr Phe
405 410 415

Lys Phe Val Lys Leu Ser Ser Ser Val Ser Gly Ala Asp Tyr Tyr Leu
420 425 430

Glu Ile Gly Phe Lys Ser Gly Ala Gly Gln Leu Gln Pro Gly Lys Asp
435 440 445

Thr Gly Glu Ile Gln Ile Arg Phe Asn Lys Asp Asp Trp Ser Asn Tyr
450 455 460

Asn Gln Gly Asn Asp Trp Ser Trp Ile Gln Ser Met Thr Ser Tyr Gly
465 470 475 480

Glu Asn Glu Lys Val Thr Ala Tyr Ile Asp Gly Val Leu Val Trp Gly
485 490 495

Gln Glu Pro Ser Gly Thr Thr Pro Ala
500 505

<210> SEQ ID NO 161
<211> LENGTH: 162
<212> TYPE: PRT
<213> ORGANISM: artificial sequence
<220> FEATURE:
<223> OTHER INFORMATION: synthetic construct

<400> SEQUENCE: 161

Thr Pro Ala Thr Ser Gly Gln Ile Lys Val Leu Tyr Ala Asn Lys Glu
1 5 10 15

Thr Asn Ser Thr Thr Asn Thr Ile Arg Pro Trp Leu Lys Val Val Asn
20 25 30

Ser Gly Ser Ser Ser Ile Asp Leu Ser Arg Val Thr Ile Arg Tyr Trp
35 40 45

Tyr Thr Val Asp Gly Glu Arg Ala Gln Ser Ala Ile Ser Asp Trp Ala
50 55 60

Gln Ile Gly Ala Ser Asn Val Thr Phe Lys Phe Val Lys Leu Ser Ser
65 70 75 80

Ser Val Ser Gly Ala Asp Tyr Tyr Leu Glu Ile Gly Phe Lys Ser Gly
85 90 95

Ala Gly Gln Leu Gln Pro Gly Lys Asp Thr Gly Glu Ile Gln Ile Arg
100 105 110

Phe Asn Lys Asp Asp Trp Ser Asn Tyr Asn Gln Gly Asn Asp Trp Ser
115 120 125

Trp Ile Gln Ser Met Thr Ser Tyr Gly Glu Asn Glu Lys Val Thr Ala
130 135 140

Tyr Ile Asp Gly Val Leu Val Trp Gly Gln Glu Pro Ser Gly Thr Thr
145 150 155 160

Pro Ala

<210> SEQ ID NO 162
<211> LENGTH: 216
<212> TYPE: PRT
<213> ORGANISM: Mycobacterium smegmatis

<400> SEQUENCE: 162

```
Met Ala Lys Arg Ile Leu Cys Phe Gly Asp Ser Leu Thr Trp Gly Trp
1               5                   10                  15

Val Pro Val Glu Asp Gly Ala Pro Thr Glu Arg Phe Ala Pro Asp Val
            20                  25                  30

Arg Trp Thr Gly Val Leu Ala Gln Gln Leu Gly Ala Asp Phe Glu Val
        35                  40                  45

Ile Glu Glu Gly Leu Val Ala Arg Thr Thr Asn Ile Asp Asp Pro Thr
    50                  55                  60

Asp Pro Arg Leu Asn Gly Ala Ser Tyr Leu Pro Ser Cys Leu Ala Thr
65                  70                  75                  80

His Leu Pro Leu Asp Leu Val Ile Ile Met Leu Gly Thr Asn Asp Thr
                85                  90                  95

Lys Ala Tyr Phe Arg Arg Thr Pro Leu Asp Ile Ala Leu Gly Met Ser
            100                 105                 110

Val Leu Val Thr Gln Val Leu Thr Ser Ala Gly Gly Val Gly Thr Thr
        115                 120                 125

Tyr Pro Ala Pro Lys Val Leu Val Val Ser Pro Pro Pro Leu Ala Pro
    130                 135                 140

Met Pro His Pro Trp Phe Gln Leu Ile Phe Glu Gly Gly Glu Gln Lys
145                 150                 155                 160

Thr Thr Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
            180                 185                 190

Gly Ile His Phe Thr Glu Ala Asn Asn Arg Asp Leu Gly Val Ala Leu
        195                 200                 205

Ala Glu Gln Val Arg Ser Leu Leu
    210                 215


<210> SEQ ID NO 163
<211> LENGTH: 272
<212> TYPE: PRT
<213> ORGANISM: Pseudomonas fluorescens

<400> SEQUENCE: 163

Met Ser Thr Phe Val Ala Lys Asp Gly Thr Gln Ile Tyr Phe Lys Asp
1               5                   10                  15

Trp Gly Ser Gly Lys Pro Val Leu Phe Ser His Gly Trp Pro Leu Asp
            20                  25                  30

Ala Asp Met Trp Glu Tyr Gln Met Glu Tyr Leu Ser Ser Arg Gly Tyr
        35                  40                  45

Arg Thr Ile Ala Phe Asp Arg Arg Gly Phe Gly Arg Ser Asp Gln Pro
    50                  55                  60

Trp Thr Gly Asn Asp Tyr Asp Thr Phe Ala Asp Asp Ile Ala Gln Leu
65                  70                  75                  80

Ile Glu His Leu Asp Leu Lys Glu Val Thr Leu Val Gly Phe Ser Met
                85                  90                  95

Gly Gly Gly Asp Val Ala Arg Tyr Ile Ala Arg His Gly Ser Ala Arg
            100                 105                 110

Val Ala Gly Leu Val Leu Leu Gly Ala Val Thr Pro Leu Phe Gly Gln
        115                 120                 125

Lys Pro Asp Tyr Pro Gln Gly Val Pro Leu Asp Val Phe Ala Arg Phe
    130                 135                 140

Lys Thr Glu Leu Leu Lys Asp Arg Ala Gln Phe Ile Ser Asp Phe Asn
145                 150                 155                 160
```

```
Ala Pro Phe Tyr Gly Ile Asn Lys Gly Gln Val Val Ser Gln Gly Val
                165                 170                 175

Gln Thr Gln Thr Leu Gln Ile Ala Leu Leu Ala Ser Leu Lys Ala Thr
            180                 185                 190

Val Asp Cys Val Thr Ala Phe Ala Glu Thr Asp Phe Arg Pro Asp Met
        195                 200                 205

Ala Lys Ile Asp Val Pro Thr Leu Val Ile His Gly Asp Gly Asp Gln
    210                 215                 220

Ile Val Pro Phe Glu Thr Thr Gly Lys Val Ala Ala Glu Leu Ile Lys
225                 230                 235                 240

Gly Ala Glu Leu Lys Val Tyr Lys Asp Ala Pro His Gly Phe Ala Val
                245                 250                 255

Thr His Ala Gln Gln Leu Asn Glu Asp Leu Leu Ala Phe Leu Lys Arg
            260                 265                 270


<210> SEQ ID NO 164
<211> LENGTH: 1545
<212> TYPE: DNA
<213> ORGANISM: artificial sequence
<220> FEATURE:
<223> OTHER INFORMATION: synthetic construct

<400> SEQUENCE: 164

atgcagctgt tcgatttgag cctggaagaa ttgaaaaagt acaaaccgaa aaagacggcg      60

cgtccggact tttctgattt ttggaaaaag tctctggagg aactgcgtca ggtcgaggcg     120

gagccgaccc tggaaagcta cgactaccct gtcaagggcg ttaaggtgta ccgcctgacc     180

taccagagct tcggtcatag caaaatcgag ggtttctatg cggtgccgga ccaaaccggt     240

ccgcacccgg cactggttcg tttccacggt tataacgcca gctatgatgg cggtatccat     300

gacatcgtca attgggcact gcatggttac gcaacgtttg gcatgctggt tcgcggccaa     360

ggcggtagcg aggataccag cgttaccccg ggtggccacg cgctgggctg gatgaccaag     420

ggtattctgt ccaaggatac ctattactac cgtggtgtat acttggatgc agttcgtgcg     480

ctggaggtca ttcaaagctt tccggaagtt gacgagcatc gtatcggtgt gattggtggt     540

agccagggtg gcgcgctggc gattgcagct gccgcgttga gcgatattcc gaaagtcgtg     600

gttgcggact atccgtatct gtcgaacttt gagcgcgctg tcgacgtggc actggaacaa     660

ccgtacctgg agattaacag ctacttccgc cgtaatagcg acccgaaagt ggaggagaag     720

gcgtttgaaa ctctgagcta ttttgatctg atcaatctgg cgggttgggt gaaacaaccg     780

accctgatgg ccattggcct gatcgataag atcactccgc cgtctacggt gttcgcggca     840

tataaccacc tggaaaccga caaagacttg aaagtttacc gttatttcgg ccacgagttt     900

atcccagcct tccagacgga aaagttgagc ttcctgcaga aacacctgct gctgagcacg     960

ggtccgggca gcggcggtgc tggttcccct ggcagcgccg gtggtccagg atccatggcg    1020

aatacgccgg tgtctggcaa tctgaaagtg gagttttaca atagcaaccc gagcgatacc    1080

acgaattcca tcaacccaca attcaaggtg acgaatacgg gcagcagcgc gattgatctg    1140

agcaaattga cgctgcgcta ttactatacc gttgatggtc agaaggacca gacctttttgg   1200

gcggatcatg cggcaatcat cggcagcaat ggcagctaca acggcattac ctctaatgtg    1260

aagggtactt tcgtcaaaat gagcagcagc accaacaacg ctgacaccta cctggaaatc    1320

agcttcaccg gtggcactct ggagccgggt gcccacgtgc agatccaggg ccgtttcgcg    1380

aagaatgact ggtccaatta cacccaaagc aatgattaca gctttaagag ccgctcgcaa    1440
```

tttgttgagt gggaccaggt taccgcgtat ctgaacggtg tcttggtttg gggtaaagag 1500
ccaggcggtt cggtggtggg tggcggtcac catcaccacc atcac 1545

<210> SEQ ID NO 165
<211> LENGTH: 515
<212> TYPE: PRT
<213> ORGANISM: artificial sequence
<220> FEATURE:
<223> OTHER INFORMATION: synthetic construct

<400> SEQUENCE: 165

Met Gln Leu Phe Asp Leu Ser Leu Glu Glu Leu Lys Lys Tyr Lys Pro
1 5 10 15

Lys Lys Thr Ala Arg Pro Asp Phe Ser Asp Phe Trp Lys Lys Ser Leu
20 25 30

Glu Glu Leu Arg Gln Val Glu Ala Glu Pro Thr Leu Glu Ser Tyr Asp
35 40 45

Tyr Pro Val Lys Gly Val Lys Val Tyr Arg Leu Thr Tyr Gln Ser Phe
50 55 60

Gly His Ser Lys Ile Glu Gly Phe Tyr Ala Val Pro Asp Gln Thr Gly
65 70 75 80

Pro His Pro Ala Leu Val Arg Phe His Gly Tyr Asn Ala Ser Tyr Asp
85 90 95

Gly Gly Ile His Asp Ile Val Asn Trp Ala Leu His Gly Tyr Ala Thr
100 105 110

Phe Gly Met Leu Val Arg Gly Gln Gly Gly Ser Glu Asp Thr Ser Val
115 120 125

Thr Pro Gly Gly His Ala Leu Gly Trp Met Thr Lys Gly Ile Leu Ser
130 135 140

Lys Asp Thr Tyr Tyr Tyr Arg Gly Val Tyr Leu Asp Ala Val Arg Ala
145 150 155 160

Leu Glu Val Ile Gln Ser Phe Pro Glu Val Asp Glu His Arg Ile Gly
165 170 175

Val Ile Gly Gly Ser Gln Gly Gly Ala Leu Ala Ile Ala Ala Ala Ala
180 185 190

Leu Ser Asp Ile Pro Lys Val Val Val Ala Asp Tyr Pro Tyr Leu Ser
195 200 205

Asn Phe Glu Arg Ala Val Asp Val Ala Leu Glu Gln Pro Tyr Leu Glu
210 215 220

Ile Asn Ser Tyr Phe Arg Arg Asn Ser Asp Pro Lys Val Glu Glu Lys
225 230 235 240

Ala Phe Glu Thr Leu Ser Tyr Phe Asp Leu Ile Asn Leu Ala Gly Trp
245 250 255

Val Lys Gln Pro Thr Leu Met Ala Ile Gly Leu Ile Asp Lys Ile Thr
260 265 270

Pro Pro Ser Thr Val Phe Ala Ala Tyr Asn His Leu Glu Thr Asp Lys
275 280 285

Asp Leu Lys Val Tyr Arg Tyr Phe Gly His Glu Phe Ile Pro Ala Phe
290 295 300

Gln Thr Glu Lys Leu Ser Phe Leu Gln Lys His Leu Leu Leu Ser Thr
305 310 315 320

Gly Pro Gly Ser Gly Gly Ala Gly Ser Pro Gly Ser Ala Gly Gly Pro
325 330 335

Gly Ser Met Ala Asn Thr Pro Val Ser Gly Asn Leu Lys Val Glu Phe
340 345 350

```
Tyr Asn Ser Asn Pro Ser Asp Thr Thr Asn Ser Ile Asn Pro Gln Phe
        355                 360                 365

Lys Val Thr Asn Thr Gly Ser Ser Ala Ile Asp Leu Ser Lys Leu Thr
    370                 375                 380

Leu Arg Tyr Tyr Tyr Thr Val Asp Gly Gln Lys Asp Gln Thr Phe Trp
385                 390                 395                 400

Ala Asp His Ala Ala Ile Ile Gly Ser Asn Gly Ser Tyr Asn Gly Ile
                405                 410                 415

Thr Ser Asn Val Lys Gly Thr Phe Val Lys Met Ser Ser Ser Thr Asn
            420                 425                 430

Asn Ala Asp Thr Tyr Leu Glu Ile Ser Phe Thr Gly Gly Thr Leu Glu
        435                 440                 445

Pro Gly Ala His Val Gln Ile Gln Gly Arg Phe Ala Lys Asn Asp Trp
    450                 455                 460

Ser Asn Tyr Thr Gln Ser Asn Asp Tyr Ser Phe Lys Ser Arg Ser Gln
465                 470                 475                 480

Phe Val Glu Trp Asp Gln Val Thr Ala Tyr Leu Asn Gly Val Leu Val
                485                 490                 495

Trp Gly Lys Glu Pro Gly Gly Ser Val Val Gly Gly Gly His His His
            500                 505                 510

His His His
        515
```

<210> SEQ ID NO 166
<211> LENGTH: 1521
<212> TYPE: DNA
<213> ORGANISM: artificial sequence
<220> FEATURE:
<223> OTHER INFORMATION: synthetic construct

<400> SEQUENCE: 166

```
atgaccaaaa tcaacaattg gcaagactac caaggtagct ctctgaaacc ggaggacttc      60

gataagtttt gggacgagaa aatcaatctg gtgagcaatc atcagtttga gtttgagctg     120

atcgaaaaga acctgagcag caaggttgtg aatttctatc atctgtggtt caccgcaatt     180

gacggtgcaa aaatccacgc gcaattgatc gtcccgaaaa acctgaaaga aaagtatcct     240

gccatcctgc aatttcacgg ttatcactgc gatagcggcg actgggttga caaaattggc     300

atcgtggcgg aaggcaacgt agtgctggca ctggattgtc gcggtcaggg tggcctgagc     360

caagacaata tccagacgat gggtatgact atgaaaggtc tgattgttcg cggcattgac     420

gagggttatg agaacctgta ctacgtccgt caattcatgg atctgatcac cgcgacgaag     480

attctgagcg aattcgattt tgtcgatgaa accaacatca gcgcgcaggg cgccagccaa     540

ggtggtgcgc tggcggttgc gtgcgcggca ctgagcccgc tgattaagaa ggtcacggct     600

acgtacccgt tcttgtccga ctaccgtaaa gcgtacgaac tgggtgccga ggaaagcgcc     660

tttgaggagc tgccatattg gttccagttt aaagacccgt tgcacttgcg tgaggattgg     720

ttcttcaacc agctggaata catcgacatt cagaatctgg ctccgcgtat taaggcagag     780

gttatttgga tcttgggcgg taaagatacc gtggtgccgc cgattaccca aatggctgcg     840

tacaacaaga ttcagtccaa gaaaagcctg tatgttctgc ctgaatacgg ccacgagtat     900

ctgccgaaga tttcggattg gctgcgcgaa aatcagggtc cgggtagcgg cggtgcgggt     960

tctccgggca gcgcaggcgg tccgggatcc atggcgaata cgccggtgtc tggcaatctg    1020

aaagtggagt tttacaatag caacccgagc gataccacga attccatcaa cccacaattc    1080

aaggtgacga atacgggcag cagcgcgatt gatctgagca aattgacgct gcgctattac    1140
```

```
tataccgttg atggtcagaa ggaccagacc ttttgggcgg atcatgcggc aatcatcggc   1200

agcaatggca gctacaacgg cattacctct aatgtgaagg gtactttcgt caaaatgagc   1260

agcagcacca acaacgctga cacctacctg gaaatcagct tcaccggtgg cactctggag   1320

ccgggtgccc acgtgcagat ccagggccgt ttcgcgaaga atgactggtc caattacacc   1380

caaagcaatg attacagctt taagagccgc tcgcaatttg ttgagtggga ccaggttacc   1440

gcgtatctga acggtgtctt ggtttggggt aaagagccag gcggttcggt ggtgggtggc   1500

ggtcaccatc accaccatca c                                             1521
```

<210> SEQ ID NO 167
<211> LENGTH: 507
<212> TYPE: PRT
<213> ORGANISM: artificial sequence
<220> FEATURE:
<223> OTHER INFORMATION: synthetic construct

<400> SEQUENCE: 167

```
Met Thr Lys Ile Asn Asn Trp Gln Asp Tyr Gln Gly Ser Ser Leu Lys
1               5                   10                  15

Pro Glu Asp Phe Asp Lys Phe Trp Asp Glu Lys Ile Asn Leu Val Ser
            20                  25                  30

Asn His Gln Phe Glu Phe Glu Leu Ile Glu Lys Asn Leu Ser Ser Lys
        35                  40                  45

Val Val Asn Phe Tyr His Leu Trp Phe Thr Ala Ile Asp Gly Ala Lys
    50                  55                  60

Ile His Ala Gln Leu Ile Val Pro Lys Asn Leu Lys Glu Lys Tyr Pro
65                  70                  75                  80

Ala Ile Leu Gln Phe His Gly Tyr His Cys Asp Ser Gly Asp Trp Val
                85                  90                  95

Asp Lys Ile Gly Ile Val Ala Glu Gly Asn Val Val Leu Ala Leu Asp
            100                 105                 110

Cys Arg Gly Gln Gly Gly Leu Ser Gln Asp Asn Ile Gln Thr Met Gly
        115                 120                 125

Met Thr Met Lys Gly Leu Ile Val Arg Gly Ile Asp Glu Gly Tyr Glu
    130                 135                 140

Asn Leu Tyr Tyr Val Arg Gln Phe Met Asp Leu Ile Thr Ala Thr Lys
145                 150                 155                 160

Ile Leu Ser Glu Phe Asp Phe Val Asp Glu Thr Asn Ile Ser Ala Gln
                165                 170                 175

Gly Ala Ser Gln Gly Gly Ala Leu Ala Val Ala Cys Ala Ala Leu Ser
            180                 185                 190

Pro Leu Ile Lys Lys Val Thr Ala Thr Tyr Pro Phe Leu Ser Asp Tyr
        195                 200                 205

Arg Lys Ala Tyr Glu Leu Gly Ala Glu Glu Ser Ala Phe Glu Glu Leu
    210                 215                 220

Pro Tyr Trp Phe Gln Phe Lys Asp Pro Leu His Leu Arg Glu Asp Trp
225                 230                 235                 240

Phe Phe Asn Gln Leu Glu Tyr Ile Asp Ile Gln Asn Leu Ala Pro Arg
                245                 250                 255

Ile Lys Ala Glu Val Ile Trp Ile Leu Gly Gly Lys Asp Thr Val Val
            260                 265                 270

Pro Pro Ile Thr Gln Met Ala Ala Tyr Asn Lys Ile Gln Ser Lys Lys
        275                 280                 285

Ser Leu Tyr Val Leu Pro Glu Tyr Gly His Glu Tyr Leu Pro Lys Ile
```

```
    290                 295                 300

Ser Asp Trp Leu Arg Glu Asn Gln Gly Pro Gly Ser Gly Gly Ala Gly
305                 310                 315                 320

Ser Pro Gly Ser Ala Gly Gly Pro Gly Ser Met Ala Asn Thr Pro Val
                325                 330                 335

Ser Gly Asn Leu Lys Val Glu Phe Tyr Asn Ser Asn Pro Ser Asp Thr
            340                 345                 350

Thr Asn Ser Ile Asn Pro Gln Phe Lys Val Thr Asn Thr Gly Ser Ser
        355                 360                 365

Ala Ile Asp Leu Ser Lys Leu Thr Leu Arg Tyr Tyr Tyr Thr Val Asp
    370                 375                 380

Gly Gln Lys Asp Gln Thr Phe Trp Ala Asp His Ala Ala Ile Ile Gly
385                 390                 395                 400

Ser Asn Gly Ser Tyr Asn Gly Ile Thr Ser Asn Val Lys Gly Thr Phe
                405                 410                 415

Val Lys Met Ser Ser Ser Thr Asn Asn Ala Asp Thr Tyr Leu Glu Ile
            420                 425                 430

Ser Phe Thr Gly Gly Thr Leu Glu Pro Gly Ala His Val Gln Ile Gln
        435                 440                 445

Gly Arg Phe Ala Lys Asn Asp Trp Ser Asn Tyr Thr Gln Ser Asn Asp
    450                 455                 460

Tyr Ser Phe Lys Ser Arg Ser Gln Phe Val Glu Trp Asp Gln Val Thr
465                 470                 475                 480

Ala Tyr Leu Asn Gly Val Leu Val Trp Gly Lys Glu Pro Gly Gly Ser
                485                 490                 495

Val Val Gly Gly Gly His His His His His His
            500                 505
```

<210> SEQ ID NO 168
<211> LENGTH: 1554
<212> TYPE: DNA
<213> ORGANISM: artificial sequence
<220> FEATURE:
<223> OTHER INFORMATION: synthetic construct

<400> SEQUENCE: 168

```
atgccgtttc cggatctgat ccagccggag ctgggcgcat acgtcagctc cgtcggtatg      60

ccggacgatt tcgctcaatt ctggaccagc accattgccg aagctcgtca ggcaggtggc     120

gaggttagca tcgtccaagc tcagacgact ctgaaagcag tccagagctt cgacgttacc     180

ttcccgggct acggcggtca cccgatcaag ggttggctga tcctgccaac ccaccacaaa     240

ggtcgcctgc cgctggtggt acagtacatt ggttatggcg gtggtcgtgg cttggcgcat     300

gaacagttgc actgggcagc atccggcttt gcgtacttcc gcatggacac ccgtggtcaa     360

ggtagcgatt ggtcggttgg tgagactgcc gacccggttg gtagcaccag cagcatcccg     420

ggctttatga cccgtggtgt gctggataag aatgactact attaccgtcg cttgttcacg     480

gacgcggtcc gtgctattga tgcgctgctg ggtctggact ttgtggaccc ggagcgcatt     540

gccgtctgcg gtgacagcca gggtggcggt atcagcctgg cggttggcgg catcgatccg     600

cgtgttaaag cggttatgcc ggatgtgccg ttcctgtgtg attttccgcg tgccgtccag     660

acggccgttc gcgacccgta cctggagatt gtgcgctttt tggcacaaca ccgtgaaaag     720

aaagcagcgg tgttcgaaac cctgaactat tttgactgtg tgaattttgc gcgtcgtagc     780

aaagcgcctg cgctgtttag cgtggcgctg atggatgaag tgtgcccgcc atctaccgtt     840

tatggtgcct tcaacgcgta tgcgggcgaa aagaccatta cggagtacga gttcaataac     900
```

```
cacgagggtg gccaaggcta tcaagaacgt cagcaaatga cgtggctgtc tcgcctgttc    960

ggtgtcggcg gtccgggtag cggtggtgcg ggcagccctg gcagcgcagg tggtccggga   1020

tccatggcga atacgccggt gtctggcaat ctgaaagtgg agttttacaa tagcaacccg   1080

agcgatacca cgaattccat caacccacaa ttcaaggtga cgaatacggg cagcagcgcg   1140

attgatctga gcaaattgac gctgcgctat tactataccg ttgatggtca gaaggaccag   1200

acctttttggg cggatcatgc ggcaatcatc ggcagcaatg gcagctacaa cggcattacc   1260

tctaatgtga agggtacttt cgtcaaaatg agcagcagca ccaacaacgc tgacacctac   1320

ctggaaatca gcttcaccgg tggcactctg gagccgggtg cccacgtgca gatccagggc   1380

cgtttcgcga agaatgactg gtccaattac acccaaagca atgattacag ctttaagagc   1440

cgctcgcaat ttgttgagtg ggaccaggtt accgcgtatc tgaacggtgt cttggtttgg   1500

ggtaaagagc caggcggttc ggtggtgggt ggcggtcacc atcaccacca tcac         1554
```

```
<210> SEQ ID NO 169
<211> LENGTH: 518
<212> TYPE: PRT
<213> ORGANISM: artificial sequence
<220> FEATURE:
<223> OTHER INFORMATION: synthetic construct

<400> SEQUENCE: 169

Met Pro Phe Pro Asp Leu Ile Gln Pro Glu Leu Gly Ala Tyr Val Ser
1               5                   10                  15

Ser Val Gly Met Pro Asp Asp Phe Ala Gln Phe Trp Thr Ser Thr Ile
            20                  25                  30

Ala Glu Ala Arg Gln Ala Gly Gly Glu Val Ser Ile Val Gln Ala Gln
        35                  40                  45

Thr Thr Leu Lys Ala Val Gln Ser Phe Asp Val Thr Phe Pro Gly Tyr
    50                  55                  60

Gly Gly His Pro Ile Lys Gly Trp Leu Ile Leu Pro Thr His His Lys
65                  70                  75                  80

Gly Arg Leu Pro Leu Val Val Gln Tyr Ile Gly Tyr Gly Gly Gly Arg
                85                  90                  95

Gly Leu Ala His Glu Gln Leu His Trp Ala Ala Ser Gly Phe Ala Tyr
            100                 105                 110

Phe Arg Met Asp Thr Arg Gly Gln Gly Ser Asp Trp Ser Val Gly Glu
        115                 120                 125

Thr Ala Asp Pro Val Gly Ser Thr Ser Ser Ile Pro Gly Phe Met Thr
    130                 135                 140

Arg Gly Val Leu Asp Lys Asn Asp Tyr Tyr Tyr Arg Arg Leu Phe Thr
145                 150                 155                 160

Asp Ala Val Arg Ala Ile Asp Ala Leu Leu Gly Leu Asp Phe Val Asp
                165                 170                 175

Pro Glu Arg Ile Ala Val Cys Gly Asp Ser Gln Gly Gly Gly Ile Ser
            180                 185                 190

Leu Ala Val Gly Gly Ile Asp Pro Arg Val Lys Ala Val Met Pro Asp
        195                 200                 205

Val Pro Phe Leu Cys Asp Phe Pro Arg Ala Val Gln Thr Ala Val Arg
    210                 215                 220

Asp Pro Tyr Leu Glu Ile Val Arg Phe Leu Ala Gln His Arg Glu Lys
225                 230                 235                 240

Lys Ala Ala Val Phe Glu Thr Leu Asn Tyr Phe Asp Cys Val Asn Phe
                245                 250                 255
```

```
Ala Arg Arg Ser Lys Ala Pro Ala Leu Phe Ser Val Ala Leu Met Asp
            260                 265                 270

Glu Val Cys Pro Pro Ser Thr Val Tyr Gly Ala Phe Asn Ala Tyr Ala
        275                 280                 285

Gly Glu Lys Thr Ile Thr Glu Tyr Glu Phe Asn Asn His Glu Gly Gly
    290                 295                 300

Gln Gly Tyr Gln Glu Arg Gln Gln Met Thr Trp Leu Ser Arg Leu Phe
305                 310                 315                 320

Gly Val Gly Gly Pro Gly Ser Gly Gly Ala Gly Ser Pro Gly Ser Ala
                325                 330                 335

Gly Gly Pro Gly Ser Met Ala Asn Thr Pro Val Ser Gly Asn Leu Lys
            340                 345                 350

Val Glu Phe Tyr Asn Ser Asn Pro Ser Asp Thr Thr Asn Ser Ile Asn
        355                 360                 365

Pro Gln Phe Lys Val Thr Asn Thr Gly Ser Ser Ala Ile Asp Leu Ser
    370                 375                 380

Lys Leu Thr Leu Arg Tyr Tyr Tyr Thr Val Asp Gly Gln Lys Asp Gln
385                 390                 395                 400

Thr Phe Trp Ala Asp His Ala Ala Ile Ile Gly Ser Asn Gly Ser Tyr
                405                 410                 415

Asn Gly Ile Thr Ser Asn Val Lys Gly Thr Phe Val Lys Met Ser Ser
            420                 425                 430

Ser Thr Asn Asn Ala Asp Thr Tyr Leu Glu Ile Ser Phe Thr Gly Gly
        435                 440                 445

Thr Leu Glu Pro Gly Ala His Val Gln Ile Gln Gly Arg Phe Ala Lys
    450                 455                 460

Asn Asp Trp Ser Asn Tyr Thr Gln Ser Asn Asp Tyr Ser Phe Lys Ser
465                 470                 475                 480

Arg Ser Gln Phe Val Glu Trp Asp Gln Val Thr Ala Tyr Leu Asn Gly
                485                 490                 495

Val Leu Val Trp Gly Lys Glu Pro Gly Gly Ser Val Val Gly Gly Gly
            500                 505                 510

His His His His His His
        515
```

<210> SEQ ID NO 170
<211> LENGTH: 1233
<212> TYPE: DNA
<213> ORGANISM: artificial sequence
<220> FEATURE:
<223> OTHER INFORMATION: synthetic construct

<400> SEQUENCE: 170

```
atggcgaaac gcattctgtg cttcggcgac agcctgacct ggggttgggt tccggtcgag     60

gatggcgcac cgacggaacg ttttgcgccg gatgtgcgtt ggacgggtgt gctggctcag    120

caactgggtg ccgattttga ggtcatcgaa gagggtctgg tcgcacgtac gaccaacatt    180

gatgacccga ccgacccgcg tctgaacggc gcaagctatt tgccgagctg tctggcgacc    240

cacctgccgc tggatctggt gattatcatg ttgggcacca atgataccaa agcttatttc    300

cgccgcaccc cgctggacat cgcgctgggc atgagcgtct tggtgacgca ggttctgact    360

agcgctggcg gtgtcggtac tacgtaccct gcgccgaaag tcctggtggt tagcccgcca    420

ccgctggcgc cgatgccgca cccgtggttc caactgattt ttgaaggcgg tgagcaaaag    480

acgaccgagt tggcccgtgt ttacagcgcg ttggcgagct ttatgaaagt tccgtttttc    540
```

```
gacgcgggca gcgttattag caccgatggc gtggacggta tccatttcac cgaagcaaat    600

aaccgtgacc tgggtgtggc cctggctgaa caagtgcgca gcctgctggg tccgggctcc    660

ggtggtgccg gttcgccggg tagcgcaggc ggtcctggat ccatggcgaa tacgccggtg    720

tctggcaatc tgaaagtgga gttttacaat agcaacccga gcgataccac gaattccatc    780

aacccacaat tcaaggtgac gaatacgggc agcagcgcga ttgatctgag caaattgacg    840

ctgcgctatt actataccgt tgatggtcag aaggaccaga ccttttgggc ggatcatgcg    900

gcaatcatcg gcagcaatgg cagctacaac ggcattacct ctaatgtgaa gggtactttc    960

gtcaaaatga gcagcagcac caacaacgct gacacctacc tggaaatcag cttcaccggt   1020

ggcactctgg agccgggtgc ccacgtgcag atccagggcc gtttcgcgaa gaatgactgg   1080

tccaattaca cccaaagcaa tgattacagc tttaagagcc gctcgcaatt tgttgagtgg   1140

gaccaggtta ccgcgtatct gaacggtgtc ttggtttggg gtaaagagcc aggcggttcg   1200

gtggtgggtg gcggtcacca tcaccaccat cac                                1233


<210> SEQ ID NO 171
<211> LENGTH: 411
<212> TYPE: PRT
<213> ORGANISM: artificial sequence
<220> FEATURE:
<223> OTHER INFORMATION: synthetic construct

<400> SEQUENCE: 171

Met Ala Lys Arg Ile Leu Cys Phe Gly Asp Ser Leu Thr Trp Gly Trp
1               5                   10                  15

Val Pro Val Glu Asp Gly Ala Pro Thr Glu Arg Phe Ala Pro Asp Val
            20                  25                  30

Arg Trp Thr Gly Val Leu Ala Gln Gln Leu Gly Ala Asp Phe Glu Val
        35                  40                  45

Ile Glu Glu Gly Leu Val Ala Arg Thr Thr Asn Ile Asp Asp Pro Thr
    50                  55                  60

Asp Pro Arg Leu Asn Gly Ala Ser Tyr Leu Pro Ser Cys Leu Ala Thr
65                  70                  75                  80

His Leu Pro Leu Asp Leu Val Ile Ile Met Leu Gly Thr Asn Asp Thr
                85                  90                  95

Lys Ala Tyr Phe Arg Arg Thr Pro Leu Asp Ile Ala Leu Gly Met Ser
            100                 105                 110

Val Leu Val Thr Gln Val Leu Thr Ser Ala Gly Gly Val Gly Thr Thr
        115                 120                 125

Tyr Pro Ala Pro Lys Val Leu Val Val Ser Pro Pro Pro Leu Ala Pro
    130                 135                 140

Met Pro His Pro Trp Phe Gln Leu Ile Phe Glu Gly Gly Glu Gln Lys
145                 150                 155                 160

Thr Thr Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
            180                 185                 190

Gly Ile His Phe Thr Glu Ala Asn Asn Arg Asp Leu Gly Val Ala Leu
        195                 200                 205

Ala Glu Gln Val Arg Ser Leu Leu Gly Pro Gly Ser Gly Gly Ala Gly
    210                 215                 220

Ser Pro Gly Ser Ala Gly Gly Pro Gly Ser Met Ala Asn Thr Pro Val
225                 230                 235                 240

Ser Gly Asn Leu Lys Val Glu Phe Tyr Asn Ser Asn Pro Ser Asp Thr
```

-continued

```
                245                 250                 255

Thr Asn Ser Ile Asn Pro Gln Phe Lys Val Thr Asn Thr Gly Ser Ser
            260                 265                 270

Ala Ile Asp Leu Ser Lys Leu Thr Leu Arg Tyr Tyr Tyr Thr Val Asp
        275                 280                 285

Gly Gln Lys Asp Gln Thr Phe Trp Ala Asp His Ala Ala Ile Ile Gly
    290                 295                 300

Ser Asn Gly Ser Tyr Asn Gly Ile Thr Ser Asn Val Lys Gly Thr Phe
305                 310                 315                 320

Val Lys Met Ser Ser Ser Thr Asn Asn Ala Asp Thr Tyr Leu Glu Ile
                325                 330                 335

Ser Phe Thr Gly Gly Thr Leu Glu Pro Gly Ala His Val Gln Ile Gln
            340                 345                 350

Gly Arg Phe Ala Lys Asn Asp Trp Ser Asn Tyr Thr Gln Ser Asn Asp
        355                 360                 365

Tyr Ser Phe Lys Ser Arg Ser Gln Phe Val Glu Trp Asp Gln Val Thr
    370                 375                 380

Ala Tyr Leu Asn Gly Val Leu Val Trp Gly Lys Glu Pro Gly Gly Ser
385                 390                 395                 400

Val Val Gly Gly Gly His His His His His His
                405                 410


<210> SEQ ID NO 172
<211> LENGTH: 1188
<212> TYPE: DNA
<213> ORGANISM: artificial sequence
<220> FEATURE:
<223> OTHER INFORMATION: synthetic construct

<400> SEQUENCE: 172

atggcgaaac gcattctgtg cttcggcgac agcctgacct ggggttgggt tccggtcgag     60

gatggcgcac cgacggaacg ttttgcgccg gatgtgcgtt ggacgggtgt gctggctcag    120

caactgggtg ccgattttga ggtcatcgaa gagggtctgg tcgcacgtac gaccaacatt    180

gatgacccga ccgacccgcg tctgaacggc gcaagctatt tgccgagctg tctggcgacc    240

cacctgccgc tggatctggt gattatcatg ttgggcacca atgataccaa agcttatttc    300

cgccgcaccc cgctggacat cgcgctgggc atgagcgtct tggtgacgca ggttctgact    360

agcgctggcg gtgtcggtac tacgtaccct gcgccgaaag tcctggtggt tagcccgcca    420

ccgctggcgc cgatgccgca cccgtggttc caactgattt ttgaaggcgg tgagcaaaag    480

acgaccgagt tggcccgtgt ttacagcgcg ttggcgagct ttatgaaagt tccgtttttc    540

gacgcgggca gcgttattag caccgatggc gtggacggta tccatttcac cgaagcaaat    600

aaccgtgacc tgggtgtggc cctggctgaa caagtgcgca gcctgctggg tccgggctcc    660

ggtggtgccg gttcgccggg tagcgcaggc ggtcctggat ccaccccagc gacgtctggt    720

caaatcaagg ttctgtatgc gaacaaagag actaattcca ccacgaacac tatccgtccg    780

tggctgaaag tggtcaatag cggtagcagc agcattgatc tgagccgtgt cacgattcgc    840

tattggtaca cggtcgacgg cgagcgtgcg cagagcgcga tctccgattg ggctcaaatt    900

ggcgcgtcca acgttacctt taagtttgtg aaactgagct ctagcgtgag cggtgcagac    960

tactatttgg aaattggttt caagagcggt gccggccaac tgcagccggg taaagatacc   1020

ggcgagatcc agatccgttt caacaaggac gactggagca attacaatca gggtaatgat   1080

tggagctgga ttcagtcgat gaccagctac ggtgaaaacg aaaaagtgac cgcctacatc   1140
```

-continued gacggcgttc tggtttgggg tcaagagccg agcggcacca ccccggca 1188

<210> SEQ ID NO 173
<211> LENGTH: 396
<212> TYPE: PRT
<213> ORGANISM: artificial sequence
<220> FEATURE:
<223> OTHER INFORMATION: synthetic construct

<400> SEQUENCE: 173

Met Ala Lys Arg Ile Leu Cys Phe Gly Asp Ser Leu Thr Trp Gly Trp
1 5 10 15

Val Pro Val Glu Asp Gly Ala Pro Thr Glu Arg Phe Ala Pro Asp Val
20 25 30

Arg Trp Thr Gly Val Leu Ala Gln Gln Leu Gly Ala Asp Phe Glu Val
35 40 45

Ile Glu Glu Gly Leu Val Ala Arg Thr Thr Asn Ile Asp Asp Pro Thr
50 55 60

Asp Pro Arg Leu Asn Gly Ala Ser Tyr Leu Pro Ser Cys Leu Ala Thr
65 70 75 80

His Leu Pro Leu Asp Leu Val Ile Ile Met Leu Gly Thr Asn Asp Thr
85 90 95

Lys Ala Tyr Phe Arg Arg Thr Pro Leu Asp Ile Ala Leu Gly Met Ser
100 105 110

Val Leu Val Thr Gln Val Leu Thr Ser Ala Gly Gly Val Gly Thr Thr
115 120 125

Tyr Pro Ala Pro Lys Val Leu Val Val Ser Pro Pro Pro Leu Ala Pro
130 135 140

Met Pro His Pro Trp Phe Gln Leu Ile Phe Glu Gly Gly Glu Gln Lys
145 150 155 160

Thr Thr Glu Leu Ala Arg Val Tyr Ser Ala Leu Ala Ser Phe Met Lys
165 170 175

Val Pro Phe Phe Asp Ala Gly Ser Val Ile Ser Thr Asp Gly Val Asp
180 185 190

Gly Ile His Phe Thr Glu Ala Asn Asn Arg Asp Leu Gly Val Ala Leu
195 200 205

Ala Glu Gln Val Arg Ser Leu Leu Gly Pro Gly Ser Gly Gly Ala Gly
210 215 220

Ser Pro Gly Ser Ala Gly Gly Pro Gly Ser Thr Pro Ala Thr Ser Gly
225 230 235 240

Gln Ile Lys Val Leu Tyr Ala Asn Lys Glu Thr Asn Ser Thr Thr Asn
245 250 255

Thr Ile Arg Pro Trp Leu Lys Val Val Asn Ser Gly Ser Ser Ser Ile
260 265 270

Asp Leu Ser Arg Val Thr Ile Arg Tyr Trp Tyr Thr Val Asp Gly Glu
275 280 285

Arg Ala Gln Ser Ala Ile Ser Asp Trp Ala Gln Ile Gly Ala Ser Asn
290 295 300

Val Thr Phe Lys Phe Val Lys Leu Ser Ser Ser Val Ser Gly Ala Asp
305 310 315 320

Tyr Tyr Leu Glu Ile Gly Phe Lys Ser Gly Ala Gly Gln Leu Gln Pro
325 330 335

Gly Lys Asp Thr Gly Glu Ile Gln Ile Arg Phe Asn Lys Asp Asp Trp
340 345 350

Ser Asn Tyr Asn Gln Gly Asn Asp Trp Ser Trp Ile Gln Ser Met Thr
355 360 365

Ser Tyr Gly Glu Asn Glu Lys Val Thr Ala Tyr Ile Asp Gly Val Leu
370 375 380

Val Trp Gly Gln Glu Pro Ser Gly Thr Thr Pro Ala
385 390 395

<210> SEQ ID NO 174
<211> LENGTH: 1266
<212> TYPE: DNA
<213> ORGANISM: artificial sequence
<220> FEATURE:
<223> OTHER INFORMATION: synthetic construct

<400> SEQUENCE: 174
atggcgaaac gcattctgtg cttcggcgac agcctgacct ggggttgggt tccggtcgag 60
gatggcgcac cgacggaacg ttttgcgccg gatgtgcgtt ggacgggtgt gctggctcag 120
caactgggtg ccgattttga ggtcatcgaa gagggtctgg tcgcacgtac gaccaacatt 180
gatgacccga ccgacccgcg tctgaacggc gcaagctatt tgccgagctg tctggcgacc 240
cacctgccgc tggatctggt gattatcatg ttgggcacca atgataccaa agcttatttc 300
cgccgcaccc cgctggacat cgcgctgggc atgagcgtct tggtgacgca ggttctgact 360
agcgctggcg gtgtcggtac tacgtaccct gcgccgaaag tcctggtggt tagcccgcca 420
ccgctggcgc cgatgccgca cccgtggttc caactgattt ttgaaggcgg tgagcaaaag 480
acgaccgagt tggcccgtgt ttacagcgcg ttggcgagct ttatgaaagt tccgtttttc 540
gacgcgggca gcgttattag caccgatggc gtggacggta tccatttcac cgaagcaaat 600
aaccgtgacc tgggtgtggc cctggctgaa caagtgcgca gcctgctggg tccgggctcc 660
ggtggtgccg gttcgccggg tagcgcaggc ggtcctggat ccgtggcaac tgctaagtat 720
ggcacgcctg ttattgacgg cgagattgat gagatctgga ataccaccga agagattgaa 780
acgaaggcag tcgcgatggg ttctttggat aagaatgcga ctgcgaaagt tcgtgtgctg 840
tgggacgaaa actacctgta cgtgctggcg attgtgaaag atccggttct gaacaaggat 900
aacagcaatc cgtgggaaca ggactccgtc gagattttca ttgacgagaa caatcacaaa 960
accggttact atgaggacga cgacgcacag ttccgcgtta actatatgaa cgagcaaacc 1020
tttggtacgg gcggtagccc ggctcgtttc aagacggccg ttaaactgat cgagggcggt 1080
tacattgtcg aagcggcgat caaatggaaa acgatcaaac caaccccgaa taccgtcatc 1140
ggcttcaata tccaggtgaa tgatgccaat gaaaagggtc aacgtgtggg catcattagc 1200
tggagcgatc cgaccaacaa cagctggcgc gacccgagca agtttggtaa cctgcgtctg 1260
atcaaa 1266

<210> SEQ ID NO 175
<211> LENGTH: 422
<212> TYPE: PRT
<213> ORGANISM: artificial sequence
<220> FEATURE:
<223> OTHER INFORMATION: synthetic construct

<400> SEQUENCE: 175

Met Ala Lys Arg Ile Leu Cys Phe Gly Asp Ser Leu Thr Trp Gly Trp
1 5 10 15

Val Pro Val Glu Asp Gly Ala Pro Thr Glu Arg Phe Ala Pro Asp Val
20 25 30

Arg Trp Thr Gly Val Leu Ala Gln Gln Leu Gly Ala Asp Phe Glu Val
35 40 45

```
Ile Glu Glu Gly Leu Val Ala Arg Thr Thr Asn Ile Asp Asp Pro Thr
    50                  55                  60

Asp Pro Arg Leu Asn Gly Ala Ser Tyr Leu Pro Ser Cys Leu Ala Thr
65                  70                  75                  80

His Leu Pro Leu Asp Leu Val Ile Ile Met Leu Gly Thr Asn Asp Thr
                85                  90                  95

Lys Ala Tyr Phe Arg Arg Thr Pro Leu Asp Ile Ala Leu Gly Met Ser
            100                 105                 110

Val Leu Val Thr Gln Val Leu Thr Ser Ala Gly Gly Val Gly Thr Thr
        115                 120                 125

Tyr Pro Ala Pro Lys Val Leu Val Val Ser Pro Pro Pro Leu Ala Pro
    130                 135                 140

Met Pro His Pro Trp Phe Gln Leu Ile Phe Glu Gly Gly Glu Gln Lys
145                 150                 155                 160

Thr Thr Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
            180                 185                 190

Gly Ile His Phe Thr Glu Ala Asn Asn Arg Asp Leu Gly Val Ala Leu
        195                 200                 205

Ala Glu Gln Val Arg Ser Leu Leu Gly Pro Gly Ser Gly Gly Ala Gly
    210                 215                 220

Ser Pro Gly Ser Ala Gly Gly Pro Gly Ser Val Ala Thr Ala Lys Tyr
225                 230                 235                 240

Gly Thr Pro Val Ile Asp Gly Glu Ile Asp Glu Ile Trp Asn Thr Thr
                245                 250                 255

Glu Glu Ile Glu Thr Lys Ala Val Ala Met Gly Ser Leu Asp Lys Asn
            260                 265                 270

Ala Thr Ala Lys Val Arg Val Leu Trp Asp Glu Asn Tyr Leu Tyr Val
        275                 280                 285

Leu Ala Ile Val Lys Asp Pro Val Leu Asn Lys Asp Asn Ser Asn Pro
    290                 295                 300

Trp Glu Gln Asp Ser Val Glu Ile Phe Ile Asp Glu Asn Asn His Lys
305                 310                 315                 320

Thr Gly Tyr Tyr Glu Asp Asp Asp Ala Gln Phe Arg Val Asn Tyr Met
                325                 330                 335

Asn Glu Gln Thr Phe Gly Thr Gly Gly Ser Pro Ala Arg Phe Lys Thr
            340                 345                 350

Ala Val Lys Leu Ile Glu Gly Gly Tyr Ile Val Glu Ala Ala Ile Lys
        355                 360                 365

Trp Lys Thr Ile Lys Pro Thr Pro Asn Thr Val Ile Gly Phe Asn Ile
    370                 375                 380

Gln Val Asn Asp Ala Asn Glu Lys Gly Gln Arg Val Gly Ile Ile Ser
385                 390                 395                 400

Trp Ser Asp Pro Thr Asn Asn Ser Trp Arg Asp Pro Ser Lys Phe Gly
                405                 410                 415

Asn Leu Arg Leu Ile Lys
            420
```

<210> SEQ ID NO 176
<211> LENGTH: 1401
<212> TYPE: DNA
<213> ORGANISM: artificial sequence
<220> FEATURE:
<223> OTHER INFORMATION: synthetic construct -continued

<400> SEQUENCE: 176

```
atgtccacct tcgttgcgaa agatggcacc cagatttact ttaaagactg gggcagcggc     60
aagccggttc tgtttagcca cggctggccg ctggacgcgg atatgtggga gtatcagatg    120
gagtacctga gcagccgtgg ttaccgtacc atcgccttcg atcgccgtgg ttttggtcgc    180
agcgatcaac cgtggaccgg caatgattat gacacgttcg cagatgacat tgcccagctg    240
atcgagcacc tggacctgaa agaggttacc ctggtcggtt tcagcatggg cggtggtgac    300
gtcgcgcgct acattgcgcg tcatggttcc gctcgtgtgg cgggtctggt cctgctgggt    360
gctgtaacgc cactgtttgg tcaaaagccg gattatccgc agggtgtgcc gttggatgtg    420
tttgcgcgct tcaaaaccga gttgctgaaa gaccgtgcgc aattcatcag cgacttcaac    480
gcaccgtttt acggtatcaa caaaggccaa gttgtcagcc agggcgttca aacgcagacg    540
ctgcagattg cgctgctggc aagcctgaag gcgaccgttg actgcgtgac ggcttttgcg    600
gaaactgatt ttcgtccgga catggcgaag attgatgttc cgaccttggt gattcacggt    660
gacggcgatc agatcgtgcc gttcgaaacc accggtaagg ttgcggccga gctgatcaaa    720
ggtgcggagc tgaaagtgta caaggacgcg cctcacggct tcgcagtcac tcatgcacag    780
caactgaacg aggacttgct ggccttcttg aaacgcggtc cgggctccgg tggcgcaggc    840
agcccgggta gcgcaggtgg tccgggatcc atggcgaata cgccggtgtc tggcaatctg    900
aaagtggagt tttacaatag caacccgagc gataccacga attccatcaa cccacaattc    960
aaggtgacga atacgggcag cagcgcgatt gatctgagca aattgacgct gcgctattac   1020
tataccgttg atggtcagaa ggaccagacc ttttgggcgg atcatgcggc aatcatcggc   1080
agcaatggca gctacaacgg cattacctct aatgtgaagg gtactttcgt caaaatgagc   1140
agcagcacca acaacgctga cacctacctg gaaatcagct tcaccggtgg cactctggag   1200
ccgggtgccc acgtgcagat ccagggccgt ttcgcgaaga atgactggtc caattacacc   1260
caaagcaatg attacagctt taagagccgc tcgcaatttg ttgagtggga ccaggttacc   1320
gcgtatctga acggtgtctt ggtttggggt aaagagccag gcggttcggt ggtgggtggc   1380
ggtcaccatc accaccatca c                                              1401
```

<210> SEQ ID NO 177
<211> LENGTH: 467
<212> TYPE: PRT
<213> ORGANISM: artificial sequence
<220> FEATURE:
<223> OTHER INFORMATION: synthetic construct

<400> SEQUENCE: 177

```
Met Ser Thr Phe Val Ala Lys Asp Gly Thr Gln Ile Tyr Phe Lys Asp
1               5                   10                  15

Trp Gly Ser Gly Lys Pro Val Leu Phe Ser His Gly Trp Pro Leu Asp
            20                  25                  30

Ala Asp Met Trp Glu Tyr Gln Met Glu Tyr Leu Ser Ser Arg Gly Tyr
        35                  40                  45

Arg Thr Ile Ala Phe Asp Arg Arg Gly Phe Gly Arg Ser Asp Gln Pro
    50                  55                  60

Trp Thr Gly Asn Asp Tyr Asp Thr Phe Ala Asp Asp Ile Ala Gln Leu
65                  70                  75                  80

Ile Glu His Leu Asp Leu Lys Glu Val Thr Leu Val Gly Phe Ser Met
                85                  90                  95

Gly Gly Gly Asp Val Ala Arg Tyr Ile Ala Arg His Gly Ser Ala Arg
            100                 105                 110
```

```
Val Ala Gly Leu Val Leu Leu Gly Ala Val Thr Pro Leu Phe Gly Gln
        115                 120                 125

Lys Pro Asp Tyr Pro Gln Gly Val Pro Leu Asp Val Phe Ala Arg Phe
    130                 135                 140

Lys Thr Glu Leu Leu Lys Asp Arg Ala Gln Phe Ile Ser Asp Phe Asn
145                 150                 155                 160

Ala Pro Phe Tyr Gly Ile Asn Lys Gly Gln Val Val Ser Gln Gly Val
                165                 170                 175

Gln Thr Gln Thr Leu Gln Ile Ala Leu Leu Ala Ser Leu Lys Ala Thr
            180                 185                 190

Val Asp Cys Val Thr Ala Phe Ala Glu Thr Asp Phe Arg Pro Asp Met
        195                 200                 205

Ala Lys Ile Asp Val Pro Thr Leu Val Ile His Gly Asp Gly Asp Gln
    210                 215                 220

Ile Val Pro Phe Glu Thr Thr Gly Lys Val Ala Ala Glu Leu Ile Lys
225                 230                 235                 240

Gly Ala Glu Leu Lys Val Tyr Lys Asp Ala Pro His Gly Phe Ala Val
                245                 250                 255

Thr His Ala Gln Gln Leu Asn Glu Asp Leu Leu Ala Phe Leu Lys Arg
            260                 265                 270

Gly Pro Gly Ser Gly Gly Ala Gly Ser Pro Gly Ser Ala Gly Gly Pro
        275                 280                 285

Gly Ser Met Ala Asn Thr Pro Val Ser Gly Asn Leu Lys Val Glu Phe
    290                 295                 300

Tyr Asn Ser Asn Pro Ser Asp Thr Thr Asn Ser Ile Asn Pro Gln Phe
305                 310                 315                 320

Lys Val Thr Asn Thr Gly Ser Ser Ala Ile Asp Leu Ser Lys Leu Thr
                325                 330                 335

Leu Arg Tyr Tyr Tyr Thr Val Asp Gly Gln Lys Asp Gln Thr Phe Trp
            340                 345                 350

Ala Asp His Ala Ala Ile Ile Gly Ser Asn Gly Ser Tyr Asn Gly Ile
        355                 360                 365

Thr Ser Asn Val Lys Gly Thr Phe Val Lys Met Ser Ser Ser Thr Asn
    370                 375                 380

Asn Ala Asp Thr Tyr Leu Glu Ile Ser Phe Thr Gly Gly Thr Leu Glu
385                 390                 395                 400

Pro Gly Ala His Val Gln Ile Gln Gly Arg Phe Ala Lys Asn Asp Trp
                405                 410                 415

Ser Asn Tyr Thr Gln Ser Asn Asp Tyr Ser Phe Lys Ser Arg Ser Gln
            420                 425                 430

Phe Val Glu Trp Asp Gln Val Thr Ala Tyr Leu Asn Gly Val Leu Val
        435                 440                 445

Trp Gly Lys Glu Pro Gly Gly Ser Val Val Gly Gly Gly His His His
    450                 455                 460

His His His
465
```

<210> SEQ ID NO 178
<211> LENGTH: 1434
<212> TYPE: DNA
<213> ORGANISM: artificial sequence
<220> FEATURE:
<223> OTHER INFORMATION: synthetic construct

<400> SEQUENCE: 178
atgtccacct tcgttgcgaa agatggcacc cagatttact ttaaagactg gggcagcggc 60
aagccggttc tgtttagcca cggctggccg ctggacgcgg atatgtggga gtatcagatg 120
gagtacctga gcagccgtgg ttaccgtacc atcgccttcg atcgccgtgg ttttggtcgc 180
agcgatcaac cgtggaccgg caatgattat gacacgttcg cagatgacat tgcccagctg 240
atcgagcacc tggacctgaa agaggttacc ctggtcggtt tcagcatggg cggtggtgac 300
gtcgcgcgct acattgcgcg tcatggttcc gctcgtgtgg cgggtctggt cctgctgggt 360
gctgtaacgc cactgtttgg tcaaaagccg gattatccgc agggtgtgcc gttggatgtg 420
tttgcgcgct tcaaaaccga gttgctgaaa gaccgtgcgc aattcatcag cgacttcaac 480
gcaccgtttt acggtatcaa caaaggccaa gttgtcagcc agggcgttca aacgcagacg 540
ctgcagattg cgctgctggc aagcctgaag gcgaccgttg actgcgtgac ggcttttgcg 600
gaaactgatt ttcgtccgga catggcgaag attgatgttc cgaccttggt gattcacggt 660
gacggcgatc agatcgtgcc gttcgaaacc accggtaagg ttgcggccga gctgatcaaa 720
ggtgcggagc tgaaagtgta caaggacgcg cctcacggct tcgcagtcac tcatgcacag 780
caactgaacg aggacttgct ggccttcttg aaacgcggtc cgggctccgg tggcgcaggc 840
agcccgggta gcgcaggtgg tccgggatcc gtggcaactg ctaagtatgg cacgcctgtt 900
attgacggcg agattgatga gatctggaat accaccgaag agattgaaac gaaggcagtc 960
gcgatgggtt ctttggataa gaatgcgact gcgaaagttc gtgtgctgtg ggacgaaaac 1020
tacctgtacg tgctggcgat tgtgaaagat ccggttctga acaaggataa cagcaatccg 1080
tgggaacagg actccgtcga gattttcatt gacgagaaca atcacaaaac cggttactat 1140
gaggacgacg acgcacagtt ccgcgttaac tatatgaacg agcaaacctt tggtacgggc 1200
ggtagcccgg ctcgtttcaa gacggccgtt aaactgatcg agggcggtta cattgtcgaa 1260
gcggcgatca aatggaaaac gatcaaacca accccgaata ccgtcatcgg cttcaatatc 1320
caggtgaatg atgccaatga aaagggtcaa cgtgtgggca tcattagctg gagcgatccg 1380
accaacaaca gctggcgcga cccgagcaag tttggtaacc tgcgtctgat caaa 1434

<210> SEQ ID NO 179
<211> LENGTH: 478
<212> TYPE: PRT
<213> ORGANISM: artificial sequence
<220> FEATURE:
<223> OTHER INFORMATION: synthetic construct

<400> SEQUENCE: 179

Met Ser Thr Phe Val Ala Lys Asp Gly Thr Gln Ile Tyr Phe Lys Asp
1 5 10 15

Trp Gly Ser Gly Lys Pro Val Leu Phe Ser His Gly Trp Pro Leu Asp
20 25 30

Ala Asp Met Trp Glu Tyr Gln Met Glu Tyr Leu Ser Ser Arg Gly Tyr
35 40 45

Arg Thr Ile Ala Phe Asp Arg Arg Gly Phe Gly Arg Ser Asp Gln Pro
50 55 60

Trp Thr Gly Asn Asp Tyr Asp Thr Phe Ala Asp Asp Ile Ala Gln Leu
65 70 75 80

Ile Glu His Leu Asp Leu Lys Glu Val Thr Leu Val Gly Phe Ser Met
85 90 95

Gly Gly Gly Asp Val Ala Arg Tyr Ile Ala Arg His Gly Ser Ala Arg
100 105 110

Val Ala Gly Leu Val Leu Leu Gly Ala Val Thr Pro Leu Phe Gly Gln

-continued

```
        115                 120                 125

Lys Pro Asp Tyr Pro Gln Gly Val Pro Leu Asp Val Phe Ala Arg Phe
    130                 135                 140

Lys Thr Glu Leu Leu Lys Asp Arg Ala Gln Phe Ile Ser Asp Phe Asn
145                 150                 155                 160

Ala Pro Phe Tyr Gly Ile Asn Lys Gly Gln Val Val Ser Gln Gly Val
                165                 170                 175

Gln Thr Gln Thr Leu Gln Ile Ala Leu Leu Ala Ser Leu Lys Ala Thr
            180                 185                 190

Val Asp Cys Val Thr Ala Phe Ala Glu Thr Asp Phe Arg Pro Asp Met
        195                 200                 205

Ala Lys Ile Asp Val Pro Thr Leu Val Ile His Gly Asp Gly Asp Gln
    210                 215                 220

Ile Val Pro Phe Glu Thr Thr Gly Lys Val Ala Ala Glu Leu Ile Lys
225                 230                 235                 240

Gly Ala Glu Leu Lys Val Tyr Lys Asp Ala Pro His Gly Phe Ala Val
                245                 250                 255

Thr His Ala Gln Gln Leu Asn Glu Asp Leu Leu Ala Phe Leu Lys Arg
            260                 265                 270

Gly Pro Gly Ser Gly Gly Ala Gly Ser Pro Gly Ser Ala Gly Gly Pro
        275                 280                 285

Gly Ser Val Ala Thr Ala Lys Tyr Gly Thr Pro Val Ile Asp Gly Glu
    290                 295                 300

Ile Asp Glu Ile Trp Asn Thr Thr Glu Glu Ile Glu Thr Lys Ala Val
305                 310                 315                 320

Ala Met Gly Ser Leu Asp Lys Asn Ala Thr Ala Lys Val Arg Val Leu
                325                 330                 335

Trp Asp Glu Asn Tyr Leu Tyr Val Leu Ala Ile Val Lys Asp Pro Val
            340                 345                 350

Leu Asn Lys Asp Asn Ser Asn Pro Trp Glu Gln Asp Ser Val Glu Ile
        355                 360                 365

Phe Ile Asp Glu Asn Asn His Lys Thr Gly Tyr Tyr Glu Asp Asp Asp
    370                 375                 380

Ala Gln Phe Arg Val Asn Tyr Met Asn Glu Gln Thr Phe Gly Thr Gly
385                 390                 395                 400

Gly Ser Pro Ala Arg Phe Lys Thr Ala Val Lys Leu Ile Glu Gly Gly
                405                 410                 415

Tyr Ile Val Glu Ala Ala Ile Lys Trp Lys Thr Ile Lys Pro Thr Pro
            420                 425                 430

Asn Thr Val Ile Gly Phe Asn Ile Gln Val Asn Asp Ala Asn Glu Lys
        435                 440                 445

Gly Gln Arg Val Gly Ile Ile Ser Trp Ser Asp Pro Thr Asn Asn Ser
    450                 455                 460

Trp Arg Asp Pro Ser Lys Phe Gly Asn Leu Arg Leu Ile Lys
465                 470                 475


<210> SEQ ID NO 180
<211> LENGTH: 216
<212> TYPE: PRT
<213> ORGANISM: Mycobacterium smegmatis

<400> SEQUENCE: 180

Met Ala Lys Arg Ile Leu Cys Phe Gly Asp Ser Leu Thr Trp Gly Trp
1               5                   10                  15

Val Pro Val Glu Asp Gly Ala Pro Thr Glu Arg Phe Ala Pro Asp Val
```

```
            20                  25                  30

Arg Trp Thr Gly Val Leu Ala Gln Gln Leu Gly Ala Asp Phe Glu Val
        35                  40                  45

Ile Glu Glu Gly Leu Ser Ala Arg Thr Thr Asn Ile Asp Asp Pro Thr
    50                  55                  60

Asp Pro Arg Leu Asn Gly Ala Ser Tyr Leu Pro Ser Cys Leu Ala Thr
65                  70                  75                  80

His Leu Pro Leu Asp Leu Val Ile Ile Met Leu Gly Thr Asn Asp Thr
                85                  90                  95

Lys Ala Tyr Phe Arg Arg Thr Pro Leu Asp Ile Ala Leu Gly Met Ser
            100                 105                 110

Val Leu Val Thr Gln Val Leu Thr Ser Ala Gly Gly Val Gly Thr Thr
        115                 120                 125

Tyr Pro Ala Pro Lys Val Leu Val Val Ser Pro Pro Pro Leu Ala Pro
    130                 135                 140

Met Pro His Pro Trp Phe Gln Leu Ile Phe Glu Gly Gly Glu Gln Lys
145                 150                 155                 160

Thr Thr Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
            180                 185                 190

Gly Ile His Phe Thr Glu Ala Asn Asn Arg Asp Leu Gly Val Ala Leu
        195                 200                 205

Ala Glu Gln Val Arg Ser Leu Leu
    210                 215


<210> SEQ ID NO 181
<211> LENGTH: 272
<212> TYPE: PRT
<213> ORGANISM: Pseudomonas fluorescens

<400> SEQUENCE: 181

Met Ser Thr Phe Val Ala Lys Asp Gly Thr Gln Ile Tyr Phe Lys Asp
1               5                   10                  15

Trp Gly Ser Gly Lys Pro Val Leu Phe Ser His Gly Trp Leu Leu Asp
            20                  25                  30

Ala Asp Met Trp Glu Tyr Gln Met Glu Tyr Leu Ser Ser Arg Gly Tyr
        35                  40                  45

Arg Thr Ile Ala Phe Asp Arg Arg Gly Phe Gly Arg Ser Asp Gln Pro
    50                  55                  60

Trp Thr Gly Asn Asp Tyr Asp Thr Phe Ala Asp Asp Ile Ala Gln Leu
65                  70                  75                  80

Ile Glu His Leu Asp Leu Lys Glu Val Thr Leu Val Gly Phe Ser Met
                85                  90                  95

Gly Gly Gly Asp Val Ala Arg Tyr Ile Ala Arg His Gly Ser Ala Arg
            100                 105                 110

Val Ala Gly Leu Val Leu Leu Gly Ala Val Thr Pro Leu Phe Gly Gln
        115                 120                 125

Lys Pro Asp Tyr Pro Gln Gly Val Pro Leu Asp Val Phe Ala Arg Phe
    130                 135                 140

Lys Thr Glu Leu Leu Lys Asp Arg Ala Gln Phe Ile Ser Asp Phe Asn
145                 150                 155                 160

Ala Pro Phe Tyr Gly Ile Asn Lys Gly Gln Val Val Ser Gln Gly Val
                165                 170                 175

Gln Thr Gln Thr Leu Gln Ile Ala Leu Leu Ala Ser Leu Lys Ala Thr
```

-continued

```
            180                 185                 190

Val Asp Cys Val Thr Ala Phe Ala Glu Thr Asp Phe Arg Pro Asp Met
        195                 200                 205

Ala Lys Ile Asp Val Pro Thr Leu Val Ile His Gly Asp Gly Asp Gln
    210                 215                 220

Ile Val Pro Phe Glu Thr Thr Gly Lys Val Ala Ala Glu Leu Ile Lys
225                 230                 235                 240

Gly Ala Glu Leu Lys Val Tyr Lys Asp Ala Pro His Gly Phe Ala Val
                245                 250                 255

Thr His Ala Gln Gln Leu Asn Glu Asp Leu Leu Ala Phe Leu Lys Arg
            260                 265                 270
```

TARGETED PERHYDROLASES

CROSS-REFERENCE TO RELATED APPLICATIONS

This application claims benefit of U.S. Provisional Patent Application No. 61/424,916, filed Dec. 20, 2010, which is incorporated by reference herein in its entirety.

FIELD OF THE INVENTION

This invention relates to the field of enzymatic perhydrolysis and targeted peracid production. Compositions and methods comprising fusion proteins comprising a perhydrolytic enzyme coupled to a peptidic component having affinity for a target surface are provided. Fusion proteins ("targeted perhydrolases") are provided comprising a perhydrolytic enzyme coupled to a peptidic component having affinity for a laundry care surface for targeted enzymatic peracid production. In a preferred aspect, the targeted perhydrolase comprises a CE-7 carbohydrate esterase having perhydrolytic activity.

BACKGROUND OF THE INVENTION

Peroxycarboxylic acids ("peracids") are effective antimicrobial agents. Methods to clean, disinfect, and/or sanitize hard surfaces, food products, living plant tissues, and medical devices against undesirable microbial growth have been described (e.g., U.S. Pat. No. 6,545,047; U.S. Pat. No. 6,183,807; U.S. Pat. No. 6,518,307; U.S. Pat. No. 5,683,724; and U.S. Pat. No. 6,635,286). Peracids have also been reported to be useful in preparing bleaching compositions for laundry detergent applications (e.g., U.S. Pat. No. 3,974,082; U.S. Pat. No. 5,296,161; and U.S. Pat. No. 5,364,554).

Perhydrolytic enzymes may be used to produce peracids. U.S. Patent Application Publication Nos. 2008-0176783 A1; 2008-0176299 A1; 2009-0005590 A1; and 2010-0041752 A1 to DiCosimo et al. disclose enzymes structurally classified as members of the CE-7 family of carbohydrate esterases (i.e., cephalosporin C deacetylases [CAHs] and acetyl xylan esterases [AXEs]) that are characterized by significant perhydrolytic activity for converting carboxylic acid ester substrates (in the presence of a suitable source of peroxygen, such as hydrogen peroxide) into peracids at concentrations sufficient for use as a disinfectant and/or a bleaching agent. Some members of the CE-7 family of carbohydrate esterases have been demonstrated to have perhydrolytic activity sufficient to produce 4000-5000 ppm peracetic acid from acetyl esters of alcohols, diols, and glycerols in 1 minute and up to 9000 ppm between 5 minutes and 30 minutes once the reaction components were mixed (DiCosimo et al., U.S. 2009-0005590 A1). U.S. Patent Application Publication No. 2010-0087529 A1 describes variant CE-7 enzymes having improved perhydrolytic activity.

Peracids are powerful oxidizing agents capable of reaction with a variety of materials. As such, care should be taken when using peracids in applications where the oxidation of non-targeted materials may be undesirable. Certain peracid applications may benefit from a controlled delivery to a target surface to help minimize unwanted oxidation of non-targeted materials.

One way to control delivery of a peracid to a target surface is to target/localize production of the peracid on or near the target surface. Targeted peracid production may decrease the amount of unwanted oxidation of non-targeted materials and may reduce the amount of peracid (or peracid generating components, including perhydrolase) required to achieve the desired effect (such as bleaching, destaining, deodorizing, sanitizing, disinfecting, and cleaning).

Peptidic affinity materials having affinity for a target surface (large peptidic materials such as antibodies, antibody fragments ($F_{ab}$), single chain fused variable region antibodies (scFc), *Camelidae* antibodies, and scaffold display proteins) have been used to direct benefit agents to a target surface. Typically the benefit agent is coupled directly to the peptidic material having affinity for the target surface. However, the cost and complexity of using these large peptidic affinity materials may exclude them for use in certain applications.

The use of shorter peptides having strong affinity for a target surface to target a benefit agent to a target surface has been described (U.S. Pat. Nos. 7,220,405; 7,309,482; 7,285,264 and 7,807,141; U.S. Patent Application Publication Nos. 2005-0226839 A1; 2007-0196305 A1; 2006-0199206 A1; 2007-0065387 A1; 2008-0107614 A1; 2007-0110686 A1; 2006-0073111 A1; 2010-0158846; and 2010-0158847; and published PCT applications WO2008/054746; WO2004/048399, and WO2008/073368). However, the use of such a peptidic material having affinity for a target surface to couple a perhydrolytic enzyme catalyst (i.e., "targeted perhydrolases") to the surface for the production of a peracid benefit agent has not been described.

Some target surfaces that may benefit from a peracid treatment may be comprised of a cellulosic material. As such, materials having affinity for cellulosic materials may be useful for targeted peracid treatment. Cellulose-binding domains (CBDs) have been identified in a large number of proteins typically associated with cellulose degradation. Tomme et al. (*J. Chromatogr. B* (1998) 7125: 283-296) discloses 13 families of cellulose-binding domains and their use in affinity purification applications. EP1224270B1 discloses synthetic "mimic" cellulose-binding domains that are typically no more than 30 amino acids in length and have strong affinity for cellulosic substances. WO2005/042735 A1 discloses non-catalytic carbohydrate-binding molecules from glucosyl hydrolase family 61 having affinity for cellulose. Han et al. (*Shengwu Huaxue Yu Shengwu Wuli Xuebao* 30:263 266 (1998)) describes the identification of peptides that specifically bind to a cellulose matrix using the phage display method. The deduced amino acid sequences of these cellulose-binding peptides have a conserved aromatic residue, tyrosine or phenylalanine, which is similar to the normal cellulose binding domain of some cellulose-binding proteins.

The use of cellulose-binding domains in the creation of fusion proteins and chimeric peptidic constructs for the targeted delivery of a benefit agent in laundry care applications has been reported. U.S. Pat. No. 7,361,487 discloses cellulase fusion proteins comprising an endoglucanase core coupled to a heterologous cellulose binding domain for use in denim finishing. CN101591648A discloses a fusion protein comprising a cutinase fused to a cellulose binding domain for cotton fiber finishing. U.S. Patent Application Publication 2006-0246566 discloses cellulase fusion proteins comprising a neutral cellulase core of a *Melanocarpus* sp. and a tail consisting of a linker/cellulose binding domain of an acid cellobiohydrolase I of *Trichoderma reesei*.

WO97/40229 and WO97/40127 disclose a method of treating fabrics with a cellulase and a hybrid enzyme comprising a phenol oxidizing enzyme fused a cellulose binding domain. U.S. Pat. No. 6,017,751 discloses a fusion protein comprising a cellulose-binding domain fused to an α-amylase, a lipase, a peroxidase or a laccase.

U.S. Pat. No. 6,586,384 and U.S. Pat. No. 6,579,842 disclose methods of delivering a benefit agent to a selected area of fabric for exerting a predetermined activity using a multispecific binding molecule that is pre-treated on the fabric followed by contacting the pre-treated fabric with the benefit agent. The binding molecule may be a fusion protein comprising a cellulose-binding domain fused to a second portion having affinity for the benefit agent.

U.S. Pat. No. 6,919,428 discloses a fusion protein comprising a cellulose-binding domain and a protein having affinity for another ligand and detergent compositions comprising such fusion proteins. U.S. Pat. No. 7,041,793 discloses detergent compositions comprising a fusion protein having a cellulose-binding domain coupled to an antibody or antibody fragment which has affinity for another ligand. U.S. Pat. No. 6,410,498 discloses laundry detergent and fabric care compositions comprising a modified transferase comprising a cellulose-binding domain. WO99/57250 discloses modified enzymes comprising a catalytically active amino acid sequence linked via a non-amino acid linker to a region comprising a cellulose-binding domain.

U.S. Pat. No. 6,465,410 discloses laundry detergents and fabric care compositions comprising modified proteins having a catalytically active amino acid sequence of an antimicrobial peptide or protein linked to an amino acid sequence comprising a cellulose-binding domain for improved sanitization benefits. U.S. Pat. No. 6,906,024 discloses fabric care compositions comprising a fabric softening peptide coupled via a non-amino acid linker to one of four specific cellulose binding domains.

WO2000/018865 and EP1115828B1 disclose a chemical entity comprising a cellulose-binding domain coupled to a chemical component for use in laundry care applications. WO2005/051997 discloses a fusion protein comprising a cellulose-binding domain from a fungal enzyme and a domain having affinity for a melamine-type polymer used to encapsulate a benefit agent.

Some woven and non-woven materials may be comprised of synthetic materials such as polyamides, nylons, polyurethanes, polyacrylates, polyesters, polyolefins, polylactides, and semi-synthetic materials such as cellulose acetate. As such, peptide-binding domains having affinity for any of these and other synthetic or semi-synthetic materials used in the manufacture of textiles may also aid in the targeted delivery of a perhydrolytic enzyme.

Biopanned peptides having affinity for cellulose and non-cellulosic materials such as cotton fabrics, polyester/cotton blends, cellulose acetate, paper, polymethyl methacrylate, Nylon, polypropylene, polyethylene, polystyrene, and polytetrafluoroethylene have been reported (U.S. Pat. Nos. 7,709,601; 7,700,716; 7,632,919; 7,858,581; 7,928,076; and 7,906,617; and U.S. Patent Application Publication NOs. 2005-0054752; 2010-0310495; 2010-0298231; 2010-0298240; 2010-0298241; 2010-0298531; 2010-0298532; 2010-0298533; 2010-0298534; and 2010-0298535. The use of such peptides in fusion proteins for targeted peracid production has not been described.

WO 01/79479 to Estell et al. discloses a modified phage display screening method that comprises contacting a peptide library with an anti-target to remove peptides that bind to the anti-target, then contacting the non-binding peptides with the target. Using this method, peptide sequences that bind to collar soil, but not to polyester/cotton and peptide sequences that bind to polyurethane, but not to cotton, polyester, or polyester/cotton fabrics were identified. No peptide sequences that bind to fabrics are reported in that disclosure.

The problem to be solved it to provide compositions and methods to target enzymatic peracid production to the surface of a target material to provide a peracid-based benefit to the target surface.

SUMMARY OF THE INVENTION

Compositions and methods are provided herein for targeting enzymatic peracid production to a target surface. Fusion proteins comprising an enzyme having perhydrolytic activity coupled to at least one peptidic component having affinity for the surface of a target material are provided. The targeted surface is contacted with the fusion protein having perhydrolytic activity whereby the perhydrolytic enzyme is bound to the target surface. The bound fusion protein can be combined with suitable reaction components to enzymatically generate a peracid on or near the target surface.

In one embodiment, a method is provided comprising:

1) providing a set of reaction components comprising:

a) at least one substrate selected from the group consisting of:

i) esters having the structure $[X]_mR_5$ wherein X=an ester group of the formula $R_6C(O)O$ $R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;

$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;

m is an integer ranging from 1 to the number of carbon atoms in $R_5$; and wherein said esters have solubility in water of at least 5 ppm at 25° C.;

ii) glycerides having the structure

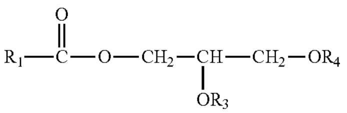

wherein $R_1$=C1 to C7 straight chain or branched chain alkyl optionally substituted with an hydroxyl or a C1 to C4 alkoxy group and $R_3$ and $R_4$ are individually H or $R_1C(O)$;

iii) one or more esters of the formula

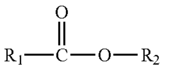

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10; and iv) acetylated saccharides selected from the group consisting of acetylated monosaccharides, acetylated disaccharides, and acetylated polysaccharides;

b) a source of peroxygen; and c) a fusion protein having perhydrolytic activity comprising the general structure PAH-$[L]_y$-TSBD or TSBD-$[L]_y$-PAH wherein PAH is an enzyme having perhydrolytic activity;

TSBD is a peptidic component having affinity for a surface of a target material; wherein the surface is not a body surface or an oral cavity surface;

L is an optional peptide linker ranging from 1 to 100 amino acids in length; and y is 0 or 1; and 2) combining the reaction components of (1) under suitable reaction conditions whereby;

a) the fusion protein binds to the target surface; and b) at least one peracid is enzymatically produced and contacted with the target surface; whereby the target surface receives a peracid-based benefit selected from the group consisting of bleaching, whitening, disinfecting, sanitizing, destaining, deodorizing, and combinations thereof.

In one embodiment, the enzyme having perhydrolytic activity used in present methods is a protease, a lipase, an esterase, an acyl transferase, an aryl esterase, a carbohydrate esterase, a cephalosporin acetyl hydrolase, an acetyl xylan esterase or any combination thereof.

In one embodiment, the enzyme having perhydrolytic activity used in the present methods is a carbohydrate esterase comprising a CE-7 signature motif that aligns with a reference sequence SEQ ID NO: 2, said signature motif comprising:

i) an RGQ motif at positions corresponding to positions 118-120 of SEQ ID NO:2;

ii) a GXSQG motif at positions corresponding to positions 179-183 of SEQ ID NO:2; and iii) an HE motif at positions corresponding to positions 298-299 of SEQ ID NO:2.

In another embodiment, a fusion protein is provided comprising the following general structure:

PAH-$[L]_y$-TSBD or

TSBD-$[L]_y$-PAH wherein

PAH is an enzyme having perhydrolytic activity;

TSBD is a peptidic component having affinity for a surface of a target material; wherein the surface is not a body surface or an oral cavity surface;

L is an optional peptide linker ranging from 1 to 100 amino acids in length; and y is 0 or 1.

In one embodiment, the enzyme portion of the fusion protein having perhydrolytic activity is a protease, a lipase, an esterase, an acyl transferase, an aryl esterase, a carbohydrate esterase, a cephalosporin acetyl hydrolase, an acetyl xylan esterase or any combination thereof. In another embodiment, the enzymatic portion having perhydrolytic activity is not a protease.

In one embodiment, the fusion protein comprises a carbohydrate esterase having a CE-7 signature motif that aligns with a reference sequence SEQ ID NO: 2, said signature motif comprising:

i) an RGQ motif at positions corresponding to positions 118-120 of SEQ ID NO:2;

ii) a GXSQG motif at positions corresponding to positions 179-183 of SEQ ID NO:2; and iii) an HE motif at positions corresponding to positions 298-299 of SEQ ID NO:2.

In some embodiments, the peptidic component having affinity for a target material may be an antibody, an $F_{ab}$ antibody fragment, a single chain variable fragment (scFv) antibody, a *Camelidae* antibody, a scaffold display protein or a single chain polypeptide lacking an immunoglobulin fold. In another embodiment, the target material may be comprised of a cellulosic material. In a preferred embodiment, the peptidic component having affinity for a target material is a cellulose-binding domain or a single chain peptide having affinity for cellulosic material.

In another embodiment, a peracid generation system is provided comprising:

a set of reaction components comprising:

a) at least one substrate selected from the group consisting of:

i) esters having the structure $[X]_mR_5$ wherein X=an ester group of the formula $R_6C(O)O$ $R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;

$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;

m is an integer ranging from 1 to the number of carbon atoms in $R_5$; and wherein said esters have solubility in water of at least 5 ppm at 25° C.;

ii) glycerides having the structure

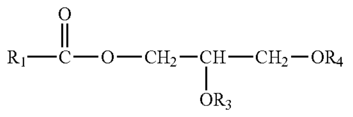

wherein $R_1$=C1 to C7 straight chain or branched chain alkyl optionally substituted with an hydroxyl or a C1 to C4 alkoxy group and $R_3$ and $R_4$ are individually H or $R_1C(O)$;

iii) one or more esters of the formula

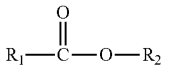

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10; and iv) acetylated saccharides selected from the group consisting of acetylated monosaccharides, acetylated disaccharides, and acetylated polysaccharides;

b) a source of peroxygen; and c) a fusion protein having perhydrolytic activity comprising the general structure $PAH-[L]_y-TSBD$ or $TSBD-[L]_y-PAH$;

wherein

PAH is an enzyme having perhydrolytic activity; wherein said enzyme having perhydrolytic activity is a lipase, a protease, an esterase, an acyl transferase, an aryl esterase, a carbohydrate esterase, a cephalosporin acetyl hydrolase, an acetyl xylan esterase or any combination thereof;

TSBD is a peptidic component having affinity for a surface of a target material; wherein the surface is not a body surface or an oral cavity surface;

L is an optional peptide linker ranging from 1 to 100 amino acids in length; and y is 0 or 1.

In one embodiment, the fusion protein component of the peracid generation system comprises a carbohydrate esterase having a CE-7 signature motif that aligns with a reference sequence SEQ ID NO: 2, said signature motif comprising:

i) an RGQ motif at positions corresponding to positions 118-120 of SEQ ID NO:2;

ii) a GXSQG motif at positions corresponding to positions 179-183 of SEQ ID NO:2; and iii) an HE motif at positions corresponding to positions 298-299 of SEQ ID NO:2.

In another embodiment, the fusion protein component of the peracid generation system comprises a perhydrolytic aryl esterase having at least 95% amino acid identity to SEQ ID NO: 162.

In another embodiment, a method is provided comprising:

1) providing a set of reaction components comprising:

a) at least one substrate selected from the group consisting of:

i) esters having the structure $[X]_mR_5$ wherein X=an ester group of the formula $R_6C(O)O$ $R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;

$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;

m is an integer ranging from 1 to the number of carbon atoms in $R_5$; and wherein said esters have solubility in water of at least 5 ppm at 25° C.;

ii) glycerides having the structure

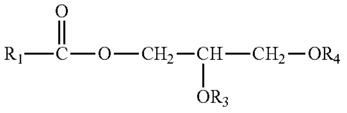

wherein $R_1$=C1 to C7 straight chain or branched chain alkyl optionally substituted with an hydroxyl or a C1 to C4 alkoxy group and $R_3$ and $R_4$ are individually H or $R_1C(O)$;

iii) one or more esters of the formula

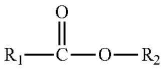

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10; and iv) acetylated saccharides selected from the group consisting of acetylated monosaccharides, acetylated disaccharides, and acetylated polysaccharides;

b) a source of peroxygen; and c) a fusion protein having perhydrolytic activity comprising the general structure $PAH-[L]_y-TSBD$ or $TSBD-[L]_y-PAH$ wherein PAH is an enzyme having perhydrolytic activity;

TSBD is a peptidic component having affinity for a surface of a target material; wherein the surface is not a body surface or an oral cavity surface;

L is an optional peptide linker ranging from 1 to 100 amino acids in length; and y is 0 or 1;

wherein the enzyme having perhydrolytic activity comprises a CE-7 signature motif that aligns with a reference sequence SEQ ID NO: 2, said signature motif comprising:

i) an RGQ motif at positions corresponding to positions 118-120 of SEQ ID NO:2;

ii) a GXSQG motif at positions corresponding to positions 179-183 of SEQ ID NO:2; and iii) an HE motif at positions corresponding to positions 298-299 of SEQ ID NO:2;

2) contacting that target surface with the fusion protein having perhydrolytic activity whereby the fusion protein binds to the target surface;

3) optionally rinsing the target surface; and 4) contacting the target surface having the bound fusion protein with said at least one substrate and the source of peroxygen whereby at least one peracid is enzymatically produced by the fusion protein; whereby the target surface receives a peracid-based benefit selected from the group consisting of bleaching, whitening, disinfecting, destaining, deodorizing, decreasing or removing biofilm, and combinations thereof.

In a preferred embodiment, the target surface comprises a cellulosic material. In another embodiment, the cellulosic material comprises cellulose, wood, wood pulp, paper, paper pulp, cotton, rayon, lyocell or any combination thereof.

In another embodiment, the target surface comprises a target material such as polymethyl methacrylate, polypropylene, polytetrafluoroethylene, polyethylene, polyamide, polyester, polystyrene, cellulose acetate or any combination thereof.

Many of the above materials are commonly found in the manufacture of fibers, yarns, textiles (woven and non-woven), and articles of clothing wherein a peracid may provide a benefit selected from the group consisting of bleaching, whitening, cleaning, sanitizing, disinfecting, destaining, deodorizing, and combinations thereof.

In another embodiment, a laundry care product is provided comprising at least one fusion having the general structure PAH-$[L]_y$-TSBD or TSBD-$[L]_y$-PAH;

wherein

PAH is an enzyme having perhydrolytic activity;

TSBD is a peptidic component having affinity for a surface of a target material; wherein the surface is not a body surface or an oral cavity surface;

L is an optional peptide linker ranging from 1 to 100 amino acids in length; and y is 0 or 1.

In another embodiment, a laundry care product is provided wherein the fusion protein comprises a CE-7 carbohydrate esterase having a CE-7 signature motif that aligns with a reference sequence SEQ ID NO: 2, said signature motif comprising:

i) an RGQ motif at positions corresponding to positions 118-120 of SEQ ID NO:2;

ii) a GXSQG motif at positions corresponding to positions 179-183 of SEQ ID NO:2; and iii) an HE motif at positions corresponding to positions 298-299 of SEQ ID NO:2.

In another embodiment, a method for the production of a fusion protein comprising a perhydrolytic enzyme coupled to at least one a peptidic component having affinity for a cellulosic material is provided, said method comprising:

a) providing a recombinant microbial host cell comprising an expressible genetic construct encoding a fusion protein, said fusion protein comprising an enzyme having perhydrolytic activity coupled to a peptidic component having affinity for a cellulosic material;

b) growing the recombinant microbial host cell under suitable conditions whereby the fusion protein is produced; and c) optionally recovering the fusion protein.

In one aspect the of the above method, the enzyme having perhydrolytic activity comprises an amino acid sequence having at least 95% identity to SEQ ID NO: 162.

In another aspect of the above method, the enzyme having perhydrolytic activity comprises a CE-7 carbohydrate esterase having a CE-7 signature motif that aligns with a reference sequence SEQ ID NO: 2, said signature motif comprising:

i) an RGQ motif at positions corresponding to positions 118-120 of SEQ ID NO:2;

ii) a GXSQG motif at positions corresponding to positions 179-183 of SEQ ID NO:2; and iii) an HE motif at positions corresponding to positions 298-299 of SEQ ID NO:2.

In another aspect, the use of one or more of the present fusion proteins in a laundry product to enzymatically produce an efficacious concentration of at least one peracid for bleaching, whitening, disinfecting, sanitizing, destaining or deodorizing a target surface is also provided.

BRIEF DESCRIPTION OF THE FIGURE

FIG. 1. Comparison of fabric bleaching vs amount of enzyme added for a targeted perhydrolase and an untargeted perhydrolase.

BRIEF DESCRIPTION OF THE BIOLOGICAL SEQUENCES

The following sequences comply with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. §1.822.

SEQ ID NO: 1 is the nucleic acid sequence encoding a cephalosporin C deacetylase from *Bacillus subtilis* ATCC® 31954™.

SEQ ID NO: 2 is the amino acid sequence of a cephalosporin C deacetylase from *Bacillus subtilis* ATCC® 31954™.

SEQ ID NO: 3 is the nucleic acid sequence encoding a cephalosporin C deacetylase from *Bacillus subtilis* subsp. *subtilis* strain 168.

SEQ ID NO: 4 is the amino acid sequence of a cephalosporin C deacetylase from *Bacillus subtilis* subsp. *subtilis* strain 168.

SEQ ID NO: 5 is the nucleic acid sequence encoding a cephalosporin C deacetylase from *B. subtilis* ATCC® 6633™.

SEQ ID NO: 6 is the acid sequence of a cephalosporin C deacetylase from *B. subtilis* ATCC® 6633™.

SEQ ID NO: 7 is the nucleic acid sequence encoding a cephalosporin C deacetylase from *B. licheniformis* ATCC® 14580™.

SEQ ID NO: 8 is the deduced amino acid sequence of a cephalosporin C deacetylase from *B. licheniformis* ATCC® 14580™.

SEQ ID NO: 9 is the nucleic acid sequence encoding an acetyl xylan esterase from *B. pumilus* PS213.

SEQ ID NO: 10 is the deduced amino acid sequence of an acetyl xylan esterase from *B. pumilus* PS213.

SEQ ID NO: 11 is the nucleic acid sequence encoding an acetyl xylan esterase from *Clostridium thermocellum* ATCC®27405™.

SEQ ID NO: 12 is the deduced amino acid sequence of an acetyl xylan esterase from *Clostridium thermocellum* ATCC®27405™.

SEQ ID NO: 13 is the nucleic acid sequence encoding an acetyl xylan esterase from *Thermotoga neapolitana*.

SEQ ID NO: 14 is the amino acid sequence of an acetyl xylan esterase from *Thermotoga neapolitana*.

SEQ ID NO: 15 is the nucleic acid sequence encoding an acetyl xylan esterase from *Thermotoga maritima* MSB8.

SEQ ID NO: 16 is the amino acid sequence of an acetyl xylan esterase from *Thermotoga maritima* MSB8.

SEQ ID NO: 17 is the nucleic acid sequence encoding an acetyl xylan esterase from *Thermoanaerobacterium* sp. JW/SL YS485.

SEQ ID NO: 18 is the deduced amino acid sequence of an acetyl xylan esterase from *Thermoanaerobacterium* sp. JW/SL YS485.

SEQ ID NO: 19 is the nucleic acid sequence of a cephalosporin C deacetylase from *Bacillus* sp. NRRL B-14911. It should be noted that the nucleic acid sequence encoding the cephalosporin C deacetylase from *Bacillus* sp. NRRL B-14911 as reported in GENBANK® Accession number ZP_01168674 appears to encode a 15 amino acid N-terminal addition that is likely incorrect based on sequence alignments with other cephalosporin C deacetylases and a comparison of the reported length (340 amino acids) versus the observed length of other CAH enzymes (typically 318-325 amino acids in length; see U.S. Patent Application Publication No. US-2010-0087528-A1; herein incorporated by reference). As such, the nucleic acid sequence as reported herein encodes the cephalosporin C deacetylase sequence from *Bacillus* sp. NRRL B-14911 without the N-terminal 15 amino acids reported under GENBANK® Accession number ZP_01168674.

SEQ ID NO: 20 is the deduced amino acid sequence of the cephalosporin C deacetylase from *Bacillus* sp. NRRL B-14911 encoded by the nucleic acid sequence of SEQ ID NO: 19.

SEQ ID NO: 21 is the nucleic acid sequence encoding a cephalosporin C deacetylase from *Bacillus halodurans* C-125.

SEQ ID NO: 22 is the deduced amino acid sequence of a cephalosporin C deacetylase from *Bacillus halodurans* C-125.

SEQ ID NO: 23 is the nucleic acid sequence encoding a cephalosporin C deacetylase from *Bacillus clausii* KSM-K16.

SEQ ID NO: 24 is the deduced amino acid sequence of a cephalosporin C deacetylase from *Bacillus clausii* KSM-K16.

SEQ ID NO: 25 is the nucleic acid sequence encoding a *Bacillus subtilis* ATCC® 29233™ cephalosporin C deacetylase (CAH).

SEQ ID NO: 26 is the deduced amino acid sequence of a *Bacillus subtilis* ATCC® 29233™ cephalosporin C deacetylase (CAH).

SEQ ID NO: 27 is the deduced amino acid sequence of a *Thermotoga neapolitana* acetyl xylan esterase variant from U.S. Patent Application Publication No. 2010-0087529 (incorporated herein by reference in its entirety), where the Xaa residue at position 277 is Ala, Val, Ser, or Thr.

SEQ ID NO: 28 is the deduced amino acid sequence of a *Thermotoga maritima* MSB8 acetyl xylan esterase variant from U.S. Patent Application Publication No. 2010-0087529, where the Xaa residue at position 277 is Ala, Val, Ser, or Thr.

SEQ ID NO: 29 is the deduced amino acid sequence of a *Thermotoga lettingae* acetyl xylan esterase variant from U.S. Patent Application Publication No. 2010-0087529, where the Xaa residue at position 277 is Ala, Val, Ser, or Thr.

SEQ ID NO: 30 is the deduced amino acid sequence of a *Thermotoga petrophila* acetyl xylan esterase variant from U.S. Patent Application Publication No. 2010-0087529, where the Xaa residue at position 277 is Ala, Val, Ser, or Thr.

SEQ ID NO: 31 is the deduced amino acid sequence of a *Thermotoga* sp. RQ2 acetyl xylan esterase variant derived from "RQ2(a)" from U.S. Patent Application Publication No. 2010-0087529, where the Xaa residue at position 277 is Ala, Val, Ser, or Thr.

SEQ ID NO: 32 is the deduced amino acid sequence of a *Thermotoga* sp. RQ2 acetyl xylan esterase variant derived from "RQ2(b)" from U.S. Patent Application Publication No. 2010-0087529, where the Xaa residue at position 278 is Ala, Val, Ser, or Thr.

SEQ ID NO: 33 is the deduced amino acid sequence of a *Thermotoga* lettingae acetyl xylan esterase.

SEQ ID NO: 34 is the deduced amino acid sequence of a *Thermotoga* petrophila acetyl xylan esterase.

SEQ ID NO: 35 is the deduced amino acid sequence of a first acetyl xylan esterase from *Thermotoga* sp. RQ2 described herein as "RQ2(a)".

SEQ ID NO: 36 is the deduced amino acid sequence of a second acetyl xylan esterase from *Thermotoga* sp. RQ2 described herein as "RQ2(b)".

SEQ ID NO: 37 is the codon optimized nucleic acid sequence encoding a *Thermoanearobacterium saccharolyticum* cephalosporin C deacetylase.

SEQ ID NO: 38 is the deduced amino acid sequence of a *Thermoanearobacterium saccharolyticum* cephalosporin C deacetylase.

SEQ ID NO: 39 is the nucleic acid sequence encoding the acetyl xylan esterase from *Lactococcus lactis* (GENBANK® accession number EU255910).

SEQ ID NO: 40 is the amino acid sequence of the acetyl xylan esterase from *Lactococcus lactis* (GENBANK® accession number ABX75634.1).

SEQ ID NO: 41 is the nucleic acid sequence encoding the acetyl xylan esterase from *Mesorhizobium loti* (GENBANK® accession number NC_002678.2).

SEQ ID NO: 42 is the amino acid sequence of the acetyl xylan esterase from *Mesorhizobium loti* (GENBANK® accession number BAB53179.1).

SEQ ID NO: 43 is the nucleic acid sequence encoding the acetyl xylan esterase from *Geobacillus stearothermophilus* (GENBANK® accession number AF038547.2).

SEQ ID NO: 44 is the amino acid sequence of the acetyl xylan esterase from *Geobacillus stearothermophilus* (GENBANK® accession number AAF70202.1).

SEQ ID NO: 45 is the nucleic acid sequence encoding a variant acetyl xylan esterase (a.k.a. variant "A3") having the following substitutions relative to the wild-type *Thermotoga maritima* acetyl xylan esterase amino acid sequence: (F24I/S35T/Q179L/N275D/C277S/S308G/F317S).

SEQ ID NO: 46 is the amino acid sequence of the "A3" variant acetyl xylan esterase.

SEQ ID NO: 47 is the nucleic acid sequence encoding the N275D/C277S variant acetyl xylan esterase.

SEQ ID NO: 48 is the amino acid sequence of the N275D/C277S variant acetyl xylan esterase.

SEQ ID NO: 49 is the nucleic acid sequence encoding the C277S/F317S variant acetyl xylan esterase.

SEQ ID NO: 50 is the amino acid sequence of the C277S/F317S variant acetyl xylan esterase.

SEQ ID NO: 51 is the nucleic acid sequence encoding the S35T/C277S variant acetyl xylan esterase.

SEQ ID NO: 52 is the amino acid sequence of the S35T/C277S variant acetyl xylan esterase.

SEQ ID NO: 53 is the nucleic acid sequence encoding the Q179L/C277S variant acetyl xylan esterase.

SEQ ID NO: 54 is the amino acid sequence of the Q179L/C277S variant acetyl xylan esterase.

SEQ ID NO: 55 is the nucleic acid sequence encoding the variant acetyl xylan esterase 843H9 having the following substitutions relative to the wild-type *Thermotoga maritima* acetyl xylan esterase amino acid sequence: (L8R/L125Q/Q176L/V183D/F2471/C277S/P292L).

SEQ ID NO: 56 is the amino acid sequence of the 843H9 variant acetyl xylan esterase.

SEQ ID NO: 57 is the nucleic acid sequence encoding the variant acetyl xylan esterase 843F12 having the following substitutions relative to the wild-type *Thermotoga maritima* acetyl xylan esterase amino acid sequence: K77E/A266E/C277S.

SEQ ID NO: 58 is the amino acid sequence of the 843F12 variant acetyl xylan esterase.

SEQ ID NO: 59 is the nucleic acid sequence encoding the variant acetyl xylan esterase 843C12 having the following substitutions relative to the wild-type *Thermotoga maritima* acetyl xylan esterase amino acid sequence: F27Y/1149V/A266V/C277S/1295T/N302S.

SEQ ID NO: 60 is the amino acid sequence of the 843C12 variant acetyl xylan esterase.

SEQ ID NO: 61 is the nucleic acid sequence encoding the variant acetyl xylan esterase 842H3 having the following substitutions relative to the wild-type *Thermotoga maritima* acetyl xylan esterase amino acid sequence: L195Q/C277S.

SEQ ID NO: 62 is the amino acid sequence of the 842H3 variant acetyl xylan esterase.

SEQ ID NO: 63 is the nucleic acid sequence encoding the variant acetyl xylan esterase 841A7 having the following substitutions relative to the wild-type *Thermotoga maritima* acetyl xylan esterase amino acid sequence: Y110F/C277S.

SEQ ID NO: 64 is the amino acid sequence of the 841A7 variant acetyl xylan esterase.

SEQ ID NOs: 65-127 are the amino acid sequences of various peptides having affinity for various polymers and cellulosic materials. SEQ ID NOs: 65-79 are examples of peptides having affinity for polymethyl methacrylate, SEQ ID NOs: 80-86 are examples of peptides having affinity for polypropylene, SEQ ID NOs: 87-95 are examples of peptides having affinity for polytetrafluoroethylene, SEQ ID NOs: 96-102 are examples of peptides having affinity for polyethylene, SEQ ID NOs: 103-108 are examples of peptides having affinity for polyamides (Nylon), SEQ ID NOs 109-111 are examples of peptides having affinity for polystyrene, SEQ ID NOs: 112-115 are examples of peptides having affinity for cellulose acetate, SEQ ID NOs: 116-117 are examples of peptides having affinity for cotton, SEQ ID NOs: 116 and 118 are examples of peptides having affinity for polyester/cotton blends, SEQ ID NOs: 119-121 are examples of peptides having affinity for paper, and SEQ ID NOs: 122-127 are examples of peptides having affinity for cellulose.

SEQ ID NOs: 128-140 and 143 are the amino acid sequences of peptide linkers/spacers.

SEQ ID ON: 141 if the nucleic acid sequence of expression plasmid pLD001.

SEQ ID NO: 142 is the amino acid sequence of *T. maritima* variant C277S ("PAH").

SEQ ID NO: 143 is the amino acid sequence of the flexible linker joining the *Thermotoga maritima* variant C277S perhydrolase to binding domain HC263.

SEQ ID NO: 144 is the nucleic acid sequence encoding fusion peptide C277S-HC263.

SEQ ID NO: 145 is the amino acid sequence of fusion peptide C277S-HC263 ("PAH-HC263").

SEQ ID NO: 146 is the amino acid of hair-binding domain HC263.

SEQ ID NO: 147 is the nucleic acid sequence encoding the fusion construct C277S-CIP.

SEQ ID NO: 148 is the amino acid sequence of fusion peptide C277S-CIP.

SEQ ID NO: 149 is the amino acid sequence of the cellulose-binding domain "CIP" of *Clostridium thermocellum* with a C-terminal His tag.

SEQ ID NO: 150 is the nucleotide sequence of the synthetic gene encoding the *Thermotoga maritima* variant C277S perhydrolase fused at its C-terminus to the *Clostridium cellulovorans* CBM17 cellulose-binding domain via a flexible linker.

SEQ ID NO: 151 is the amino acid sequence of the *Thermotoga maritima* variant C277S perhydrolase fused at its C-terminus to the *Clostridium cellulovorans* CBM17 cellulose-binding domain via a flexible linker.

SEQ ID NO: 152 is the amino acid sequence of the *Clostridium cellulovorans* CBM17 cellulose-binding domain with a C-terminal His tag.

SEQ ID NO: 153 is the nucleotide sequence of the synthetic gene encoding the *Thermotoga maritima* variant C277S perhydrolase fused at its C-terminus to the *Bacillus* sp. CBM28 cellulose-binding domain via a flexible linker.

SEQ ID NO: 154 is the amino acid sequence of the *Thermotoga maritima* variant C277S perhydrolase fused at its C-terminus to the *Bacillus* sp. CBM28 cellulose-binding domain via a flexible linker.

SEQ ID NO: 155 is the amino acid sequence of the *Bacillus* sp. CBM28 cellulose-binding domain with a C-terminal His tag.

SEQ ID NO: 156 is the polynucleotide sequence of the synthetic gene encoding the *Thermotoga maritima* variant C277S perhydrolase fused at its C-terminus to the *Thermotoga maritima* CBM9-2 cellulose-binding domain via a flexible linker.

SEQ ID NO: 157 is the amino acid sequence of the *Thermotoga maritima* variant C277S perhydrolase fused at its C-terminus to the *Thermotoga maritima* CBM9-2 cellulose-binding domain via a flexible linker.

SEQ ID NO: 158 is the amino acid sequence of the *Thermotoga maritima* CBM9-2 cellulose-binding.

SEQ ID NO: 159 is the nucleotide sequence of the synthetic gene encoding the *Thermotoga maritima* variant C277S perhydrolase fused at its C-terminus to the *Caldicellulosiruptor saccharolyticus* CBD1 cellulose-binding domain via a flexible linker.

SEQ ID NO: 160 is the amino acid sequence of the *Thermotoga maritima* variant C277S perhydrolase fused at its C-terminus to the *Caldicellulosiruptor saccharolyticus* CBD1 cellulose-binding domain via a flexible linker.

SEQ ID NO: 161 is the amino acid sequence of the *Caldicellulosiruptor saccharolyticus* CBD1 cellulose-binding.

SEQ ID NO: 162 is the amino acid sequence of the S54V variant of the aryl esterase from *Mycobacterium smegmatis* (U.S. Pat. No. 7,754,460; WO2005/056782; and EP1689859 B1).

SEQ ID NO: 163 is the amino acid sequence of the L29P variant of the *Pseudomonas fluorescens* esterase (U.S. Pat. No. 7,384,787).

SEQ ID NO: 164 is the nucleotide sequence of the synthetic gene encoding the acetyl xylan esterase from *Bacillus pumilus* fused at its C-terminus to the cellulose binding domain *Clostridium thermocellum* (CIP) via a flexible linker.

SEQ ID NO: 165 is the amino acid sequence of the acetyl xylan esterase from *Bacillus pumilus* to the cellulose binding domain *Clostridium thermocellum* (CIP) via a flexible linker.

SEQ ID NO: 166 is the nucleotide sequence of the synthetic gene encoding the acetyl xylan esterase from *Lactococcus lactis* subsp. *lactis* fused at its C-terminus to the cellulose binding domain *Clostridium thermocellum* (CIP) via a flexible linker.

SEQ ID NO: 167 is the amino acid sequence of the acetyl xylan esterase from *Lactococcus lactis* subsp. *lactis* to the cellulose binding domain *Clostridium thermocellum* (CIP) via a flexible linker.

SEQ ID NO: 168 is the nucleotide sequence of the synthetic gene encoding the acetyl xylan esterase from *Mesorhizobium loti* fused at its C-terminus to the cellulose binding domain *Clostridium thermocellum* (CIP) via a flexible linker.

SEQ ID NO: 169 is the amino acid sequence of the acetyl xylan esterase from *Mesorhizobium loti* to the cellulose binding domain *Clostridium thermocellum* (CIP) via a flexible linker.

SEQ ID NO: 170 is the nucleotide sequence of the synthetic gene encoding the acetyl xylan esterase from the S54V variant of the aryl esterase from *Mycobacterium smegmatis* fused at its C-terminus to the cellulose binding domain *Clostridium thermocellum* (CIP) via a flexible linker SEQ ID NO: 171 is the amino acid sequence of the acetyl xylan esterase from the S54V variant of the aryl esterase from *Mycobacterium smegmatis* to the cellulose binding domain *Clostridium thermocellum* (CIP) via a flexible linker.

SEQ ID NO: 172 is the nucleotide sequence of the synthetic gene encoding the acetyl xylan esterase from the S54V variant of the aryl esterase from *Mycobacterium smegmatis* fused at its C-terminus to the *Caldicellulosiruptor saccharolyticus* CBD1 cellulose-binding domain via a flexible linker.

SEQ ID NO: 173 is the amino acid sequence of the acetyl xylan esterase from the S54V variant of the aryl esterase from *Mycobacterium smegmatis* to the *Caldicellulosiruptor saccharolyticus* CBD1 cellulose-binding domain via a flexible linker.

SEQ ID NO: 174 is the nucleotide sequence of the synthetic gene encoding the acetyl xylan esterase from the S54V variant of the aryl esterase from *Mycobacterium smegmatis* fused at its C-terminus to the *Thermotoga maritima* CBM9-2 cellulose-binding domain via a flexible linker.

SEQ ID NO: 175 is the amino acid sequence of the acetyl xylan esterase from the S54V variant of the aryl esterase from *Mycobacterium smegmatis* to the *Thermotoga maritima* CBM9-2 cellulose-binding domain via a flexible linker.

SEQ ID NO: 176 is the nucleotide sequence of the synthetic gene encoding the acetyl xylan esterase from the L29P variant of the hydrolase from *Pseudomonas fluorescens* fused at its C-terminus to the cellulose binding domain *Clostridium thermocellum* (CIP) via a flexible linker.

SEQ ID NO: 177 is the amino acid sequence of the acetyl xylan esterase from the L29P variant of the hydrolase from *Pseudomonas fluorescens* to the cellulose binding domain *Clostridium thermocellum* (CIP) via a flexible linker.

SEQ ID NO: 178 is the nucleotide sequence of the synthetic gene encoding the acetyl xylan esterase the L29P variant of the hydrolase from *Pseudomonas fluorescens* fused at its C-terminus to the *Thermotoga maritima* CBM9-2 cellulose-binding domain via a flexible linker.

SEQ ID NO: 179 is the amino acid sequence of the acetyl xylan esterase from the L29P variant of the hydrolase from *Pseudomonas fluorescens* to the *Thermotoga maritima* CBM9-2 cellulose-binding domain via a flexible linker.

SEQ ID NO: 180 is the amino acid sequence of the wild type aryl esterase from *Mycobacterium smegmatis* (U.S. Pat. No. 7,754,460; WO2005/056782; and EP1689859 B1).

SEQ ID NO: 181 is the amino acid sequence of the wild type *Pseudomonas fluorescens* esterase (U.S. Pat. No. 7,384,787).

DETAILED DESCRIPTION OF THE INVENTION

In this disclosure, a number of terms and abbreviations are used. The following definitions apply unless specifically stated otherwise.

As used herein, the articles “a”, “an”, and “the” preceding an element or component of the invention are intended to be nonrestrictive regarding the number of instances (i.e., occurrences) of the element or component. Therefore “a”, “an”, and “the” should be read to include one or at least one, and the singular word form of the element or component also includes the plural unless the number is obviously meant to be singular.

As used herein, the term “comprising” means the presence of the stated features, integers, steps, or components as referred to in the claims, but that it does not preclude the presence or addition of one or more other features, integers, steps, components or groups thereof. The term “comprising” is intended to include embodiments encompassed by the terms “consisting essentially of” and “consisting of”. Similarly, the term “consisting essentially of” is intended to include embodiments encompassed by the term “consisting of”.

As used herein, the term “about” modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term “about” also encompasses amounts that differ due to different equilibrium conditions for a composition resulting from a particular initial mixture. Whether or not modified by the term “about”, the claims include equivalents to the quantities.

Where present, all ranges are inclusive and combinable. For example, when a range of “1 to 5” is recited, the recited range should be construed as including ranges “1 to 4”, “1 to 3”, “1-2”, “1-2 & 4-5”, “1-3 & 5”, and the like.

As used herein, “contacting” refers to placing a composition in contact with the target surface for a period of time sufficient to achieve the desired result (target surface binding, peracid based effects, etc). By proviso, the target surfaces do not include body surface (such as hair, nail, skin, etc.) and oral care surface (such as gums, teeth, etc.). In one embodiment, “contacting” may refer to placing a composition comprising (or capable of producing) an efficacious concentration of peracid in contact with a target surface for a period of time sufficient to achieve the desired result. In another embodiment, “contacting” may also refer to the placing at least one component of a laundry care composition, such as one or more of the reaction components used to enzymatic perhydrolysis, in contact with a target surface. Contacting includes spraying, treating, immersing, flushing, pouring on or in, mixing, combining, painting, coating, applying, affixing to and otherwise communicating a peracid solution or a composition comprising an efficacious concentration of peracid, a solution or composition that forms an efficacious concentration of peracid or a component of the composition that forms an efficacious concentration of peracid with the target surface.

As used herein, the terms "substrate", "suitable substrate", and "carboxylic acid ester substrate" interchangeably refer specifically to:

(a) one or more esters having the structure $$[X]_mR_5$$

wherein

X is an ester group of the formula $R_6C(O)O$;

$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;

$R_5$ is a C1 to C6 linear, branched, or cyclic hydrocarbyl moiety or a five-membered cyclic heteroaromatic moiety or six-membered cyclic aromatic or heteroaromatic moiety optionally substituted with a hydroxyl group, wherein each carbon atom in $R_5$ individually comprises no more than one hydroxyl group or no more than one ester group or carboxylic acid group, and wherein $R_5$ optionally comprises one or more ether linkages;

m is an integer ranging from 1 to the number of carbon atoms in $R_5$, said one or more esters having solubility in water of at least 5 ppm at 25° C.; or (b) one or more glycerides having the structure

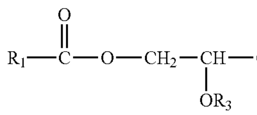

wherein $R_1$ is a C1 to C7 straight chain or branched chain alkyl optionally substituted with an hydroxyl or a C1 to C4 alkoxy group and $R_3$ and $R_4$ are individually H or $R_1C(O)$;

or (c) one or more esters of the formula

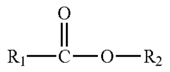

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10; or (d) one or more acetylated monosaccharides, acetylated disaccharides, or acetylated polysaccharides; or (e) any combination of (a) through (d).

As used herein, the term "peracid" is synonymous with peroxyacid, peroxycarboxylic acid, peroxy acid, percarboxylic acid and peroxoic acid.

As used herein, the term "peracetic acid" is abbreviated as "PAA" and is synonymous with peroxyacetic acid, ethaneperoxoic acid and all other synonyms of CAS Registry Number 79-21-0.

As used herein, the term "monoacetin" is synonymous with glycerol monoacetate, glycerin monoacetate, and glyceryl monoacetate.

As used herein, the term "diacetin" is synonymous with glycerol diacetate; glycerin diacetate, glyceryl diacetate, and all other synonyms of CAS Registry Number 25395-31-7.

As used herein, the term "triacetin" is synonymous with glycerin triacetate; glycerol triacetate; glyceryl triacetate, 1,2,3-triacetoxypropane; 1,2,3-propanetriol triacetate and all other synonyms of CAS Registry Number 102-76-1.

As used herein, the term "monobutyrin" is synonymous with glycerol monobutyrate, glycerin monobutyrate, and glyceryl monobutyrate.

As used herein, the term "dibutyrin" is synonymous with glycerol dibutyrate and glyceryl dibutyrate.

As used herein, the term "tributyrin" is synonymous with glycerol tributyrate, 1,2,3-tributyrylglycerol, and all other synonyms of CAS Registry Number 60-01-5.

As used herein, the term "monopropionin" is synonymous with glycerol monopropionate, glycerin monopropionate, and glyceryl monopropionate.

As used herein, the term "dipropionin" is synonymous with glycerol dipropionate and glyceryl dipropionate.

As used herein, the term "tripropionin" is synonymous with glyceryl tripropionate, glycerol tripropionate, 1,2,3-tripropionylglycerol, and all other synonyms of CAS Registry Number 139-45-7.

As used herein, the terms "acetylated sugar" and "acetylated saccharide" refer to mono-, di- and polysaccharides comprising at least one acetyl group. Examples include, but are not limited to glucose pentaacetate; xylose tetraacetate; acetylated xylan; acetylated xylan fragments; β-D-ribofuranose-1,2,3,5-tetraacetate; tri-O-acetyl-D-galactal; and tri-O-acetyl-glucal.

As used herein, the terms "hydrocarbyl", "hydrocarbyl group", and "hydrocarbyl moiety" is meant a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, pentyl, cyclopentyl, methylcyclopentyl, hexyl, cyclohexyl, benzyl, and phenyl. In a preferred embodiment, the hydrocarbyl moiety is a straight chain, branched or cyclic arrangement of carbon atoms connected by single carbon to carbon bonds and/or by ether linkages, and substituted accordingly with hydrogen atoms.

As used herein, the terms "monoesters" and "diesters" of 1,2-ethanediol; 1,2-propanediol; 1,3-propanediol; 1,2-butanediol; 1,3-butanediol; 2,3-butanediol; 1,4-butanediol; 1,2-pentanediol; 1,5-pentanediol; 2,5-pentanediol; 1,6-pentanediol; 1,2-hexanediol; 2,5-hexanediol; 1,6-hexanediol; and mixtures thereof, refer to said compounds comprising at least one ester group of the formula RC(O)O, wherein R is a C1 to C7 linear hydrocarbyl moiety. In one embodiment, the carboxylic acid ester substrate is selected from the group consisting of propylene glycol diacetate (PGDA), ethylene glycol diacetate (EDGA), and mixtures thereof.

As used herein, the term "propylene glycol diacetate" is synonymous with 1,2-diacetoxypropane, propylene diacetate, 1,2-propanediol diacetate, and all other synonyms of CAS Registry Number 623-84-7.

As used herein, the term "ethylene glycol diacetate" is synonymous with 1,2-diacetoxyethane, ethylene diacetate, glycol diacetate, and all other synonyms of CAS Registry Number 111-55-7.

As used herein, the terms "suitable enzymatic reaction mixture", "components suitable for in situ generation of a peracid", "suitable reaction components", "suitable aqueous reaction mixture", "reaction mixture", and "peracid-generating components" refer to the materials and water in which the reactants and the perhydrolytic enzyme catalyst come into contact. The peracid-generating components will include at least one perhydrolase in the form of a fusion protein that is not targeted to a human or animal body surface, at least one suitable carboxylic acid ester substrate, a source of peroxygen, and water (aqueous solution comprising a source of peroxygen, such as hydrogen peroxide). In a preferred aspect, the perhydrolase is a CE-7 perhydrolase in the form of a fusion protein targeted to a non-body surface. In a preferred embodiment, the non-body surface is a laundry care surface. In a further preferred aspect, the target surface comprises cellulose and/or a cellulosic material.

As used herein, the term "perhydrolysis" is defined as the reaction of a selected substrate with peroxide to form a peracid. Typically, inorganic peroxide is reacted with the selected substrate in the presence of a catalyst to produce the peroxycarboxylic acid. As used herein, the term "chemical perhydrolysis" includes perhydrolysis reactions in which a substrate (a peroxycarboxylic acid precursor) is combined with a source of hydrogen peroxide wherein peroxycarboxylic acid is formed in the absence of an enzyme catalyst. As used herein, the term "enzymatic perhydrolysis" includes perhydrolysis reactions in which a carboxylic acid ester substrate (a peracid precursor) is combined with a source of hydrogen peroxide and water whereby the enzyme catalyst catalyzes the formation of peracid.

As used herein, the term "perhydrolase activity" refers to the catalyst activity per unit mass (for example, milligram) of protein, dry cell weight, or immobilized catalyst weight.

As used herein, "one unit of enzyme activity" or "one unit of activity" or "U" is defined as the amount of perhydrolase activity required for the production of 1 μmol of peroxycarboxylic acid product per minute at a specified temperature.

As used herein, the terms "enzyme catalyst" and "perhydrolase catalyst" refer to a catalyst comprising an enzyme having perhydrolysis activity and may be in the form of a whole microbial cell, permeabilized microbial cell(s), one or more cell components of a microbial cell extract, partially purified enzyme, or purified enzyme. The enzyme catalyst may also be chemically modified (such as by pegylation or by reaction with cross-linking reagents). The perhydrolase catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997.

As used herein, the term "targeted perhydrolase" or "targeted perhydrolytic enzyme" will refer to a perhydrolytic fusion protein comprising a first portion having at least enzyme having perhydrolytic activity and at least one second portion comprising a peptidic component having affinity for the surface of a target material which, by proviso, does not include human hair, human skin, human nail or a human oral cavity surface. The aforementioned proviso excluding body and oral cavity surfaces has been included as there are co-pending applications directed to targeted perhydrolases for use in personal care applications (see co-owned and co-pending United States patent applications entitled "ENZYMATIC PERACID GENERATION FOR USE IN ORAL CARE PRODUCTS" (Ser. No. 13/330,261) and "ENZYMATIC PERACID GENERATION FOR USE IN HAIR CARE PRODUCTS" (Ser. No. 13/330,105). The first portion may be coupled to the peptidic component(s) having affinity for the surface of a target material through one or more optional peptide linkers. The peptidic component having affinity for a target surface is chosen to localize or target enzymatic peracid production on or near the target surface. In one embodiment, the target material is a yard, fiber, textile or fabric comprising a natural fiber, semi-synthetic fiber or synthetic fiber or blend of fibers. In another embodiment, the target surface comprises a cellulosic material such as cellulose, wood, wood pulp, paper, paper pulp, cotton, rayon, and lyocell. In another embodiment, the target material is in the form of a fiber, yarn, textile or fabric (woven or non-woven) comprising a cellulosic material.

As used herein, the term "cellulosic" refers to a material comprising or derived from cellulose. As used herein, "cellulose" is a polysaccharide consisting of a linear chain β(1→4) linked D-glucose units, typically comprising several hundred to several thousand units. Examples of cellulosic materials may include cellulose, wood, wood pulp, paper, cotton, rayon, and lyocell (a cellulose fiber obtained by an organic solvent spinning process).

As used herein, the term "cellulose-binding domain" refers to a naturally-occurring binding domain having strong affinity for cellulose this is present in many cellulose degrading enzymes (Tomme et al., supra). The non-targeted perhydrolytic enzymes described herein do not naturally contain a cellulose-binding domain. As such, a targeted perhydrolase designed to have affinity for a cellulosic material is a fusion protein comprising a perhydrolytic enzyme and at least one peptidic component having affinity for a cellulosic material. In one embodiment, the peptidic component may include the use of a cellulose-binding domain.

As used herein, "acetyl xylan esterases" refers to an enzyme (E.C. 3.1.1.72; AXEs) that catalyzes the deacetylation of acetylated xylans and other acetylated saccharides. As illustrated herein, several enzymes classified as acetyl xylan esterases are provided having significant perhydrolytic activity.

As used herein, the terms "cephalosporin C deacetylase" and "cephalosporin C acetyl hydrolase" refer to an enzyme (E.C. 3.1.1.41) that catalyzes the deacetylation of cephalosporins such as cephalosporin C and 7-aminocephalosporanic acid (Mitsushima et al., (1995) *Appl. Env. Microbiol.* 61(6):2224-2229). The amino acid sequences of several cephalosporin C deacetylases having significant perhydrolytic activity are provided herein.

As used herein, the term "*Bacillus subtilis* ATCC® 31954™" refers to a bacterial cell deposited to the American Type Culture Collection (ATCC) having international depository accession number ATCC® 31954™. *Bacillus subtilis* ATCC® 31954™ has been reported to have an ester hydrolase ("diacetinase") activity capable of hydrolyzing glycerol esters having 2 to 8 carbon acyl groups, especially diacetin (U.S. Pat. No. 4,444,886; herein incorporated by reference in its entirety). As described herein, an enzyme having significant perhydrolase activity from *B. subtilis* ATCC® 31954™ is provided as SEQ ID NO: 2 (see United States Patent Application Publication No. 2010-0041752). The amino acid sequence of the isolated enzyme has 100% amino acid identity to the cephalosporin C deacetylase provided by GENBANK® Accession No. BAA01729.1 (Mitsushima et al., supra).

As used herein, the term "*Thermotoga maritima* MSB8" refers to a bacterial cell reported to have acetyl xylan esterase activity (GENBANK® NP_227893.1; see U.S. Patent Application Publication No. 2008-0176299). The amino acid sequence of the enzyme having perhydrolase activity from *Thermotoga maritima* MSB8 is provided as SEQ ID NO: 16.

As used herein, an "isolated nucleic acid molecule", "isolated polynucleotide", and "isolated nucleic acid fragment" will be used interchangeably and refer to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid or as defined herein | Xaa | X |

For example, it is well known in the art that alterations in a gene which result in the production of a chemically equivalent amino acid at a given site, but do not affect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, and Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products.

As used herein, the terms "signature motif" and "diagnostic motif" refer to conserved structures shared among a family of enzymes having a defined activity. The signature motif can be used to define and/or identify the family of structurally-related enzymes having similar enzymatic activity for a defined family of substrates. The signature motif can be a single contiguous amino acid sequence or a collection of discontiguous, conserved motifs that together form the signature motif. Typically, the conserved motif(s) is represented by an amino acid sequence. In a preferred aspect, the signature motif is a "CE-7 signature motif", a conserved structural motif shared amount members of the carbohydrate esterase family 7 ("CE-7 carbohydrate esterases") having "perhydrolytic activity."

As used herein, the term "codon optimized", as it refers to genes or coding regions of nucleic acid molecules for transformation of various hosts, refers to the alteration of codons in the gene or coding regions of the nucleic acid molecules to reflect the typical codon usage of the host organism without altering the polypeptide for which the DNA codes.

As used herein, "synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as pertaining to a DNA sequence, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequences to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, "gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different from that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure.

As used herein, the term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., the coding sequence is under the transcriptional control of the promoter. Coding sequences can be operably linked to regulatory sequences in sense or antisense orientation.

As used herein, the term "expression" refers to the transcription and stable accumulation of sense (mRNA) or antisense RNA derived from the nucleic acid molecule of the invention. Expression may also refer to translation of mRNA into a polypeptide.

As used herein, "transformation" refers to the transfer of a nucleic acid molecule into the genome of a host organism, resulting in genetically stable inheritance. In the present invention, the host cell's genome includes chromosomal and extrachromosomal (e.g., plasmid) genes. Host organisms containing the transformed nucleic acid molecules are referred to as "transgenic", "recombinant" or "transformed" organisms.

As used herein, the terms "plasmid", "vector" and "cassette" refer to an extrachromosomal element often carrying genes which are typically not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

As used herein, the term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990)), and DNASTAR (DNASTAR, Inc. 1228 S. Park St. Madison, Wis. 53715 USA), CLUSTALW (for example, version 1.83; Thompson et al., *Nucleic Acids Research,* 22(22):4673-4680 (1994)), and the FASTA program incorporating the Smith-Waterman algorithm (W. R. Pearson, *Comput. Methods Genome Res., [Proc. Int. Symp.*] (1994), Meeting Date 1992, 111-20. Editor(s): Suhai, Sandor. Publisher: Plenum, New York, N.Y.), Vector NTI (Informax, Bethesda, Md.) and Sequencher v. 4.05. Within the context of this application it will be understood that where sequence analysis software is used for analysis, that the results of the analysis will be based on the "default values" of the program referenced, unless otherwise specified. As used herein "default values" will mean any set of values or parameters set by the software manufacturer that originally load with the software when first initialized.

As used herein, the term "biological contaminants" refers to one or more unwanted and/or pathogenic biological entities including, but not limited to, microorganisms, spores, viruses, prions, and mixtures thereof. In one embodiment, a process is provided to enzymatically produce an efficacious concentration of at least one peracid useful to reduce and/or eliminate the presence of the biological contaminants.

As used herein, the term "disinfect" refers to the process of destruction of or prevention of the growth of biological contaminants. As used herein, the term "disinfectant" refers to an agent that disinfects by destroying, neutralizing, or inhibiting the growth of biological contaminants. As used herein, the term "disinfection" refers to the act or process of disinfecting. As used herein, the term "antiseptic" refers to a chemical agent that inhibits the growth of disease-carrying microorganisms. In one aspect, the biological contaminants are pathogenic microorganisms.

As used herein, the term "sanitary" means of or relating to the restoration or preservation of health, typically by removing, preventing or controlling an agent that may be injurious to health. As used herein, the term "sanitize" means to make sanitary. As used herein, the term "sanitizer" refers to a sanitizing agent. As used herein the term "sanitization" refers to the act or process of sanitizing.

As used herein, the term "biocide" refers to a chemical agent, typically broad spectrum, which inactivates or destroys microorganisms. A chemical agent that exhibits the ability to inactivate or destroy microorganisms is described as having "biocidal" activity. Peracids can have biocidal activity. Typical alternative biocides known in the art, which may be suitable for use in the present invention include, for example, chlorine, chlorine dioxide, chloroisocyanurates, hypochlorites, ozone, acrolein, amines, chlorinated phenolics, copper salts, organo-sulphur compounds, and quaternary ammonium salts.

As used herein, the phrase "minimum biocidal concentration" refers to the minimum concentration of a biocidal agent that, for a specific contact time, will produce a desired lethal, irreversible reduction in the viable population of the targeted microorganisms. The effectiveness can be measured by the $\log_{10}$ reduction in viable microorganisms after treatment. In one aspect, the targeted reduction in viable microorganisms after treatment is at least a 3-$\log_{10}$ reduction, more preferably at least a 4-$\log_{10}$ reduction, and most preferably at least a 5-$\log_{10}$ reduction. In another aspect, the minimum biocidal concentration is at least a 6-$\log_{10}$ reduction in viable microbial cells.

As used herein, the terms "peroxygen source" and "source of peroxygen" refer to compounds capable of providing hydrogen peroxide at a concentration of about 1 mM or more when in an aqueous solution including, but not limited to, hydrogen peroxide, hydrogen peroxide adducts (e.g., urea-hydrogen peroxide adduct (carbamide peroxide)), perborates, and percarbonates. As described herein, the concentration of the hydrogen peroxide provided by the peroxygen compound in the aqueous reaction formulation is initially at least 0.1 mM or more upon combining the reaction components. In one embodiment, the hydrogen peroxide concentration in the aqueous reaction formulation is at least 0.5 mM. In another embodiment, the hydrogen peroxide concentration in the aqueous reaction formulation is at least mM. In another embodiment, the hydrogen peroxide concentration in the aqueous reaction formulation is at least 100 mM. In another embodiment, the hydrogen peroxide concentration in the aqueous reaction formulation is at least 200 mM. In another embodiment, the hydrogen peroxide concentration in the aqueous reaction formulation is 500 mM or more. In yet another embodiment, the hydrogen peroxide concentration in the aqueous reaction formulation is 1000 mM or more. The molar ratio of the hydrogen peroxide to enzyme substrate, e.g., triglyceride, ($H_2O_2$:substrate) in the aqueous reaction formulation may be from about 0.002 to 20, preferably about 0.1 to 10, and most preferably about 0.5 to 5.

As used herein, the term "oligosaccharide" refers to compounds containing between 2 and at least 24 monosaccharide units linked by glycosidic linkages. The term "monosaccharide" refers to a compound of empirical formula $(CH_2O)_n$, where n≥3, the carbon skeleton is unbranched, each carbon atom except one contains a hydroxyl group, and the remaining carbon atom is an aldehyde or ketone at carbon atom 1. The term "monosaccharide" also refers to intracellular cyclic hemiacetal or hemiketal forms.

As used herein, the term "excipient" refers to inactive substance used as a carrier for active ingredients in a formulation. The excipient may be used to stabilize the active ingredient in a formulation, such as the storage stability of the active ingredient. Excipients are also sometimes used to bulk up formulations that contain active ingredients. As described herein, the "active ingredient" is typically the peracid produced by the perhydrolytic enzyme. In some embodiments, the active ingredient may be an enzyme having perhydrolytic activity, a peracid produced by the perhydrolytic enzyme under suitable reaction conditions, or a combination thereof.

The term "substantially free of water" will refer to a concentration of water in a formulation that does not adversely impact the storage stability of the enzyme or an enzyme powder when present in the carboxylic acid ester. The carboxylic acid ester may contain a very low concentration of water, for example, triacetin typically has between 180 ppm and 300 ppm of water. In one embodiment, the perhydrolytic enzyme is stored in the carboxylic acid ester substrate that is substantially free of water. In a further embodiment, "substantially free of water" may mean less than 2000 ppm, preferably less than 1000 ppm, more preferably less than 500 ppm, and even more preferably less than 250 ppm of water in the formulation comprising the enzyme (or enzyme powder) and the carboxylic acid ester. In one embodiment, the perhydrolytic enzyme may be stored in an aqueous solution if the generation system is designed such that the enzyme is stable in the aqueous solution (for example, a solution that does not contain a significant concentration of a carboxylic acid ester substrate capable of being hydrolyzed by the enzyme during storage). In one embodiment, the perhydrolytic enzyme may be stored in a mixture comprising the carboxylic acid ester substrate that is substantially free of water and one or more buffers (e.g., sodium and/or potassium salts of bicarbonate, citrate, acetate, phosphate, pyrophosphate, methylphosphonate, succinate, malate, fumarate, tartrate, and maleate).

As used herein, the term "benefit agent" refers to a material that promotes or enhances a useful advantage, a favorable/desirable effect or benefit. The peracid benefit agent generated using the present targeted perhydrolase-based compositions and methods provide a benefit to a target material (hard surfaces, wood pulp, paper, paper pulp, fibers, yarns, textile, and fabrics as well as polymers and copolymers used to produce fibers) such as disinfecting, sanitizing, bleaching, whitening, destaining, deodorizing, and any combination thereof with the proviso that the target material is not human or animal body surface (hair, skin, nails) as well as surfaces within an oral cavity. In one embodiment, a process is provided whereby a peracid benefit agent is enzymatically generated by a targeted perhydrolase on a textile or article of clothing to achieve a desired benefit, such as disinfecting, sanitizing, bleaching, destaining, deodorizing, and any combination thereof.

Enzymes Having Perhydrolytic Activity

Enzymes having perhydrolytic activity may include some enzymes classified as lipases, proteases, esterases, acyl transferases, aryl esterases, carbohydrate esterases, and combinations so long as the enzyme has perhydrolytic activity for one or more of the present substrates. Examples may include, but are not limited to perhydrolytic proteases (subtilisin Carlsberg variant; U.S. Pat. No. 7,510,859), perhydrolytic aryl esterases (*Pseudomonas fluorescens*; SEQ ID NO: 163 [L29P variant] and 181 [wild type]; U.S. Pat. No. 7,384,787), the perhydrolytic aryl esterase/acyl transferases from *Mycobacterium smegmatis* (SEQ ID NOs: 162 [S54V variant] and 180 [wild type]; U.S. Pat. No. 7,754,460; WO2005/056782; and EP1689859 B1), and the perhydrolytic carbohydrate esterases. In a preferred aspect, the perhydrolytic carbohydrate esterase is a CE-7 carbohydrate esterase. In another embodiment, the perhydrolytic enzyme does not include by proviso, perhydrolytic proteases.

In one embodiment, suitable perhydrolases may include enzymes comprising an amino acid sequence having at least 30%, 33%, 40%, 50%, 60%, 70%, 80%, 85%, 90%, 91%, 92%, 93%, 94%, 95%, 96%, 97%, 98%, or 99% amino acid identity to any of the amino acid sequences reported herein.

In another embodiment, the suitable perhydrolases may include enzymes comprising an amino acid sequence having at least 30%, 33%, 40%, 50%, 60%, 70%, 80%, 85%, 90%, 91%, 92%, 93%, 94%, 95%, 96%, 97%, 98%, or 99% amino acid identity to SEQ ID NO: 162, 163, 180, and 181. In one embodiment, the perhydrolytic enzyme comprises an amino acid sequence having at least 95% identity to SEQ ID NO: 162.

In another embodiment, substantially similar perhydrolytic enzymes may include those encoded by polynucleotide sequences that hybridize under highly stringent hybridization conditions (0.1×SSC, 0.1% SDS, 65° C. and washed with 2×SSC, 0.1% SDS followed by a final wash of 0.1×SSC, 0.1% SDS, 65° C.) to the polynucleotide sequences encoding any of the present perhydrolytic enzymes.

CE-7 Perhydrolases

In one embodiment, the present compositions and methods comprise at least one fusion protein having at least one perhydrolytic enzyme having perhydrolytic activity that is structurally classified as members of the carbohydrate family esterase family 7 (CE-7 family) of enzymes (see Coutinho, P.M., Henrissat, B. "Carbohydrate-active enzymes: an integrated database approach" in *Recent Advances in Carbohydrate Bioengineering*, H.J. Gilbert, G. Davies, B. Henrissat and B. Svensson eds., (1999) The Royal Society of Chemistry, Cambridge, pp. 3-12.). The CE-7 family of enzymes has been demonstrated to be particularly effective for producing peroxycarboxylic acids from a variety of carboxylic acid ester substrates when combined with a source of peroxygen (WO2007/070609 and U.S. Patent Application Publication Nos. 2008-0176299, 2008-176783, 2009-0005590, 2010-0041752, and 2010-0087529, as well as U.S. patent application Ser. No. 12/571,702 and U.S. Provisional Patent Application No. 61/318,016 to DiCosimo et al.; each incorporated herein by reference).

Members of the CE-7 family include cephalosporin C deacetylases (CAHs; E.C. 3.1.1.41) and acetyl xylan esterases (AXEs; E.C. 3.1.1.72). Members of the CE-7 esterase family share a conserved signature motif (Vincent et al., *J. Mol. Biol.,* 330:593-606 (2003)). Perhydrolases comprising the CE-7 signature motif ("CE-7 perhydrolases") and/or a substantially similar structure are suitable for the preparation and use as perhydrolytic fusion peptides ("targeted perhydrolase") in the compositions and methods described herein. Means to identify substantially similar biological molecules are well known in the art (e.g., sequence alignment protocols, nucleic acid hybridizations and/or the presence of a conserved signature motif; with the proviso that substantially similar polynucleotides and polypeptides encoding or associated with perhydrolytic enzymes are identified using the sequences associated with the perhydrolytic enzyme without the targeting domain). In one aspect, the perhydrolase includes an enzyme comprising the CE-7 signature motif and at least 20%, preferably at least 30%, more preferably at least 33%, more preferably at least 40%, more preferably at least 42%, more preferably at least 50%, more preferably at least 60%, more preferably at least 70%, more preferably at least 80%, more preferably at least 90%, and most preferably at least 90%, 91%, 92%, 93%, 94%, 95%, 96%, 97%, 98%, or 99% amino acid identity to one of the sequences provided herein.

As used herein, the phrase "enzyme is structurally classified as a CE-7 enzyme", "CE-7 perhydrolase" or "structurally classified as a carbohydrate esterase family 7 enzyme" will be used to refer to enzymes having perhydrolysis activity which are structurally classified as a CE-7 carbohydrate esterase. This family of enzymes can be defined by the presence of a signature motif (Vincent et al., supra). The signature motif for CE-7 esterases comprises three conserved motifs (residue position numbering relative to reference sequence SEQ ID NO: 2; the CE-7 perhydrolase from *B. subtilis* ATCC® 31954™):

a) Arg118-Gly119-Gln120;

b) Gly179-Xaa180-Ser181-Gln182-Gly183; and c) His298-Glu299.

Typically, the Xaa at amino acid residue position 180 is glycine, alanine, proline, tryptophan, or threonine. Two of the three amino acid residues belonging to the catalytic triad are in bold. In one embodiment, the Xaa at amino acid residue position 180 is selected from the group consisting of glycine, alanine, proline, tryptophan, and threonine.

Further analysis of the conserved motifs within the CE-7 carbohydrate esterase family indicates the presence of an additional conserved motif (LXD at amino acid positions 267-269 of SEQ ID NO: 2) that may be used to further define a perhydrolase belonging to the CE-7 carbohydrate esterase family. In a further embodiment, the signature motif defined above may include an additional (fourth) conserved motif defined as:

Leu267-Xaa268-Asp269.

The Xaa at amino acid residue position 268 is typically isoleucine, valine, or methionine. The fourth motif includes the aspartic acid residue (bold) belonging to the catalytic triad (Ser181-Asp269-His298).

The targeted CE-7 perhydrolases are fusion proteins having at least one peptidic component having affinity for at least one target surface. In one embodiment, alignments used to determine if a targeted perhydrolase (fusion protein) comprises the CE-7 signature motif will be based on the amino acid sequence of the perhydrolytic enzyme without the peptidic component having the affinity for a body surface.

A number of well-known global alignment algorithms (i.e., sequence analysis software) may be used to align two or more amino acid sequences representing enzymes having perhydrolase activity to determine if the enzyme is comprised of the CE-7 signature motif. The aligned sequence(s) are compared to the reference sequence (SEQ ID NO: 2) to determine the existence of the signature motif. In one embodiment, a CLUSTAL alignment (such as CLUSTALW) using a reference amino acid sequence (as used herein the perhydrolase sequence (SEQ ID NO: 2) from the *Bacillus subtilis* ATCC® 31954™) is used to identify perhydrolases belonging to the CE-7 esterase family. The relative numbering of the conserved amino acid residues is based on the residue numbering of the reference amino acid sequence to account for small insertions or deletions (for example, typically five amino acids of less) within the aligned sequence.

Examples of other suitable algorithms that may be used to identify sequences comprising the CE-7 signature motif (when compared to the reference sequence) may include, but are not limited to, Needleman and Wunsch (*J. Mol. Biol.* 48, 443-453 (1970); a global alignment tool) and Smith-Waterman (*J. Mol. Biol.* 147:195-197 (1981); a local alignment tool). In one embodiment, a Smith-Waterman alignment is implemented using default parameters. An example of suitable default parameters include the use of a BLOSUM62 scoring matrix with GAP open penalty=10 and a GAP extension penalty=0.5.

Enzymes having relatively low overall amino acid identity to SEQ ID NO: 2 (while retaining the CE-7 signature motif) may exhibit significant perhydrolase activity. In one embodiment, suitable perhydrolases may include enzymes comprising the CE-7 signature motif and at least 20%, preferably at least 30%, 33%, 40%, 50%, 60%, 70%, 80%, 85%, 90%, 91%, 92%, 93%, 94%, 95%, 96%, 97%, 98%, or 99% amino acid identity to SEQ ID NO: 2.

Examples of suitable CE-7 carbohydrate esterases having perhydrolytic activity include, but are not limited to, enzymes having an amino acid sequence such as SEQ ID NOs: 2, 4, 6, 8, 10, 12, 14, 16, 18, 20, 22, 24, 26, 27, 28, 29, 30, 31, 32, 33, 34, 35, 36, 38, 40, 42, 44, 46, 48, 50, 52, 54, 56, 58, 60, 62, and 64. In one embodiment, the enzyme comprises an amino acid sequence selected from the group consisting of 14, 16, 27, 28, 29, 30, 31, 32, 33, 34, 35, 36, 46, 48, 50, 52, 54, 56, 58, 60, 62, and 64.

As used herein, the term "CE-7 variant", "variant perhydrolase" or "variant" will refer to CE-7 perhydrolases having a genetic modification that results in at least one amino acid addition, deletion, and/or substitution when compared to the corresponding enzyme (typically the wild type enzyme) from which the variant was derived; so long as the CE-7 signature motif and the associated perhydrolytic activity are maintained. CE-7 variant perhydrolases may also be used in the present compositions and methods. Examples of CE-7 variants are provided as SEQ ID NOs: 27, 28, 29, 30, 31, 32, 48, 50, 52, 54, 56, 58, 60, 62, and 64. In one embodiment, the variants may include SEQ ID NOs: 27, 28, 50, 52, 54, 56, 58, 60, 62, and 64.

The skilled artisan recognizes that substantially similar CE-7 perhydrolase sequences (retaining the signature motifs) may also be used in the present compositions and methods. In one embodiment, substantially similar sequences are defined by their ability to hybridize, under highly stringent conditions with the nucleic acid molecules associated with sequences exemplified herein. In another embodiment, sequence alignment algorithms may be used to define substantially similar enzymes based on the percent identity to the DNA or amino acid sequences provided herein.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J. and Russell, D., T. *Molecular Cloning: A Laboratory Manual*, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms. Post-hybridization washes typically determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of conditions uses higher temperatures in which the washes are identical to those above except for the temperature of the final two 30 min washes in 0.2×SSC, 0.5% SDS was increased to 60° C. Another preferred set of highly stringent hybridization conditions is 0.1×SSC, 0.1% SDS, 65° C. and washed with 2×SSC, 0.1% SDS followed by a final wash of 0.1×SSC, 0.1% SDS, 65° C.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (Sambrook and Russell, supra). For hybridizations with shorter nucleic acids, i.e., oligonucleotides, the position of mismatches becomes more important, and the length of the oligonucleotide determines its specificity (Sambrook and Russell, supra). In one aspect, the length for a hybridizable nucleic acid is at least about 10 nucleotides. Preferably, a minimum length for a hybridizable nucleic acid is at least about 15 nucleotides in length, more preferably at least about 20 nucleotides in length, even more preferably at least 30 nucleotides in length, even more preferably at least 300 nucleotides in length, and most preferably at least 800 nucleotides in length. Furthermore, the skilled artisan will recognize that the temperature and wash solution salt concentration may be adjusted as necessary according to factors such as length of the probe.

As used herein, the term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs. Sequence alignments and percent identity calculations may be performed using the Megalign program of the LASERGENE bioinformatics computing suite (DNASTAR Inc., Madison, Wis.), the AlignX program of Vector NTI v. 7.0 (Informax, Inc., Bethesda, Md.), or the EMBOSS Open Software Suite (EMBL-EBI; Rice et al., *Trends in Genetics* 16, (6):276-277 (2000)). Multiple alignment of the sequences can be performed using the CLUSTAL method (such as CLUSTALW; for example version 1.83) of alignment (Higgins and Sharp, CABIOS, 5:151-153 (1989); Higgins et al., Nucleic Acids Res. 22:4673-4680 (1994); and Chema et al., *Nucleic Acids Res* 31 (13):3497-500 (2003)), available from the European Molecular Biology Laboratory via the European Bioinformatics Institute) with the default parameters. Suitable parameters for CLUSTALW protein alignments include GAP Existence penalty=15, GAP extension=0.2, matrix=Gonnet (e.g., Gonnet250), protein ENDGAP=−1, protein GAPDIST=4, and KTUPLE=1. In one embodiment, a fast or slow alignment is used with the default settings where a slow alignment is preferred. Alternatively, the parameters using the CLUSTALW method (e.g., version 1.83) may be modified to also use KTUPLE=1, GAP PENALTY=10, GAP extension=1, matrix=BLOSUM (e.g., BLOSUM64), WINDOW=5, and TOP DIAGONALS SAVED=5.

In one aspect, suitable isolated nucleic acid molecules encode a polypeptide having an amino acid sequence that is at least about 20%, preferably at least 30%, 33%, 40%, 50%, 60%, 70%, 80%, 85%, 90%, 91%, 92%, 93%, 94%, 95%, 96%, 97%, 98%, or 99% identical to the amino acid sequences reported herein. In another aspect, suitable isolated nucleic acid molecules encode a polypeptide having an amino acid sequence that is at least about 20%, preferably at least 30%, 33%, 40%, 50%, 60%, 70%, 80%, 85%, 90%, 91%, 92%, 93%, 94%, 95%, 96%, 97%, 98%, or 99% identical to the amino acid sequences reported herein; with the proviso that the polypeptide retains the CE-7 signature motif. Suitable nucleic acid molecules not only have the above homologies, but also typically encode a polypeptide having about 300 to about 340 amino acids, more preferably about 310 to about 330 amino acids, and most preferably about 318 to about 325 amino acids in length wherein each polypeptide is characterized as having perhydrolytic activity.

Single Chain Peptides Having Affinity for a Target Surface

Single chain peptides lacking an immunoglobulin fold that are capable of binding to a target surface are referred to as "target surface-binding peptides" and may include, for example, peptides that bind to any target surface with the proviso that the target surface does not include human hair, human skin, human nail, or a human oral cavity surface (such as tooth enamel, tooth pellicle, gums, etc.).

Short peptides having strong affinity for at least one body surface or benefit agent have been reported (U.S. Pat. Nos. 7,220,405; 7,309,482; 7,285,264 and 7,807,141; U.S. Patent Application Publication Nos. 2005-0226839; 2007-0196305; 2006-0199206; 2007-0065387; 2008-0107614; 2007-0110686; 2006-0073111; 2010-0158846 and 2010-0158847; and published PCT applications WO2008/054746; WO2004/048399, and WO2008/073368). These peptides have been used to construct peptide-based reagents capable of binding benefit agents to a target body surface for use primarily in cosmetic applications.

Biopanned peptides having affinity for various natural and synthetic polymeric materials such as cotton fabrics, polyester/cotton blends, cellulose acetate, paper, polymethyl methacrylate, polyesters such as Nylon, polypropylene, polyethylene, polystyrene, and polytetrafluoroethylene have been reported (U.S. Pat. Nos. 7,709,601; 7,700,716; and 7632919; and U.S. Patent Application Publication NOs. 2005-0054752; 2007-0265431; 2007-0264720; 2007-0141628; and 2010-0158823, and U.S. patent application Ser. Nos. 12/785,694; 12/778,167; 12/778,169; 12/778,174; 12/778,178; 12/778,180; 12/778,186; 12/778,194; and 12/778,199).

Short peptides having affinity for various pigments, polymers, cellulosic materials, and print media have also been reported in the creation of diblock and triblock dispersants (United States Patent Application Publication No. 2005-0054752). However, the use of such peptides to couple an active perhydrolase to the surface of a target material (i.e., "targeted perhydrolases") for the production of a peracid benefit agent has not been described. In a preferred aspect, the use of a targeted CE-7 perhydrolase to the surface of a target material for the production of a peracid benefit agent has not been described.

In some embodiments, target surface-binding domains are comprised of target surface-binding peptides that are up to about 60 amino acids in length. In one embodiment the target surface-binding peptides are 5 to 60 amino acids in length. In other embodiments the target surface-binding peptides are 7 to 50 amino acids in length or 7 to 30 amino acids in length. In still other embodiments are the target surface-binding peptides that are 7 to 27 amino acids in length.

In some embodiments, the use of multiple target surface-binding peptides can provide a peptidic component (a target surface-binding "domain") that is more durable than any individual target surface-binding peptide. In some embodiments, the target surface-binding domain comprises from 2 to about 50, preferably 2 to about 25, more preferably 2 to about 10, and most preferably 2 to about 5 target surface-binding peptides.

Multiple peptidic binding elements can be linked directly together or linked together using one or more peptide spacers/linkers. Certain peptide spacers are from 1 to 100 or 1 to 50 amino acids in length. In some embodiments, the peptide spacers are about 1 to about 25, 3 to about 40, or 3 to about 30 amino acids in length. In other embodiments are spacers that are about 5 to about 20 amino acids in length. Examples of peptide linkers are provided by amino acid sequences 128, 129, 130, 131, 132, 133, 134, 135, 136, 137, 138, 139, 140, and 143. The peptide spacers/linkers may be repeated up to 10 times.

Additional target surface-binding domains, and the shorter target surface-binding peptides of which they are comprised, can be identified using any number of methods known to those skilled in the art, including, for example, any known biopanning techniques such as phage display, bacterial display, yeast display, ribosome display, mRNA display, and combinations thereof. Typically a random or substantially random (in the event bias exists) library of peptides is biopanned against the target surface to identify peptides within the library having affinity for the target surface. Short target surface-binding peptides and/or target surface-binding domains may also be empirically generated to have an electrostatic affinity for the target surface.

The generation of random libraries of peptides is well known and may be accomplished by a variety of techniques including, bacterial display (Kemp, D. J.; *Proc. Natl. Acad. Sci. USA* 78(7):4520-4524 (1981), and Helfman et al., *Proc. Natl. Acad. Sci. USA* 80(1):31-35, (1983)), yeast display (Chien et al., *Proc Natl. Acad. Sci. USA* 88(21):9578-82 (1991)), combinatorial solid phase peptide synthesis (U.S. Pat. Nos. 5,449,754; 5,480,971; 5,585,275; and 5,639,603), and phage display technology (U.S. Pat. Nos. 5,223,409; 5,403,484; 5,571,698 and 5,837,500); ribosome display (U.S. Pat. Nos. 5,643,768; 5,658,754; and 7,074,557), and mRNA display technology (PROFUSION™; see U.S. Pat. Nos. 6,258,558; 6,518,018; 6,281,344; 6,214,553; 6,261,804; 6,207,446; 6,846,655; 6,312,927; 6,602,685; 6,416,950; 6,429,300; 7,078,197; and 6,436,665).

Targeted Perhydrolases

As used herein, the term "targeted perhydrolase" and "targeted enzyme having perhydrolytic activity" will refer to a fusion proteins comprising at least one perhydrolytic enzyme (wild type or variant thereof) fused/coupled to at least one peptidic component having affinity for a surface of a target material; wherein the surface is not a body surface or an oral cavity surface. In a preferred aspect, the target surface is a The perhydrolytic enzyme within the targeted perhydrolase may be any perhydrolytic enzyme and may include lipases, proteases, esterases, acyl transferases, aryl esterases, carbohydrate esterases, and combinations so long as the enzyme has perhydrolytic activity for one or more of the present substrates. Examples may include, but are not limited to perhydrolytic proteases (subtilisin variant; U.S. Pat. No. 7,510,859), perhydrolytic esterase (*Pseudomonas fluorescens*; U.S. Pat. No. 7,384,787; SEQ ID NO: 163 and 181), and perhydrolytic aryl esterase (*Mycobacterium smegmatis*; U.S. Pat. No. 7,754,460; WO2005/056782; and EP1689859 B1; SEQ ID NOs: 162 [S54V variant] and 180 [wild type]).

As used herein the terms "peptidic component", "peptidic component having affinity for a target surface", and "TSBD" will refer to component of the fusion protein that is not part of the perhydrolytic enzyme comprising at least one polymer of two or more amino acids joined by a peptide bond; wherein the component has affinity for a surface of a target material; wherein the surface is not a body surface or an oral cavity surface.

In one embodiment, the target material is the surface of wood, wood pulp, a fiber, a yarn, a textile or garment made from natural fibers, semi-synthetic fibers, synthetic fibers or a fiber blend. In one embodiment, the target material is a cellulosic material such as cellulose, wood, wood pulp, paper, paper pulp, cotton, rayon, and lyocell (a cellulose fiber obtained by an organic solvent spinning process). In another embodiment, the target material is a cellulosic material, a polymer or copolymer capable of being used in paper, fibers, yarns, textiles (woven or non-woven) or garments. Examples of these materials may include, but are not limited to, polymethyl methacrylate, polypropylene, polytetrafluoroethylene, polyethylene, polyamides (Nylon), polystyrene, cellulose acetate, cotton, polyester/cotton blends, wood pulp, paper, and cellulose.

The peptidic component may have affinity for a cellulosic material. As such, the peptidic component may be a naturally occurring cellulose-binding domain (Tomme et al., supra), a target-binding domain derived from a naturally-occurring cellulose-binding domain, or a mimic cellulose binding domain (EP1224270B1). Examples of cellulose-binding domains may belong to various classes and families (Guillen et al., *Appl. Microbiol. Biotechnol.* (2010) V85 pp. 1241-1249). They may be obtained from various microorganisms including, but not limited to, *Clostridium thermocellum, Clostridium cellulovorans, Bacillus* sp., *Thermotoga maritima*, and *Caldicellulosiruptor saccharolyticus*. In one embodiment, the cellulose-binding domain is obtained from *Clostridium thermocellum* ("CIP", class 3 superfamily of cellulose binding domains; a CBD3), *Clostridium cellulovorans* (CBM17, carbohydrate binding domain superfamily 17), *Bacillus* sp. (CBM28, carbohydrate binding motif superfamily 28), *Thermotoga maritima* (CBM9-2, cellulose binding domains class 9; CBM9) or *Caldicellulosiruptor saccharolyticus* (CBD1, class 3 superfamily of cellulose binding domains; a CBD3). In one embodiment, the peptidic component having affinity for the target surface is a cellulose-binding domain belonging to cellulose-binding domain family CBM9, CBM17, CBM28, or CBD3. In a further embodiment, the cellulose-binding domain comprises a polypeptide having an amino acid sequence selected from the group consisting of SEQ ID NOs: 149, 152, 155, 158 and 161; wherein SEQ ID NOs: 149, 152, 155, 158, and 161 may optionally not include on their C-terminus peptide linkers and/or hexa-his tags.

In one embodiment, the peptidic component having affinity for a target surface may be an antibody, an $F_{ab}$ antibody fragment, a single chain variable fragment (scFv) antibody, a *Camelidae* antibody (Muyldermans, S., *Rev. Mol. Biotechnol.* (2001) 74:277-302), a non-antibody scaffold display protein (Hosse et al., *Prot. Sci.* (2006) 15(1): 14-27 and Binz, H. et al. (2005) *Nature Biotechnology* 23, 1257-1268 for a review of various scaffold-assisted approaches) or a single chain polypeptide lacking an immunoglobulin fold. In another aspect, the peptidic component having affinity for a target surface (wherein the surface is not a body surface or an oral cavity surface) is a single chain peptide lacking an immunoglobulin fold (i.e., a target surface-binding peptide or a target surface-binding domain comprising at least one target surface-binding peptide having affinity for a target surface; wherein the surface is not a body surface or an oral cavity surface. In a preferred embodiment, the peptidic component is a single chain peptide comprising one or more target surface-binding peptides having affinity for a target surface.

The peptidic component having affinity for the target surface may be separated from the perhydrolytic enzyme by an optional peptide linker. Certain peptide linkers/spacers are from 1 to 100 or 1 to 50 amino acids in length. In some embodiments, the peptide spacers are about 1 to about 25, 3 to about 40, or 3 to about 30 amino acids in length. In other embodiments are spacers that are about 5 to about 20 amino acids in length. Multiple peptide linkers may be used. In one embodiment, at least one peptide linker is present and may be repeated up to 10 times.

In one embodiment, the targeted perhydrolase is a fusion protein having perhydrolytic activity comprising the general structure $$PAH\text{-}[L]_y\text{-}TSBD$$

or $$TSBD\text{-}[L]_y\text{-}PAH$$

wherein

PAH is the enzyme having perhydrolytic activity;

TSBD is a peptidic component having affinity for a surface of a target material; wherein the surface is not a body surface or an oral cavity surface;

L is an optional peptide linker ranging from 1 to 100 amino acids in length; and y is 0 or 1.

In a preferred aspect, the target material is of wood, wood pulp, a fiber, a yarn, a textile or garment made from natural fibers, semi-synthetic fibers, synthetic fibers or a fiber blend. In one embodiment, the target material is a cellulosic material such as cellulose, wood, wood pulp, paper, cotton, rayon, and lyocell (a cellulose fiber obtained by an organic solvent spinning process). In another embodiment, the target material is a cellulosic material, a polymer or copolymer capable of being used in paper, fibers, yarns, textiles (woven or non-woven) or garments.

Examples single chain peptides having affinity for various materials have been previous described. For example, SEQ ID NOs: 65-127 are amino acid sequences of various peptides having affinity for various polymers and cellulosic materials. SEQ ID NOs: 65-79 are examples of peptides having affinity for polymethyl methacrylate, SEQ ID NOs: 80-86 are examples of peptides having affinity for polypropylene, SEQ ID NOs: 87-95 are examples of peptides having affinity for polytetrafluoroethylene, SEQ ID NOs: 96-102 are examples of peptides having affinity for polyethylene, SEQ ID NOs: 103-108 are examples of peptides having affinity for polyamides (Nylon), SEQ ID NOs 109-111 are examples of peptides having affinity for polystyrene, SEQ ID NOs: 112-115 are examples of peptides having affinity for cellulose acetate, SEQ ID NOs: 116-117 are examples of peptides having affinity for cotton, SEQ ID NOs: 116 and 118 are examples of peptides having affinity for polyester/cotton blends, SEQ ID NOs: 119-121 are examples of peptides having affinity for paper, and SEQ ID NOs: 122-127 are examples of peptides having affinity for cellulose.

The peptidic component having affinity for the surface of the target material may be separated from the perhydrolase by an optional peptide linker. Certain peptide linkers/spacers are from 1 to 100 or 1 to 50 amino acids in length. In some embodiments, the peptide spacers are about 1 to about 25, 3 to about 40, or 3 to about 30 amino acids in length. In other embodiments are spacers that are about 5 to about 20 amino acids in length. Multiple peptide linkers may be used. In one embodiment, at least one peptide linker is present and may be repeated up to 10 times. As such, examples of targeted perhydrolases may include, but are not limited to, any of perhydrolases having an amino acid sequence selected from the group consisting of SEQ ID NOs 2, 4, 6, 8, 10, 12, 14, 16, 18, 20, 22, 24, 26, 27, 28, 29, 30, 31, 32, 33, 34, 35, 36, 38, 40, 42, 44, 46, 48, 50, 52, 54, 56, 58, 60, 62, 64, 162, 163, 180, and 181 coupled to a peptidic component having affinity for the surface of a target material.

In another embodiment, the targeted perhydrolase comprises an amino acid sequence selected from the group consisting of SEQ ID NOs 2, 4, 6, 8, 10, 12, 14, 16, 18, 20, 22, 24, 26, 27, 28, 29, 30, 31, 32, 33, 34, 35, 36, 38, 40, 42, 44, 46, 48, 50, 52, 54, 56, 58, 60, 62, 64, 162, 163, 180, and 181 coupled to one or more cellulose-binding domains. In another aspect, the targeted perhydrolase comprises a non-CE-7 perhydrolase having an amino acid sequence selected from the group consisting of SEQ ID NOs 162, 163, 180, and 181 coupled to one or more cellulose-binding domains having an amino acid sequence selected from the group consisting of SEQ ID NO: 149, 152, 155, 158, and 161. In yet another aspect, the targeted perhydrolase comprises an amino acid sequence selected from the group consisting of SEQ ID NOs 148, 151, 154, 157, 160, 165, 167, 169, 171, 173, 175, 177, and 179. In yet another aspect, the targeted perhydrolase comprises an amino acid sequence selected from the group consisting of SEQ ID NOs 171, 173, 175, 177, and 179.

Targeted CE-7 Perhydrolases

In one embodiment, the targeted perhydrolase is a CE-7 perhydrolase. As used herein, the terms "targeted CE-7 perhydrolase" and "targeted CE-7 carbohydrate esterase" refer to fusion proteins comprising at least one CE-7 perhydrolase (wild type or variant perhydrolase) fused/coupled to at least one peptidic component having affinity for a target surface.

In one embodiment, a fusion peptide is provided comprising the general structure:

PAH-[L]$_y$-TSBD or

TSBD-[L]$_y$-PAH;

wherein

PAH is a CE-7 carbohydrate esterase having perhydrolytic activity; the PAH having a CE-7 signature motif that aligns with a reference sequence SEQ ID NO: 2, said CE-7 signature motif comprising:

i) an RGQ motif that aligns with amino acid residues 118-120 of SEQ ID NO:2;

ii) a GXSQG motif that aligns with amino acid residues 179-183 of SEQ ID NO:2; and iii) an HE motif that aligns with amino acid residues 298-299 of SEQ ID NO:2;

TSBD is a peptidic component having affinity for a surface on a target material; wherein the target material is not human hair, human skin, human nail or a human oral cavity surface;

L is an optional peptide linker; and y is an integer ranging from 0 to 10.

In anther embodiment, the CE-7 signature motif further includes an LXD motif that aligns with amino acid residues 267-269 of SEQ ID NO: 2.

It should be noted that the alignment to determine the presence of the CE-7 signature motif is conducted without the optional linker or the TSBD. In one embodiment, the alignment is conducted using CLUSTALW.

In one embodiment, the target material is the surface of wood, wood pulp, a fiber, a yarn, a textile or garment made from natural fibers, semi-synthetic fibers, synthetic fibers or a fiber blend. In one embodiment, the target material is a cellulosic material such as cellulose, wood, wood pulp, paper, paper pulp, cotton, rayon, and lyocell (a cellulose fiber obtained by an organic solvent spinning process). In another embodiment, the target material is a cellulosic material, a polymer or copolymer capable of being used in paper, fibers, yarns, textiles (woven or non-woven) or garments. Examples of these materials may include, but are not limited to, polymethyl methacrylate, polypropylene, polytetrafluoroethylene, polyethylene, polyamides (Nylon), polystyrene, cellulose acetate, cotton, polyester/cotton blends, wood pulp, paper, and cellulose.

The peptidic component may have affinity for a cellulosic material. As such, the peptidic component may be a naturally occurring cellulose-binding domain (Tomme et al., supra), a target-binding domain derived from a naturally-occurring cellulose-binding domain, or a mimic cellulose binding domain (EP1224270B1). Examples of cellulose-binding domains the may be coupled to CE-7 perhydrolase may be obtained from microorganisms including, but not limited to, *Clostridium thermocellum, Clostridium cellulovorans, Bacillus* sp., *Thermotoga maritima*, and *Caldicellulosiruptor saccharolyticus*. In one embodiment, the cellulose-binding domain is obtained from *Clostridium thermocellum* (e.g., "CIP"), *Clostridium cellulovorans* CBM17, *Bacillus* sp. CBM28, *Thermotoga maritima* CBM9-2 or *Caldicellulosiruptor saccharolyticus* CBD1. In a further embodiment, the cellulose-binding domain comprises a polypeptide having an amino acid sequence selected from the group consisting of SEQ ID NOs: 149, 152, 155, 158 and 161; wherein SEQ ID NOs: 149, 152, 155, 158, and 161 may optionally not include on their C-terminus peptide linkers and/or hexa-his tags.

In one embodiment, the peptidic component having affinity for the surface of a target material coupled to the CE-7 perhydrolase may be an antibody, an $F_{ab}$ antibody fragment, a single chain variable fragment (scFv) antibody, a *Camelidae* antibody (Muyldermans, S., *Rev. Mol. Biotechnol.* (2001) 74:277-302), a non-antibody scaffold display protein (Hosse et al., *Prot. Sci.* (2006) 15(1): 14-27 and Binz, H. et al. (2005) *Nature Biotechnology* 23, 1257-1268 for a review of various scaffold-assisted approaches) or a single chain polypeptide lacking an immunoglobulin fold. In another aspect, the peptidic component having affinity for the target surface is a single chain peptide lacking an immunoglobulin fold (i.e., a target surface-binding peptide or a target surface-binding domain comprising at least one target surface-binding peptide). In another embodiment, the peptidic component is a single chain peptide comprising one or more target surface-binding peptides having affinity for the surface of a target material.

CE-7 perhydrolases may be coupled to one or more single chain peptides having affinity for a target material to create a targeted CE-7 perhydrolase. Examples of such single chain peptides have been previous described. For example, SEQ ID NOs: 65-127 are amino acid sequences of various peptides having affinity for various polymers and cellulosic materials. SEQ ID NOs: 65-79 are examples of peptides having affinity for polymethyl methacrylate, SEQ ID NOs: 80-86 are examples of peptides having affinity for polypropylene, SEQ ID NOs: 87-95 are examples of peptides having affinity for polytetrafluoroethylene, SEQ ID NOs: 96-102 are examples of peptides having affinity for polyethylene, SEQ ID NOs: 103-108 are examples of peptides having affinity for polyamides (Nylon), SEQ ID NOs 109-111 are examples of peptides having affinity for polystyrene, SEQ ID NOs: 112-115 are examples of peptides having affinity for cellulose acetate, SEQ ID NOs: 116-117 are examples of peptides having affinity for cotton, SEQ ID NOs: 116 and 118 are examples of peptides having affinity for polyester/cotton blends, SEQ ID NOs: 119-121 are examples of peptides having affinity for paper, and SEQ ID NOs: 122-127 are examples of peptides having affinity for cellulose.

The peptidic component having affinity for the surface of the target material may be separated from the CE-7 perhydrolase by an optional peptide linker. Certain peptide linkers/spacers are from 1 to 100 or 1 to 50 amino acids in length. In some embodiments, the peptide spacers are about 1 to about 25, 3 to about 40, or 3 to about 30 amino acids in length. In other embodiments are spacers that are about 5 to about 20 amino acids in length. Multiple peptide linkers may be used. As such, examples of targeted perhydrolases may include, but are not limited to, any of the CE-7 perhydrolases having an amino acid sequence selected from the group consisting of SEQ ID NOs 2, 4, 6, 8, 10, 12, 14, 16, 18, 20, 22, 24, 26, 27, 28, 29, 30, 31, 32, 33, 34, 35, 36, 38, 40, 42, 44, 46, 48, 50, 52, 54, 56, 58, 60, 62, and 64 coupled to a peptidic component having affinity for the surface of a target material. In a preferred embodiment, examples of targeted perhydrolases may include, but are not limited to, any of CE-7 perhydrolases having an amino acid sequence selected from the group consisting of SEQ ID NOs 2, 4, 6, 8, 10, 12, 14, 16, 18, 20, 22, 24, 26, 27, 28, 29, 30, 31, 32, 33, 34, 35, 36, 38, 40, 42, 44, 46, 48, 50, 52, 54, 56, 58, 60, 62, and 64 coupled to one or more target surface-binding peptides having affinity for a target surface (optionally through a peptide spacer).

In one embodiment, the targeted perhydrolase comprises a CE-7 perhydrolase having an amino acid sequence selected from the group consisting of SEQ ID NOs 2, 4, 6, 8, 10, 12, 14, 16, 18, 20, 22, 24, 26, 27, 28, 29, 30, 31, 32, 33, 34, 35, 36, 38, 40, 42, 44, 46, 48, 50, 52, 54, 56, 58, 60, 62, and 64 coupled to one or more target surface-binding peptides selected from the group consisting of SEQ ID NOs: 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, and 127.

In another embodiment, the targeted perhydrolase comprises a CE-7 perhydrolase having an amino acid sequence selected from the group consisting of SEQ ID NOs 2, 4, 6, 8, 10, 12, 14, 16, 18, 20, 22, 24, 26, 27, 28, 29, 30, 31, 32, 33, 34, 35, 36, 38, 40, 42, 44, 46, 48, 50, 52, 54, 56, 58, 60, 62, and 64 coupled to one or more cellulose-binding domains. In another aspect, the targeted perhydrolase comprises a CE-7 perhydrolase having an amino acid sequence selected from the group consisting of SEQ ID NOs 2, 4, 6, 8, 10, 12, 14, 16, 18, 20, 22, 24, 26, 27, 28, 29, 30, 31, 32, 33, 34, 35, 36, 38, 40, 42, 44, 46, 48, 50, 52, 54, 56, 58, 60, 62, and 64 coupled to one or more cellulose-binding domains having an amino acid sequence selected from the group consisting of SEQ ID NO: 149, 152, 155, 158, and 161. In yet another aspect, the targeted perhydrolase comprises an amino acid sequence selected from the group consisting of SEQ ID NOs 148, 151, 154, 157, 160, 165, 167, and 169.

Binding Affinity

The peptidic component having affinity for the target surface comprises a binding affinity for the target surface of $10^{-5}$ molar (M) or less. In certain embodiments, the peptidic component is one or more target surface-binding peptides and/or binding domain(s) having a binding affinity of $10^{-5}$ molar (M) or less. In some embodiments, the target surface-binding peptides or domains will have a binding affinity value of $10^{-5}$ M or less in the presence of at least about 50-500 mM salt. The term "binding affinity" refers to the strength of the interaction of a binding peptide with its respective substrate. Binding affinity can be defined or measured in terms of the binding peptide's dissociation constant ("$K_D$"), or "$MB_{50}$."

"$K_D$" corresponds to the concentration of peptide at which the binding site on the target is half occupied, i.e., when the concentration of target with peptide bound (bound target material) equals the concentration of target with no peptide bound. The smaller the dissociation constant, the more tightly the peptide is bound. For example, a peptide with a nanomolar (nM) dissociation constant binds more tightly than a peptide with a micromolar (μM) dissociation constant. Certain embodiments of the invention will have a $K_D$ value of $10^{-5}$ or less.

"$MB_{50}$" refers to the concentration of the binding peptide that gives a signal that is 50% of the maximum signal obtained in an ELISA-based binding assay. See, e.g., Example 3 of U.S. Patent Application Publication 2005/022683; hereby incorporated by reference. The $MB_{50}$ provides an indication of the strength of the binding interaction or affinity of the components of the complex. The lower the value of $MB_{50}$, the stronger, i.e., "better," the interaction of the peptide with its corresponding substrate. For example, a peptide with a nanomolar (nM) $MB_{50}$ binds more tightly than a peptide with a micromolar (μM) $MB_{50}$. Certain embodiments of the invention will have a $MB_{50}$ value of $10^{-5}$ M or less.

In some embodiments, the peptidic component having affinity for a target surface may have a binding affinity, as measured by $K_D$ or $MB_{50}$ values, of less than or equal to about $10^{-5}$ M, less than or equal to about $10^{-6}$ M, less than or equal to about $10^{-7}$ M, less than or equal to about $10^{-8}$ M, less than or equal to about $10^{-9}$ M, or less than or equal to about $10^{-10}$ M.

As used herein, the term "strong affinity" will refer to a binding affinity having a $K_D$ or $MB_{50}$ value of less than or equal to about $10^{-5}$ M, preferably less than or equal to about $10^{-6}$ M, more preferably less than or equal to about $10^{-7}$ M, more preferably less than or equal to about $10^{-8}$ M, less than or equal to about $10^{-9}$ M, or most preferably less than or equal to about $10^{-10}$ M.

Multicomponent Peroxycarboxylic Acid Generation Systems

The design of systems and means for separating and combining multiple active components are known in the art and generally will depend upon the physical form of the individual reaction components. For example, multiple active fluids (liquid-liquid) systems typically use multi-chamber dispenser bottles or two-phase systems (e.g., U.S. Patent Application Publication No. 2005/0139608; U.S. Pat. No. 5,398,846; U.S. Pat. No. 5,624,634; U.S. Pat. No. 6,391,840; E.P. Patent 0807156B1; U.S. Patent Application. Pub. No. 2005/0008526; and PCT Publication No. WO 00/61713) such as found in some bleaching applications wherein the desired bleaching agent is produced upon mixing the reactive fluids. Other forms of multicomponent systems used to generate peroxycarboxylic acid may include, but are not limited to, those designed for one or more solid components or combinations of solid-liquid components, such as powders (e.g., U.S. Pat. No. 5,116,575), multi-layered tablets (e.g., U.S. Pat. No. 6,210,639), water dissolvable packets having multiple compartments (e.g., U.S. Pat. No. 6,995,125) and solid agglomerates that react upon the addition of water (e.g., U.S. Pat. No. 6,319,888).

In another embodiment, the carboxylic acid ester in the first component is selected from the group consisting of monoacetin, diacetin, triacetin, and combinations thereof. In another embodiment, the carboxylic acid ester in the first component is an acetylated saccharide. In another embodiment, the enzyme catalyst in the first component may be a particulate solid. In another embodiment, the first reaction component may be a solid tablet or powder Peroxycarboxylic acids are quite reactive and generally decrease in concentration over time. This is especially true for commercial pre-formed peroxycarboxylic acid compositions that often lack long term stability. Aqueous solutions of pre-formed peroxycarboxylic acids may also present handling and/or shipping difficulties, especially when shipping large containers and/or highly concentrated peroxycarboxylic acid solutions over longer distances. Further, pre-formed peroxycarboxylic acid solutions may not be able to provide the desired concentration of peroxycarboxylic acid for a particular target application. As such, it is highly desirable to keep the various reaction components separated, especially for liquid formulations.

The use of multi-component peroxycarboxylic acid generation systems comprising two or more components that are combined to produce the desired peroxycarboxylic acid has been reported. The individual components should be safe to handle and stable for extended periods of time (i.e., as measured by the concentration of peroxycarboxylic acid produced upon mixing). In one embodiment, the storage stability of a multi-component enzymatic peroxycarboxylic acid generation system may be measured in terms of enzyme catalyst stability.

Products (e.g., laundry care products) comprising a multi-component peroxycarboxylic acid generation formulation are provided herein that use an targeted enzyme catalyst to rapidly produce an aqueous peracid solution having a desired peroxycarboxylic acid concentration on or near the target surface. The mixing may occur immediately prior to use and/or at the site (in situ) of application. In one embodiment, the product formulation will be comprised of at least two components that remain separated until use. Mixing of the components rapidly forms an aqueous peracid solution. Each component is designed so that the resulting aqueous peracid solution comprises an efficacious peracid concentration suitable for the intended end use. The composition of the individual components should be designed to (1) provide extended storage stability and/or (2) provide the ability to enhance formation of a suitable aqueous reaction formulation comprised of peroxycarboxylic acid.

The multi-component formulation may be comprised of at least two substantially liquid components. In one embodiment, the multi-component formulation may be a two component formulation comprises a first liquid component and a second liquid component. The use of the terms "first" or "second" liquid component is relative provided that two different liquid components comprising the specified ingredients remain separated until use. At a minimum, the multi-component peroxycarboxylic acid formulation comprises (1) at least one enzyme catalyst having a fusion protein (i.e., targeted perhydrolase) having perhydrolytic activity, (2) a carboxylic acid ester substrate, and (3) a source of peroxygen and water wherein the formulation enzymatically produces the desired peracid upon combining the components. In one embodiment, the enzyme having perhydrolytic activity in the multi-component peroxycarboxylic acid formulation is a targeted CE-7 perhydrolase.

The type and amount of the various ingredients used within two component formulation should to be carefully selected and balanced to provide (1) storage stability of each component, especially the perhydrolysis activity of the enzyme catalyst and (2) physical characteristics that enhance solubility and/or the ability to effectively form the desired aqueous peroxycarboxylic acid solution (e.g., ingredients that enhance the solubility of the ester substrate in the aqueous reaction mixture and/or ingredients that modify the viscosity and/concentration of at least one of the liquid components [i.e., at least one cosolvent that does not have a significant, adverse effect on the enzymatic perhydrolysis activity]).

Various methods to improve the performance and/or catalyst stability of enzymatic peracid generation systems have been disclosed. U.S. Patent Application Publication No. 2010-0048448 A1 describes the use of at least one cosolvent to enhance solubility and/or the mixing characteristics of certain ester substrates. The present compositions and methods may also use a cosolvent. In one embodiment, the component comprising the carboxylic acid ester substrate and the perhydrolase catalyst comprises an organic solvent having a Log P value of less than about 2, wherein Log P is defined as the logarithm of the partition coefficient of a substance between octanol and water, expressed as $P=[solute]_{octanol}/[solute]_{water}$. Several cosolvents having a log P value of 2 or less that do not have a significant adverse impact on enzyme activity are described. In another embodiment, the cosolvent is about 20 wt % to about 70 wt % within the reaction component comprising the carboxylic acid ester substrate and the enzyme. The reaction component comprising the carboxylic acid ester substrate and the enzyme may optionally comprise one or more buffers (e.g., sodium and/or potassium salts of bicarbonate, citrate, acetate, phosphate, pyrophosphate, methylphosphonate, succinate, malate, fumarate, tartrate, and maleate).

U.S. Patent Application Publication No. 2010-0086534 A1 describes the use of a two component system wherein the first component comprises a formulation of a liquid carboxylic acid ester and solid enzyme powder; wherein said enzyme powder comprises a formulation of (a) at least one CE-7 esterase having perhydrolysis activity and (b) at least one oligosaccharide excipient; and the second component comprises water having a source of peroxygen and a hydrogen peroxide stabilizer. The present compositions and methods may use a two component formulation similar to the system described in US 2010-0086534 A1. As such, an oligosaccharide excipient may be used to help stabilize enzyme activity. In one embodiment, the oligosaccharide excipient may have a number average molecular weight of at least about 1250 and a weight average molecular weight of at least about 9000. In another embodiment, the oligosaccharide excipient has have a number average molecular weight of at least about 1700 and a weight average molecular weight of at least about 15000. In another embodiment, the oligosaccharide is maltodextrin.

U.S. Patent Application Publication No. 2010-0086535 A1 also describes a two component system wherein the first component comprises a formulation of a liquid carboxylic acid ester and solid enzyme powder, said formulation comprising (a) an enzyme powder comprising at least one CE-7 esterase having perhydrolysis activity and at least one oligosaccharide excipient and at least one surfactant; and (b) at least one buffer, where in a preferred embodiment the buffer is added as a separate (i.e. separate from the enzyme powder) insoluble component to the carboxylic acid ester substrate; and the second component comprises water having a source of peroxygen and a hydrogen peroxide stabilizer. The present compositions and methods may use a two component formulation similar to the system described in US 2010-0086535 A1. In one embodiment, the excipient may be an oligosaccharide excipient that has a number average molecular weight of at least about 1250 and a weight average molecular weight of at least about 9000. In another embodiment, the oligosaccharide excipient may have a number average molecular weight of at least about 1700 and a weight average molecular weight of at least about 15000. In another embodiment, the oligosaccharide is maltodextrin. In a further embodiment, the pH buffer is a bicarbonate buffer. In yet a further embodiment, the hydrogen peroxide stabilizer is TURPINAL® SL.

Enzyme Powders

In some embodiments, the present compositions may use an enzyme catalyst in form of a stabilized enzyme powder. Methods to make and stabilize formulations comprising an enzyme powder are described in U.S. Patent Application Publication Nos. 2010-0086534 and 2010-0086535.

In one embodiment, the enzyme may be in the enzyme powder in an amount in a range of from about 5 weight percent (wt %) to about 75 wt % based on the dry weight of the enzyme powder. A preferred weight percent range of the enzyme in the enzyme powder/spray-dried mixture is from about wt % to 50 wt %, and a more preferred weight percent range of the enzyme in the enzyme powder/spray-dried mixture is from about 20 wt % to 33 wt %

In one embodiment, the enzyme powder may further comprise an excipient. In one aspect, the excipient is provided in an amount in a range of from about 95 wt % to about 25 wt % based on the dry weight of the enzyme powder. A preferred wt % range of excipient in the enzyme powder is from about 90 wt % to 50 wt %, and a more preferred wt % range of excipient in the enzyme powder is from about 80 wt % to 67 wt %.

In one embodiment, the excipient used to prepare an enzyme powder may be an oligosaccharide excipient. In one embodiment, the oligosaccharide excipient has a number average molecular weight of at least about 1250 and a weight average molecular weight of at least about 9000. In some embodiments, the oligosaccharide excipient has a number average molecular weight of at least about 1700 and a weight average molecular weight of at least about 15000. Specific oligosaccharides may include, but are not limited to, maltodextrin, xylan, mannan, fucoidan, galactomannan, chitosan, raffinose, stachyose, pectin, insulin, levan, graminan, amylopectin, sucrose, lactulose, lactose, maltose, trehalose, cellobiose, nigerotriose, maltotriose, melezitose, maltotriulose, raffinose, kestose, and mixtures thereof. In a preferred embodiment, the oligosaccharide excipient is maltodextrin. Oligosaccharide-based excipients may also include, but are not limited to, water-soluble non-ionic cellulose ethers, such as hydroxymethyl-cellulose and hydroxypropylmethylcellulose, and mixtures thereof. In yet a further embodiment, the excipient may be selected from, but not limited to, one or more of the following compounds: trehalose, lactose, sucrose, mannitol. sorbitol, glucose, cellobiose, α-cyclodextrin, and carboxymethylcellulose.

The formulations may comprise at least one optional surfactant, where the presence of at least one surfactant is preferred. Surfactants may include, but are not limited to, ionic and nonionic surfactants or wetting agents, such as ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides or ethoxylated derivatives thereof, diglycerides or polyoxyethylene derivatives thereof, sodium docusate, sodium lauryl sulfate, cholic acid or derivatives thereof, lecithins, phospholipids, block copolymers of ethylene glycol and propylene glycol, and non-ionic organosilicones. Preferably, the surfactant is a polyoxyethylene sorbitan fatty acid ester, with polysorbate 80 being more preferred.

When the formulation comprises an enzyme powder, the surfactant used to prepare the powder may be present in an amount ranging from about 5 wt % to 0.1 wt % based on the weight of protein present in the enzyme powder, preferably from about 2 wt % to 0.5 wt % based on the weight of protein present in the enzyme powder.

The enzyme powder may additionally comprise one or more buffers (e.g., sodium and/or potassium salts of bicarbonate, citrate, acetate, phosphate, pyrophosphate, methylphosphonate, succinate, malate, fumarate, tartrate, and maleate), and an enzyme stabilizer (e.g., ethylenediaminetetraacetic acid, (1-hydroxyethylidene)bisphosphonic acid)).

Spray drying of the formulation to form the enzyme powder is carried out, for example, as described generally in *Spray Drying Handbook*, 5th ed., K. Masters, John Wiley & Sons, Inc., NY, N.Y. (1991), and in PCT Patent Publication Nos. WO 97/41833 and WO 96/32149 to Platz, R. et al.

In general spray drying consists of bringing together a highly dispersed liquid, and a sufficient volume of hot air to produce evaporation and drying of the liquid droplets. Typically the feed is sprayed into a current of warm filtered air that evaporates the solvent and conveys the dried product to a collector. The spent air is then exhausted with the solvent. Those skilled in the art will appreciate that several different types of apparatus may be used to provide the desired product. For example, commercial spray dryers manufactured. by Buchi Ltd. (Postfach, Switzerland) or GEA Niro Corp. (Copenhagen, Denmark) will effectively produce particles of desired size. It will further be appreciated that these spray dryers, and specifically their atomizers, may be modified or customized for specialized applications, such as the simultaneous spraying of two solutions using a double nozzle technique. More specifically, a water-in-oil emulsion can be atomized from one nozzle and a solution containing an antiadherent such as mannitol can be co-atomized from a second nozzle. In other cases it may be desirable to push the feed solution though a custom designed nozzle using a high pressure liquid chromatography (HPLC) pump. Provided that microstructures comprising the correct morphology and/or composition are produced the choice of apparatus is not critical and would be apparent to the skilled artisan in view of the teachings herein.

The temperature of both the inlet and outlet of the gas used to dry the sprayed material is such that it does not cause degradation of the enzyme in the sprayed material. Such temperatures are typically determined experimentally, although generally, the inlet temperature will range from about 50° C. to about 225° C., while the outlet temperature will range from about 30° C. to about 150° C. Preferred parameters include atomization pressures ranging from about 20-150 psi (0.14 MPa-1.03 MPa), and preferably from about 30-40 to 100 psi (0.21-0.28 MPa to 0.69 MPa). Typically the atomization pressure employed will be one of the following (MPa) 0.14, 0.21, 0.28, 0.34, 0.41, 0.48, 0.55, 0.62, 0.69, 0.76, 0.83 or above.

When using an enzyme powder, the enzyme powder or a formulation of the enzyme powder in carboxylic acid ester may be required to substantially retain its enzymatic activity for an extended period of time when stored at ambient temperature. The enzyme powder or a formulation of the enzyme powder in carboxylic acid ester substantially retains its enzymatic activity at elevated temperatures for short periods of time. In one embodiment, "substantially retains its enzymatic activity" is meant that the enzyme powder or a formulation of the enzyme powder in carboxylic acid ester retains at least about 75 percent of the enzyme activity of the enzyme in the enzyme powder or a formulation of the enzyme powder after an extended storage period at ambient temperature and/or after a short storage period at an elevated temperature (above ambient temperature) in a formulation comprised of a carboxylic acid ester and the enzyme powder as compared to the initial enzyme activity of the enzyme powder prior to the preparation of a formulation comprised of the carboxylic acid ester and the enzyme powder. The extended storage period is a period of time of from about one year to about two years at ambient temperature. In one embodiment, the short storage period is at an elevated temperature is a period of time of from when the formulation comprised of a carboxylic acid ester and the enzyme powder is produced at 40° C. to about eight weeks at 40° C. In another embodiment, the elevated temperature is in a range of from about 30° C. to about 52° C. In a preferred embodiment, the elevated temperature is in a range of from about 30° C. to about 40° C.

In some embodiments, the enzyme powder retains at least 75 percent of the enzyme activity after eight weeks storage at 40° C. in a formulation comprised of a carboxylic acid ester and the enzyme powder as compared to the initial enzyme activity of the enzyme powder prior to the preparation of a formulation comprised of the carboxylic acid ester and the enzyme powder at 40° C. In other embodiments, the enzyme powder retains at least 76, 77, 78, 79, 80, 81, 82, 83, 84, 85, 86, 87, 88, 89, 90, 91, 92, 93, 94, 95, 96, 97, 98, 99, or 100 percent of the enzyme activity of the at least one enzyme after eight weeks storage at 40° C. in a formulation comprised of a carboxylic acid ester and the enzyme powder as compared to the initial enzyme activity of the enzyme powder prior to the preparation of a formulation comprised of the carboxylic acid ester and the enzyme powder at 40° C. Preferably, perhydrolysis activity is measured as described in Examples 8-13 of U.S. Patent Application Publication No. 2010-0086510; but any method of measuring perhydrolysis activity may used.

A further improvement in enzyme activity over the stated periods of time can be achieved by adding a buffer having a buffering capacity in a pH range of from about 5.5 to about 9.5 to the formulation comprised of the carboxylic acid ester and the spray-dried enzyme powder as described in U.S. Patent Application Publication No. 2010-0086534. A suitable buffer may include, but is not limited to, sodium salt, potassium salt, or mixtures of sodium or potassium salts of bicarbonate, pyrophosphate, phosphate, methylphosphonate, citrate, acetate, malate, fumarate, tartrate maleate or succinate. Preferred buffers for use in the formulation comprised of the carboxylic acid ester and the spray-dried enzyme powder include the sodium salt, potassium salt, or mixtures of sodium or potassium salts of bicarbonate, pyrophosphate, phosphate, methylphosphonate, citrate, acetate, malate, fumarate, tartrate maleate or succinate. In preferred embodiment, the buffer comprises the sodium and/or potassium salts of bicarbonate.

In embodiments where a buffer may be present in the carboxylic acid ester and enzyme powder formulation, the buffer may be present in an amount in a range of from about 0.01 wt % to about 50 wt % based on the weight of carboxylic acid ester in the formulation comprised of carboxylic acid ester and enzyme powder. The buffer may be present in a more preferred range of from about 0.10% to about 10% based on the weight of carboxylic acid ester in the formulation comprised of carboxylic acid ester and enzyme powder. Further, in these embodiments, the comparison between perhydrolysis activity of the enzyme is determined as between an enzyme powder which retains at least 75 percent of the perhydrolysis activity of the at least one enzyme after eight weeks storage at 40° C. in a formulation comprised of a carboxylic acid ester, a buffer having a buffering capacity in a pH range of from about 5.5 to about 9.5, and the enzyme powder as compared to the initial perhydrolysis activity of the enzyme powder prior to the preparation of a formulation comprised of the carboxylic acid ester, the buffer having a buffering capacity in a pH range of from about 5.5 to about 9.5, and the enzyme powder.

It is intended that the dried enzyme powder be stored as a formulation in the organic compound that is a substrate for the at least one enzyme, such as triacetin. In the absence of added hydrogen peroxide, triacetin is normally hydrolyzed in aqueous solution by a hydrolytic enzyme (e.g., a CE-7 carbohydrate esterase) to produce diacetin and acetic acid, and the production of acetic acid results in a decrease in the pH of the reaction mixture. One requirement for long term storage stability of the enzyme in triacetin is that there is not a significant reaction of the triacetin with any water that might be present in the triacetin; the specification for water content in one commercial triacetin (supplied by Tessenderlo Group, Brussels, Belgium) is 0.03 wt % water (300 ppm). Any hydrolysis of triacetin that occurs during storage of the enzyme in triacetin would produce acetic acid, which could result in a decrease in activity or inactivation of the CE-7 perhydrolases; the perhydrolases are typically inactivated at or below a pH of 5.0 (see U.S. Patent Application Publication No. 2009-0005590 to DiCosimo, R., et al.). The excipient selected for use in the present application must provide stability of the enzyme in the organic substrate for the enzyme under conditions where acetic acid might be generated due to the presence of low concentrations of water in the formulation. The dried enzyme powder be stored as a formulation in the organic compound that is a substrate for the at least one enzyme, where the formulation additionally comprises an excipient and one or more buffers (e.g., sodium and/or potassium salts of bicarbonate, citrate, acetate, phosphate, pyrophosphate, methylphosphonate, succinate, malate, fumarate, tartrate, and maleate)

Suitable Reaction Conditions for the Targeted Enzyme-Catalyzed Preparation of Peracids from Carboxylic Acid Esters and Hydrogen Peroxide One or more targeted enzymes having perhydrolytic activity may be used to generate an efficacious concentration of the desired peracid in the present compositions and methods. The desired peracid may be prepared by reacting carboxylic acid esters with a source of peroxygen including, but not limited to, hydrogen peroxide, sodium perborate or sodium percarbonate, in the presence of an enzyme catalyst comprising a fusion protein having perhydrolytic activity.

The enzyme catalyst comprises at least one fusion protein (targeted perhydrolase) having perhydrolytic activity. In one embodiment, the perhydrolytic enzyme within the targeted perhydrolase may be any perhydrolytic enzyme and may include lipases, proteases, esterases, acyl transferases, aryl esterases, carbohydrate esterases, and combinations so long as the enzyme has perhydrolytic activity for one or more of the present substrates. Examples may include, but are not limited to perhydrolytic proteases (e.g., subtilisin variant; U.S. Pat. No. 7,510,859), perhydrolytic esterases (e.g. *Pseudomonas fluorescens*; U.S. Pat. No. 7,384,787; SEQ ID NO: 163 and 181), and perhydrolytic aryl esterases (e.g. *Mycobacterium smegmatis*; U.S. Pat. No. 7,754,460; WO2005/056782; and EP1689859 B1; SEQ ID NOs: 162 [S54V variant] and 180 [wild type]).

In another embodiment, the enzyme used to prepare the fusion protein is structurally classified as a member of the CE-7 carbohydrate esterase family (CE-7; see Coutinho, P. M., and Henrissat, B., supra). In another embodiment, the targeted perhydrolase comprises a perhydrolytic enzyme that is structurally classified as a cephalosporin C deacetylase. In another embodiment, the targeted perhydrolase comprises a perhydrolytic enzyme that is structurally classified as an acetyl xylan esterase. When targeting a CE-7 acetyl xylan esterase to a cellulosic material is it understood that the CE-7 acetyl xylan esterase does not naturally contain a cellulose-binding domain. As such, acetyl xylan esterase targeted to a cellulosic surface is chimeric fusion protein designed to have an additional peptidic component having affinity for cellulose.

In one embodiment, the perhydrolase catalyst comprises an enzyme having perhydrolysis activity and a CE-7 signature motif comprising:

a) an RGQ motif that aligns with amino acid residues 118-120 of SEQ ID NO: 2;
b) a GXSQG motif that aligns with amino acid residues 179-183 of SEQ ID NO: 2; and
c) an HE motif that aligns with amino acid residues 298-299 of SEQ ID NO: 2.

In a preferred embodiment, the alignment to reference SEQ ID NO: 2 is performed using CLUSTALW.

In a further embodiment, the CE-7 signature motif additional may comprise and additional (i.e., fourth) motif defined as an LXD motif that aligns with amino acid residues 267-269 of reference sequence SEQ ID NO:2.

In another embodiment, the perhydrolase catalyst comprises an enzyme having perhydrolase activity, said enzyme having an amino acid sequence selected from the group consisting of SEQ ID NOs: 2, 4, 6, 8, 10, 12, 14, 16, 18, 20, 22, 24, 26, 27, 28, 29, 30, 31, 32, 33, 34, 35, 36, 38, 40, 42, 44, 46, 48, 50, 52, 54, 56, 58, 60, 62, and 64.

In another embodiment, the perhydrolase catalyst comprises an enzyme having perhydrolase activity, said enzyme having an amino acid sequence selected from the group consisting of SEQ ID NOs: 2, 4, 6, 8, 10, 12, 14, 16, 18, 20, 22, 24, 26, 27, 28, 29, 30, 31, 32, 33, 34, 35, 36, 38, 40, 42, 44, 46, 48, 50, 52, 54, 56, 58, 60, 62, and 64, wherein said enzyme may have one or more additions, deletions, or substitutions so long as the signature motif is conserved and perhydrolase activity is retained.

As described above, the CE-7 perhydrolase is used in the form of a fusion protein having a first portion comprising CE-7 perhydrolase and a second portion comprising a peptidic component having affinity for a target body surface such at that perhydrolase is "targeted" to a surface. In one embodiment, any CE-7 perhydrolase (as defined by the presence of the CE-7 signature motifs) may be fused to any peptidic component/binding element capable of targeting the enzyme to a target surface. In one aspect, the peptidic component having affinity for a target surface may include antibodies, antibody fragments ($F_{ab}$), as well as single chain variable fragments (scFv; a fusion of the variable regions of the heavy ($V_H$) and light chains ($V_L$) of immunoglobulins), single domain camelid antibodies, scaffold display proteins, cellulose-binding domains (when targeting cellulosic materials), and single chain affinity peptides lacking immunoglobulin folds. The compositions comprising antibodies, antibodies fragments and other immunoglobulin-derived binding elements, as well as large scaffold display proteins, are often not economically viable. As such, and in a preferred aspect, the peptidic component/binding element is a cellulose-binding domain or single chain affinity peptide lacking an immunoglobulin fold and/or immunoglobulin domain.

Cellulose-binding domains are typically associated with cellulose degrading enzymes. Over a dozen families of CBDs have been reported (Tomme et al., supra). In one embodiment, a cellulose-binding domain is used as the peptidic component to target the CE-7 perhydrolase to a cellulosic material.

Short single chain body surface-binding peptides may be empirically generated (e.g., positively charged polypeptides targeted to negatively charged surfaces) or generated using biopanning against a target surface. Methods to identify/obtain affinity peptides using any number of display techniques (e.g., phage display, yeast display, bacterial display, ribosome display, and mRNA display) are well known in the art. Individual target surface-binding peptides may be coupled together, via optional spacers/linkers, to form larger binding domains (also referred to herein as binding "hands") to enhance attachment/localization of the perhydrolytic enzyme to the target surface.

The fusion proteins may also include one or more peptide linkers/spacers separating the CE-7 perhydrolase enzyme from the target surface-binding domain and/or between different target surface-binding peptides (e.g., when a plurality of target surface-binding peptides are coupled together to form a larger target surface-binding domain). In one embodiment, the peptide spacers/linkers may be repeated up to 10 times. A non-limiting list of exemplary peptide spacers are provided by the amino acid sequences of SEQ ID NOs: 128-140 and 143.

Suitable carboxylic acid ester substrates may include esters having the following formula:

(a) one or more esters having the structure $[X]_m R_5$ wherein

X is an ester group of the formula $R_6C(O)O$;

$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;

$R_5$ is a C1 to C6 linear, branched, or cyclic hydrocarbyl moiety or a five-membered cyclic heteroaromatic moiety or six-membered cyclic aromatic or heteroaromatic moiety optionally substituted with a hydroxyl group, wherein each carbon atom in $R_5$ individually comprises no more than one hydroxyl group or no more than one ester group or carboxylic acid group, and wherein $R_5$ optionally comprises one or more ether linkages;

m is an integer ranging from 1 to the number of carbon atoms in $R_5$, said one or more esters having solubility in water of at least 5 ppm at 25° C.; or (b) one or more glycerides having the structure

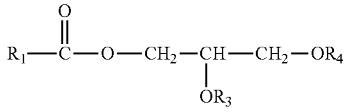

wherein $R_1$ is a C1 to C7 straight chain or branched chain alkyl optionally substituted with an hydroxyl or a C1 to C4 alkoxy group and $R_3$ and $R_4$ are individually H or $R_1C(O)$; or (c) one or more esters of the formula

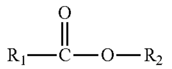

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10; or (d) one or more acetylated monosaccharides, acetylated disaccharides, or acetylated polysaccharides; or (e) any combination of (a) through (d).

Suitable substrates may also include one or more acylated saccharides selected from the group consisting of acylated mono-, di-, and polysaccharides. In another embodiment, the acylated saccharides are selected from the group consisting of acetylated xylan; fragments of acetylated xylan; acetylated xylose (such as xylose tetraacetate); acetylated glucose (such as α-D-glucose pentaacetate; β-D-glucose pentaacetate; 1-thio-β-D-glucose-2,3,4,6-tetraacetate); β-D-galactose pentaacetate; sorbitol hexaacetate; sucrose octaacetate; β-D-ribofuranose-1,2,3,5-tetraacetate; β-D-ribofuranose-1,2,3,4-tetraacetate; tri-O-acetyl-D-galactal; tri-O-acetyl-D-glucal; β-D-xylofuranose tetraacetate, α-D-glucopyranose pentaacetate; β-D-glucopyranose-1,2,3,4-tetraacetate; β-D-glucopyranose-2,3,4,6-tetraacetate; 2-acetamido-2-deoxy-1,3,4,6-tetracetyl-β-D-glucopyranose; 2-acetamido-2-deoxy-3,4,6-triacetyl-1-chloride-α-D-glucopyranose; α-D-mannopyranose pentaacetate, and acetylated cellulose. In a preferred embodiment, the acetylated saccharide is selected from the group consisting of β-D-ribofuranose-1,2,3,5-tetraacetate; tri-O-acetyl-D-galactal; tri-O-acetyl-D-glucal; sucrose octaacetate; and acetylated cellulose.

In another embodiment, additional suitable substrates may also include 5-acetoxymethyl-2-furaldehyde; 3,4-diacetoxy-1-butene; 4-acetoxybenezoic acid; vanillin acetate; propylene glycol methyl ether acetate; methyl lactate; ethyl lactate;

methyl glycolate; ethyl glycolate; methyl methoxyacetate; ethyl methoxyacetate; methyl 3-hydroxybutyrate; ethyl 3-hydroxybutyrate; and triethyl 2-acetyl citrate.

In another embodiment, suitable substrates are selected from the group consisting of: monoacetin; diacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-D-glucal; monoesters or diesters of 1,2-ethanediol; 1,2-propanediol; 1,3-propanediol; 1,2-butanediol; 1,3-butanediol; 2,3-butanediol; 1,4-butanediol; 1,2-pentanediol; 2,5-pentanediol; 1,5-pentanediol; 1,6-pentanediol; 1,2-hexanediol; 2,5-hexanediol; 1,6-hexanediol; and mixtures thereof. In another embodiment, the substrate is a C1 to C6 polyol comprising one or more ester groups. In a preferred embodiment, one or more of the hydroxyl groups on the C1 to C6 polyol are substituted with one or more acetoxy groups (such as 1,3-propanediol diacetate; 1,2-propanediol diacetate; 1,4-butanediol diacetate; 1,5-pentanediol diacetate, etc.). In a further embodiment, the substrate is propylene glycol diacetate (PGDA), ethylene glycol diacetate (EGDA), or a mixture thereof. In a further embodiment, suitable substrates are selected from the group consisting of monoacetin, diacetin, triacetin, monopropionin, dipropionin, tripropionin, monobutyrin, dibutyrin, and tributyrin. In yet another aspect, the substrate is selected from the group consisting of diacetin and triacetin. In a most preferred embodiment, the suitable substrate comprises triacetin.

In a preferred embodiment, the carboxylic acid ester is a liquid substrate selected from the group consisting of monoacetin, diacetin, triacetin, and combinations (i.e., mixtures) thereof. The carboxylic acid ester is present in the reaction formulation at a concentration sufficient to produce the desired concentration of peroxycarboxylic acid upon enzyme-catalyzed perhydrolysis. The carboxylic acid ester need not be completely soluble in the reaction formulation, but has sufficient solubility to permit conversion of the ester by the perhydrolase catalyst to the corresponding peroxycarboxylic acid. The carboxylic acid ester is present in the reaction formulation at a concentration of 0.05 wt % to 40 wt % of the reaction formulation, preferably at a concentration of 0.1 wt % to 20 wt % of the reaction formulation, and more preferably at a concentration of 0.5 wt % to 10 wt % of the reaction formulation.

The peroxygen source may include, but is not limited to, hydrogen peroxide, hydrogen peroxide adducts (e.g., urea-hydrogen peroxide adduct (carbamide peroxide)) perborate salts and percarbonate salts. The concentration of peroxygen compound in the reaction formulation may range from 0.0033 wt % to about 50 wt %, preferably from 0.033 wt % to about 40 wt %, more preferably from 0.33 wt % to about 30 wt %.

Many perhydrolase catalysts (whole cells, permeabilized whole cells, and partially purified whole cell extracts) have been reported to have catalase activity (EC 1.11.1.6). Catalases catalyze the conversion of hydrogen peroxide into oxygen and water. In one aspect, the perhydrolysis catalyst lacks catalase activity. In another aspect, a catalase inhibitor may be added to the reaction formulation. Examples of catalase inhibitors include, but are not limited to, sodium azide and hydroxylamine sulfate. One of skill in the art can adjust the concentration of catalase inhibitor as needed. The concentration of the catalase inhibitor typically ranges from 0.1 mM to about 1 M; preferably about 1 mM to about 50 mM; more preferably from about 1 mM to about 20 mM. In one aspect, sodium azide concentration typically ranges from about 20 mM to about 60 mM while hydroxylamine sulfate concentration is typically about 0.5 mM to about 30 mM, preferably about 10 mM.

In another embodiment, the enzyme catalyst lacks significant catalase activity or may be engineered to decrease or eliminate catalase activity. The catalase activity in a host cell can be down-regulated or eliminated by disrupting expression of the gene(s) responsible for the catalase activity using well known techniques including, but not limited to, transposon mutagenesis, RNA antisense expression, targeted mutagenesis, and random mutagenesis. In a preferred embodiment, the gene(s) encoding the endogenous catalase activity are down-regulated or disrupted (i.e., knocked-out). As used herein, a "disrupted" gene is one where the activity and/or function of the protein encoded by the modified gene is no longer present. Means to disrupt a gene are well-known in the art and may include, but are not limited to, insertions, deletions, or mutations to the gene so long as the activity and/or function of the corresponding protein is no longer present. In a further preferred embodiment, the production host is an *E. coli* production host comprising a disrupted catalase gene selected from the group consisting of katG and katE (see U.S. Patent Application Publication No. 2008-0176299). In another embodiment, the production host is an *E. coli* strain comprising a down-regulation and/or disruption in both katG and a katE catalase genes.

The concentration of the catalyst in the aqueous reaction formulation depends on the specific catalytic activity of the catalyst, and is chosen to obtain the desired rate of reaction. The weight of catalyst in perhydrolysis reactions typically ranges from 0.0001 mg to 10 mg per mL of total reaction volume, preferably from 0.001 mg to 2.0 mg per mL. The catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. The use of immobilized catalysts permits the recovery and reuse of the catalyst in subsequent reactions. The enzyme catalyst may be in the form of whole microbial cells, permeabilized microbial cells, microbial cell extracts, partially-purified or purified enzymes, and mixtures thereof.

In one aspect, the concentration of peroxycarboxylic acid generated by the combination of chemical perhydrolysis and enzymatic perhydrolysis of the carboxylic acid ester is sufficient to provide an effective concentration of peroxycarboxylic acid for the chosen application. In another aspect, the present methods provide combinations of enzymes and enzyme substrates to produce the desired effective concentration of peroxycarboxylic acid, where, in the absence of added enzyme, there is a significantly lower concentration of peroxycarboxylic acid produced. Although there may in some cases be substantial chemical perhydrolysis of the enzyme substrate by direct chemical reaction of inorganic peroxide with the enzyme substrate, there may not be a sufficient concentration of peroxycarboxylic acid generated to provide an effective concentration of peroxycarboxylic acid in the desired applications, and a significant increase in total peroxycarboxylic acid concentration is achieved by the addition of an appropriate perhydrolase catalyst to the reaction formulation.

The concentration of peroxycarboxylic acid generated (e.g. peracetic acid) by the perhydrolysis of at least one carboxylic acid ester is at least about 0.1 ppm, preferably at least 0.5 ppm, 1 ppm, 5 ppm, 10 ppm, 20 ppm, 100 ppm, 200 ppm, 300 ppm, 500 ppm, 700 ppm, 1000 ppm, 2000 ppm, 5000 ppm or 10,000 ppm of peracid within 10 minutes, preferably within 5 minutes, of initiating the perhydrolysis reaction. The product formulation comprising the peroxycarboxylic acid may be optionally diluted with water, or a solution predominantly comprised of water, to produce a formulation with the desired lower concentration of peroxycarboxylic acid base on the target application. One of skill in the art can adjust the reaction components and/or dilution amounts to achieve the desired peracid concentration for the chosen product.

In one aspect, the reaction time required to produce the desired concentration of peracid is not greater than about two hours, preferably not greater than about 30 minutes, more preferably not greater than about 10 minutes, and most preferably in about 5 minutes or less. In other aspects, the target surface is contacted with the peracid formed in accordance with the processes described herein within 5 minutes of combining the reaction components. In one embodiment, the target surface is contacted with the peracid produced with the processes described herein within about 5 minutes to about 168 hours of combining said reaction components, or within about 5 minutes to about 48 hours, or within about 5 minutes to 2 hours of combining said reaction components, or any such time interval therein.

The peracid formed in accordance with the processes describe herein is used in a product/application wherein the peracid is contacted with a target surface to provide a peracid-based benefit to the target material. In one embodiment, the process to produce a peracid for a target surface is conducted in situ.

The temperature of the reaction may be chosen to control both the reaction rate and the stability of the enzyme catalyst activity. The temperature of the reaction may range from just above the freezing point of the reaction formulation (approximately 0° C.) to about 95° C., with a preferred range of 5° C. to about 75° C., and a more preferred range of reaction temperature of from about 5° C. to about 55° C.

The pH of the final reaction formulation containing peroxycarboxylic acid is from about 2 to about 9, preferably from about 3 to about 8, more preferably from about 5 to about 8, even more preferably about 5.5 to about 8, and yet even more preferably about 6.0 to about 7.5. The pH of the reaction, and of the final reaction formulation, may optionally be controlled by the addition of a suitable buffer including, but not limited to, phosphate, pyrophosphate, bicarbonate, acetate, or citrate. The concentration of buffer, when employed, is typically from 0.1 mM to 1.0 M, preferably from 1 mM to 300 mM, most preferably from 10 mM to 100 mM.

In another aspect, the enzymatic perhydrolysis reaction formulation may contain an organic solvent that acts as a dispersant to enhance the rate of dissolution of the carboxylic acid ester in the reaction formulation. Such solvents include, but are not limited to, propylene glycol methyl ether, acetone, cyclohexanone, diethylene glycol butyl ether, tripropylene glycol methyl ether, diethylene glycol methyl ether, propylene glycol butyl ether, dipropylene glycol methyl ether, cyclohexanol, benzyl alcohol, isopropanol, ethanol, propylene glycol, and mixtures thereof.

Single Step vs. Multi-Step Application Methods

Typically the minimum set of reaction components to enzymatically produce a peracid benefit agent will include (1) at least one perhydrolase in the form of a targeted fusion protein, (2) at least one suitable carboyxlic acid ester substrate, and (3) a source of peroxygen (and water).

The peracid-generating reaction components of the present compositions may remain separated until use. In one embodiment, the peracid-generating components are combined and then contacted with the target surface whereby the resulting peracid-based benefit agent provides a benefit to the target surface. The components may be combined and then contacted with the target surface or may be combined on the target surface. In one embodiment, the peracid-generating components are combined such that the peracid is produced in situ.

A multi-step application may also be used. One or two of the individual components of the peracid-generating system (i.e., a sequential application on the target surface of at least one of the three basic reaction components) composition may be contacted with the target surface prior to applying the remaining components required for enzymatic peracid production. In one embodiment, the targeted perhydrolytic enzyme is contacted with the target surface prior to contacting the surface with the carboyxlic acid ester substrate and/or the source of peroxygen (i.e., a "two-step application"). The targeted perhydrolase is contacted with the target surface under suitable conditions to promote non-covalent bonding of the fusion protein to the target surface. An optional rinsing step may be used to remove excess and/or unbound fusion protein prior to combining the remaining reaction components.

In a further embodiment, the targeted perhydrolytic enzyme and the carboxylic acid ester are applied to the target surface prior to the addition of the source of peroxygen.

In a further embodiment, the targeted perhydrolytic enzyme and the source of peroxygen (e.g., an aqueous solution comprising hydrogen peroxide) are applied to the target surface prior to the addition of the carboxylic acid ester substrate.

In a further embodiment, the carboxylic acid ester substrate and the source of peroxygen (e.g., an aqueous solution comprising hydrogen peroxide) are applied to the target surface prior to the addition of the targeted perhydrolytic enzyme.

Uses of Targeted Perhydrolase Prepared Peroxycarboxylic acid Compositions

The targeted enzyme catalyst-generated peracid produced according to the present method can be used in a variety of hard surface/inanimate object applications for reduction of concentrations of biological contaminants, such as decontamination of medical instruments (e.g., endoscopes), textiles (such as garments and carpets), food preparation surfaces, food storage and food-packaging equipment, materials used for the packaging of food products, chicken hatcheries and grow-out facilities, animal enclosures, and spent process waters that have microbial and/or virucidal activity. The targeted enzyme-generated peroxycarboxylic acids may be used in formulations designed to inactivate prions (e.g., certain proteases) to additionally provide biocidal activity (see U.S. Pat. No. 7,550,420 to DiCosimo et al.).

In one aspect, the peracid composition is useful as a disinfecting agent for non-autoclavable medical instruments and food packaging equipment. As the peracid-containing formulation may be prepared using GRAS or food-grade components (targeted perhydrolase, enzyme substrate, hydrogen peroxide, and buffer), the targeted perhydrolase-generated peracid may also be used for decontamination of animal carcasses, meat, fruits and vegetables, or for decontamination of prepared foods. The targeted perhydrolase-generated peracid may be incorporated into a product whose final form is a powder, liquid, gel, film, solid or aerosol. The targeted perhydrolase-generated peracid may be diluted to a concentration that still provides an efficacious decontamination.

Fusion proteins comprising a perhydrolytic enzyme and at least one peptidic component having affinity for a targeted surface are used to produce an efficacious concentration of peracid on or near the surface to be disinfected or bleached. The target surface may be a surface or object contaminated (or suspected of being contaminated) with biological contaminants, such as pathogenic microbial contaminants. In one embodiment, the peptidic component used to target the perhydrolytic enzyme has affinity for a contaminated surface, a surface suspected of being contaminated, or the actual contaminant (i.e., peptidic component has affinity for the actual biological contaminant).

As used herein, "contacting" refers to placing a disinfecting composition comprising an effective concentration of peracid (produce by the targeted perhydrolase) in contact with the target surface for a period of time sufficient to achieve the desired effect. Contacting includes spraying, treating, immersing, flushing, pouring on or in, mixing, combining, painting, coating, applying, affixing to and otherwise communicating a solution or composition that forms an efficacious concentration of peroxycarboxylic acid with the target surface. The disinfectant compositions comprising the targeted perhydrolase may be combined with a cleaning composition to provide both cleaning and disinfection. Alternatively, a cleaning agent (e.g., a surfactant or detergent) may be incorporated into the formulation to provide both cleaning and disinfection in a single composition.

The compositions can also contain at least one additional antimicrobial agent, combinations of prion-degrading proteases, a virucide, a sporicide, or a biocide. Combinations of these agents with the peracid produced by the claimed processes can provide for increased and/or synergistic effects when used to clean and disinfect surfaces and/or objects contaminated (or suspected of being contaminated) with biological contaminants. Suitable antimicrobial agents include carboxylic esters (e.g., p-hydroxy alkyl benzoates and alkyl cinnamates), sulfonic acids (e.g., dodecylbenzene sulfonic acid), iodo-compounds or active halogen compounds (e.g., elemental halogens, halogen oxides (e.g., NaOCl, HOCl, HOBr, $ClO_2$), iodine, interhalides (e.g., iodine monochloride, iodine dichloride, iodine trichloride, iodine tetrachloride, bromine chloride, iodine monobromide, or iodine dibromide), polyhalides, hypochlorite salts, hypochlorous acid, hypobromite salts, hypobromous acid, chloro- and bromo-hydantoins, chlorine dioxide, and sodium chlorite), organic peroxides including benzoyl peroxide, alkyl benzoyl peroxides, ozone, singlet oxygen generators, and mixtures thereof, phenolic derivatives (e.g., o-phenyl phenol, o-benzyl-p-chlorophenol, tert-amyl phenol and $C_1$-$C_6$ alkyl hydroxy benzoates), quaternary ammonium compounds (e.g., alkyldimethylbenzyl ammonium chloride, dialkyldimethyl ammonium chloride and mixtures thereof), and mixtures of such antimicrobial agents, in an amount sufficient to provide the desired degree of microbial protection. Effective amounts of antimicrobial agents include about 0.001 wt % to about 60 wt % antimicrobial agent, about 0.01 wt % to about 15 wt % antimicrobial agent, or about 0.08 wt % to about 2.5 wt % antimicrobial agent.

In one aspect, the peracids formed by the process can be used to reduce the concentration of viable biological contaminants (such as a microbial population) when enzymatically generated on (or near) the target locus. As used herein, a "locus" comprises part or all of a target surface suitable for the desired peracid-based benefit. Target surfaces may include all surfaces that can potentially be contaminated with biological contaminants. Non-limiting examples include equipment surfaces found in the food or beverage industry (such as tanks, conveyors, floors, drains, coolers, freezers, equipment surfaces, walls, valves, belts, pipes, drains, joints, crevasses, combinations thereof, and the like); building surfaces (such as walls, floors and windows); non-food-industry related pipes and drains, including water treatment facilities, pools and spas, and fermentation tanks; hospital or veterinary surfaces (such as walls, floors, beds, equipment (such as endoscopes), clothing worn in hospital/veterinary or other healthcare settings, including clothing, scrubs, shoes, and other hospital or veterinary surfaces); restaurant surfaces; bathroom surfaces; toilets; clothes and shoes; surfaces of barns or stables for livestock, such as poultry, cattle, dairy cows, goats, horses and pigs; hatcheries for poultry or for shrimp; and pharmaceutical or biopharmaceutical surfaces (e.g., pharmaceutical or biopharmaceutical manufacturing equipment, pharmaceutical or biopharmaceutical ingredients, pharmaceutical or biopharmaceutical excipients). Additional hard surfaces include food products, such as beef, poultry, pork, vegetables, fruits, seafood, combinations thereof, and the like. The locus can also include water absorbent materials such as infected linens or other textiles. The locus also includes harvested plants or plant products including seeds, corms, tubers, fruit, and vegetables, growing plants, and especially crop growing plants, including cereals, leaf vegetables and salad crops, root vegetables, legumes, berried fruits, citrus fruits and hard fruits.

Non-limiting examples of hard surface materials may include metals (e.g., steel, stainless steel, chrome, titanium, iron, copper, brass, aluminum, and alloys thereof), minerals (e.g., concrete), polymers and plastics (e.g., polyolefins, such as polyethylene, polypropylene, polystyrene, poly(meth) acrylate, polyacrylonitrile, polybutadiene, poly(acrylonitrile, butadiene, styrene), poly(acrylonitrile, butadiene), acrylonitrile butadiene; polyesters such as polyethylene terephthalate; and polyamides such as nylon). Additional surfaces include brick, tile, ceramic, porcelain, wood, wood pulp, paper, vinyl, linoleum, and carpet.

The peracids formed by the present process may be used to provide a benefit to a fiber, yarn, article of clothing or a textile including, but not limited to disinfecting, sanitizing, bleaching, destaining, and deodorizing. The peracids formed by the present process may be used in any number of laundry care products including, but not limited to textile pre-wash treatments, laundry detergents, laundry detergents or additives, stain removers, bleaching compositions, deodorizing compositions, and rinsing agents, to name a few.

The peracids formed by the present process can be used in one or more steps of the wood pulp or paper pulp bleaching/delignification process, particularly where peracetic acid is used (for example, see EP1040222 B1 and U.S. Pat. No. 5,552,018 to Devenyns, J.)

Laundry Care Compositions

The present compositions and method may be used in laundry care applications for targeted peracid production. The targeted perhydrolase may be targeted a fiber, yarn, textile (woven or non-woven), or article of clothing. The peracid produced by the targeted peracid-generating system results in a targeted surface that is disinfected, sanitized, bleached, destained, deodorized or any combination thereof.

The fusion protein having perhydrolytic activity is designed to have affinity for a target material used in the manufacture of fibers, yarns, textiles (woven or non-woven) or articles of clothing. The target material may include natural, semi-synthetic, and synthetic materials used in the manufacture of articles to be laundered. The target materials may include polymers and copolymers typically used in the preparation of fibers, yarns, textiles and articles of clothing.

Target materials may include cellulosic materials, non-cellulosic materials (e.g., polyesters, polyacrylics), and blends thereof. In one embodiment, the target surface comprises a cellulosic material. As such, a peptidic component having affinity for the cellulosic material may be used to couple the targeted perhydrolase to the cellulosic material. The remaining peracid-generating reaction components may be added before, in combination with, or after coupling the targeted perhydrolase to the target surface.

Targeting Perhydrolases to a First Material/Surface or Object for Controlled Delivery of a Peracid Benefit Agent to a Secondary Material/Surface or Object In some embodiments it may be desirable to target the perhydrolytic enzymes to a primary target material/surface or object that is not the beneficiary of the peracid based benefit agent. For example, it may be desirable to first target the perhydrolytic enzyme to a primary material/surface such as a tool, utensil, applicator, fabric, bandage, sponge, mop, a non-respirable particle, and the like, which is subsequently used delivery a peracid based benefit to a secondard material/surface (e.g., a perhydrolytic fusion protein bound to a mop head that is subsequently contacted with a floor) for cleaning, bleaching, whitening, disinfecting, sanitizing, destaining, deodorizing, or any combination thereof. In another aspect, the targeted perhydrolytic enzyme is targeted to a particle (using a binding domain having affinity for the particle) which is subsequently used as a delivery vehicle for the active fusion protein. In a further aspect, the particle comprising the fusion protein is non-respirable and of low toxicity. In another embodiment, the particle or surface comprises a cellulosic material capable of binding to a perhydrolytic fusion protein via a peptidic component having affinity for cellulose.

HPLC Assay Method for Determining the Concentration of Peroxycarboxylic Acid and Hydrogen Peroxide.

A variety of analytical methods can be used in the present methods to analyze the reactants and products including, but not limited to, titration, high performance liquid chromatography (HPLC), gas chromatography (GC), mass spectroscopy (MS), capillary electrophoresis (CE), the analytical procedure described by Pinkernell et al., (*Anal. Chem.*, 69(17): 3623-3627 (1997)), and the 2,2'-azino-bis(3-ethylbenzothazoline)-6-sulfonate (ABTS) assay (Pinkernell et al., *Analyst,* 122:567-571 (1997) and Dinu et al., *Adv. Funct. Mater.,* 20:392-398 (2010)) and as described in the present examples.

Determination of Minimum Biocidal Concentration of Peroxycarboxylic Acids

Certain personal care applications may be associated with the removal of unwanted microbes, such as those associated with body order, fungal infections, and the development of dental caries, to name a few. As such, one may want to measure the minimum biocidal concentration for the target personal care application. The method described by J. Gabrielson, et al. (*J. Microbiol. Methods* 50: 63-73 (2002)) can be employed for determination of the Minimum Biocidal Concentration (MBC) of peroxycarboxylic acids, or of hydrogen peroxide and enzyme substrates. The assay method is based on XTT reduction inhibition, where XTT ((2,3-bis[2-methoxy-4-nitro-5-sulfophenyl]-5-[(phenylamino)carbonyl]-2H-tetrazolium, inner salt, monosodium salt) is a redox dye that indicates microbial respiratory activity by a change in optical density (OD) measured at 490 nm or 450 nm. However, there are a variety of other methods available for testing the activity of disinfectants and antiseptics including, but not limited to, viable plate counts, direct microscopic counts, dry weight, turbidity measurements, absorbance, and bioluminescence (see, for example Brock, Semour S., *Disinfection, Sterilization, and Preservation,* 5$^{th}$ edition, Lippincott Williams & Wilkins, Philadelphia, Pa., USA; 2001).

Recombinant Microbial Expression

The genes and gene products of the instant sequences may be produced in heterologous host cells, particularly in the cells of microbial hosts. Preferred heterologous host cells for expression of the instant genes and nucleic acid molecules are microbial hosts that can be found within the fungal or bacterial families and which grow over a wide range of temperature, pH values, and solvent tolerances. For example, it is contemplated that any of bacteria, yeast, and filamentous fungi may suitably host the expression of the present nucleic acid molecules. The perhydrolase may be expressed intracellularly, extracellularly, or a combination of both intracellularly and extracellularly, where extracellular expression renders recovery of the desired protein from a fermentation product more facile than methods for recovery of protein produced by intracellular expression. Transcription, translation and the protein biosynthetic apparatus remain invariant relative to the cellular feedstock used to generate cellular biomass; functional genes will be expressed regardless. Examples of host strains include, but are not limited to, bacterial, fungal or yeast species such as *Aspergillus, Trichoderma, Saccharomyces, Pichia, Phaffia, Kluyveromyces, Candida, Hansenula, Yarrowia, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. In one embodiment, bacterial host strains include *Escherichia, Bacillus, Kluyveromyces*, and *Pseudomonas*. In a preferred embodiment, the bacterial host cell is *Bacillus subtilis* or *Escherichia coli.*

Large-scale microbial growth and functional gene expression may use a wide range of simple or complex carbohydrates, organic acids and alcohols or saturated hydrocarbons, such as methane or carbon dioxide in the case of photosynthetic or chemoautotrophic hosts, the form and amount of nitrogen, phosphorous, sulfur, oxygen, carbon or any trace micronutrient including small inorganic ions. The regulation of growth rate may be affected by the addition, or not, of specific regulatory molecules to the culture and which are not typically considered nutrient or energy sources.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell and/or native to the production host, although such control regions need not be so derived.

Initiation control regions or promoters which are useful to drive expression of the present cephalosporin C deacetylase coding region in the desired host cell are numerous and familiar to those skilled in the art. Virtually any promoter capable of driving these genes is suitable for the present invention including but not limited to, CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, araB, tet, trp, $IP_L$, $IP_R$, T7, tac, and trc (useful for expression in *Escherichia coli*) as well as the amy, apr, npr promoters and various phage promoters useful for expression in *Bacillus.*

Termination control regions may also be derived from various genes native to the preferred host cell. In one embodiment, the inclusion of a termination control region is optional. In another embodiment, the chimeric gene includes a termination control region derived from the preferred host cell.

Industrial Production

A variety of culture methodologies may be applied to produce the perhydrolase catalyst. For example, large-scale production of a specific gene product over expressed from a recombinant microbial host may be produced by batch, fed-batch, and continuous culture methodologies. Batch and fed-batch culturing methods are common and well known in the art and examples may be found in Thomas D. Brock in *Biotechnology: A Textbook of Industrial Microbiology*, Second Edition, Sinauer Associates, Inc., Sunderland, Mass. (1989) and Deshpande, Mukund V., *Appl. Biochem. Biotechnol.*, 36:227-234 (1992).

Commercial production of the desired perhydrolase catalyst may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Recovery of the desired perhydrolase catalysts from a batch fermentation, fed-batch fermentation, or continuous culture, may be accomplished by any of the methods that are known to those skilled in the art. For example, when the enzyme catalyst is produced intracellularly, the cell paste is separated from the culture medium by centrifugation or membrane filtration, optionally washed with water or an aqueous buffer at a desired pH, then a suspension of the cell paste in an aqueous buffer at a desired pH is homogenized to produce a cell extract containing the desired enzyme catalyst. The cell extract may optionally be filtered through an appropriate filter aid such as celite or silica to remove cell debris prior to a heat-treatment step to precipitate undesired protein from the enzyme catalyst solution. The solution containing the desired enzyme catalyst may then be separated from the precipitated cell debris and protein by membrane filtration or centrifugation, and the resulting partially-purified enzyme catalyst solution concentrated by additional membrane filtration, then optionally mixed with an appropriate carrier (for example, maltodextrin, phosphate buffer, citrate buffer, or mixtures thereof) and spray-dried to produce a solid powder comprising the desired enzyme catalyst.

When an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope be limited to the specific values recited when defining a range.

GENERAL METHODS

The following examples are provided to demonstrate preferred aspects of the invention. It should be appreciated by those of skill in the art that the techniques disclosed in the examples follow techniques to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the presently disclosed methods and examples.

All reagents and materials were obtained from DIFCO Laboratories (Detroit, Mich.), GIBCO/BRL (Gaithersburg, Md.), TCI America (Portland, Oreg.), Roche Diagnostics Corporation (Indianapolis, Ind.), Thermo Scientific (Pierce Protein Research Products; Rockford, Ill.) or Sigma-Aldrich Chemical Company (St. Louis, Mo.), unless otherwise specified.

The following abbreviations in the specification correspond to units of measure, techniques, properties, or compounds as follows: "sec" or "s" means second(s), "min" means minute(s), "h" or "hr" means hour(s), "μL" means microliter(s), "mL" means milliliter(s), "L" means liter(s), "mM" means millimolar, "M" means molar, "mmol" means millimole(s), "ppm" means part(s) per million, "wt" means weight, "wt %" means weight percent, "g" means gram(s), "mg" means milligram(s), "μg" means microgram(s), "ng" means nanogram(s), "g" means gravity, "HPLC" means high performance liquid chromatography, "dd $H_2O$" means distilled and deionized water, "dcw" means dry cell weight, "ATCC" or "ATCC®" means the American Type Culture Collection (Manassas, Va.), "U" means unit(s) of perhydrolase activity, "rpm" means revolution(s) per minute, "PAH" means perhydrolase, and "EDTA" means ethylenediaminetetraacetic acid.

HPLC Perhydrolase Assay

Determination of the peracetic acid (PAA) concentration in the reaction mixtures was performed according to the method described by Pinkernell et al. Aliquots (0.040 mL) of the reaction mixture were removed at predetermined times and mixed with 0.960 mL of 5 mM phosphoric acid in water; adjustment of the pH of the diluted sample to less than pH 4 immediately terminated the reaction. The resulting solution was filtered using an ULTRAFREE® MC-filter unit (30,000 Normal Molecular Weight Limit (NMWL), Millipore cat #UFC3LKT 00) by centrifugation for 2 min at 12,000 rpm. An aliquot (0.100 mL) of the resulting filtrate was transferred to 1.5-mL screw cap HPLC vial (Agilent Technologies, Palo Alto, Calif.; #5182-0715) containing 0.300 mL of deionized water, then 0.100 mL of 20 mM MTS (methyl-p-tolyl-sulfide) in acetonitrile was added, the vials capped, and the contents briefly mixed prior to a 10 min incubation at ca. 25° C. in the absence of light. To each vial was then added 0.400 mL of acetonitrile and 0.100 mL of a solution of triphenylphosphine (TPP, 40 mM) in acetonitrile, the vials re-capped, and the resulting solution mixed and incubated at ca. 25° C. for 30 min in the absence of light. To each vial was then added 0.100 mL of 10 mM N,N-diethyl-m-toluamide (DEET; HPLC external standard) and the resulting solution analyzed by HPLC (Waters Alliance e2695, Waters Corporation; MA).

HPLC Method:

Supelco Discovery C8 column (10 cm×4.0-mm, 5 μm) (cat. #569422-U) w/precolumn Supelco Supelguard Discovery C8 (Sigma-Aldrich; cat #59590-U); 10 microliter injection volume; gradient method with $CH_3CN$ (Sigma-Aldrich; #270717) and deionized water at 1.0 mL/min and ambient temperature:

| Time (min:sec) | (% CH3CN) |
|---|---|
| 0:00 | 40 |
| 3:00 | 40 |
| 3:10 | 100 |
| 4:00 | 100 |
| 4:10 | 40 |
| 7:00 (stop) | 40 |

Expression Vector pLD001

Plasmid pLD001 (SEQ ID NO: 141) has been previous reported as a suitable expression vector for *E. coli* (see U.S. Patent Application Publication No. 2010-0158823 A1 to Wang et al.; incorporated herein by reference).

The vector pLD001 was derived from the commercially available vector pDEST17 (Invitrogen, Carlsbad, Calif.). The vector pLD001 was derived from the commercially available vector pDEST17 (Invitrogen, Carlsbad, Calif.) and includes sequences that encode a fragment of the enzyme ketosteroid isomerase (KSI).

Using standard recombinant DNA methods, the coding sequences for the various hydrolases/perhydrolases bounded by NdeI and BamHI sites may be ligated between NdeI and BamHI sites of pLD001 replacing the KSI fragment. Similarly the coding sequences of the binding domains bounded by the BamHI and AscI sites may be ligated between BamHI and AscI sites of pLD001.

Example 1

Construction of Cotton-Targeted Perhydrolase Fusions

This example describes the design of an expression system for the production of perhydrolases targeted to cellulose and specifically targeted to cotton via cellulose-binding sequences.

The polynucleotides (SEQ ID NOs: 147, 150, and 153) encoding fusions of a perhydrolase to cellulose-binding domains (SEQ ID NOs: 148, 151, and 154; respectively) were designed to have the nucleotide sequence of the C277S variant of the *Thermotoga maritima* perhydrolase (SEQ ID NO: 142) fused at the 3'-end to the nucleotide sequence encoding a 18 amino acid flexible linker (SEQ ID NO: 143); itself fused to the nucleotide sequence encoding the cellulose-binding domains of cellulases from *Clostridium thermocellum* (SEQ ID NO: 149), *Clostridium cellulovorans* (SEQ ID NO: 152) and *Bacillus* sp. (SEQ ID NO: 155) with a Met at the N-terminus and a His6 at the C-terminus. The genes were codon-optimized for expression in *E. coli* and synthesized by DNA2.0 (Menlo Park, Calif.). The coding sequences were cloned behind the T7 promoter in the expression vector pLD001 (SEQ ID NO: 141) between the NdeI and AscI restriction sites yielding plasmids pLR988, pLR1049, and pLR1050; respectively. To express the fusion proteins, the plasmids were transferred to the *E. coli* strain BL21AI (Invitrogen, Carlsbad, Calif.) yielding strains LR3310, LR3504, and LR3505; respectively.

The non-targeted C277S variant of the *Thermotoga maritima* perhydrolase (SEQ ID NO: 142) was cloned similarly. Production of the untargeted perhydrolase has been described previously in U.S. Patent Application Publication No. 2010-0087529 to DiCosimo et al.

The gene coding (SEQ ID NO: 144) for another perhydrolase fusion ("PAH-HC263"; SEQ ID NO: 145) that was initially designed for binding to hair was used as a negative control in the following experiments (see co-filed, co-pending U.S. Provisional patent application entitled "ENZYMATIC PERACID GENERATION FOR USE IN HAIR CARE PRODUCTS" Ser. No. 61/424,847.

Example 2

Production of a Fusion Protein Comprising a Perhydrolase Fused to a Thermophilic Cellulose-Binding Domain This example describes the expression and purification of a perhydrolase targeted to cellulose via a thermostable cellulose-binding domain.

Strain LR3310 was grown in 1 L of autoinduction medium (10 g/L Tryptone, 5 g/L Yeast Extract, 5 g/L NaCl, 50 mM $Na_2HPO_4$, 50 mM $KH_2PO_4$, mM $(NH_4)_2SO_4$, 3 mM $MgSO_4$, 0.75% glycerol, 0.075% glucose and 0.05% arabinose) containing 50 mg/L spectinomycin at 37° C. for 20 hours under 200 rpm agitation. The preparation and recombinant expression of the non-targeted *Thermotoga maritima* C277S variant has previously been reported by DiCosimo et al. in U.S. Patent Application Publication No. 2010-0087529.

The cells were harvested by centrifugation at 8000 rpm at 4° C. and washed by resuspending the cell pellets in 300 mL of ice chilled lysis buffer (50 mM Tris pH 7.5, 5 mM EDTA, 100 mM NaCl) using a tissue homogenizer (Brinkman Homogenizer model PCU11) at 3500 rpm followed by centrifugation (8000 rpm, 4° C.). The cells were then lysed by resuspension in chilled lysis buffer containing 75 mg of chicken egg white lysozyme (Sigma) using the tissue homogenizer. The cell suspensions were allowed to rest on ice for 3 hrs to allow the digestion of the cell wall by the lysozyme, with periodic homogenization with the tissue homogenizer. At this stage, care was taken to avoid any foaming of the extracts. The extracts were split (150 mL per 500-mL bottle) and frozen at −20° C. The frozen cell extracts were thawed at room temperature (~22° C.), homogenized with the tissue homogenizer, and disrupted by sonication using a sonicator (Branson Ultrasonics Corporation, Sonifier model 450) equipped with a 5 mm probe at 20% maximum output, 2 pulses per second for 1 min repeat once. The lysed cell extracts were transferred to 4×50-mL conical polypropylene centrifuge tubes and then centrifuged at 10,000 rpm for 10 min at 4° C. The pellet containing cell debris as well as unbroken cells was frozen. Aliquots of the lysate were transferred to 15-mL conical polypropylene (12×5-mL) and heated to 60° C. for 15 min, chilled on ice and pooled into 4×50-mL conical polypropylene centrifuge tubes. The soluble fraction containing the thermostable enzyme and the precipitated *E. coli* proteins were separated by centrifugation at 10,000 rpm for 10 min at 4° C. If the cell disruption was incomplete after the sonication step, the frozen pellet was thawed again and subjected to a second round of sonication, centrifugation and heat treatment. The output of this purification protocol typically yielded 2-4 mg of protein per mL with a purity of the fusion perhydrolase between 90% and 75% of the protein as estimated by polyacrylamide gel electrophoresis (PAGE) analysis. Total protein was quantitated by the BCA assay (Sigma-Aldrich, St Louis, Mo.) using a solution of Bovine Serum Albumin as a standard (Sigma-Aldrich).

Example 3

Production of Other Fusion Proteins Comprising Perhydrolase Fused to a Cellulose-Binding Domain This example describes the expression and purification of a perhydrolase targeted to cellulose via non-thermostable cellulose-binding domains.

Strains LR3504 and LR3505 were grown in 1 L autoinduction medium as described in Example 2 for strain LR3310. Cells were harvested and whole cell extracts were prepared by lysozyme/freeze-thaw cycles as described for cells of strain LR3310.

The soluble cell extracts containing the perhydrolase fusion were subjected to metal chelation affinity chromatography. Five mL of lysates were loaded onto a 5-mL Co-NTA chromatography column (Co-NTA Cat#89965, Thermo Scientific, Rockford, Ill.) equilibrated with 20 mL of equilibration/wash buffer (10 mM Tris HCl pH 7.5, 10% glycerol, 150 mM NaCl, 1 mM imidazole). The column was then washed with 15 mL of equilibration/wash buffer and the bound fusion proteins were eluted with 15 mL of elution buffer (10 mM Tris HCl pH 7.5, 10% glycerol, 150 mM NaCl, 150 mM imidazole). The perhydrolase fusions were tested without additional purification.

Example 4

Quantitation of the Enzyme Hydrolase Activity

This example describes the method for the detection and quantitation of a perhydrolase via its hydrolase activity using a non-specific esterase substrate.

The hydrolase activity of the perhydrolase fusions was determined with pNPA (p-nitrophenyl acetyl ester). Typically the enzyme was diluted in hydrolase assay buffer (50 mM $KH_2$ $PO_4$, pH 7.2) to a concentration between 1 and 0.01 μg/mL. The reaction was initiated by addition of pNPA to a final concentration of 3 mM (30 μL/mL of 100 mM pNPA dissolved in acetonitrile) at 25° C. or 30° C. Change in absorption at 400 nm with time was recorded. Due to a background level of non-enzymatic hydrolysis of pNPA, a no-enzyme control was included in the analysis. Activity was measured as Δ400/min (sample)−Δ400/min (no-enzyme control) and converted into μmol of pNPA hydrolyzed/mg of proteins×min (pNPA molar absorption: 10909 $M^{-1}$). The specific activity of the fusion proteins was typically between 10 and 30 μmol/mg×min.

Example 5

Binding of the Cellulose-Targeted Perhydrolase Fusion to Cotton Fabric

This example describes the binding of the perhydrolase to cellulose in a manner dependent on the fusion of cellulose-binding sequences to the perhydrolase.

For cotton binding experiments, cotton fabric stained with blueberry juice was used as received (Test Fabrics Inc., West Pittson, Pa.). Swatches (1 $cm^2$, ~27 mg) were added into a 1.8-mL microfuge tube. Hydrolase assay buffer (1 mL) as added to the swatch followed by the addition of the perhydrolase enzymes to the solution. The enzymes, added in excess, were allowed to bind the cotton swatches for 30 min with gentle agitation (24 rpm) on an Adams Nutator (model 1105; Becton Dickinson, Franklin Lakes, N.J.). No enzyme controls, with and without swatch, were included in the binding experiment to account for non-enzymatic hydrolysis of the pNPA hydrolase reagent. After the binding step, a 0.8 mL aliquot of the binding buffer was transferred to a new tube containing 9.2 mL buffer to quantitate the amount of unbound enzyme. Additional binding buffer was removed and the swatches were washed 4 times with 1 mL of 1% TWEEN®-20 in hydrolase buffer, followed by 2 washes with 1 mL each in hydrolase buffer. The swatches were then resuspended in 10 mL of hydrolase assay and the hydrolase activity that remained bound to the swatch was measured. The C277S variant of *Thermotoga maritima* perhydrolase (also referred to herein as "PAH"; SEQ ID NO: 142) was used as a control (a non-targeted perhydrolase). The results are provided in Table 1.

TABLE 1

Retention of Cellulose-Targeted Perhydrolase on Cotton Fabric

| Enzyme ID (SEQ ID NO:) | Activity not retained on swatches (nmol pNPA hydrolyzed/min) | Activity retained on swatches after 4 TWEEN ®-20 washes (nmol pNPA hydrolyzed/min)[a] |
|---|---|---|
| Untagged C277S (SEQ ID NO: 142) | 647.2 | 0.0 |
| C277S-HC263 (SEQ ID NO: 145) | 223.7 | 1.8 |
| C277S-CIP (SEQ ID NO: 148) | 334.6 | 77.9 |

[a]= The retention of the enzymes on the swatch is measured by the amount of hydrolase activity retained expressed in nmol pNPA hydrolyzed/min in a 10 mL assay.

This experiment demonstrates that the perhydrolase fusion targeted to cellulose by the CIP cellulose-binding domain was retained on cotton fabric after extensive washes in 1% TWEEN®-20 while the untargeted perhydrolase or a fusion protein comprising a perhydrolase targeted to another surface were not.

Example 6

Binding of the Cellulose-Targeted Perhydrolase Fusions to Cellulosic Materials This example describes the binding of cellulose-targeted perhydrolase fusions to several cotton blend fabrics.

The binding of the targeted perhydrolase fusion proteins C277S-CIP, (SEQ ID NO: 148), C277S-CBM17 (SEQ ID NO: 151), and C277S-CBM28 (SEQ ID NO: 154) were tested on the cotton blends fabrics indicated in Table 2. Swatches (1 $cm^2$) were exposed to 1 mL the fusion protein solution as described above. The swatches were washed as described above and the enzyme was detected by its hydrolase activity using the pNPA assay.

TABLE 2

Binding of the Cellulose-targeted Perhydrolases to Cotton Blends Fabrics

| Hydrolase activity retained on: | C277S-CIP (nmol pNPA hydrolyzed/min)[b] | C277S-CBM17 (nmol pNPA hydrolyzed/min)[b] | C277S-CBM28 (nmol pNPA hydrolyzed/min)[b] |
|---|---|---|---|
| Cotton/Spandex (96%/4%) | 147 | 174 | 83 |
| Rayon/Spandex (95%/5%) | 101 | 128 | 64 |
| Poly/Cotton (65%/35%) | 248 | 248 | 73 |
| Cellulose Acetate (100%) | 110 | 0 | 0 |
| Cotton | 202 | 18 | 110 |

[b]= The retention of the enzymes on the swatch is measured by the amount of hydrolase activity retained expressed in nmol pNPA hydrolyzed/min in a 10 mL assay.

This example demonstrates the usefulness and applicability of targeting the perhydrolase to cellulose based or cellulose containing fabrics.

Example 7

Bleaching Activity of the C277S-CIP Cellulose-Targeted Perhydrolase on Stained Cotton Fabric This example describes the benefit of a cellulose targeting domain fused to the perhydrolase in bleaching stained cotton fabric in applications where the enzyme is washed from the fabric.

Blueberry-stained swatches (1 $cm^2$) were placed in 50-mL polypropylene tubes (3 swatches per tube) containing 3 mL of PAH buffer. Three tubes received respectively 14 μL of C277S-CIP (4.7 μg/mL), 27 μL of untargeted ("untagged") *Thermotoga maritima* C277S (9 μg/mL), and no enzyme.

The enzyme was allowed to bind for 30 min under gentle agitation. The swatches were then washed 4 times with 5 mL of C277S buffer containing 1% TWEEN®-20 and 2 more times with C277S buffer. The swatches were dried at room temperature (~22° C.) for 30 min and their color was measured with a colorimeter (SP64 Portable Sphere Spectrophotometer, model SP64, X-Rite Inc. Grandville, Mich.)(settings: wave length range 400 nm to 700 nm, every 10 nm, aperture 8 mm). Two color measurements were made on the front and on back of each swatch and the four values were averaged.

Each swatch was then placed in a 1.8-mL microfuge tube with 1 mL of 50 mM Tris pH 7.5 buffer containing 11 mM hydrogen peroxide+100 mM triacetin and incubated for 10 min at room temperature with gentle swirling. The solutions were removed; the swatches washed with 50 mM Tris pH 7.5, air dried and their color measured with a colorimeter.

TABLE 3

Bleaching of Stained Cotton Fabric Mediated by a Targeted Perhydrolase

| | Color before treatment | | | Color after treatment | | | Average color change (ΔE) | |
|---|---|---|---|---|---|---|---|---|
| | | | | | | | vs no | vs no |
| | L | a | b | L | a | b | treatment | enzyme |
| No Enzyme | 64.9 | −1.4 | 0.6 | 69.4 | −0.3 | 2.5 | 5.1 | 0.0 |
| Untargeted C277S (SEQ ID NO: 142) | 65.2 | −1.4 | 0.8 | 69.9 | −0.3 | 2.7 | 5.1 | 0.0 |
| C277S-CIP (SEQ ID NO: 148) | 64.8 | −1.3 | 0.6 | 77.9 | 2.1 | 7.4 | 15.0 | 9.9 |

Values are the average of measurement triplicate swatches.

This example shows that, under the conditions of the assay, the presence of the targeted enzyme enhances bleaching significantly over that provided by the hydrogen peroxide and triacetin solution. No enhancement in bleaching was generated by the untargeted perhydrolase indicating that it did not bind to the cotton fabric following the washing steps, thus demonstrating the advantage of targeting the perhydrolase to retain it onto the cotton fabric.

TABLE 4

Bleaching of Stained Cotton Fabric Mediated by Targeted Perhydrolase

| | | | | Average color change (ΔE) | |
|---|---|---|---|---|---|
| | L | a | b | vs no treatment | vs no enzyme |
| Color before treatment | 62.48 | 0.30 | 3.47 | 0.0 | Not applicable |
| Color after treatment without enzyme | 68.57 | 0.73 | 5.39 | 6.4 | 0.0 |
| C277S-CIP | 75.6 | 2.1 | 9.0 | 14.4 | 8.0 |
| C277S-CBM17 | 76.0 | 2.7 | 9.7 | 15.1 | 8.8 |
| C277S-CBM28 | 76.4 | 2.5 | 9.5 | 15.3 | 9.0 |

This example shows that the improved bleaching due to the targeting of the perhydrolase to cellulose can be implemented when other cellulose-binding domains are fused to the perhydrolase.

Example 8

Bleaching Improvement by Perhydrolase Targeting

This example describes the benefit of a cellulose targeting domain fused to the perhydrolase in bleaching stained cotton fabric in applications where the enzyme is not washed from the fabric.

In this experiment, the bleaching due to the production of peracetic by the targeted perhydrolase bound to cotton fabric was compared to that due to unbound untargeted perhydrolase, at equal total amount of enzyme added. The total amount of enzyme added was assessed by measuring the hydrolase activity of the enzyme.

Swatches (1 $cm^2$) of blueberry-strained cotton were placed in 2-mL centrifuge tubes containing 1 mL of PAH buffer. A set of tubes received increasing amounts of the CIP targeted perhydrolase (C277S-CIP): 0, 20, 40 and 80 μL of enzyme (1:20 dilution of 4 μg/μL at an estimated 90% purity). A set of tubes that will later receive the untargeted enzyme were prepared in the same manner except that they only received PAH buffer. Duplicate tubes were set up for each enzyme concentration to be tested, for both the targeted enzyme and the untargeted enzyme to be added later, one to measure the amount of enzyme retained on the swatch and one to measure bleaching. All the tubes were agitated gently for 30 min at room temperature (~22° C.).

For all the C277S-CIP containing tubes, 0.8 mL of enzyme solution was transferred to a 15-mL polypropylene tube containing 9.2 mL of PAH-buffer to measure hydrolase activity representing the unbound enzyme fraction. The swatches were washed 3 times with 1 mL of 1% TWEEN® in PAH-buffer with hand agitation then 2 times with 1 mL buffer PAH-buffer. One swatch for each C277S-CIP concentration was transferred to a 15-mL polypropylene tube containing 10 mL of PAH buffer to measure bound hydrolase activity. The second swatch for each C277S-CIP (SEQ ID NO: 148) concentration and all the other swatches to later receive untargeted *Thermotoga maritima* C277S enzyme (SEQ ID NO: 142) were transferred to a new 2-mL centrifuge tube.

Half of the swatches that did not receive the C277S-CIP enzyme, were transferred to a 15-mL polypropylene tube containing 10 mL of PAH-buffer and increasing amounts of the untargeted enzyme (0, 10, 20, 30, 40, 50 and 60 μL of a 13.6 μg/mL enzyme solution at an estimated 25% purity) to measure bound hydrolase activity.

Hydrolase activity of the swatches with the bound C277S-CIP and the unbound untargeted C277S was measured by addition of the 300 μL of 100 mM pNPA in acetonitrile and monitoring the change of absorption at 400 nm with time.

To the second set of swatches that had not received C277S-CIP, increasing amounts of the untargeted perhydrolase were added (0, 10, 20, 30, 40, 50 and 60 μL of a 13.6 μg/mL enzyme solution at an estimated 25% purity). These swatches and the swatches that had been previously been contacted by the targeted C277S-CIP received 1 mL of 11 mM hydrogen peroxide+100 mM triacetin in 50 mM Tris pH 7.5 to evaluate bleaching by the peracetic acid produces. After an initial mixing, the tubes were left to stand for 10 min at room temperature. The bleaching reaction was stopped after 10 min by removal of solution and rinsing 2×1-mL 50 mM Tris pH 7.5. The swatches were air dried and their color was measured with a colorimeter. This experiment was repeated. As shown in Table 5, for an equal amount of enzyme activity added and for an equal duration of reaction, the cellulose targeted perhydrolase was more effective at bleaching the stained swatches that the untargeted perhydrolase.

This example demonstrated the utility of targeting the perhydrolase to a cellulose substrate for increasing the efficacy of the enzyme.

TABLE 5

Comparison of Bleaching vs. Amount of Enzyme Added for the Targeted and Untargeted Perhydrolase.

| | Untargeted enzyme Amount of enzyme added (μL of 1/20 enzyme dilution) | | | | | | | Targeted enzyme | | | |
|---|---|---|---|---|---|---|---|---|---|---|---|
| | 0 | 10 | 20 | 30 | 40 | 50 | 60 | 0 | 20 | 40 | 80 |
| Experiment 1 | | | | | | | | | | | |
| Bleaching (ΔE) | 0 | 2.34 | 4.10 | 4.68 | 4.86 | 5.61 | 5.99 | 0.09 | 6.55 | 6.43 | 6.85 |
| Hydrolase[1] (ΔA400/min) | 0 | 0.045 | 0.077 | 0.118 | 0.154 | 0.180 | 0.22 | 0.00 | 0.050 | 0.084 | 0.109 |
| Experiment 2 | | | | | | | | | | | |
| Bleaching (ΔE) | 0 | 1.92 | 3.33 | 4.01 | 5.02 | 5.35 | 5.33 | 0.04 | 6.17 | 6.65 | 7.05 |
| Hydrolase (ΔA400/min) | 0 | 0.038 | 0.068 | 0.096 | 0.123 | 0.158 | 0.183 | 0.00 | 0.038 | 0.075 | 0.106 |

[1]Hydrolase activity representing the amount of enzyme present is expressed as ΔA400/min (enzymatic reaction)-ΔA400/min (non-enzymatic reaction). The bleaching is expressed as ΔE over the non-enzymatic reaction. Two experiments are reported.

Example 9

Construction of Perhydrolase Fusions to Additional Thermophilic Cellulose Binding Domains This example describes the design of an expression system for the production of additional perhydrolases targeted to cellulose, and specifically targeted to cotton via cellulose-binding sequences in which the cellulose binding domains are thermophilic.

The polynucleotides (SEQ ID NOs: 156, and 159) encoding fusions of a perhydrolase to cellulose-binding domains (SEQ ID NOs: 157 and 160, respectively) were designed to have the nucleotide sequence of the C277S variant of the *Thermotoga maritima* perhydrolase (SEQ ID NO: 142) fused at the 3'-end to the nucleotide sequence encoding a 18 amino acid flexible linker (SEQ ID NO: 143); itself fused to the nucleotide sequence encoding the cellulose-binding domains CBM9-2 of endo-1,4-beta-xylanase A from *Thermotoga maritima* (SEQ ID NO: 159) and CBD1 of the Cellulase A from *Caldicellulosiruptor saccharolyticus* (SEQ ID NO: 161) with a Met at the N-terminus. The genes were codon-optimized for expression in *E. coli* and synthesized by DNA2.0 (Menlo Park, Calif.). The coding sequences were cloned into an expression vector behind the pBAD promoter using the NdeI and AscI restriction sites yielding plasmids pLR1069 and pLR1071 respectively. To express the fusion proteins, the plasmids were transferred to the *E. coli* strain LR3728 (MG1655 $araBAD^-$ $ackA^-$ $pta^-$ $msbB^-$ $katE^-$ $katG^-$).

Example 10

Production of Fusion Proteins Comprising a Perhydrolase and a Thermophilic Cellulose-Binding Domain This example describes the expression and purification of a perhydrolase targeted to cellulose via a thermostable cellulose-binding domain.

Strains expressing the genes encoding fusions of the *Thermotoga maritima* perhydrolase to the cellulose-binding domains CBM9-2 of endo-1,4-beta-xylanase A from *Thermotoga maritima* (SEQ ID NO: 159) and CBD1 of the cellulase A from *Caldicellulosiruptor saccharolyticus* (SEQ ID NO: 161) were grown in autoinduction medium as described in Example 2. The cells were harvested by centrifugation at 8000 rpm at 4° C. and washed by resuspending the cell pellets in 300 mL of ice-chilled 50 mM $KH_2PO_4$, pH 7.2 buffer containing 10,000 Units Benzonase (Sigma-Aldrich St Louis, Mo.)

The cells were disrupted by two passes through a French pressure cell. The lysed cell extracts were transferred to 4×50-mL conical polypropylene centrifuge tubes and centrifuged at 10,000 rpm for 10 min at 4° C. Five mL of the soluble fraction were transferred to 15-mL conical polypropylene tubes and heated to 80° C. for 15 min, chilled on ice and pooled into 4×50-mL conical polypropylene centrifuge tubes. The soluble fraction containing the thermostable enzyme and the precipitated *E. coli* proteins were separated by centrifugation at 10,000 rpm for 10 min at 4° C. The output of this purification protocol typically yielded 2-4 mg of protein per mL with a purity of the fusion perhydrolase between 90% and 75% of the protein as estimated by polyacrylamide gel electrophoresis (PAGE) analysis. Total protein was quantitated by the BCA assay (Sigma-Aldrich, St Louis, Mo.) using a solution of Bovine Serum Albumin as a standard (Sigma-Aldrich). The perhydrolase activity was measured with the ABTS (2,2'- azino-bis(3-ethylbenzothiazoline)-6-sulfonate). The specific activity of the fusion perhydrolases were 482 μmol PAA/min/mg and 629 μmol PAA/min/mg respectively.

The fusion of the *Thermotoga maritima* perhydrolase to both thermophilic cellulose binding domains remained soluble indicating that they could be produced by the same process as the un-targeted perhydrolase.

Example 11

Demonstration of Functionality of the Perhydrolase Fused to Thermophilic Cellulose-Binding Domains This example demonstrates the activity of perhydrolases targeted to cellulose via a thermostable cellulose-binding domain as well as their binding to cellulose.

The perhydrolase fusions engineered to contain a thermophilic binding domain were contacted to a cellulose slurry (AVICEL® microcrystalline cellulose, (FMC Corp., Philadelphia, Pa.) 20 mg in 1 mL of 50 mM potassium phosphate buffer pH 7.2) (2.5 mg of enzyme/g cellulose). After 30 min of gentle agitation, the cellulose was pelleted by centrifugation. The supernatant (unbound fraction) was transferred to a new tube and the cellulose was washed 5 times with 1 mL of phosphate buffer. The perhydrolase activity was measured in the unbound fraction as well as in the bound fraction (cellulose slurry after the fifth buffer wash). Ninety six % of the activity of perhydrolase fused to the *Thermotoga* CBM9-2 cellulose-binding domain and 98% of that of the perhydrolase fused to the *Caldicellulosiruptor* CBD-1 cellulose-binding domain were retained on the cellulose. Denaturing polyacrylamide gel electrophoresis of proteins present in the bound and unbound fractions showed a protein band corresponding to fusion perhydrolase the washed AVICEL® slurries and not in the unbound fractions confirming their binding to cellulose and thus the functionality of the cellulose binding domain when fused to the perhydrolase.

This example demonstrates that other cellulose binding domains can be engineered in perhydrolase binding domains and allow the perhydrolase to retain its activity and bind to cellulose.

Example 12

Construction of Fusions of Additional to Perhydrolases to Cellulose Binding Domains This example describes the design of expression systems for the production of additional perhydrolases targeted to cellulose.

TABLE 6

Description of various hydrolase/perhydrolases fused to cellulose binding domains

| Organism source of perhydrolase | Targeting sequence (SEQ ID NO:) | Nucleotide sequence of targeted perhydrolase (SEQ ID NO:) | Amino acid sequence of targeted perhydrolase (SEQ ID NO:) |
|---|---|---|---|
| *Bacillus pumilus* | CIP (SEQ ID NO: 149) | 164 | 165 |
| *Lactobacillus lactis* | CIP (SEQ ID NO: 149) | 166 | 167 |
| *Mesorhizobium loti* | CIP (SEQ ID NO: 149) | 168 | 169 |
| *Mycobacterium smegmatis* | CIP (SEQ ID NO: 149) | 170 | 171 |
| *Mycobacterium smegmatis* | CBD1 (SEQ ID NO: 161) | 172 | 173 |
| *Mycobacterium smegmatis* | CBM9-2 (SEQ ID NO: 158) | 174 | 175 |
| *Pseudomonas fluorescens* | CIP (SEQ ID NO: 149) | 176 | 177 |
| *Pseudomonas fluorescens* | CBM9-2 (SEQ ID NO: 158) | 178 | 179 |

The polynucleotide sequences (SEQ ID NOs: 164, 166, and 168) were designed to encode fusions of xylan esterases from *Bacillus pumilus, Lactococcus lactis* and *Mesorhizobium loti* (SEQ ID NOs: 10, 40, and 42) to a 18 amino acid flexible linker (SEQ ID NO: 143); itself fused to the CIP cellulose binding domain *Clostridium thermocellum* (SEQ ID NO: 149). These enzymes belong to the CE-7 family of hydrolases as does the *Thermotoga maritima* perhydrolase.

The polynucleotide sequences (SEQ ID NOs: 170, 172, and 174) were designed to encode fusions of the S54V variant of the aryl esterase from *Mycobacterium smegmatis* (SEQ ID NO: 162) to a 18 amino acid flexible linker (SEQ ID NO: 143); itself fused to the cellulose binding domains CIP from *Clostridium thermocellum* (SEQ ID NO: 149), CBD1 (SEQ ID NO: 161) from *Caldicellulosiruptor saccharolyticus* and CBM9-2 (SEQ ID NO: 158) from *Thermotoga maritima*. The aryl esterase from *Mycobacterium smegmatis* belongs to a different class of hydrolytic enzyme than that of the *Thermotoga maritima* perhydrolase.

The polynucleotide sequences (SEQ ID NOs: 176 and 178) were designed to encode fusions of the L29P variant of the hydrolase from *Pseudomonas fluorescens* (SEQ ID NO: 163) to a 18 amino acid flexible linker (SEQ ID NO: 143); itself fused to the cellulose binding domains CIP from *Clostridium thermocellum* (SEQ ID NO: 149) and CBM9-2 (SEQ ID NO: 158) from *Thermotoga maritima*. The hydrolase/esterase from *Pseudomonas fluorescens* belongs to a different class of hydrolytic enzymes than that of the *Thermotoga maritima* perhydrolase or of *Mycobacterium smegmatis.*

The genes were codon-optimized for expression in *E. coli* and synthesized by DNA2.0 (Menlo Park, Calif.). The coding sequences were cloned in plasmids behind the T7 promoter or the pBAD promoter in a manner similar as that described in Examples 1 and 9. The plasmids were transferred in an appropriate expression host: *E. coli* strain BL21AI (Invitrogen, Carlsbad, Calif.) for constructs under the T7 promoter or in an araBAD derivative of *E. coli* MG1655 for constructs under the pBAD promoter.

Example 13

Production of Fusion Proteins Comprising Alternative Esterase/Perhydrolase and a Cellulose-Binding Domain This example describes the expression and purification of various alternative esterase/perhydrolase targeted to cellulose.

Strains expressing the genes encoding fusions to the hydrolase/perhydrolases in Table 6 of Example 12 were grown in 1 L of autoinduction medium (10 g/L Tryptone, 5 g/L Yeast Extract, 5 g/L NaCl, 50 mM $Na_2HPO_4$, 50 mM $KH_2PO_4$, 25 mM $(NH_4)_2SO_4$, 3 mM $MgSO_4$, 0.75% glycerol, 0.075% glucose and 0.05% arabinose) containing 50 mg/L spectinomycin at 37° C. for 20 hours under 200 rpm agitation. All protein fusions expressed well in *E. coli*. The cells were harvested by centrifugation at 8000 rpm at 4° C. and washed by resuspending the cell pellets in 300 mL of ice chilled lysis buffer (50 mM Tris pH 7.5 100 mM NaCl) using a tissue homogenizer (Brinkman Homogenizer model PCU11) at 3500 rpm followed by centrifugation (8000 rpm, 4° C.). The cells were disrupted by two passes through a French pressure cell at 16,000 psi (~110.32 MPa). The lysed cell extracts were transferred to 4×50-mL conical polypropylene centrifuge tubes and centrifuged at 10,000 rpm for 10 min at 4° C. The supernatant containing the enzymes were transferred to new tubes. The approximate amount of fusion protein in each extract was estimated by comparison to bands of Bovine Serum Albumin standard on a Coomassie stained PAGE gel.

This example demonstrates the production of various combination of hydrolases/perhydrolases to various cellulose binding domains.

Example 14

Perhydrolase Activity of Alternative Perhydrolases Fused to a Cellulose-Binding Domains This example describes the activity of alternative esterase/perhydrolase targeted to cellulose.

The perhydrolase activity of the enzymes targeted to cellulose with a variety of targeting domains produced as described in Example 13 was measured with the ABTS assay. The results are reported in Table 7 and show that targeted CE7 as well as non-CE7 hydrolases have perhydrolytic activity.

TABLE 7

Perhydrolase activity of various cellulose-targeted hydrolytic enzymes.

| Organism source of perhydrolase | Targeting sequence (SEQ ID NO:) | Amino acid sequence of targeted perhydrolase (SEQ ID NO:) | Perhydrolase activity (μmol/mg PAA/min/mg) |
|---|---|---|---|
| *Bacillus pumilus* | CIP (SEQ ID NO: 149) | 165 | 53 |
| *Lactobacillus lactis* | CIP (SEQ ID NO: 149) | 167 | 27 |
| *Mesorhizobium loti* | CIP (SEQ ID NO: 149) | 169 | Not done [1] |
| *Mycobacterium smegmatis* | CIP (SEQ ID NO: 149) | 171 | 54 |
| *Mycobacterium smegmatis* | CBD1 (SEQ ID NO: 161) | 173 | 69 |
| *Mycobacterium smegmatis* | CBM9-2 (SEQ ID NO: 158) | 175 | 75 |
| *Pseudomonas fluorescens* | CIP (SEQ ID NO: 149) | 177 | 1.5 [2] |
| *Pseudomonas fluorescens* | CBM9-2 (SEQ ID NO: 158) | 179 | 1.6 [2] |

Note

[1] The perhydrolase of the *Mesorhizobium loti* fusion was not measured but the enzyme was found to be active using the pNPA hydrolase assay.

Note

[2] The perhydrolase activity of the various fusions was measured with the ABTS assay using 64 mM Triacetin as a substrate at pH 7.5 except for the *Pseudomonas fluorescens* hydrolase fusions that were assayed using 1M Na acetate as a substrate at pH 5.5. Fusions to the *Thermotoga* perhydrolase had no activity with Acetate as a substrate.

This example demonstrates that other cellulose-targeted fusions of hydrolase enzymes, from the CE-7 family or from other families can be produced and have perhydrolytic activity, and could be used directly or after enzyme evolution in applications involving cellulosic materials.

Example 15

Binding of Alternative Perhydrolase Fused to Cellulose Binding Domains

This example describes the binding of alternative esterase/perhydrolase targeted to cellulose.

Crude extracts of *E. coli* expressing various combinations of hydrolase/perhydrolases fused to various cellulose binding domains were contacted to a cellulose slurry. The extracts were loaded in excess as to saturate the cellulose (AVICEL®, 20 mg in 1 mL of 50 mM potassium phosphate buffer pH7.2; perhydrolase fusions approximately 300 μg of enzyme/20 mg cellulose). After 30 min of gentle agitation, the cellulose was pelleted by centrifugation. The supernatants (unbound fractions) were removed and the cellulose pellets were washed three times with 1 mL of phosphate buffer. After the third wash, the cellulose was resuspended in 1 mL of phosphate buffer. Twenty μL of resuspended slurry were mixed with 20 μL of denaturing SDS PAGE sample buffer and boiled for 5 min. The binding of the cellulose-targeted perhydrolases was assessed by denaturing polyacrylamide gel electrophoresis of proteins present in the bound fraction (20 μL sample loaded per lane). All fusions showed a protein band with the appropriate size corresponding to the fusion perhydrolase binding the washed AVICEL® slurry. All the bands all had a similar intensity thus demonstrating the functionality of the cellulose binding domain when fused to the perhydrolase.

This example demonstrates that diverse perhydrolases from different hydrolase families can be targeted to cellulose via different cellulose binding domains and that cellulose binding domains are functional in the context of fusions to perhydrolases other than the *Thermotoga* perhydrolase.

What is claimed is:

1. A method comprising:

1) providing a set of reaction components comprising:

a) at least one substrate selected from the group consisting of:

i) esters having the structure $[X]_mR_5$ wherein X=an ester group of the formula $R_6C(O)O$ $R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;

$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;

m is an integer ranging from 1 to the number of carbon atoms in $R_5$; and wherein said esters have solubility in water of at least 5 ppm at 25° C.;

ii) glycerides having the structure

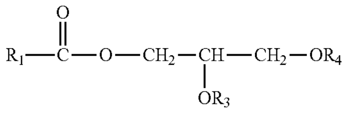

wherein $R_1$=$C_1$ to $C_7$ straight chain or branched chain alkyl optionally substituted with an hydroxyl or a C1 to C4 alkoxy group and $R_3$ and $R_4$ are individually H or $R_1C(O)$;

iii) one or more esters of the formula

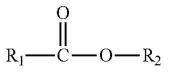

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10; and iv) acetylated saccharides selected from the group consisting of acetylated monosaccharides, acetylated disaccharides, and acetylated polysaccharides;

b) a source of peroxygen; and a fusion protein comprising the following general structure:

PAH-[L]y-TSBD or

TSBD-[L]y-PAH wherein

PAH is an enzyme having perhydrolytic activity; wherein said enzyme is a carbohydrate esterase having a CE-7 signature motif that aligns with a reference sequence SEQ ID NO: 2, said signature motif comprising:

i) an RGQ motif at positions corresponding to positions 118-120 of SEQ ID NO:2;

ii) a GXSQG motif at positions corresponding to positions 179-183 of SEQ ID NO:2; and iii) an HE motif at positions corresponding to positions 298-299 of SEQ ID NO:2; TSBD is a peptidtc component having affinity for a surface of a target material; wherein the surface is not a body surface or an oral cavity surface; wherein the peptidic component is a single chain variable fragment (scFv) antibody, a single chain polypeptide lacking an immunoglobulin fold comprising at least one target surface-binding peptide ranging from 5 to 60 amino acids in length, or a cellulose binding domain; L is an optional peptide linker ranging from 1 to 100 amino acids in length; and y is 0 or 1; and 2) combining the reaction components of (1) under suitable reaction conditions whereby;

a) the fusion protein binds to the target surface; and b) at least one peracid is enzymatically produced and contacted with the target surface; whereby the target surface receives a peracid-based benefit selected from the group consisting of bleaching, whitening, disinfecting, sanitizing, destaining, deodorizing, and combinations thereof.

2. The method of claim 1 wherein the reaction components are combined on the target surface.

3. The method of claim 1 wherein the reaction components are combined prior to contacting the target surface.

4. The method of claim 1 wherein the fusion protein having perhydrolytic activity is present on the target surface prior to enzymatically producing the peracid.

5. The method of claim 1 wherein the cellulose-binding domain is obtained from a cellulose-binding enzyme from *Clostridium thermocellum, Clostridium cellulovorans, Bacillus* sp., *Thermotoga maritima*, or *Caldicellulosiruptor saccharolyticus.*

6. The method of claim 5 wherein the cellulose-binding domain is a member of cellulose-binding domain family CBM9, CBM17, CBM28, or CBD3.

7. The method of claim 1 wherein the target material comprises a cellulosic material.

8. The method of claim 7 wherein the cellulosic material comprises cellulose, wood, wood pulp, paper, cotton, rayon, lyocell or any combination thereof.

9. The method of claim 1 or claim 8 wherein the target material comprises polymethyl methacrylate, polypropylene, polytetrafluoroethylene, polyethylene, polyamide, polyester, polystyrene, cellulose acetate or any combination thereof.

10. The method of claim 1 where the peracid is produced at a concentration of 500 ppb to 10,000 ppm within 5 minutes of combining the set of reaction components.

11. The method of claim 10 wherein the peracid is contacted with the target surface for less than 1 hour.

12. The method of claim 1, claim 10 or claim 11 wherein the peracid is peracetic acid.

13. The method of claim 1 wherein the substrate comprises triacetin.

14. A fusion protein comprising the following general structure:

$$PAH\text{-}M_y\text{-}TSBD$$

or $$TSBD\text{-}[L]_y\text{-}PAH$$

wherein

PAH is an enzyme having perhydrolytic activity; wherein said enzyme is a carbohydrate esterase having a CE-7 signature motif that aligns with a reference sequence SEQ ID NO: 2, said signature motif comprising:

1) an RGQ motif at positions corresponding to positions 118-120 of SEQ ID NO:2;

2) a GXSQG motif at positions corresponding to positions 179-183 of SEQ ID NO:2; and 3) an HE motif at positions corresponding to positions 298-299 of SEQ ID NO:2;

TSBD is a peptidic component having affinity for a surface of a target material; wherein the surface is not a body surface or an oral cavity surface; wherein the peptidic component is a single chain variable fragment (scFv) antibody, a single chain polypeptide lacking an immunoglobulin fold comprising at least one target surface-binding peptide ranging from 5 to 60 amino acids in length, or a cellulose binding domain;

L is an optional peptide linker ranging from 1 to 100 amino acids in length; and y is 0 or 1.

15. The fusion protein of claim 14 wherein said at least one target surface-binding peptide has a $K_D$ value or an $MB_{50}$ value of $10^{-5}$ M or less for said target surface.

16. The fusion protein of claim 14 wherein the single chain polypeptide comprises 2 to 50 target surface-binding peptides, wherein the target surface-binding peptides are independently and optionally separated by a polypeptide spacer ranging from 1 to 100 amino acids in length.

17. The fusion protein of claim 14 wherein the peptidic component comprises a length of no more than 200 amino acids.

18. A peracid generation system comprising:

a set of reaction components comprising:

1) at least one substrate selected from the group consisting of:

i) esters having the structure $$[X]_mR_5$$

wherein X=an ester group of the formula $R_6C(O)O$ $R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;

$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;

m is an integer ranging from 1 to the number of carbon atoms in $R_5$; and wherein said esters have solubility in water of at least 5 ppm at 25° C.;

ii) glycerides having the structure

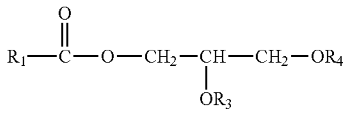

wherein $R_1$=C1 to C7 straight chain or branched chain alkyl optionally substituted with an hydroxyl or a C1 to C4 alkoxy group and $R_3$ and $R_4$ are individually H or $R_1C(O)$;

iii) one or more esters of the formula

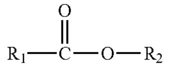

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10; and iv) acetylated saccharides selected from the group consisting of acetylated monosaccharides, acetylated disaccharides, and acetylated polysaccharides;

2) a source of peroxygen; and 3) a fusion protein having perhydrolytic activity comprising the general structure $$PAH\text{-}[L]_y\text{-}TSBD$$

or $$TSBD\text{-}[L]_y\text{-}PAH$$

wherein

PAH is an enzyme having perhydrolytic activity; wherein said enzyme having perhydrolytic activity is a carbohydrate esterase having a CE-7 signature motif that aligns with a reference sequence SEQ ID NO: 2, said signature motif comprising:

1) an RGQ motif at positions corresponding to positions 118-120 of SEQ ID NO:2;

2) a GXSQG motif at positions corresponding to positions 179-183 of SEQ ID NO:2; and 3) an HE motif at positions corresponding to positions 298-299 of SEQ ID NO:2;

TSBD is a peptidic component having affinity for a surface of a target material; wherein the surface is not a body surface or an oral cavity surface; wherein the peptidic component is a single chain variable fragment (scFv) antibody, a single chain polypeptide lacking an immunoglobulin fold comprising at least one target surface-binding peptide ranging from 5 to 60 amino acids in length, or a cellulose binding domain;

L is an optional peptide linker ranging from 1 to 100 amino acids in length; and y is 0 or 1.

19. A laundry care product comprising the fusion protein of claim 14.

20. The laundry care product of claim 19 wherein the laundry care product is in the form of a powder, granule, paste, gel, liquid, tablet, rinse or any combination thereof.

21. A method comprising:

1) providing a set of reaction components comprising:

a) at least one substrate selected from the group consisting of:

i) esters having the structure $[X]_mR_5$ wherein X=an ester group of the formula $R_6C(O)O$ $R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;

$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;

m is an integer ranging from 1 to the number of carbon atoms in $R_5$; and wherein said esters have solubility in water of at least 5 ppm at 25° C.;

ii) glycerides having the structure

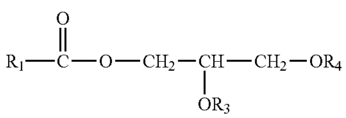

wherein $R_1$=C1 to C7 straight chain or branched chain alkyl optionally substituted with an hydroxyl or a C1 to C4 alkoxy group and $R_3$ and $R_4$ are individually H or $R_1C(O)$;

iii) one or more esters of the formula

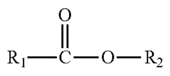

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10; and iv) acetylated saccharides selected from the group consisting of acetylated monosaccharides, acetylated disaccharides, and acetylated polysaccharides;

b) a source of peroxygen; and c) the fusion protein of claim 14;

2) contacting that target surface with the fusion protein having perhydrolytic activity whereby the fusion protein binds to the target surface;

3) optionally rinsing the target surface; and 4) contacting the target surface having the bound fusion protein with said at least one substrate and the source of peroxygen whereby at least one peracid is enzymatically produced by the fusion protein; whereby the target surface receives a peracid-based benefit selected from the group consisting of bleaching, whitening, disinfecting, destaining, deodorizing, decreasing or removing biofilm, and combinations thereof.

22. A method for the production of a fusion protein comprising a perhydrolytic enzyme coupled to at least one a peptidic component having affinity for a cellulosic material, said method comprising:

a) providing a recombinant microbial host cell comprising an expressible genetic construct encoding the fusion protein of claim 14;

b) growing the recombinant microbial host cell under suitable conditions whereby the fusion protein is produced; and c) optionally recovering the fusion protein.

23. The method of claim 22 wherein the recombinant microbial host cell is *Escherichia coli* or *Bacillus subtilis*.

24. The method of claim 22 wherein the peptidic component having affinity for a cellulosic material a cellulose-binding domain.

25. The method of claim 24 wherein the cellulose-binding domain is obtained from a cellulose-binding enzyme from *Clostridium thermocellum, Clostridium cellulovorans, Bacillus* sp., *Thermotoga maritima*, or *Caldicellulosiruptor saccharolyticus*.

26. The method of claim 24 wherein the cellulose-binding domain is a member of cellulose-binding domain family CBM9, CBM17, CBM28, or CBD3.

27. The method of claim 22 wherein the peptidic component having affinity for a target surface is a single chain polypeptide lacking an immunoglobulin fold.

* * * * *